US011576906B2

(12) United States Patent
Kelly et al.

(10) Patent No.: US 11,576,906 B2
(45) Date of Patent: *Feb. 14, 2023

(54) INHIBITING MUTANT IDH-1

(71) Applicant: FORMA Therapeutics, Inc., Watertown, MA (US)

(72) Inventors: Patrick F. Kelly, Concord, MA (US); Alan Collis, Lexington, MA (US); Jeff Davis, Hingham, MA (US); Duncan Walker, Boulder, CO (US); Susan Ashwell, Carlisle, MA (US); Blythe Thomson, Newton, MA (US); Wei Lu, Newton, MA (US)

(73) Assignee: FORMA Therapeutics, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/414,505

(22) Filed: May 16, 2019

(65) Prior Publication Data
US 2019/0350919 A1 Nov. 21, 2019

Related U.S. Application Data

(60) Provisional application No. 62/812,367, filed on Mar. 1, 2019, provisional application No. 62/798,677, filed on Jan. 30, 2019, provisional application No. 62/798,681, filed on Jan. 30, 2019, provisional application No. 62/798,684, filed on Jan. 30, 2019, provisional application No. 62/798,687, filed on Jan. 30, 2019, provisional application No. 62/798,690, filed on Jan. 30, 2019, provisional application No. 62/773,562, filed on Nov. 30, 2018, provisional application No. 62/692,591, filed on Jun. 29, 2018, provisional application No. 62/692,598, filed on Jun. 29, 2018, provisional application No. 62/692,601, filed on Jun. 29, 2018, provisional application No. 62/692,604, filed on Jun. 29, 2018, provisional application No. 62/692,605, filed on Jun. 29, 2018, provisional application No. 62/680,566, filed on Jun. 4, 2018, provisional application No. 62/680,571, filed on Jun. 4, 2018, provisional application No. 62/680,560, filed on Jun. 4, 2018, provisional application No. 62/680,562, filed on Jun. 4, 2018, provisional application No. 62/672,462, filed on May 16, 2018, provisional application No. 62/672,461, filed on May 16, 2018.

(51) Int. Cl.
A61K 31/4709 (2006.01)
A61P 35/00 (2006.01)
A61K 9/00 (2006.01)
A61K 9/20 (2006.01)
A61K 9/48 (2006.01)
A61K 31/7068 (2006.01)

(52) U.S. Cl.
CPC ........ *A61K 31/4709* (2013.01); *A61K 9/0053* (2013.01); *A61K 9/2054* (2013.01); *A61K 9/4866* (2013.01); *A61P 35/00* (2018.01); *A61K 31/7068* (2013.01)

(58) Field of Classification Search
CPC .... A61K 31/4709; A61K 9/0053; A61P 35/00
USPC ................................................. 514/312, 314
See application file for complete search history.

(56) References Cited

U.S. PATENT DOCUMENTS

| | | |
|---|---|---|
| 5,262,564 A | 11/1993 | Kun et al. |
| 5,984,882 A | 11/1999 | Rosenschein et al. |
| 6,410,516 B1 | 6/2002 | Baltimore et al. |
| 6,914,128 B1 | 7/2005 | Salfeld et al. |
| 6,979,675 B2 | 12/2005 | Tidmarsh |
| 7,217,286 B2 | 5/2007 | Falotico et al. |
| 8,367,347 B2 | 2/2013 | Hartmann et al. |
| 8,469,749 B2 | 6/2013 | Ladouceur et al. |
| 8,685,660 B2 | 4/2014 | Vogelstein et al. |
| 8,876,991 B2 | 11/2014 | Luebke |
| 8,882,892 B2 | 11/2014 | Hoversten et al. |
| 8,883,438 B2 | 11/2014 | Cantley et al. |
| 8,933,395 B2 | 1/2015 | Mueth et al. |
| 9,073,941 B2 | 7/2015 | Wong et al. |
| 9,335,332 B2 | 5/2016 | Kumaravel et al. |
| 9,353,418 B2 | 5/2016 | Vogelstein et al. |
| 9,624,175 B2 | 4/2017 | Lin et al. |
| 9,624,216 B2 | 4/2017 | Lin et al. |
| 9,771,349 B2 | 9/2017 | Lin et al. |
| 9,815,817 B2 | 11/2017 | Lin et al. |
| 9,834,539 B2 * | 12/2017 | Lin .......................... A61P 35/00 |
| 10,005,734 B2 | 6/2018 | Lin et al. |
| 10,253,015 B2 | 4/2019 | Lin et al. |
| 10,266,495 B2 | 4/2019 | Lin et al. |
| 10,280,150 B2 | 5/2019 | Lin et al. |
| 10,414,752 B2 | 9/2019 | Lin et al. |

(Continued)

FOREIGN PATENT DOCUMENTS

| | | |
|---|---|---|
| CN | 102558049 A | 7/2012 |
| CN | 103814020 A | 5/2014 |
| EP | 0481802 A1 | 4/1992 |
| JP | 2013-513613 A | 4/2013 |
| JP | 2017-528487 A | 9/2017 |

(Continued)

OTHER PUBLICATIONS

Brandon Nicolay et al . The IDH1 mutant inhibitor AG120 show a strong inhibition of 2-HG production in an orthotopic IDH1 mutant glioma model in vivo. (Year: 2017).*

(Continued)

*Primary Examiner* — Charanjit Aulakh
(74) *Attorney, Agent, or Firm* — James J. Diehl

(57) ABSTRACT

Methods of treating patients diagnosed with cancer harboring an IDH-1 mutation are provided, including the therapeutic administration of a certain inhibitor of a mutant IDH-1 as a single agent, or in combination with azacitidine (AZA).

3 Claims, 34 Drawing Sheets

(56) References Cited

U.S. PATENT DOCUMENTS

| | | | |
|---|---|---|---|
| 10,532,047 | B2 | 1/2020 | Luke |
| 10,550,098 | B2 | 2/2020 | Lin et al. |
| 10,610,125 | B2 | 4/2020 | Dang et al. |
| 10,704,108 | B2 | 7/2020 | Vogelstein et al. |
| 10,837,064 | B2 | 11/2020 | Vogelstein et al. |
| 10,889,567 | B2 | 1/2021 | Lin et al. |
| 2003/0105124 | A1 | 6/2003 | Sobolov-Jaynes |
| 2004/0106645 | A1 | 6/2004 | Blackburn et al. |
| 2006/0281122 | A1 | 12/2006 | Bryant et al. |
| 2008/0300208 | A1 | 12/2008 | Einat et al. |
| 2012/0184548 | A1 | 7/2012 | Dominique et al. |
| 2012/0184562 | A1 | 7/2012 | Luk |
| 2014/0235620 | A1 | 8/2014 | Caferro et al. |
| 2016/0083349 | A1 | 3/2016 | Lin et al. |
| 2016/0083365 | A1 | 3/2016 | Lin et al. |
| 2016/0083366 | A1* | 3/2016 | Lin .................. C07D 401/14 514/249 |
| 2016/0083367 | A1 | 3/2016 | Lin et al. |
| 2016/0311774 | A1 | 10/2016 | Lin et al. |
| 2016/0311818 | A1 | 10/2016 | Lin et al. |
| 2017/0081730 | A1 | 3/2017 | Vogelstein et al. |
| 2017/0157132 | A1 | 6/2017 | Wu et al. |
| 2017/0174658 | A1 | 6/2017 | Lin et al. |
| 2018/0086733 | A1 | 3/2018 | Lin et al. |
| 2018/0118732 | A1 | 5/2018 | Lin et al. |
| 2018/0134682 | A1 | 5/2018 | Lin et al. |
| 2018/0141910 | A1 | 5/2018 | Lin et al. |
| 2018/0312487 | A1 | 11/2018 | Lin et al. |
| 2018/0327361 | A1 | 11/2018 | Lin et al. |
| 2018/0327382 | A1 | 11/2018 | Lin et al. |
| 2019/0135781 | A1 | 5/2019 | Lin et al. |
| 2019/0263778 | A1 | 8/2019 | Lin et al. |
| 2019/0350919 | A1 | 11/2019 | Kelly et al. |
| 2019/0350920 | A1 | 11/2019 | Luke et al. |
| 2019/0350921 | A1 | 11/2019 | Ashwell |
| 2019/0350922 | A1 | 11/2019 | Kelly et al. |
| 2020/0085815 | A1 | 3/2020 | Luke et al. |
| 2020/0108060 | A1 | 4/2020 | Kelly et al. |
| 2020/0223822 | A1 | 7/2020 | Lin et al. |
| 2020/0297717 | A1 | 9/2020 | Kelly et al. |

FOREIGN PATENT DOCUMENTS

| | | |
|---|---|---|
| JP | 2017-528491 A | 9/2017 |
| JP | 2017-528492 A | 9/2017 |
| RU | 2284325 C2 | 9/2006 |
| WO | WO-00/40749 A2 | 7/2000 |
| WO | WO-2006/054912 A1 | 5/2006 |
| WO | WO-2007/117778 A2 | 10/2007 |
| WO | WO-2008/010964 A1 | 1/2008 |
| WO | WO-2008/069242 A1 | 6/2008 |
| WO | WO-2008/131547 A1 | 11/2008 |
| WO | WO-2010/028099 A1 | 3/2010 |
| WO | WO-2010/105243 A1 | 9/2010 |
| WO | WO-2010/144338 A1 | 12/2010 |
| WO | WO-2011/050210 A1 | 4/2011 |
| WO | WO-2011/050211 A2 | 4/2011 |
| WO | WO-2011/072174 A1 | 6/2011 |
| WO | WO-2012/040332 A2 | 3/2012 |
| WO | WO-2012/054915 A2 | 4/2012 |
| WO | WO-2012/079532 A1 | 6/2012 |
| WO | WO-2012/129562 A2 | 9/2012 |
| WO | WO-2012/171337 A1 | 12/2012 |
| WO | WO-2012/171506 A1 | 12/2012 |
| WO | WO-2012/173682 A2 | 12/2012 |
| WO | WO-2013/046136 A1 | 4/2013 |
| WO | WO-2013/096820 A1 | 6/2013 |
| WO | WO-2013/102431 A1 | 7/2013 |
| WO | WO-2013/102431 A1 | 7/2013 |
| WO | WO-2013/107291 A1 | 7/2013 |
| WO | WO-2013/107405 A1 | 7/2013 |
| WO | WO-2013/127997 A1 | 9/2013 |
| WO | WO-2014/141153 A1 | 9/2014 |
| WO | WO-2014/141153 A1 | 9/2014 |
| WO | WO-2014/147586 A1 | 9/2014 |
| WO | WO-2014/184272 A2 | 11/2014 |
| WO | WO-2015/003146 A1 | 1/2015 |
| WO | WO-2015/121210 A1 | 8/2015 |
| WO | WO-2016/044781 A1 | 3/2016 |
| WO | WO-2016/044782 A1 | 3/2016 |
| WO | WO-2016/044787 A1 | 3/2016 |
| WO | WO-2016/044789 A1 | 3/2016 |
| WO | WO-2016/106331 A1 | 6/2016 |
| WO | WO-2016/108045 A2 | 7/2016 |
| WO | WO-2016/171755 A1 | 10/2016 |
| WO | WO-2016/171756 A1 | 10/2016 |
| WO | WO-2017/019429 A1 | 2/2017 |
| WO | WO-2017/146795 A1 | 8/2017 |
| WO | WO-2017/213910 A1 | 12/2017 |
| WO | WO-2017/223202 A1 | 12/2017 |
| WO | WO-2018/111707 A1 | 6/2018 |
| WO | WO-PCT/US19/32742 | 5/2019 |
| WO | WO-PCT/US19/32747 | 5/2019 |
| WO | WO-2019/222551 A1 | 11/2019 |
| WO | WO-2019/222553 A1 | 11/2019 |
| WO | WO-2020/232381 A1 | 11/2020 |

OTHER PUBLICATIONS

Wolfgang Wick et al New (alternative) temozolomide regimens for the treatment of glioma (Year: 2009).*

Young Shin Cho et al. Discovery and Evaluation of Clinical Candidate IDH305, a brain Penetrant Mutant IDH1 inhibitor. (Year: 2017).*

Young Shin-Cho et al. Discovery and evaluation of IDH305 (Year: 2017).*

U.S. Appl. No. 16/414,716, filed May 16, 2019, Luke et al.

Abbas, S. et al., Acquired mutations in the genes encoding IDH1 and IDH2 both are recurrent aberrations in acute myeloid leukemia: prevalence and prognostic value, Blood, 116(12): 2122-2126 (2010).

Aghili, M. et al., Hydroxyglutaric aciduria and malignant brain tumor: a case report and literature review, J. Neurooncol., 91: 233-236 (2009).

Amary, M.F. et al., IDH1 and IDH2 mutations are frequent events in central chondrosarcoma and central and periosteal chondromas but not in other mesenchymal tumours, J Pathol, 224: 334-343 (2011).

Amary, M.F. et al., Ollier disease and Maffucci syndrome are caused by somatic mosaic mutations of IDH1 and IDH2, Nature Genetics, 43(12): 1262-1265 (2011).

Amidon, G.L. et al., A Theoretical Basis for a Biopharmaceutical Drug Classification: The Correlation of in Vitro Drug Product Dissolution and in Vivo Bioavailability, Pharmaceutical Research, 12(3): 413-420 (1995).

Andrones, O.C. et al., Pharmacodynamics of mutant-IDH1 inhibitors in glioma patients probed by in vivo 3D MRS imaging of 2-hydroxyglutarate, Nature Communications, 9: 1474, 9 pages (2018).

Asteian, A. et al., Design, Synthesis, and Biological Evaluation of Indole Biphenylcarboxylic Acids as PPARγ Antagonists, ACS Med. Chem. Lett., 6: 998-1003 (2015).

Badr, M.Z.A. et al., Reaction of Quinoxaline Derivatives with Nucleophilic Reagents, , Bull Chem Soc Jpn, 56(1): 326-330 (1983).

Baer, M.R. et al., A Phase 1 Dose Escalation Study of the IDH1m Inhibitor, FT-2102, in Patients with Acute Myeloid Leukemia (AML) or Myelodysplastic Syndrome (MDS), Abstract for Congress of EHA, EHA-1757: 1 page (Jun. 2018).

Baer, M.R. et al., A Phase 1 Dose Escalation Study of the IDH1m Inhibitor, FT-2102, in Patients with Acute Myeloid Leukemia (AML) or Myelodysplastic Syndrome (MDS), Presented at the 2018 Congress of EHA, Poster PF236, Stockholm (Jun. 15, 2018).

Bai, H. et al., Integrated genomic characterization of IDH1-mutant glioma malignant progression, Nature Genetics, 48(1): 59-66 (2016).

Balss, J. et al., Analysis of the *IDH1* codon 132 mutation in brain tumors, Acta Neuropathol, 116: 597-602 (2008).

(56) References Cited

OTHER PUBLICATIONS

Bertus, P. and Szymoniak, J., A direct synthesis of 1-aryl- and 1-alkenylcyclopropylamines from aryl and alkenyl Nitriles, Journal of Organic Chemistry, 68(18): 7133-7136 (2003).
Bleeker, F.E. et al., Recent advances in the molecular understanding of glioblastoma, J. Neurooncol, 108: 11-27 (2012).
Boddu, P. and Borthakur, G., Therapeutic targeting of isocitrate dehydrogenase mutant AML, Expert Opinion on Investigational Drugs, 26(5): 525-529 (2017).
Borg, G. et al., One-pot asymmetric synthesis of tert-butanesulfinyl-protected amines from ketones by the in situ reduction of tert-butanesulfinyl ketimines, Tetrahedron Letters, 40: 6709-6712 (1999).
Borger, D.R. et al., Circulating Oncometabolite 2-Hydroxyglutarate is a Potential Surrogate Biomarker in Patients with Isocitrate Dehydrogenase-Mutant Intrahepatic Cholangiocarcinoma, Clin Cancer Res, 20(7): 1884-1890 (2014).
Borger, D.R., et al., Frequent mutation of isocitrate dehydrogenase (IDH)1 and IDH2 in cholangiocarcinoma identified through broad-based tumor genotyping, The Oncologist 17, 72-79 (2012).
Borodovsky, A. et al., 5-azacytidine reduces methylation, promotes differentiation and induces tumor regression in a patient-derived IDH1 mutant glioma xenograft, Oncotarget, 4(10): 1737-1747 (2013).
Brooks, E. et al., Identification and Characterization of Small-Molecule Inhibitors of the R132H/R132H Mutant Isocitrate Dehydrogenase 1 Homodimer and R132H/Wild-Type Heterodimer, Journal of Biomolecular Screening, 19(8): 1193-1200 (2014).
Bunse, L. et al., Suppression of antitumor T cell immunity by the oncometabolite (R)-2-hydroxyglutarate, Nature Medicine, 25 pages (2018).
Cairns, R.A. and Mak, T.W., Oncogenic Isocitrate Dehydrogenase Mutations: Mechanisms, Models, and Clinical Opportunities, Cancer Discover, 730-741 (2013).
Chaturvedi, A. et al., Mutant IDH1 promotes leukemogenesis in vivo and can be specifically targeted in human AML, Blood, 122(16): 2877-2887 (2013).
Chaturvedi, A. et al., Pan-mutant-IDH1 inhibitor BAY1436032 is highly effective against human IDH1 mutant acute myeloid leukemia in vivo, Leukemia, 31: 2020-2028 (2017).
Chiou, W.L., and Barve, A., Linear Correlation of the Fraction of Oral Dose Absorbed of 64 Drugs Between Humans and Rats, Pharmaceutical Research, 15(11): 1792-1795 (1998).
Cho, Y.S. et al., Discovery and Evaluation of Clinical Candidate IDH305, a Brain Penetrant Mutant IDH1 Inhibitor, ACS Med Chem Lett., 8(10): 1116-1121 (2017). Supporting Information, 31 pages.
Chowdhury, R. et al., The oncometabolite 2-hydroxyglutarate inhibits histone lysine demethylases, EMBO Reports, 12(5): 463-469 (2011).
Claus, E.B. et al., Survival and low grade glioma: the emergence of genetic Information, Neurosurg Focus, 38(1): E6, 19 pages (2015).
ClinicalTrials.gov Identifier: NCT02719574, "Open-label Study of FT-2102 With or Without Azacitidine or Cytarabine in Patients With AML or MDS With an IDH1 Mutation," (v1 dated Mar. 21, 2016, published Mar. 24, 2016, and first posted Mar. 25, 2016 at https://clinicaltrials.gov/ct2/history/NCT02719574?V_1=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v10 dated Nov. 6, 2017, published Nov. 7, 2017, and update posted Nov. 8, 2017 at https://clinicaltrials.gov/ct2/history/NCT02719574?V_10=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v11 dated Dec. 6, 2017, published Dec. 7, 2017, and update posted Dec. 8, 2017 at https://clinicaltrials.gov/ct2/history/NCT02719574?V_11=View#StudyPageTop).

ClinicalTrials.gov Identifier: NCT02719574, "Open-label Study of FT-2102 With or Without Azacitidine or Cytarabine in Patients With AML or MDS With an IDH1 Mutation," (v12 dated May 17, 2018, Published May 18, 2018, and update posted May 21, 2018 at https://clinicaltrials.gov/ct2/history/NCT02719574?V_12=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v13 dated Nov. 27, 2018, published Nov. 28, 2018, and update posted Nov. 29, 2018 at https://clinicaltrials.gov/ct2/history/NCT02719574?V_13=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v2 dated Apr. 21, 2016 published Apr. 21, 2016, and update posted Apr. 22, 2016 at https://clinicaltrials.gov/ct2/history/NCT02719574?V_2=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v3 dated Jun. 8, 2016, published Jun. 8, 2016, and update posted Jun. 9, 2016 at https://clinicaltrials.gov/ct2/history/NCT02719574?V_3=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v4 dated Jul. 1, 2016, published Jul. 1, 2016, and update posted Jul. 4, 2016 at https://clinicaltrials.gov/ct2/history/NCT02719574?V_4=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v5 dated Jul. 12, 2016, published Jul. 12, 2016, and update posted Jul. 13, 2016 at https://clinicaltrials.gov/ct2/history/NCT02719574?V_5=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v6 dated Aug. 17, 2016, published Aug. 18, 2016, and update posted Aug. 19, 2016 at https://clinicaltrials.gov/ct2/history/NCT02719574?V_6=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v7 dated Dec. 8, 2016, published Dec. 8, 2016, and update posted Dec. 9, 2016 at https://clinicaltrials.gov/ct2/history/NCT02719574?V_7=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v8 dated Feb. 15, 2017, published Feb. 16, 2017, and update posted Feb. 16, 2017 at https://clinicaltrials.gov/ct2/history/NCT02719574?V_8=View#StudyPageTop).
ClinicalTrials.gov Identifier: NCT02719574, "Open-label Study of FT-2102 With or Without Azacitidine or Cytarabine in Patients With AML or MDS With an IDH1 Mutation," (v9 dated May 5, 2017, published May 5, 2017, and update posted May 8, 2017 at https://clinicaltrials.gov/ct2/history/NCT02719574?V_9=View#StudyPageTop).
ClinicalTrials.gov Identifier: NCT02719574, "Open-label Study of FT-2102 With or Without Azacitidine or Cytarabine in Patients With AML or MDS With an IDH1 Mutation," Study Details, (First Posted May 18, 2018, Last Update Posted Nov. 29, 2018).
ClinicalTrials.gov Identifier: NCT03684811, "A Study of FT-2102 in Participants with Advanced Solid Tumors and Gliomas With an IDH1 Mutation," (v1 dated Sep. 24, 2018; update published on Sep. 25, 2018, and posted on Sep. 26, 2018 https://clinicaltrials.gov/ct2/history/NCT03684811?V_1=View#StudyPageTop.
ClinicalTrials.gov Identifier: NCT03684811, "A Study of FT-2102 in Participants with Advanced Solid Tumors and Gliomas With an IDH1 Mutation," (v2 dated Nov. 12, 2018; update published on Nov. 13, 2018, and posted on Nov. 14, 2018 https://clinicaltrials.gov/ct2/history/NCT03684811?V_2=View#StudyPageTop.

(56) References Cited

OTHER PUBLICATIONS

ClinicalTrials.gov Identifier: NCT03684811, "A Study of FT-2102 in Participants with Advanced Solid Tumors and Gliomas With an IDH1 Mutation," (v3 dated Feb. 12, 2019; update published on Feb. 12, 2019 and posted on Feb. 15, 2019 https://clinicaltrials.gov/ct2/history/NCT03684811?V_3=View#StudyPageTop.
ClinicalTrials.gov Identifier: NCT03684811, "A Study of FT-2102 in Participants with Advanced Solid Tumors and Gliomas With an IDH1 Mutation," (v4 dated Feb. 15, 2019; update published on Feb. 18, 2019, and posted on Feb. 19, 2019 https://clinicaltrials.gov/ct2/history/NCT03684811?V_4=View#StudyPageTop.
ClinicalTrials.gov Identifier: NCT03684811, "A Study of FT-2102 in Participants with Advanced Solid Tumors and Gliomas With an IDH1 Mutation," (v5 dated Mar. 13, 2019; update published on Mar. 13, 2019, and posted on Mar. 14, 2019 https://clinicaltrials.gov/ct2/history/NCT03684811?V_5=View#StudyPageTop.
ClinicalTrials.gov Identifier: NCT03684811, "A Study of FT-2102 in Participants with Advanced Solid Tumors and Gliomas With an IDH1 Mutation," Study Details (First Posted Sep. 26, 2018, Last Update Posted May 1, 2019).
Cohen, A. et al., IDH1 and IDH2 Mutations in Gliomas, Curr Neurol Neurosci Rep., 13(5): 345, 13 pages (2013).
Cortes, J.E. et al., FT-2102, an IDH1m Inhibitor, Combined with Azacitidine in Patients with Acute Myeloid Leukemia (AML) or Myelodysplastic Syndrome (MDS): Results from a Phase 1 Study, Congress of EHA 2019 Abstract Submission, 4. Acute myeloid leukemia—Clinical, EHA-3328, 2 pages (submitted Mar. 1, 2019).
Cortes, J.E. et al., FT-2102, an IDH1m Inhibitor, in Combination with Azacitidine in Patients with Acute Myeloid Leukemia (AML) or Myelodysplastic Syndrome (MDS): Results from a Phase 1 Study, ASH abstract available on online meeting program, 9 pages (submitted Jul. 31, 2018, published Nov. 1, 2018).
Cortes, J.E. et al., FT-2102, an IDH1m Inhibitor, in Combination with Azacitidine in Patients with Acute Myeloid Leukemia (AML) or Myelodysplastic Syndrome (MDS): Results from a Phase 1 Study, Poster 1452, Presented at the 60th Annual Meeting of the American Society of Hematology, San Diego, CA (Dec. 1, 2018).
Cui, Z. et al., Structure and properties of N-heterocycle-containing benzotriazoles as UV absorbers, Journal of Molecular Structure, 1054: 94-99 (2013).
Cytosar-U, Sterile Cytarabine, USP; Drug Description, Pharmacia & Upjohn Company, Revised Sep. 1997, 6 pages (Approved Oct. 15, 1998).
Dai, D. et al., Clinical pharmacokinetics/pharmacodynamics (PK/PD) of ivosidenib in patients with IDH1-mutant advanced hematologic malignancies from a phase 1 study, 2018 ASCO Annual Meeting, J Clin Oncol., 36 (Abstract 2581), 1 page (Jun. 4, 2018). URL: https://meetinglibrary.asco.org/record/158639/abstract [Retrieved Jun. 7, 2018].
Damato, S. et al., IDH1 mutations are not found in cartilaginous tumours other than central and periosteal chondrosarcomas and enchondromas, Histopathology, 60: 357-376 (2011).
Dang, L. et al., Cancer-associated IDH1 mutations produce 2-hydroxyglutarate, Nature, 462: 739-744 (2009).
Dang, L. et al., IDH mutations in cancer and progress toward development of targeted therapeutics, Annals of Oncology, 27: 599-608 (2016).
Dang, L. et al., IDH mutations in glioma and acute myeloid leukemia, Trends Mol. Med., 16(9): 387-397 (2010).
Database Caplus (Online) Chemical Abstracts Service, Columbus, Ohio, US; retrieved from STN Database accession No. 1987: 407040 abstract, Prostakov, N.S. et al., Synthesis of substituted 2-pyridones and 4-aza-3-fluorenones, Khimiya Geterotsiklicheskikh Soedinenii, 7: 939-942 (1986).
Database Registry (Online) Chemical Abstracts Service, Columbus, Ohio, US; Database accession No. 1434379-53-9 (Jun. 5, 2013).
Database Registry (Online) Chemical Abstracts Service, Columbus, Ohio, US; Database accession No. 1497653-96-9 (Dec. 18, 2013).
Database Registry (Online) Chemical Abstracts Service, Columbus, Ohio, US; Database accession No. 1567357-55-4 (Mar. 12, 2014).
Database Registry (Online) Chemical Abstracts Service, Columbus, Ohio, US; Database accession No. 1567456-94-3 (Mar. 12, 2014).
De Botton, S. et al., FT-2102, An IDH1m Inhibitor, Induces Mutation Clearance in Patients With Acute Myeloid Leukemia (AML) or Myelodysplastic Syndrome (MDS) Treated in Phase 1 Dose Escalation and Expansion Study, Abstract Submission, 4. Acute myeloid leukemia—Clinical, EHA-3251, 2 pages (submitted Mar. 1, 2019).
Deng, G. et al., Selective Inhibition of Mutant Isocitrate Dehydrogenase 1 (IDH1) via Disruption of a Metal Binding Network by an Allosteric Small Molecule, The Journal of Biological Chemistry, 290:762-774 (2014).
Derissen, E.J.B. et al., ConciseDrug Review: Azacitidine and-Decitabine, The Oncologist; 18: 619-624 (2013).
Diao, L. and Meibohm, B., Pharmacometric Applications and Challenges in the Development of Therapeutic Antibodies in Immuno-Oncology, Current Pharmacology Reports, 4: 285-291 (2018).
Dohner, H., Diagnosis and management of AML in adults: 2017 ELN recommendations from an international expert panel, Blood, 129: 424-447 (2017).
Eckmann, K.R. et al., Chemotherapy Outcomes for the Treatment of Unresectable Intrahepatic and Hilar Cholangiocarcinoma: A Retrospective Analysis, Gastrointest Cancer Res 4: 155-160 (2011).
El-Khoueiry, A.B. et al., Nivolumab in patients with advanced hepatocellular carcinoma (CheckMate 040): results of phase 1/2 dose escalation and expansion, USC Norris Comprehensive Cancer Center, 36 pages (2017).
Estekizadeh, A. et al., Increased cytomegalovirus replication by 5-Azacytidine and viral-induced cytoplasmic expression of DNMT-1 in medulloblastoma and endothelial cells, International Journal of Oncology, 52: 1317-1327 (2018).
Estey E., Acute myeloid leukemia and myelodysplastic syndromes in older patients, JCO, 25: 1908-1915 (2007).
Faderl, S. et al., Clofarabine plus cytarabine compared with cytarabine alone in older patients with relapsed or refractory acute myelogenous leukemia: results from the CLASSIC I trial, J Clin Oncol., 30: 2492-2499 (2012).
Fatima, S., Molecular docking and 3D-QSAR studies on inhibitors of DNA damage signaling enzyme human PARP-1, J Receptors and Signal Transduction, 32(4) 214-224 (2012).
Fernandez, H.F. et al., Anthracycline dose intensification in acute myeloid leukemia, NEJM, 361:1249-1259 (2009).
Figueroa, M.E. et al., Leukemic IDH1 and IDH2 mutations result in a hypermethylation phenotype, disrupt TET2 function, and impair hematopoietic differentiation, Cancer Cell, 18:553-567 (2010).
Flavahan, W.A. et al., Insulator dysfunction and oncogene activation in IDH mutant gliomas, Nature, 1-16 (2015).
FORMA Therapeutics, Discovery and Optimization of a Novel Series of Inhibitors of mt-IDH1, 7th Annual Advances in Chemical Sciences Symposium, Presentation, 21 slides (May 4, 2018).
FORMA Therapeutics, FORMA Therapeutics and the University of Oxford Announce Multi-Year Collaboration to Advance the Development of Deubiquitinating Enzyme (DUB) Inhibitors for the Treatment of Neurodegenerative Diseases, Press Release, 2 pages (May 9, 2018).
FORMA Therapeutics, FORMA Therapeutics Announces Presentation at The 2018 American Society of Clinical Oncology (ASCO) Annual Meeting, FT-2102 IDH1m Inhibitor Clinical Data Selected for Oral Presentation, Abstract 7009: 1 page (May 10, 2018).
Frankel, S.R. et al., The "retinoic acid syndrome" in acute promyelocytic leukemia, Ann Intern Med., 117(4): 292-296 (1992).
Gaal, J. et al., Isocitrate Dehydrogenase Mutations are Rare in Pheochromocytomas and Paragangliomas, J. Clin. Endocrinol. Metab., 95(3): 1274-1278 (2010).
Ghiam, A.F. et al., IDH mutation status in prostate cancer, Oncogene, 31: 3826 (2012).
Goyal, L. et al., Prognosis and Clinicopathologic Features of Patients With Advanced Stage Isocitrate Dehydrogenase (IDH)Mutant and IDHWild-Type Intrahepatic Cholangiocarcinoma, The Oncologist, 20: 1019-1027 (2015).
Gross, S. et al., Cancer-associated metabolite 2-hydroxyglutarate accumulates in acute myelogenous leukemia with isocitrate dehydrogenase 1 and 2 mutations, J. Exp. Med., 207(2): 339-344 (2010).

(56) References Cited

OTHER PUBLICATIONS

Hayden, J.T. et al., Frequent IDH1 mutations in supratentorial primitive neuroectodermal tumors (sPNET) of adults but not children, Cell Cycle, 8(11): 1806-1807 (2009).
He, Y. et al., Asperspiropene A, a novel fungal metabolite as an inhibitor of cancer-associated mutant isocitrate dehydrogenase 1, Org. Chem. Front., 1-8 (2017).
Hondeghem, L.M. et al., Blinded Test in Isolated Female Rabbit Heart Reliably Identifies Action Potential Duration Prolongation and Proarrhythmic Drugs: Importance of Triangulation, Reverse Use Dependence, and Instability, Journal of Cardiovascular Pharmacology, 41: 14-24 (2003).
Hondeghem, L.M. et al., Instability and Triangulation of the Action Potential Predict Serious Proarrhythmia, but Action Potential Duration Prolongation is Antiarrhythmic, Circulation, 103: 2004-2013 (2001).
International Search Report for PCT/US2015/051044, 4 pages (dated Nov. 23, 2015).
International Search Report for PCT/US2015/051046, 3 pages (dated Oct. 30, 2015).
International Search Report for PCT/US2015/051053, 4 pages (dated Oct. 28, 2015).
International Search Report for PCT/US2015/051055, 3 pages (dated Nov. 13, 2015).
International Search Report for PCT/US2015/051056, 4 pages (dated Nov. 20, 2015).
International Search Report for PCT/US2015/051059, 3 pages (dated Oct. 30, 2015).
Janin, M. et al., Serum 2-Hydroxyglutarate Production in IDH1- and IDH2-Mutated De Novo Acute Myeloid Leukemia: A Study by the Acute Leukemia French Association Group, Journal of Clinical Oncology, 32(4): 297-305 (2014).
Jiang, K. et al., Primary Liver Cancers, Part 2: Progression Pathways and Carcinogenesis, Cancer Control, 25(1): 1-9 (2018).
Jones, S.; et al., Discovery and Optimization of Allosteric Inhibitors of Mutant Isocitrate Dehydrogenase 1 (R132H IDH1) Displaying Activity in Human Acute Myeloid Leukemia Cells, J. Med. Chem., 59(24): 11120-11137 (2016).
Kang, M.R. et al., Mutational analysis of IDH1 codon 132 in glioblastomas and other common cancers, Int. J. Cancer, 125: 353-355 (2009).
Kats, L.M., et al., Proto-oncogenic role of mutant IDH2 in leukemia initiation and maintenance, Cell Stem Cell, 14:329-341 (2014).
Koivunen, P. et al., Transformation by the R Enantiomer of 2-Hydroxyglutarate Linked to EgIN Activation, Nature, 483(7390): 484-488 (2013).
Kombarov, R.V. et al., CA Accession No. 138:368869, abstract only of Chem of Het Compounds, 38(9): 1154-1155 (2002).
Kopinja, J. et al., A Brain Penetrant Mutant IDH1 Inhibitor Provides In Vivo Survival Benefit, Scientific Reports, 7: 13853, 14 pages (2017).
Kurz, S.C. and Wen, P.Y., Quo Vadis-Do Immunotherapies Have a Role in Glioblastoma?, Curr Treat Options Neurol, 20: 14, 1-23 (2018).
Labussiere, M. et al., IDH1 Gene Mutations: A New Paradigm in Glioma Prognosis and Therapy?, The Oncologist, 15: 196-199 (2010).
Law, J. M.; et al., Discovery of 8-Membered Ring Sulfonamides as Inhibitors of Oncogenic Mutant Isocitrate Dehydrogenase 1. ACS Medicinal Chemistry Letters, 7(10): 944-949 (2016).
Lee, J.H. et al., IDH1 R132C mutation is detected in clear cell hepatocellular carcinoma by pyrosequencing, World Journal of Surgical Oncology, 15: 82, 8 pages (2017).
Levell, J. R. et al., Optimization of 3-pyrimidin-4-yl-oxazolidin-2-ones as allosteric and mutant specific inhibitors of IDH1, ACS Med. Chem. Lett., 8: 151-156 (2017).
Liu, G. et al., Catalytic Asymmetric Synthesis of tert-Butanesulfinamide. Application to the Asymmetric Synthesis of Amines, J. Am. Chem. Soc., 119: 9913-9914 (1997).
Liu, G. et al., Synthesis of enantiomerically pure N-tert-butanesulfinyl imines (tertbutanesulfinimines) by the direct condensation of tert-butanesulfinamide with aldehydes and ketones. J. Org. Chem., 64(6): 1278-1284 (1999).
Liu, Z. et al., Inhibition of cancerassociated mutant isocitrate dehydrogenases: synthesis, structureactivity relationship, and selective antitumor activity. J. Med. Chem., 57: 8307-8318 (2014).
Lopez, G.Y. et al., IDH1 mutation identified in human melanoma, Biochem Biophys Res Commun., 398(3): 585-587 (2010).
Losman, J.-A. et al., (R)-2-Hydroxyglutarate is Sufficient to Promote Leukemogenesis and its Effects are Reversible, Science, 339(6127): 9 pages (2013).
Lu, C. et al., IDH mutation impairs histone demethylation and results in a block to cell differentiation, Nature, 483(7390): 474-478 (2012).
Lu, C. et al., Induction of sarcomas by mutant IDH2, Genes & Development, 27: 1986-1998 (2013).
Mahmood, I., Prediction of Clearance, Volume of Distribution and Half-life by Allometric Scaling and by use of Plasma Concentrations Predicted from Pharmacokinetic Constants: a Comparative Study, J. Pharm. Pharmacol., 51: 905-910 (1999).
Mantica, M. et al., Retrospective study of nivolumab for patients with recurrent high grade gliomas, Journal of Neuro-Oncology, 139: 625-631 (2018).
Mardis, E.R. et al., Recurring Mutations Found by Sequencing an Acute Myeloid Leukemia Genome, N Engl J Med, 361(11): 1058-1066 (2009).
McBrayer, S.K. et al., Transaminase Inhibition by 2-Hydroxyglutarate Impairs Glutamate Biosynthesis and Redox Homeostasis in Glioma, Cell, 175: 101-116 (2018).
Medeiros, B.C. et al., Isocitrate dehydrogenase mutations in myeloid malignancies, Leukemia, 31: 272-281 (2017).
Meijer, D. et al., Genetic Characterization of Mesenchymal, Clear Cell, and Dedifferentiated Chondrosarcoma, Genes, Chromosomes & Cancer, 51:899-909 (2012).
Metallo, C.M. et al, Reductive glutamine metabolism by IDH1 mediates lipogenesis under hypoxia, Nature, 481(7381):380-384 (2011).
Meth-Cohn, O. and Stanforth, S. P. The Vilsmeier-Haack reaction (Review), Compr. Org. Synth., 2: 777-779 (1991).
Mohamed, E.A. et al., CA Accession No. 122:160601, abstract only of Indian J Chem, Sect B: Org Chem Inc Med Chem, 34B(1): 21-26 (1995).
Molenaar, R.J. et al., Wild-type and mutated IDH1/2 enzymes and therapy responses, Oncogene, 37: 1949-1960 (2018).
Morshed, M.N. et al., Computational approach to the identification of novel Aurora-A inhibitors, Bioorg & Med Chem, 19: 907-916 (2011).
National Comprehensive Cancer Network, Inc., NCCN Clinical Practice Guidelines in Oncology (NCCN Guidelines®), Acute Myeloid Leukemia, Version 2.2018 (Aug. 1, 2018).
Okoye-Okafor, U.C. et al., New IDH1 mutant inhibitors for treatment of acute myeloid leukemia, Nat. Chem. Biol., 11: 878-886 (2015).
Oran, B. and Weisdorf, D. Survival for older patients with acute myeloid leukemia: a population-based study, Haematologica, 97: 1916-1924 (2012).
Pansuriya, T.C. et al., Somatic mosaic IDH1 and IDH2 mutations are associated with enchondroma and spindle cell hemangioma in Ollier disease and Maffucci syndrome, Nature Genetics, 43(12): 1256-1261 (2011).
Parsons, D.W. et al., An Integrated Genomic Analysis of Human Glioblastoma Multiforme, Science, 321(5897): 1807, 15 pages (2008).
Paschka, P. et al., IDH1 and IDH2 mutations are frequent genetic alterations in acute myeloid leukemia and confer adverse prognosis in cytogenetically normal acute myeloid leukemia with NPM1 mutation without FLT3 internal tandem duplication, J Clin Oncol., 22: 3636-3643 (2010).
Pelosi, E. et al., Isocitrate dehydrogenase mutations in human cancers: physiopathologic mechanisms and therapeutic Targeting. Journal of Exploratory Research in Pharmacology, 1: 20-34 (2016).

(56) References Cited

OTHER PUBLICATIONS

Penard-Lacronique, V. and, Bernard, O.A., IDH1, Histone Methylation, and So Forth, Cancer Cell, 30: 192-194 (2016).

Peng, D. et al., Epigenetic silencing of Th1 type chemokines shapes tumor immunity and immunotherapy, Nature, 527(7577): 249-253 (2015).

Popovici-Muller, J. et al., Discovery of the First Potent Inhibitors of Mutant IDH1 That Lower Tumor 2-HG in Vivo, ACS Med. Chem. Lett., 3(10): 850-855 (2012).

Prensner, J.R. and Chinnaiyan, A.M., Metabolism unhinged: IDH mutations in cancer, Nature Medicine, 17(3): 291-293 (2011).

Prostakov, N.S. et al., Chemistry of Heterocyclic Compounds, CHCCAL, 22(7): 685-810 (1986).

Pusch, S. et al., Pan-mutant IDH1 inhibitor BAY 1436032 for effective treatment of IDH1 mutant astrocytoma in vivo. Acta Neuropathologica, 133(4): 629-644 (2017).

Ravandi, F. et al., Vosaroxin plus cytarabine versus placebo plus cytarabine in patients with first relapsed or refractory acute myeloid leukemia (VALOR): a randomized, controlled, double-blind, multinational, phase 3 study, Lancet Oncol., 16: 1025-1036 (2015).

Roboz, G.J. et al., International randomized Phase 2I study of elacytarabine versus investigator choice in patients with relapsed/refractory acute myeloid leukemia, J Clin Oncol., 20: 1919-1926 (2014).

Rohle, D. et al., An Inhibitor of Mutant IDH1 Delays Growth and Promotes Differentiation of Glioma Cells, Science, 340(6132): 626-630 (2013). Supplementary Materials, 32 pages.

Rowe, J.M., AML in 2017: Advances in clinical practice, Best Practice & Research Clinical Haematology, 30: 283-286 (2017).

Saha, S.K. et al., IDH mutations in liver cell plasticity and biliary cancer, Cell Cycle, 13(20): 3176-3182 (2014).

Saha, S.K. et al., Mutant IDH inhibits HNF-4a to block hepatocyte differentiation and promote biliary cancer, Nature, 19 pages (2014).

Sasaki, M. et al., D-2-hydroxyglutarate produced by mutant IDH1 perturbs collagen maturation and basement membrane function, Genes & Development, 26: 2038-2049 (2012).

Sasaki, M. et al., IDH1(R132H) mutation increases murine haematopoietic progenitors and alters epigenetics, Nature, 488(7413): 656-659 (2012).

Schnittger, S. et al., IDH1 mutations are detected in 6.6% of 1414 AML patients and are associated with intermediate risk karyotype and unfavorable prognosis in adults younger than 60 years and unmutated NPM1 status, Blood, 116(25): 5486-5496 (2010).

Schrader, F.C. et al., Novel Type II Fatty Acid Biosynthesis (FAS II) Inhibitors as Multistage Antimalarial Agents, Chem Med Chem, 8: 442-461 (2013).

Segall, M., Multi-parameter Optimisation in Drug Discovery: Quickly targeting compounds with a good balance of properties, Optibrium Ltd, ELRIG Drug Discovery 2011, 32 pages (Sep. 7, 2011).

Sellner, L. et al. Increased levels of 2-hydroxyglutarate in AML patients with IDH1-R132H and IDH2-R140Q mutations, Eur. J. Haematol., 85: 457-459 (2010).

Shibata, T. et al., Mutant IDH1 Confers an in Vivo Growth in a Melanoma Cell Line with BRAF Mutation, Am. J. Pathol., 178(3): 1395-1402 (2011).

Skrzypiec-Spring, M. et al., Isolated heart perfusion according to Langendorff—Still viable in the new millennium, Journal of Pharmacological and Toxicological Methods, 55:113-126 (2007).

Sri Ramya, P.V. et al., Curcumin inspired 2-chloro/phenoxy quinoline analogues: Synthesis and biological evaluation as potential anticancer agents, Bioorganic & Medicinal Chemistry Letters 28: 892-898 (2018).

Stein, E.M. et al., Molecular remission and response patterns in patients with mutant-IDH2 acute myeloid leukemia treated with enasidenib, Blood, 133(7): 676-0867 (2019).

Struys, E.A. et al., Investigations by mass isotopomer analysis of the formation of D-2-hydroxyglutarate by cultures lymphoblasts from two patients with D-2-hydroxyglytaric aciduria, FEBS Letters, 557: 115-120 (2004).

Suman, P. et al., Synthesis and evaluation of functionalized aminobenzoboroxoles as potential anti-cancer agents, Journal of Organometallic Chemistry, 798(1): 125-131 (2015).

Talati, C. and Sweet, K., Recently approved therapies in acute myeloid leukemia: A complex treatment landscape, Leukemia Research, 73: 58-66 (2018).

Thomson, B. and Lipford, K., A Phase 1b/2 Study of FT-2102 in Patients with Advanced Solid Tumors and Gliomas with an IDH1 Mutation, Poster Presented at the Cholangiocarcinoma Foundation Annual Conference, Salt Lake City, UT (Jan. 30, 2019).

Tintori, C. et al., Identification of Hck Inhibitors as Hits for the Development of Antileukemia and Anti-HIV Agents, Chem Med Chem, 8: 1353-1360 (2013).

Turcan, S. et al., Efficient induction of differentiation and growth inhibition in IDH1 mutant glioma cells by the DNMT Inhibitor Decitabine, Oncotarget, 4(10): 1729-1736 (2013).

Urban, D. J. et al., Assessing inhibitors of mutant isocitrate dehydrogenase using a suite of pre-clinical discovery assays, Scientific Reports 7(1): 12758 (2017).

Valle, J. et al., Cisplatin plus Gemcitabine versus Gemcitabine for Biliary Tract Cancer, N Engl J Med, 362: 1273-1281 (2010).

Venkanna, P. et al., 2,4,6-Trichloro-1,3,5-triazine and N,N'-dimethylformamide as an effective Vilsmeier-Haack reagent for the synthesis of 2-chloro-3-formyl quinolines from acetanilides, Tetrahedron Letters, 56(37): 5164-5167 (2015).

Vidaza, Azacitidine for injection; Drug Description, Manufactured for Pharmion Corporation, Manufactured by Ben Venue Laboratories, Inc., 19 pages (Edition Date: Jan. 9, 2007).

Wager, T.T. et al., Defining Desirable Central Nervous System Drug Space through the Alignment of Molecular Properties, in Vitro ADME, and Safety Attributes, ACS Chem. Neurosci., 1:420-434 (2010).

Wager, T.T. et al., Moving beyond Rules: The Development of a Central Nervous System Multiparameter Optimization (CNS MPO) Approach to Enable Alignment of Druglike Properties. ACS Chem. Neurosci., 1(6): 435-449 (2010).

Wahl, D.R. et al., Glioblastoma Therapy Can be Augmented by Targeting IDH1-mediated NADPH Biosynthesis, Cancer Res, 77(4): 960-970 (2017).

Wakayama, M. and Ellman, J.A., Recycling the tert-Butanesulfinyl Group in the Synthesis of Amines Using tert-Butanesulfinamide, J. Org. Chem., 74: 2646-2650 (2009).

Wakimoto, H. et al., Targetable Signaling Pathway Mutations are Associated with Malignant Phenotype in IDH-Mutant Gliomas, Clin Cancer Res, 20(11): 2898-2909 (2014).

Wang, F. et al., Targeted Inhibition of Mutant IDH2 in Leukemia Cells Induces Cellular Differentiation, Science, 340: 622-626 (2013).

Wang, P. et al., Mutations in Isocitrate Dehydrogenase 1 and 2 Occur Frequently in Intrahepatic Cholangiocarcinomas and Share Hypermetylation Targets with Glioblastomas, Oncogene, 32(25): 3091-3100 (2013).

Wang, R. et al., Rapid Ti(OiPr)4 facilitated synthesis of a,a,a-trisubstituted primary amines by the addition of Grignard reagents to nitriles under microwave heating conditions. Tetrahedron Letters, 50(50): 7070-7073 (2009).

Ward, P.S. et al., The common feature of leukemia-associated IDH1 and IDH2 mutations is a neomorphic enzymatic activity that converts α-ketoglutarate to 2-hydroxyglutarate, Cancer Cell, 17(3): 225-234 (2010).

Ward, P.S. et al., The Potential for Isocitrate Dehydrogenase Mutations to Produce 2-Hydroxyglutarate Depends on Allele Specificity and Subcellular Compartmentalization, The Journal of Biological Chemistry, 288(6): 3804-3815 (2013).

Waters, N.J. et al., Validation of a rapid equilibrium dialysis approach for the measurement of plasma protein binding, J Pharm Sci., 97(10): 4586-4595 (2008).

Watts, J.M. et al., A Phase 1 Dose Escalation Study of the IDH1m Inhibitor, FT-2102, in Patients with Acute Myeloid Leukemia or Myelodysplastic Syndrome, ASCO Abstract public release May 16, 2018, Presented Jun. 4, 2018, Clin Oncol 36, 2018 (suppl; abstr 7009).

(56) References Cited

OTHER PUBLICATIONS

Watts, J.M. et al., A Phase 1 Dose Escalation Study of the IDH1m Inhibitor, FT-2102, in Patients with Acute Myeloid Leukemia or Myelodysplastic Syndrome, Presented at the 2018 ASCO Annual Meetings, 19 pages (Jun. 4, 2018).
Watts, J.M. et al., Phase 1 Study of the IDH1m Inhibitor FT-2102 as a Single Agent in Patients with IDH1 m Acute Myeloid Leukemia (AML) or Myelodysplastic Syndrome (MDS), ASH abstract available in online meeting program, 8 pages (submitted Jul. 31, 2018, published Nov. 1, 2018).
Watts, J.M. et al., Phase 1 Study of the IDH1m Inhibitor FT-2102 as a Single Agent in Patients with IDH1m Acute Myeloid Leukemia (AML) or Myelodysplastic Syndrome (MDS), Poster 1453, Presented at the 60th Annual Meeting of the American Society of Hematology, San Diego, CA (Dec. 1, 2018).
Wheeler, D.A. and Robers, L.R., The Cancer Genome Atlas Research Network, Comprehensive and Integrative Genomic Characterization of Hepatocellular Carcinoma, Cell, 169: 1327-1341 (2017).
Wu, F. et al., Inhibition of cancer-associated mutant isocitrate dehydrogenases by 2-thiohydantoin compounds, J. Med. Chem., 58: 6899-6908 (2015).
Xu, W. et al., Oncometabolite 2-Hydroxyglutarate is a Competitive Inhibitor of a-Ketoglutarate-Dependent Dioxygenases, Cancer Cell, 19: 17-30 (2011).
Xu, X. et al., Structures of human cytosolic NADP-dependent isocitrate dehydrogenase reveal a novel self-regulatory mechanism of activity, J Biol Chem., 279(32): 33946-33957 (2004).
Yamashita, A.S. et al., Demethylation and epigenetic modification with 5-azacytidine reduces IDH1 mutant glioma growth in combination with temozolomide, Neuro-Oncology, 21(2): 189-200 (2019).
Yan, H et al., IDH1 and IDH2 Mutations in Gliomas, The New England Journal of Medicine, 360(8):765-773 (2009).
Yang, H. et al., IDH1 and IDH2 Mutations in Tumorigenesis: Mechanistic Insights and Clinical Perspectives, Clin Cancer Res, 18(20): 5562-5571 (2012).
Zhao, S. et al., Glioma-Derived Mutations in IDH1 Dominantly Inhibit IDH1 Catalytic Activity and Induce HIF-1a, Science, 324(5924): 261-265 (2009).
Zheng, B. et al., Crystallographic Investigation and Selective Inhibition of Mutant Isocitrate Dehydrogenase, ACS Medicinal Chemistry Letters, 4(6): 542-546 (2013).
U.S. Appl. No. 16/431,588, filed Jun. 4, 2019, Ashwell.
Cancer Genome Atlas Research Network, Comprehensive, Integrative Genomic Analysis of Diffuse Lower-Grade Gliomas, N Engl J Med, 372: 2481-2498 (2015).
ClinicalTrials.gov Identifier: NCT02073994, Study of Orally Administered AG-120 in Subjects With Advanced Solid Tumors, Including Glioma, With an IDH1 Mutation, First Posted Feb. 28, 2014; Last Update Posted Jun. 4, 2019. https://clinicaltrials.gov/ct2/show/NCT02073994?term=NCT02073994&rank=1.
ClinicalTrials.gov Identifier: NCT02481154, Study of Orally Administered AG-881 in Patients With Advanced Solid Tumors, Including Gliomas, With an IDH1 and/or IDH2 Mutation, First Posted Jun. 25, 2015; Last Update Posted Jun. 6, 2019. https://clinicaltrials.gov/ct2/show/NCT02481154?term=NCT02481154&rank=1.
ClinicalTrials.gov Identifier: NCT03343197, Study of AG-120 and AG-881 in Subjects With Low Grade Glioma, First Posted Nov. 17, 2017; Last Update Posted Jul. 23, 2018. https://clinicaltrials.gov/ct2/show/NCT03343197?term=NCT03343197&rank=1.
Cortes, J.E. et al., FT-2102, an IDH1m Inhibitor, Combined with Azacitidine in Patients with Acute Myeloid Leukemia (AML) or Myelodysplastic Syndrome (MDS): Results from a Phase 1 Study, Poster EHA-3328, Presented at the 24th Annual Congress of the European Hematology Association, Amsterdam, Netherlands, Jun. 14, 2019.
De Botton, S. et al., FT-2102, an IDH1m Inhibitor, Induces Mutation Clearance in Patients with Acute Myeloid Leukemia (AML) or Myelodysplastic Syndrome (MDS) Treated in Phase 1 Dose Escalation and Expansion Study, Poster EHA-3251, Presented at the 24th Annual Congress of the European Hematology Association, Amsterdam, Netherlands, Jun. 15, 2019.

Dinardo, C.D. et al., Ivosidenib (AG-120) Induced Durable Remissions and Transfusion Independence in Patients with IDH1-Mutant Relapsed or Refractory Myelodysplastic Syndrome: Results from a Phase 1 Dose Escalation and Expansion Study, 2018 ASH Annual Meeting, Poster, 132: Abstract 1812 (2018).
Dinardo, C.D. et al., Mutant IDH (MIDH) Inhibitors, Ivosidenib or Enasidenib, With Azacitidine (AZA) in Patients With Acute Myeloid Leukemia (AML), European Hematology Association, Abstract S1562, 2(S1): 719 (2018).
Emadi, A. et al., Presence of isocitrate dehydrogenase mutations may predict clinical response to hypomethylating agents in patients with acute myeloid leukemia, Am. J. Hematol., 90: E77-E79, (2015).
FORMA Therapeutics, Best-in-Class mIDH1 Inhibitor FT-2102, Presentation, 24 slides (Jan. 8-11, 2018).
Hindson, B. J. et al., High-Throughput Droplet Digital PCR System for Absolute Quantitation of DNA Copy Number, Anal. Chem., 83(22): 8604-8610 (2011).
Le, K. et al., Population Pharmacokinetics of Ivosidenib (AG-120) in Patients with IDH1-Mutant Advanced Hematologic Malignancies, POSTER, 2018 ASH Annual Meeting, 132: Abstract 1394 (2018).
Lin, J. et al., Discovery and Optimization of Quinoline Derivatives as Potent, Selective, and Orally Bioavailable Mutant Isocitrate Dehydrogenase 1 Inhibitors. J. Med. Chem. (2019).
Mellinghoff, I. et al., AG-120, A First-in-Class Mutant IDH1 Inhibitor in Patients with Recurrent or Progressive IDH1 Mutant Glioma: Updated Results from the Phase 1 Non-Enhancing Glioma Population, Presentation ACTR-46, Society for Neuro-Oncology Annual Scientific Meeting, Nov. 16-19, 2017, San Francisco, CA, USA (2017).
Mellinghoff, I. et al., Phase 1 study of AG-881, an inhibitor of mutant IDH1 and IDH2: results from the recurrent/progressive glioma population, Presentation ACTR-31, 23rd Annual Scientific Meeting and Education Day of the Society for Neuro-oncology (SNO), Nov. 15-18, 2018, New Orleans, LA, USA (2018).
Mellinghoff, I.K. et al., A phase 1, open-label perioperative study of ivosidenib (AG-120) and vorasidenib (AG-881) in recurrent, IDH1-mutant, low-grade glioma: Results from Cohort 1, Presented at the American Society of Clinical Oncology (ASCO) Annual Meeting, May 21-Jun. 3, 2019, Chicago, IL, USA.
Nicolay, B. et al., Combined use of the pan-IDH mutant inhibitor AG-881 with radiation therapy shows added benefit in an orthotopic IDH1 mutant glioma model in vivo, Poster EXTH-34, Presented at the 22nd Annual Scientific Meeting and Education Day of the Society for Neuro-oncology, Nov. 16-19, 2017, San Francisco, CA, USA (2017).
Nicolay, B. et al., The IDH1 mutant inhibitor AG-120 shows strong inhibition of 2-HG production in an orthotopic IDH1 mutant glioma model in vivo, EXTH-59, Presented at the 22nd Annual Scientific Meeting and Education Day of the Society for Neuro-oncology, Nov. 16-19, 2017, San Francisco, CA, USA (2017).
Pollyea, D.A. et al., Ivosidenib (AG-120) in Mutant IDH1 Relapsed/Refractory Acute Myeloid Leukemia: Results of a Phase 1 Study, European Hematology Association, Abstract S1560, 2(S1): 718 (2018).
Vogelstein, B. and Kinzler, K.W., Digital PCR, Proc. Natl. Acad. Sci. USA, 96: 9236-9241 (1999).
U.S. Appl. No. 16/526,593, Kelly et al.
Abbott RealTime IDH1 label, Reference No. 08N90-090, 31 pages (Jul. 2018); accessed on Jul. 29, 2019 from https://www.fda.gov/medical-devices/vitro-diagnostics/list-cleared-or-approved-companion-diagnostic-devices-vitro-and-imaging-tools.
Leese, C. L. and Rydon, H.N., Polyazanaphthalenes. Part I. Some derivatives of 1:4:5-triazanaphthalene and quinoxaline, PolyJournal of the Chemical Society, 303-309 (1995).
Mamedov, V. A. et al., Synthesis and Functionalization of 3-Ethylquinoxalin-2(1H)-one, Russian Journal of Organic Chemistry, 41(4): 599-606 (2005).
Agios Pharmaceuticals, Press Release, Agios Pharmaceuticals to Present Clinical and Preclinical Data at the 2014 American Society of Hematology Annual Meeting, 7 pages (Cambridge, Mass., Nov. 6, 2014). URL: <http://investor.agios.com/news-releases/news-release-details/agios-pharmaceuticals-present-clinical-and-preclinical-data-2014> [Retrieved May 14, 2019].

(56) References Cited

OTHER PUBLICATIONS

Agios Pharmaceuticals, Press Release, Agios to Present New Data From Lead Programs at the 2015 ASH Annual Meeting, 6 pages (Cambridge, Mass., Nov. 5, 2014). URL: <http://investor.agios.com/news-releases/news-release-details/agios-present-new-data-lead-programs-2015-ash-annual-meeting> [Retrieved May 14, 2019].
Agios Pharmaceuticals, Press Release, Agios Announces Initiation of Phase 1/2 Frontline Combination Study of AG-221 or AG-120 with VIDAZA® (azacitidine for injection) in Newly Diagnosed Acute Myeloid Leukemia (AML) Patients Not Eligible for Intensive Chemotherapy, 4 pages (Cambridge, Mass, Mar. 30, 2016).
Agios Pharmaceuticals, Press Release, Agios Announces Phase 1 Data from Dose Expansion Cohorts of AG-120 in Patients with IDH1 Mutant Positive Glioma and Chondrosarcoma, 4 pages (Cambridge, Mass, Nov. 18, 2016).
Agios Pharmaceuticals, Press Release, Agios Presents Phase 1 Data from Dose-Escalation and Expansion Cohorts of AG-120 (Ivosidenib) in Patients with Previously Treated IDH1 Mutant Positive Cholangiocarcinoma, 4 pages (Chicago, Jun. 3, 2017).
Birendra, K.C. and Dinardo, C.D., Evidence for clinical differentiation and differentiation syndrome in patients with acute myeloid leukemia and IDH1 mutations treated with the targeted mutant IDH1 inhibitor, AG-120, Clin Lymphoma Myeloma Leuk., 16(8): 460-465 (2016).
Burris, H. et al., Abstract PL04-05: The first reported results of AG-120, a first-in-class, potent inhibitor of the IDH1 mutant protein, in a Phase I study of patients with advanced IDH1-mutant solid tumors, including gliomas, Mol. Cancer Ther., 14(12 Supplement 2): 5 pages (Dec. 2015).
Center for Drug Evaluation and Research, Application No. 209606Orig11000, Multi-Discipline Review, Reference ID: 4131433,190 pages (Submission date Dec. 30, 2016).
De Botton, S. et al., Clinical Safety and Activity of AG-120, a First-in-Class, Potent Inhibitor of the IDH1-Mutant Protein, in a Phase 1 Study of Patients with Advanced IDH-Mutant Hematologic Malignancies. European Hematology Association Learning Center, p. 563 (2015).
Dinardo, C., Highlights in Acute Myeloid Leukemia From the 2017 American Society of Hematology Annual Meeting and Exposition, Clinical Advance in Hematology & Oncology, 16(3): Suppl 8 (Mar. 2018), A Review of Selected Presentations From the 2017 American Society of Hematology Annual Meeting and Exposition, Atlanta, Georgia, 24 pages (Mar. 8, 2018).
Dinardo, C.D. and Cortes, J.E., Mutations in AML: prognostic and therapeutic implications, Hematology, 348-355 (2016).
Dinardo, C.D. et al., Characteristics, clinical outcome, and prognostic significance of IDH mutations in AML, Am J Hematol., 90(8): 732-736 (2015).
Dinardo, C.D. et al., Durable Remissions with Ivosidenib in IDH1-Mutated Relapsed or Refractory AML, N Engl J Med, 378: 2386-2398 (2018).
Dinardo, C.D. et al., Ivosidenib (AG-120) in Mutant IDH1 AML and Advanced Hematologic Malignancies: Results of a Phase 1 Dose Escalation and Expansion Study. Presented at: ASH Annual Meeting and Exposition, Atlanta, Georgia. Abstract 725, 3 pages (Dec. 13, 2017).
Dinardo, C.D. et al., Ivosidenib (AG-120) Induced Durable Remissions and Transfusion Independence in Patients with IDH1-Mutant Relapsed or Refractory Myelodysplastic Syndrome: Results from a Phase 1 Dose Escalation and Expansion Study, 2018 ASH Annual Meeting, Blood, 132: Abstract 1812 (2018).
Dinardo, C.D. et al., Mutant IDH (mIDH) inhibitors, ivosidenib or enasidenib, with azacitidine (AZA) in patients with acute myeloid leukemia (AML), 2018 ASCO Annual Meeting, J Clin Oncol., 36 (Abstract 7042), 2 pages (Jun. 4, 2018). URL: https://meetinglibrary.asco.org/record/162432/abstract [Retrieved Jun. 7, 2018].
Dinardo, C.D. et al., Mutant Isocitrate Dehydrogenase (mIDH) Inhibitors, Enasidenib or Ivosidenib, in Combination with Azacitidine (AZA): Preliminary Results of a Phase 1b/2 Study in Patients with Newly Diagnosed Acute Myeloid Leukemia (AML), Ash Annual Meeting, Blood, 130: Abstract 639 (2017).

Dinardo, C.D. et al., Mutant Isocitrate Dehydrogenase (mIDH) Inhibitors, Enasidenib or Ivosidenib, in Combination with Azacitidine (AZA): Preliminary Results of a Phase 1b/2 Study in Patients with Newly Diagnosed Acute Myeloid Leukemia (AML), Presentation, ASH Annual Meeting, Abstract 639: 14 pages (2017).
Dinardo, C.D. et al., Serum 2-hydroxyglutarate levels predict isocitrate dehydrogenase mutations and clinical outcome in acute myeloid leukemia, Blood, 121(24): 4917-1924 (2013).
Fan, B. et al., Evaluation of the pharmacokinetic/pharmocodynamic (PK/PD) relationships of an oral, selective, first-in-class, potent IDH1 inhibitor, AG-221, from a phase 1 trial in patients with advanced IDH2 mutant positive hematologic malignancies, Blood, 124: 3737, 6 pages (2014). URL: http://www.bloodjournal.org/content/124/21/3737?sso-checked=true [Retrieved May 13, 2019].
Fan, B. et al., Evaluation of the pharmacokinetic/pharmocodynamic (PK/PD) relationships of an oral, selective, first-in-class, potent IDH1 inhibitor, AG-221, from a phase 1 trial in patients with advanced IDH2 mutant positive hematologic malignancies, Poster 3737, Presented at the 56th American Society of Hematology Annual Meeting and Exposition, San Francisco, CA, 1 page (Dec. 8, 2014).
Fan, B. et al., Longitudinal Pharmacokinetic/Pharmacodynamic Profile of AG-120, a Potent Inhibitor of the IDH1 Mutant Protein, in a Phase 1 Study of IDH1-Mutant Advanced Hematologic Malignancies, American Society of Hematology, 57th Annual Meeting & Exposition, Orlando, FL, Abstract 1310, 2 pages (Dec. 508, 2015). URL: https://ash.confex.com/ash/2015/webprogramscheduler/Paper82908.html [Retrieved Jun. 7, 2018].
Fan, B. et al., Longitudinal Pharmacokinetic/Pharmacodynamic Profile of AG-120, a Potent Inhibitor of the IDH1 Mutant Protein, in a Phase 1 Study of IDH1-Mutant Advanced Hematologic Malignancies, Blood, 126(23): 1310-1310 (2015).
Fan, B. et al., Longitudinal pharmacokinetic/pharmacodynamic profile of AG-120, a potent inhibitor of the IDH1 mutant protein, in a phase 1 study of IDH1-mutant advanced hematologic malignancies, Poster 1310, Presented at the 57th American Society of Hematology Annual Meeting and Exposition, Orlando, FL, 1 page (Dec. 5, 2015).
Fan, B. et al., Pharmacokinetic/pharmacodynamic (PK/PD) profile of AG-120 in patients with IDH1-mutant cholangiocarcinoma from a phase 1 study of advanced solid tumors, Poster 4082, Presented at the American Society of Clinical Oncology (ASCO) Annual Meeting, Chicago, IL, USA, 1 page (Jun. 3, 2017).
Fan, B. et al., Pharmacokinetic/Pharmacodynamic (PK/PD) Profile of AG-120 in Patients with IDH1-Mutant Cholangiocarcinoma from a Phase 1 Study of Advanced Solid Tumorsm, Journal of Clinical Oncology, 35(15_suppl): 4082-4082 (May 20, 2017).
Fan, B. et al., Pharmacokinetic/pharmacodynamic evaluation of AG-120, a potent inhibitor of the IDH1 mutant protein, in a phase 1 study of IDH1-mutant advanced hematologic malignancies, Poster P572, Presented at the 20th Congress of the European Hematology Association, Vienna, Austria, 1 page (Jun. 13, 2015).
Fan, B. et al., Pharmacokinetics/pharmacodynamics (PK/PD) of ivosidenib in patients with IDH1-mutant advanced solid tumors from a phase 1 study, 2018 ASCO Annual Meeting, J Clin Oncol., 36 (Abstract 2577), 1 page (Jun. 4, 2018). URL: https://meetinglibrary.asco.org/record/158587/abstract [Retrieved Jun. 7, 2018].
Ghazanchyan, T. et al., Developing a Genomics Model to Predict Failure of Isocitrate Dehydrogenase (IDH) Inhibitors for Treatment of Patients with IDH1- or IDH2-Mutated Acute Myeloid Leukemia, 2018 ASH Annual Meeting, Blood, 132: Abstract 2815 (2018).
Ishii, Y. et al., Abstract A071: AG-120 (ivosidenib), a first-in-class mutant IDH1 inhibitor, promotes morphologic changes and upregulates liver-specific genes in IDH1 mutant cholangiocarcinoma, Cellular Responses to Therapy, AACR-NCI-EORTC International Conference on Molecular Targets and Cancer Therapeutics, Oct. 26-30, 2017, Philadelphia, PA, 3 pages (Published Jan. 2018).
Le, K. et al., Population Pharmacokinetics of Ivosidenib (AG-120) in Patients with IDH1-Mutant Advanced Hematologic Malignancies, 2018 ASH Annual Meeting, Blood, 132: Abstract 1394 (2018).
Lowery, M.A et al., A phase 3, multicenter, randomized, double-blind study of AG-120 vs placebo in patients with an advanced cholangiocarcinoma with an IDH1 mutation, ASCO Annual Meeting 2017, J Clin Oncol, 35: suppl; Abstract TPS4142 (2017).

(56) References Cited

OTHER PUBLICATIONS

Lowery, M.A. et al., Phase I study of AG-120, an IDH1 mutant enzyme inhibitor: Results from the cholangiocarcinoma dose escalation and expansion cohorts, Abstract 4015, Journal of Clinical Oncology, 35 (15 Suppl): 4015-4015 (May 20, 2017). URL: http://ascopubs.org/doi/abs/10.1200/JCO.2017.35.15_suppl.4015 [Retrieved Mar. 21, 2018].

Ma, R. and Yun, C. H., Crystal structures of pan-IDH inhibitor AG-881 in complex with mutant human IDH1 and IDH2, Biochem Biophys Res Commun, 503(4): 2912-2917 (2018).

Mellinghoff, I.K. et al., Phase 1 study of AG-881, an inhibitor of mutant IDH1/IDH2, in patients with advanced IDH-mutant solid tumors, including glioma, 2018 ASCO Annual Meeting, J Clin Oncol., 36: (Abstract 2002), 2 pages (Jun. 1, 2018). URL: https://meetinglibrary.asco.org/record/162680/abstract [Retrieved Jun. 7, 2018].

Pollyea, D.A. et al., Ivosidenib (IVO; AG-120) in mutant IDH1 relapsed/refractory acute myeloid leukemia (R/R AML): Results of a phase 1 study, 2018 ASCO Annual Meeting, J Clin Oncol., 36 (Abstract 7000), 2 pages (Jun. 2, 2018). URL: https://meetinglibrary.asco.org/record/161682/abstract [Retrieved Jun. 7, 2018].

Popovici-Muller, J. et al., Discovery of AG-120 (Ivosidenib): A First-in-Class Mutant IDH1 Inhibitor for the Treatment of IDH1 Mutant Cancer, ACS Med. Chem. Lett., 9(4): 300-305 (2018).

Roboz, G.J. et al., Ivosidenib (AG-120) Induced Durable Remissions and Transfusion Independence in Patients with IDH1-Mutant Untreated AML: Results from a Phase 1 Dose Escalation and Expansion Study, ASH Annual Meeting, Blood, 132: Abstract 561 (2018).

Roboz, G.J. et al., Ivosidenib (AG-120) Induced Durable Remissions and Transfusion Independence in Patients with IDH1-Mutant Untreated AML: Results from a Phase 1 Dose Escalation and Expansion Study, Presentation, Presented at the 60th American Society of Hematology (ASH) Annual Meeting, Dec. 1-4, 2-18, San Diego, CA, USA, 16 pages, Abstract 561 (2018).

Stein, E. et al., AGILE: A phase 3, multicenter, randomized, placebo-controlled study of ivosidenib in combination with azacitidine in adult patients with previously untreated acute myeloid leukemia with an IDH1 mutation, Journal of Clinical Oncology, 36(15 suppl): Abstract TPS7074 (2018).

Stein, E. et al., AGILE: A phase 3, multicenter, randomized, placebo-controlled study of ivosidenib in combination with azacitidine in adult patients with previously untreated acute myeloid leukemia with an IDH1 mutation, Presented at the American Society of Clinical Oncology (ASCO) Annual Meeting, Chicago, IL, USA, Abstract TPS7074, J Clin Oncol 36, 2018 (Jun. 1-5, 2018).

Stein, E. M. et al., Ivosidenib or Enasidenib Combined with Standard Induction Chemotherapy is Well Tolerated and Active in Patients with Newly Diagnosed AML with an IDH1 or IDH2 Mutation: Initial Results from a Phase 1 Trial, 2017 ASH Annual Meeting, Blood, 130: Abstract 726 (2017).

Stein, E.M. et al., Ivosidenib or Enasidenib Combined with Induction and Consolidation Chemotherapy in Patients with Newly Diagnosed AML with an IDH1 or IDH2 Mutation is Safe, Effective, and Leads to MRD-Negative Complete Remissions, Poster Presented at the 60th American Society of Hematology (ASH) Annual Meeting, Dec. 1-4, 2018, San Diego, CA, USA, 21 pages, Abstract 560 (2018).

Stone, R.M. et al., Genetic Profiling and Deep IDH1 Mutation Clearance to ≤0.04 in Ivosidenib (AG-120)-Treated Patients with Mutant IDH1 Relapsed or Refractory and Untreated AML, 2017 ASH Annual Meeting, Blood, 130: Abstract 2684 (2017).

Thompson, C.B., Metabolic Enzymes as Oncogenes or Tumor Suppressors, N Engl J Med, 360(8): 813-815 (2009).

Watanabe, T. et al., IDH1 Mutations are early events in the Development of Astrocytomas and Oligodendrogliomas, American Journal of Pathology, 174(4): 1149-1153 (2009).

Yen, K. et al., Abstract 4956: Functional characterization of the ivosidenib (AG-120) and azacitidine combination in a mutant IDH1 AML cell model, Experimental and Molecular Therapeutics, Proceedings: AACR Annual Meeting 2018; Apr. 14-18, 2018; Chicago, IL (Published Jul. 2018).

Yen, K. et al., Abstract B126: AG-881, a brain penetrant, potent, pan-mutant IDH (mIDH) inhibitor for use in mIDH solid and hematologic malignancies, AACR-NCI-EORTC International Conference: Molecular Targets and Cancer Therapeutics (Oct. 26-30, 2017; Philadelphia, PA).

Center for Drug Evaluation and Research, Application No. 211192Orig1s000, Multi-Discipline Review, Reference ID: 4294809, 235 pages (Submission date Dec. 21, 2017).

Caira, M.R. et al., Crystalline polymorphism of organic compounds, Topics in Current Chemistry, 198: 163-208 (1998).

International Search Report for PCT/US2019/032742, 4 pages (dated Jul. 29, 2019).

International Search Report for PCT/US2019/032747, 5 pages (dated Aug. 1, 2019).

Olutasidenib, C18H15ClN4O2, PubChem, Compound Summary, 10 pages (retrieved Jul. 24, 2019).

Cortes, J.E. et al., Olutasidenib (FT-2102) Induces Rapid Remissions in Patients with IDH1-Mutant Myelodysplastic Syndrome: Results of Phase 1/2 Single Agent Treatment and Combination with Azacitidine, ASH Annual Meeting, Oral and Poster Abstract, Abstract 674 (Dec. 9, 2019).

Ribadeneira, M. et al., SCIDOT-42. FT-2102—A Potent and Selective Brain Penetrant Inhibitor of Mutant Isocitrate Dehydrogenase, Neuro-Oncology, 21(Supplement 6): vi280 3 pages (2019).

Seltzer, M.J. et al., Inhibition of Glutaminase Preferentially Slows Growth of Glioma Cells with Mutant IDH1, Cancer Research, 70(22): 8981-8987 (2010).

Watts, J.M. et al., Olutasidenib (FT-2102), an IDH1m Inhibitor as a Single Agent or in Combination with Azacitidine, Induces Deep Clinical Responses with Mutation Clearance in Patients with Acute Myeloid Leukemia Treated in a Phase 1 Dose Escalation and Expansion Study, ASH Annual Meeting, Oral and Poster Abstract, Abstract 231 (Dec. 7, 2019).

U.S. Appl. No. 16/893,147, Kelly et al.

De La Fuente, M. et al., A Phase 1b/2 Study of Olutasidenib in Patients with Relapsed/Regractory IDH1 Mutant Gliomas: Safety and Clinical Activity as a Single Agent and in Combination with Azacitidine, ASCO, slides 1-13, May 2020.

Press Release, Forma Therapeutics Announces Clinical Data to be Presented at ASCO20 Virtual Scientific Program (2020), Forma Therapeutics, <https://www.formatherapeutics.com/press-releases/forma-therapeutics-announces-clinical-data-to-be-presented-at-asco20-virtual-scientific-program>. Retrieved Jun. 5, 2020.

U.S. Appl. No. 16/712,951, Lin et al.

Blackburn, C. et al., Identification and characterization of amino-piperidinequinolones and quinazolinones as MCHr1 antagonists, Bio. and Med. Chem. Letters, 16(10):2621-2627 (2006).

Caravella, J. A. et al., Structure-based design and identification of FT-2102 (olutasidenib), a potent mutant-selective IDH1 inhibitor, J Med Chem, doi: 10.1021/acs.jmedchem.9b01423, Epub ahead of print (2020).

Cortes, J.E. et al., Olutasidenib (FT-2102) Induces Rapid Remissions in Patients with IDH1-Mutant Myelodysplastic Syndrome: Results of Phase 1/2 Single Agent Treatment and Combination with Azacitidine, ASH Annual Meeting, Oral Presentation, 12 pages (Dec. 9, 2019).

De La Fuente, M.I. et al., A phase ib/II study of olutasidenib in patients with relapsed/refractory IDH1 mutant gliomas: Safety and efficacy as single agent and in combination with azacitidine, Amer. Soc. Clin. Oncol. (2020), Abstract, <https://meetinglibrary.asco.org/record/185065/abstract>. Retrieved on May 13, 2020.

De La Fuente, M.I. et al., Phase 1b/2 Study of Olutasidenib (FT-2102), an Inhibitor of Mutant IDH1, in Patients with Relapsed/Refractory IDH1-Mutant Gliomas: Preliminary Safety and Clinical Activity, Presented at the Society for NeuroOncology, Phoenix, AZ, Nov. 20-24, 2019 (Presented on Nov. 21, 2019).

(56) References Cited

OTHER PUBLICATIONS

Golub, D. et al., Mutant Isocitrate Dehydrogenase Inhibitors as Targeted Cancer Therapeutics, Front. Oncol., Article 417, 1-25 (2019).

Huang, J. et al., Isocitrate Dehydrogenase Mutations in Glioma: From Basic Discovery to Therapeutics Development, Front. Oncol., Article 506, 9:1-7 (2019).

Jones, R.L. et al., A phase ib/II study of olutasidenib in patients with relapsed/refractory IDH1 mutant solid tumors: Safety and efficacy as single agent, Amer. Soc. Clin. Oncol. (2020), Abstract, <https://meetinglibrary.asco.org/record/186633/abstract>. Retrieved on May 13, 2020.

Megías-Vericat, J.E., et al., IDHI-mutated relapsed or refractory AML: current challenges and future prospects, Blood and Lymphatic Cancer: Targets and Therapy, 9:19-32 (2019).

Reitman, Z.J. and Yan, H, Isocitrate Dehydrogenase 1 and 2 Mutations in Cancer: Alterations at a Crossroads of Cellular Metabolism, J. Natl. Cancer Inst., 102:932-941 (2010).

Wai, J. et al., Synthesis and evaluation of 2-pyridinone derivatives as specific HIV-1 reverse transcriptase inhibitors. 3. Pyridyl and phenyl analogs of 3-aminopyridin-2(1H)-one, J. Med. Chem., 36(2):249-255 (1993).

Watts, J.M. et al., Olutasidenib (FT-2102), an IDH1m Inhibitor as a Single Agent or in Combination with Azacitidine, Induces Deep Clinical Responses with Mutation Clearance in Patients with Acute Myeloid Leukemia Treated in a Phase 1 Dose Escalation and Expansion Study, ASH Annual Meeting, Oral Presentation, 14 pages (Dec. 7, 2019).

A Study of FT-2012 in Patients with Advanced Solid Tumors and Gliomas, Spanish Clinical Studies Registry, retrieved from https://reec.aemps.es/reec/public/detail.html, 16 pages (2019).

Study to evaluate FT-2012 as a single agent or in combination with Azacitidine or Cytarabine in patients with Acute Myeloid Leukemia or Myelodysplastic Syndrome, Spanish Clinical Studies Registry, retrieved from https://reec.aemps.es/reec/public/detail.html, 14 pages (2018).

U.S. Appl. No. 17/055,278, Kelly et al.

U.S. Appl. No. 17/101,018, Lin et al.

U.S. Appl. No. 17/112,269, Kelly et al.

Abbott Molecular Inc., Summary of Safety and Effectiveness Data (SSED), 43 pages (2018). URL: <https://www.accessdata.fda.gov/cdrh_docs/pdf17/P170041B.pdf> [Retrieved Jul. 28, 2020].

Abbott Molecular Inc., U.S. Food and Drug Administration Approval Letter, 4 pages (2018). URL: https://www.accessdata.fda.gov/cdrh_docs/pdf17/P170041A.pdf.

Abbvie, AbbVie Receives EMA and FDA Orphan Drug Designation for Investigational Compound ABT-414 in the Treatment of Glioblastoma Multiforme, 4 pages (Aug. 4, 2014). URL: https://www.prnewswire.com/news-releases/abbvie-receives-ema-and-fda-orphan-drug-designation-for-investigational-compound-abt-414-in-the-treatment-of-glioblastoma-multiforme-269807321.html.

Abbvie, AbbVie Receives U.S. FDA Rare Pediatric Disease Designation for Investigational ABT-414 for the Treatment of a Type of Pediatric Brain Tumor known as Diffuse Intrinsic Pontine Glioma (DIPG), 3 pages (Jul. 11, 2016). URL: https://news.abbvie.com/article_print.cfm?article_id=11360.

Agios Pharmaceuticals, Press Release, Agios Presents Updated Data from Phase 1 Dose-Escalation Study of AG-881 in Patients with IDH Mutant Positive Advanced Glioma, 6 pages (Nov. 16, 2018). URL: https://investor.agios.com/news-releases/news-release-details/agios-presents-updated-data-phase-1-dose-escalation-study-ag-881.

Agios Pharmaceuticals, Press Release, Celgene and Agios Announce Collaborations with Abbott for Diagnostic Identification of IDH Mutations in AML, 4 pages (Summit, N.J. and Cambridge, Mass., Oct. 12, 2016). URL: <https://investor.agios.com/news-releases/news-release-details/celgene-and-agios-announce-collaborations-abbott-diagnostic> [Retrieved Jul. 28, 2020].

Agios Pharmaceuticals, Press Release, FDA Accepts New Drug Application and Grants Priority Review for Ivosidenib in Relapsed or Refractory AML with an IDH1 Mutation, 4 pages (Summit, N.J. and Cambridge, Mass., Feb. 15, 2018). URL: <https://investor.agios.com/news-releases/news-release-details/fda-accepts-new-drug-application-and-grants-priority-review-0> [Retrieved Jul. 28, 2020].

Agios Pharmaceuticals, Press Release, FDA Grants Approval of TIBSOVO®, the First Oral, Targeted Therapy for Adult Patients with Relapsed/Refractory Acute Myeloid Leukemia and an IDH1 Mutation, 9 pages (Jul. 20, 2018). URL: <https://investor.agios.com/news-releases/news-release-details/fda-grants-approval-tibsovor-first-oral-targeted-therapy-adult> [Retrieved Jul. 28, 2020].

Agios Pharmaceuticals, Third Quarter 2018 Financial Results, 27 pages (Nov. 1, 2018).

Agios Pharmaceuticals, TIBSOVO® (ivosidenib) FDA Approval, 17 pages (Jul. 20, 2018).

Bayer, Interim Report Third Quarter of 2018, 61 pages (2018).

Bleeker, F.E. et al., $IDH1^{R132}$ mutations occur frequently in high-grade gliomas but not in other solid tumors, Human Mutation, 30:84-91 (2009).

ClinicalTrials.gov Identifier: NCT00900224, Studying Tissue and Blood Samples From Patients with Acute Myeloid Leukemia, (v40 dated Dec. 15, 2010; update posted Dec. 16, 2010) URL: <https://clinicaltrials.gov/ct2/history/NCT00900224?V_40=View>.

ClinicalTrials.gov Identifier: NCT01800695, Evaluating the Safety and Pharmacokinetics of ABT-414 for Subjects With Glioblastoma Multiforme (First Posted Feb. 28, 2013, Last Update Posted Nov. 21, 2017). URL: https://clinicaltrials.gov/ct2/show/NCT01800695.

ClinicalTrials.gov Identifier: NCT02073994, Study of Orally Administered AG-120 in Subjects With Advanced Solid Tumors, Including Glioma, With an IDH1 Mutation (First Posted Feb. 28, 2014, Last Update Posted Dec. 9, 2020). URL: https://clinicaltrials.gov/ct2/show/NCT02073994.

ClinicalTrials.gov Identifier: NCT02074839, Study of Orally Administered AG-120 in Subjects With Advanced Hematologic Malignancies With an IDH1 Mutation (First Posted Feb. 28, 2014, Last Update Posted Feb. 5, 2020). URL: https://clinicaltrials.gov/ct2/show/NCT02074839?term=NCT02074839&draw=2&rank=1.

ClinicalTrials.gov Identifier: NCT02193347, IDH1 Peptide Vaccine for Recurrent Grade II Glioma (RESIST) (First Posted Jul. 17, 2014, Last Update Posted May 13, 2020). URL: https://clinicaltrials.gov/ct2/show/NCT02193347.

ClinicalTrials.gov Identifier: NCT02481154, Study of Orally Administered AG-881 in Patients With Advanced Solid Tumors, Including Gliomas, With an IDH1 and/or IDH2 Mutation (First Posted Jun. 25, 2015, Last Update Posted Dec. 17, 2020). URL: https://clinicaltrials.gov/ct2/show/NCT02481154.

ClinicalTrials.gov Identifier: NCT02492737, Study of Orally Administered AG-881 in Patients With Advanced Hematologic Malignancies With an IDH1 and/or IDH2 Mutation (First Posted Jul. 9, 2015, Last Update Posted Mar. 8, 2019). URL: https://clinicaltrials.gov/ct2/show/NCT02492737?term=NCT02492737&draw=2&rank=1.

ClinicalTrials.gov Identifier: NCT02511405, A Phase 3, Pivotal Trial of VB-111 Plus Bevacizumab vs. Bevacizumab in Patients With Recurrent Glioblastoma (GLOBE) (GLOBE) (First Posted Jul. 30, 2015, Last Update Posted Oct. 23, 2018). URL: https://clinicaltrials.gov/ct2/show/NCT02511405?term=VB-111.

ClinicalTrials.gov Identifier: NCT02573324, A Study of ABT-414 in Participants With Newly Diagnosed Glioblastoma (GBM) With Epidermal Growth Factor Receptor (EGFR) Amplification (Intellance1) (First Posted Oct. 9, 2015, Last Update Posted Dec. 21, 2020). URL: https://clinicaltrials.gov/ct2/show/NCT02573324?term=ABT-414&rank=6.

ClinicalTrials.gov Identifier: NCT02677922, A Safety and Efficacy Study of Oral AG-120 Plus Subcutaneous Azacitidine and Oral AG-221 Plus Subcutaneous Azacitidine in Subjects With Newly Diagnosed Acute Myeloid Leukemia (AML) (First Posted Feb. 9, 2016, Last Update Posted Dec. 20, 2019). URL: https://clinicaltrials.gov/ct2/show/NCT02677922.

ClinicalTrials.gov Identifier: NCT02746081, Phase I Study of BAY1436032 in IDH1-mutant Advanced Solid Tumors (First Posted Apr. 21, 2016, Last Update Posted Dec. 22, 2020). URL: https://clinicaltrials.gov/ct2/show/NCT02746081.

(56) References Cited

OTHER PUBLICATIONS

ClinicalTrials.gov Identifier: NCT02771301, Safety and Efficacy of IDH1R132H-DC Vaccine in Gliomas (First Posted May 13, 2016, Last Update Posted May 13, 2016). URL: https://clinicaltrials.gov/ct2/show/NCT02771301.
ClinicalTrials.gov Identifier: NCT02989857, Study of AG-120 in Previously Treated Advanced Cholangiocarcinoma With IDH1 Mutations (ClarIDHy) (ClarIDHy) (First Posted Dec. 12, 2016, Last Update Posted Dec. 1, 2020). URL: https://clinicaltrials.gov/ct2/show/NCT02989857.
ClinicalTrials.gov Identifier: NCT03030066, Study of DS-1001b in Patients With Gene IDH1-Mutated Gliomas (First Posted Jan. 24, 2017, Last Update Posted Feb. 28, 2020). URL: https://clinicaltrials.gov/ct2/show/NCT03030066.
ClinicalTrials.gov Identifier: NCT03149575, VAL-083 Phase 3 Study in Temozolomide-Avastin (Bevacizumab) Recurrent GBM (STAR-3) (First Posted May 11, 2017, Last Update Posted Nov. 14, 2019). URL: https://clinicaltrials.gov/ct2/show/NCT03149575?term=VAL-083&rank=6.
ClinicalTrials.gov Identifier: NCT03173248, Study of AG-120 (Ivosidenib) vs. Placebo in Combination With Azacitidine in Patients With Previously Untreated Acute Myeloid Leukemia With an IDH1 Mutation (AGILE) (First Posted Jun. 1, 2017, Last Update Posted Dec. 24, 2020). URL: https://www.clinicaltrials.gov/ct2/show/NCT03173248.
ClinicalTrials.gov Identifier: NCT03343197, Study of AG-120 and AG-881 in Subjects With Low Grade Glioma (First Posted Nov. 17, 2017, Last Update Posted Oct. 5, 2020). URL: https://clinicaltrials.gov/ct2/show/NCT03343197.
ClinicalTrials.gov Identifier: NCT03393000, Safety and Efficacy Study of Trans Sodium Crocetinate (TSC) in Newly Diagnosed Glioblastoma (GBM) Biopsy-Only Subjects (INTACT) (First Posted Jan. 8, 2018, Last Update Posted Jan. 28, 2020). URL: https://clinicaltrials.gov/ct2/show/record/NCT03393000?term=trans+sodium+crocetinate&rank=1&view=record.
ClinicalTrials.gov Identifier: NCT03398655, A Study of VB-111 With Paclitaxel vs Paclitaxel for Treatment of Recurrent Platinum-Resistant Ovarian Cancer (OVAL) (OVAL) (First Posted Jan. 12, 2018, Last Update Posted Jan. 1, 2021). URL: https://clinicaltrials.gov/ct2/show/NCT03398655?term=VB-111.
DelMar Pharmaceuticals, Inc., DelMar Pharmaceuticals Announces Fast Track Designation for VAL-083 in Recurrent Glioblastoma, 5 pages (Dec. 26, 2017).
Gainer, J.L. et al., Trans sodium crocetinate with temozolomide and radiation therapy for glioblastoma multiforme, J. Neurosurg. 126:460-466 (2017).
Gormley, G., Research and Development at Daichii Sankyo, Daiichi-Sankyo, 70 pages (2014). URL: https://www.daiichisankyo.com/files/news/ir/pdf/005258/R&D%20Day_eng.pdf.
Gruslove, A. et al., VB-111: a novel anti-vascular therapeutic for glioblastoma multiforme, J Neurooncol., 124(3):365-372 (2015).
Gu, X. et al., MicroRNA-129-5p inhibits human glioma cell proliferation and induces cell cycle arrest by directly targeting DNMT3A, Am. J. Transl. Res., 10(9):2834-2847 (2018).
International Search Report for PCT/US2020/033212, 6 pages (dated Jul. 20, 2020).
Katz, A., Novel Alkylating Agent Defies Mechanisms of Resistance in GBM Tumors, OncologyLive, 18(19): (Oct. 11, 2017).
Kintara Therapeutics, DelMar Presents Clinical Update on VAL-083 From Ongoing First- and Second-Line Trials in Patients with MGMT-unmethylated GBM at The Society for NeuroOncology Annual Meeting, 5 pages (Nov. 20, 2018). URL: https://www.kintara.com/news-media/press-releases/detail/887/delmar-presents-clinical-update-on-val-083-from-ongoing.
Lin, J. et al., Discovery and Optimization of Quinolinone Derivatives as Potent, Selective, and Orally Bioavailable Mutant Isocitrate Dehydrogenase 1 (mIDH1) Inhibitors, J. Med. Chem., 62(14):6575-6596 (2019).

Mellai, M., et al., The Distribution and Significance of IDH Mutations in Gliomas, Evolution of the Molecular Biology of Brain Tumors and the Therapeutic Implications, Terry Lichtor, IntechOpen, DOI: 10.5772/52357, 23 pages (2013).
Mellinghoff, I.K. et al., A phase 1, multicenter, randomized, open-label, perioperative study of AG-120 (ivosidenib) and AG-881 in patients with recurrent, nonenhancing, IDH1-mutant, low-grade glioma, Presented at the 23rd Annual Scientific Meeting and Education Day of the Society for Neuro-oncology (SNO), New Orleans, LA, USA, Poster RBTT-03 (Nov. 15-18, 2018).
Mellinghoff, I.K. et al., AG-120, a first-in-class mutant IDH1 inhibitor in patients with recurrent or progressive IDH1 mutant glioma: results from the phase 1 glioma expansion cohorts, Presented at the Society for Neuro-Oncology Annual Scientific Meeting, Scottsdale, AZ, ACTR-46: 19 pages (Nov. 18, 2016).
Metzker, M., Sequencing technologies—the next generation, Nature Review Genetics, 11:31-46 (2010).
Mohamed, H. and Duffy-Warren, F., FT-2102—mIDH1 Inhibitor, Forma Therapeutics presentation, 4th Paediatric Strategy Forum for Medicinal Product Development for Acute Myeloid Leukaemia in Children and Adolescents, Erasmus University Rotterdam, 7 pages (Apr. 11, 2019).
Panknin, O. et al., Abstract 2645: BAY 1436032: A highly selective, potent and orally available inhibitor of mutant forms of IDH1, AACR 107th Annual Meeting Apr. 16-26, 2016, 4 pages.
Pleyer, L., et al., Azacitidine for Front-Line Therapy of Patients with AML: Reproducible Efficacy Established by Direct Comparison of International Phase 3 Trial Data with Registry Data form the Austrian Azacitidine Registry of the AGMT Study Group, J. Mol. Sci., 18(415):1-18 (2017).
Reardon, D.A. et al., Efficacy and safety results of ABT-414 in combination with radiation and temozolomide in newly diagnosed glioblastoma, Neuro-Oncology, 19(7):965-975 (2016).
Ribadeneira, M.D. et al., Olutasidenib (FT-2102) A Potent and Selective Brain Penetrant Inhibitor of Mutant Isocitrate Dehydrogenase 1, Forma Therapeutics, Inc., Presented at 3rd SNO-SCIDOT Joint Conference on Therapeutic Delivery to the CNS, 9 pages (Nov. 20, 2019).
Shanley, M., Phase 3 Results Reveal Combination Therapy Does Not Improve Overall Survival in Glioblastoma, HCP Live, 2 pages (Mar. 8, 2018). URL: https://www.hcplive.com/view/vb-111-combination-glioblastoma-fail.
Struys, E.A. et al., Mutations in the D-2-Hydroxyglutarate Dehydrogenase Gene Cause D-2-Hydroxyglutaric Aciduria, Am. J. Hum. Genet., 76:358-360 (2005).
Szopa, W. et al., Diagnostic and Therapeutic Biomarkers in Glioblastoma: Current Status and Future Perspectives, BioMed Res. Inter., 1-14 (2017).
The Brain Tumour Charity, Positive results from a drug treating recurrent glioblastoma, (Jun. 28, 2018) URL: https://news.abbvie.com/news/abbvie-receives-us-fda-rare-pediatric-disease-designation-for-investigational-abt-414-for-treatment-type-pediatric-brain-tumor-known-as-diffuse-intrinsic-pontine-glioma-dipg.htm.
TIBSOVO Prescription Label, 20 pages (issued Jul. 20, 2018). URL:<https://www.accessdata.fda.gov/drugsatfda_docs/label/2018/211192s000lbl.pdf>.
U.S. Appl. No. 16/431,588 Non-Final Rejection, 47 pages (dated Jul. 14, 2020).
U.S. Appl. No. 16/431,588 Notice of Allowance, 20 pages (dated Dec. 15, 2020).
U.S. Appl. No. 16/431,588 Response to Non-Final Rejection, 19 pages (filed Sep. 4, 2020).
U.S. Appl. No. 16/526,593 Non-Final Rejection, 32 pages (dated Jun. 15, 2020).
U.S. Appl. No. 16/526,593 Notice of Allowance, 9 pages (dated Sep. 8, 2020).
U.S. Appl. No. 16/526,593 Response to Non-Final Rejection, 13 pages (filed Aug. 26, 2020).
U.S. Appl. No. 16/693,585 Final Rejection, 30 pages (dated Nov. 20, 2020).
U.S. Appl. No. 16/693,585 Non-Final Rejection, 16 pages (dated Sep. 2, 2020).

(56) References Cited

OTHER PUBLICATIONS

U.S. Appl. No. 16/693,585 Response to Non-Final Rejection, 16 pages (filed Sep. 23, 2020).
U.S. Appl. No. 16/893,147 Non-Final Rejection, 41 pages (dated Nov. 30, 2020).
U.S. Food and Drug Administration, FDA approves ivosidenib for relapsed or refractory acute myeloid leukemia, 2 pages (Content current as of Jan. 23, 2019). URL: https://www.fda.gov/drugs/resources-information-approved-drugs/fda-approves-ivosidenib-relapsed-or-refractory-acute-myeloid-leukemia.
U.S. Food and Drug Administration, ivosidenib, Treatment of acute myeloid leukemia (AML), 2 pages (Date Designated Jun. 9, 2015). URL: https://www.accessdata.fda.gov/scripts/opdlisting/oopd/detailedIndex.cfm?cfgridkey=481515.
U.S. Food and Drug Administration, ivosidenib, Treatment of cholangiocarcinoma, 1 page (Date Designated Apr. 26, 2017). URL: https://www.accessdata.fda.gov/scripts/opdlisting/oopd/detailedIndex.cfm?cfgridkey=562216.
U.S. Food and Drug Administration, ivosidenib, Treatment of glioma, 1 page (Date Designated May 1, 2018). URL: https://www.accessdata.fda.gov/scripts/opdlisting/oopd/detailedIndex.cfm?cfgridkey=637718.
U.S. Food and Drug Administration, vorasidenib, Treatment of glioma, 1 page (Date Designated Sep. 10, 2018). URL: https://www.accessdata.fda.gov/scripts/opdlisting/oopd/detailedIndex.cfm?cfgridkey=649318.
U.S. Food and Drug Adminsitration, Facts About the Current Good Manufacturing Practices (CGMPs), 1 page (2018), URL: https://www.fda.gov/drugs/pharmaceutical-quality-resources/facts-about-current-good-manufacturing-practices-cgmps.
VBL Therapeutics, Data Demonstrate Strengthened Overall Survival Benefit in Patients Treated With VB-111 in Combination With Bevacizumab, 4 pages (Jun. 1, 2015). URL: vblrx.com/vbl-therapeutics-reports-updated-interim-results-from-phase-2-clinical-trial-of-vb-111-in-recurrentglioblastoma-rgbm/.
VBL Therapeutics, VBL Therapeutics Announces Third Quarter 2018 Financial Results, 6 pages (Nov. 20, 2018). URL: https://www.globenewswire.com/news-release/2018/11/20/1654366/0/en/VBL-Therapeutics-Announces-Third-Quarter-2018-Financial-Results.html.
Wang, M. et al., Molecular Mutation and Their Cooccurrences in Cytogenetically Normal Acute Myeloid Leukemia, Hindawi Publishing Stem Cells International, 1-11 (2017).
Yu, J. et al., Clinical implications of recurrent gene mutations in acute myeloid leukemia, Exp. Hematol. Oncol., 9:1-11 (2020).
ICH Harmonised Tripartite Guideline, Good Manufacturing Practice Guide for Active Pharmaceutical Ingredients Q7, Current Step 4 version, 49 pages (Nov. 10, 2000).
Wick, W. et al., New (alternative) temozolomide regimens for the treatment of glioma, Neuro-Oncology, 11:69-79 (2009).

* cited by examiner

C1: Gr 3 IDH-DS Resolved with Dexamethasone and Hydroxyurea

INHIBITING MUTANT IDH-1

CROSS REFERENCE TO RELATED APPLICATIONS

This application claims the benefit of and priority to U.S. Provisional Application Serial Nos.: U.S. Provisional Application No. 62/672,461, filed May 16, 2018; U.S. Provisional Application No. 62/672,462, filed May 16, 2018; U.S. Provisional Application No. 62/680,566 filed Jun. 4, 2018; U.S. Provisional Application No. 62/680,571, filed Jun. 4, 2018; U.S. Provisional Application No. 62/680,560, filed Jun. 4, 2018; U.S. Provisional Application No. 62/680,562, filed Jun. 4, 2018; U.S. Provisional Application No. 62/692,598, filed Jun. 29, 2018; U.S. Provisional Application No. 62/692,601, filed Jun. 29, 2018; U.S. Provisional Application No. 62/692,604, filed Jun. 29, 2018; U.S. Provisional Application No. 62/692,605, filed Jun. 29, 2018; U.S. Provisional Application No. 62/692,591, filed Jun. 29, 2018, U.S. Provisional Application No. 62/773,562 filed Nov. 30, 2018; U.S. Provisional Application No. 62/798,677, filed Jan. 30, 2019; U.S. Provisional Application No. 62/798,681 filed Jan. 30, 2019; U.S. Provisional Application No. 62/798,684, filed Jan. 30, 2019; 62/798,687, filed Jan. 30, 2019; U.S. Provisional Application No. 62/798,690, filed Jan. 30, 2019; and U.S. Provisional Application No. 62/812,367, filed Mar. 1, 2019, the contents of each of which are hereby incorporated herein by reference in their entirety.

TECHNICAL FIELD

The present disclosure relates to the medical treatment of certain forms of cancer harboring a mIDH1 mutation, and related medical conditions.

BACKGROUND

The metabolic enzyme isocitrate dehydrogenase (IDH1) catalyzes the oxidative decarboxylation of isocitrate to α-ketoglutarate (α-KG). In both hematologic and solid tumor malignancies, mutated IDH1 acquires the neomorphic activity of converting α-KG to 2-hydroxyglutarate (2-HG) and thereby leads to the aberrant accumulation of 2-HG. 2-HG has been proposed to act as an "oncometabolite" that has pleotropic effects on tumorigenesis. Excess production of 2-HG has been shown to inhibit α-KG-dependent enzymes involved in epigenetic regulation, collagen synthesis, and cell signaling, thereby leading to a block in normal differentiation of progenitor cells and the subsequent development of cancer. Therefore, inhibition of mutated IDH1 in tumor cells and the concomitant decrease in 2-HG production is a therapeutic approach to the treatment of IDH1-mutated cancers.

IDH-1 mutations reported in cancer can occur at amino acid position R132, such as R132H, R132C, R132S, R132G, and R132L mutations. There remains a need for therapeutic compounds that selectively inhibit production of 2-HG from cancer cells harboring a variety of R132 IDH-1 mutations.

Indeed, mutant IDH-1 ("mIDH-1") is a key therapeutic target for the treatment of a variety of cancers and is the subject of extensive research efforts to develop therapeutic compounds useful for the inhibition of mIDH-1. Many different small molecule inhibitors of m-IDH1 have been disclosed in publications (e.g., WO2016/044789, WO2016/044787, WO2016/044782, WO2016/171755, and WO2016/171756). Among the other mIDH-1 inhibitors that have been developed are those depicted in Table 1, which includes multiple compounds that have been reported in clinical trials, and certain other compounds that have been described as being useful for the treatment of cancer.

TABLE 1

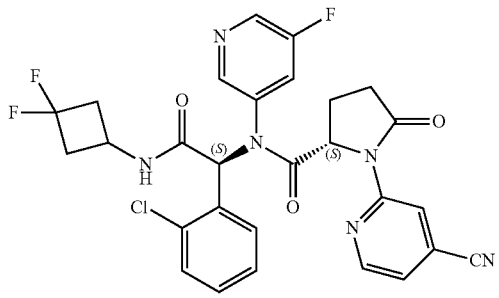

AG-120

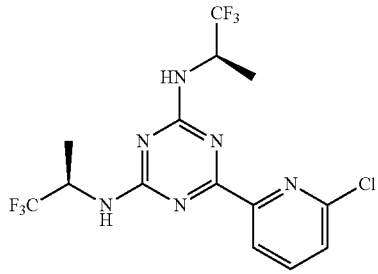 [SMILES: C[C@@H](Nc1nc(N[C@H](C)C(F)(F)F)nc(-c2cccc(Cl)n2)n1)C(F)(F)F]

AG-881

TABLE 1-continued
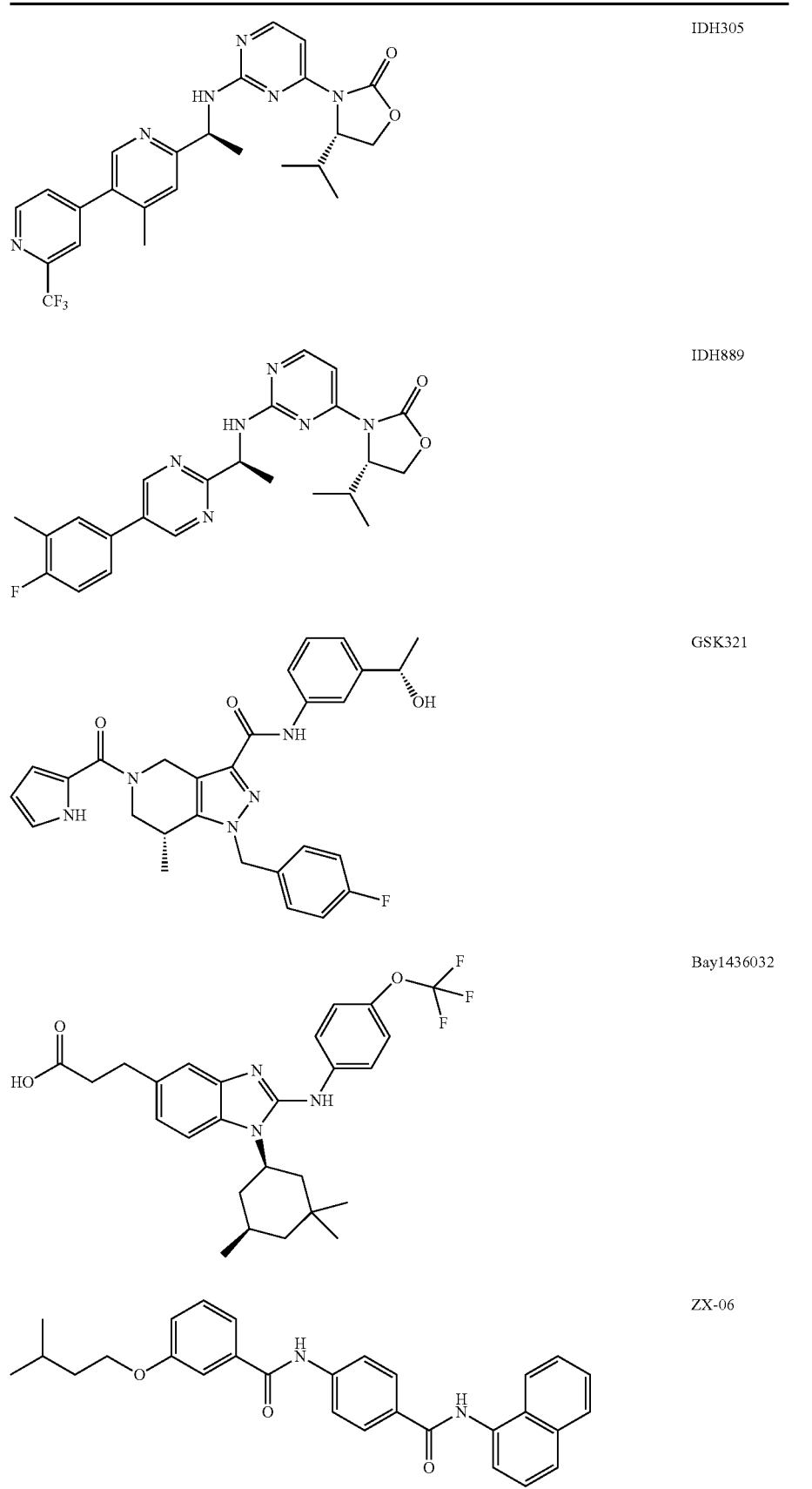
IDH305
IDH889
GSK321
Bay1436032
ZX-06

TABLE 1-continued
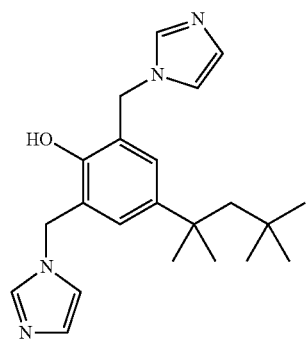
isocitrate
dehydrogenase-1
inhibitor
(Sanofi)
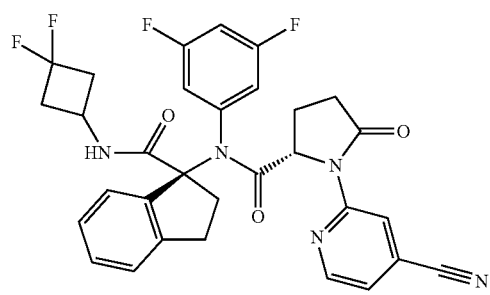
isocitrate dehydrogenase-
1 inhibitor
(Shanghai Haihe
Pharmaceutical)
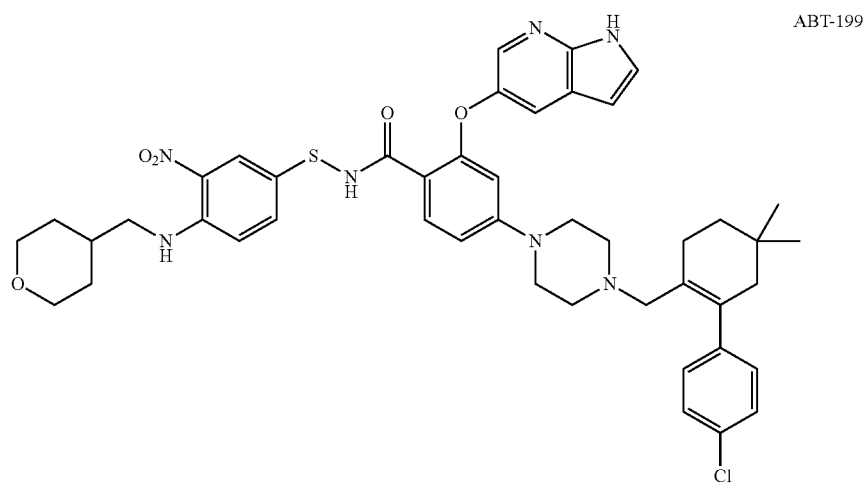
ABT-199
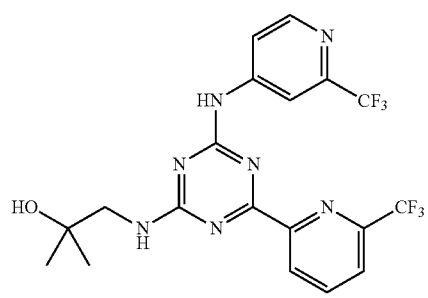 [SMILES: CC(C)(O)CNc1nc(Nc2ccnc(C(F)(F)F)c2)nc(-c2cccc(C(F)(F)F)n2)n1]
AG-221

The FDA recently approved the administration of 500 mg once daily of a mutant IDH1 inhibitor for the treatment of acute myeloid leukemia (AML) with a susceptible IDH1 mutation as detected by an FDA-approved test in (a) adult patients with newly-diagnosed AML who are ≥75 years old or who have comorbidities that preclude use of intensive induction chemotherapy and (b) adult patients with relapsed or refractory AML. However, a 2017 Multi-Discipline Review panel at the FDA noted that doubling the drug dose of this compound translates to only approximately a 40% increase in exposure, and that an increase in clearance at steady state may be related to autoinduction. A PBPK model reasonably captured the autoinduction effect of the 500 mg QD dose of this compound on CYP3A4, and described the steady-state PK profiles of this compound in patients at clinically relevant exposure levels. The fold-change in relative bioavailability of this compound from single-dose to steady-state for this compound was 0.50. In addition, following administration of a single oral dose of 50 mg/kg to rats with an intact blood-brain barrier, this compound exhibited brain penetration of 4.1% ($AUC_{0-8\,h}$ [brain]/$AUC_{0-8\,h}$ [plasma]).

There remains an unmet medical need for a therapeutically effective method of administering a mIDH-1 inhibitor providing the following benefits:

i) achieving sufficient predicted free brain drug exposure (e.g., a desirable predicted $C_{brain}$ Ratio as disclosed herein) suitable for treating mIDH1 solid tumors in the central nervous system, including forms of brain cancer such as glioma; and ii) achieving and sustaining a desired steady state drug plasma concentration within a suitable range for a patient throughout a desired course of treatment (e.g., at least six months).

Thus, there remain particular challenges associated with treating m-IDH1 forms of cancer, including the treatment of mIDH1 forms of blood cancer (e.g., AML) throughout a course of treatment (e.g., 15 days to 6 months), treatment of mIDH1 forms of cancer across the blood brain barrier (e.g., mIDH1 forms of glioma), and treatment of other mIDH1 solid tumors.

SUMMARY

The administration of a therapeutically effective amount of Compound 1 using the methods of treatment provided herein provides a treatment for patients diagnosed with a cancer harboring a mIDH1 mutation, including treatment of such conditions of the blood (e.g., AML) and within the central nervous system (e.g., glioma). In some embodiments, a total of 150 mg of Compound 1 can be administered twice per day on a daily basis to provide a therapeutically effective steady state blood concentration throughout a course of treatment (e.g., 6 months or more). This 150 mg BID dose of Compound 1 can be administered to a patient diagnosed with a cancer harboring a mIDH1 mutation and continued each day throughout a course of treatment. A course of treatment is preferably of sufficient duration to provide a therapeutically effective steady state plasma concentration in the patient diagnosed with the mIDH1 mutation (e.g., at least 15 days), and continuing until a favorable treatment outcome is achieved. In some examples, a course of treatment is up to 6 months (e.g., 15 days to 6 months).

Compound 1 has been administered in human clinical trials as a single agent or in combination with other therapeutic agents to treat multiple mIDH1 forms of cancer, including mIDH1 forms of AML and glioma. In one example provided herein, a patient diagnosed with mIDH1 AML treated with 150 mg BID of Compound 1 achieved a complete remission after a 28 day course of treatment. In another example, a patient diagnosed with mIDH1 AML was treated with 150 mg BID of Compound 1 in combination with azacitidine, as disclosed herein, for a total of eight 28-day treatment cycles and also achieved complete remission of the AML. In a third example, a patient diagnosed with mIDH1 glioma was treated with 150 mg BID of Compound 1 and demonstrated a partial response confirmed by MRI, after two consecutive 28-day treatment cycles, as determined by RANO criteria (≥50% decrease in tumor, no new lesions, on stable dose corticosteroids, no progression of measurable disease).

Compound 1 is a potent, selective, orally bioavailable, small-molecule inhibitor of mutated IDH1 and is useful as an anticancer therapeutic in patients with certain mutations in the IDH1 gene (including R132X mutations).

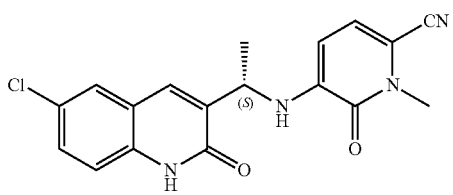

mIDH1 forms of cancer can be treated by the therapeutic administration of Compound 1 at a total daily dose of 300 mg (preferably, 150 mg twice daily, or BID) to selectively inhibit multiple clinically relevant R132X mutations of IDH-1. Compound 1 can be administered to achieve a durable effective drug plasma concentration over the course of a desired course of treatment (e.g., at least six months). Methods of administering Compound 1 for the treatment of certain cancers, including glioma, hematological cancers such as AML, and solid tumors, are provided herein.

The present disclosure identifies a particular mIDH-1 inhibitor and, furthermore, new therapeutic methods for using this compound in the treatment of cancer (e.g., AML, glioma, and various solid tumors). In the selection of the mIDH-1 inhibitor Compound 1, the present disclosure provides an insight that certain prior assessments of multiple mIDH-1 inhibitory compounds may have focused on and/or unduly prioritized one or more features (e.g., in vitro potency as measured in biochemical assays for the production of 2-HG) that can lead away from appreciation of certain unexpected properties of Compound 1 that lead to the discovery of methods of treatment as described herein.

The discovery of the methods of treatment provided herein is based in part on the selection of Compound 1 from among many compounds reported to inhibit the production of 2-HG from mIDH-1 cancer cells. Compound 1 was not initially reported as having the greatest biochemical potency compared to reports for certain other small molecule inhibitors of mIDH-1. Structurally distinct compounds (e.g., AG-120, AG-881, IDH305, IDH889, GSK321, and Bay1436032) and other certain quinolinone-based compounds were initially reported as having greater in vitro potency in biochemical assays measuring activity against certain mIDH-1 isoforms. Compound 1 not only inhibits 2-HG production from cells harboring various R132X forms of IDH-1 mutations; Compound 1 is characterized by a CNS multiparameter optimization ("CNS MPO") value supporting further development as an oral therapy for mIDH-1 forms of cancer in the central nervous system.

Compound 1 has been used according to the novel methods of treatment provided herein to achieve both complete responses in the treatment of multiple patients diagnosed with AML in a human clinical trial, and a partial response in a human clinical subject continuing on therapy. Accordingly, the Applicants have discovered meaningful and therapeutically beneficial methods of treating mIDH1 cancer that include the selection of the mIDH1 inhibitor Compound 1 and the discovery of certain methods of administering Compound 1 that can provide steady state blood plasma concentrations in a patient in need thereof throughout a course of treatment that are suitable for treatment of multiple mIDH1 forms of cancer, including conditions of the blood (e.g., AML) and the CNS (e.g., glioma).

The methods of treatment provided herein are based in part on multiple scientific discoveries, including: (1) the selection of Compound 1 as having sufficient in vitro potency against multiple R132X forms of mIDH-1 cancer, (2) the properties of Compound 1 supporting its use in mIDH1 cancers in the central nervous system (e.g., predicted free brain drug levels of Compound 1 relative to the minimum effective level of Compound 1, and subsequent partial response of a human mIDH1 glioma patient to treatment with Compound 1), (3) the discovery of a specific dose and dose regimen for administering a therapeutically effective amount of Compound 1 useful for treating multiple mIDH1 cancers (including treatment of cancers of the blood, brain and other solid tumors) after comparative testing of multiple dose and dose intervals, and (4) the discovery that desired blood plasma concentration of Compound 1 can be maintained in a patient throughout a course of treatment of 6 months or more using the preferred methods of administering Compound 1 (e.g., 300 mg total per day, preferably administered as a total of 150 mg of Compound 1 BID).

IDH-1 Selectivity of Compound 1

Compound 1 selectively inhibits the production of 2-HG in mIDH-1 cancer cells (i.e., cancer cells harboring IDH-1 R132X mutations) with desirable in vitro potencies when compared to wild type IDH-1 cells and mIDH-2 cancer cells. In addition to this selectivity for mIDH-1, Compound 1 is active against multiple IDH-1 R132X mutants, and therefore can be used to treat patients diagnosed with cancers possessing a variety of such mIDH1 mutations. Of these R132X IDH-1 mutants, R132H and R132C are the more frequently detected mutations for human mIDH-1 cancers. With respect to inhibiting 2-HG production from mIDH-1 R132C and R132H cell lines, Compound 1 shows comparable activity that is within 5-fold, compared to more disparate differences in activity ranging from about 8-fold to 240-fold for comparative compounds [see Example 4].

In addition to R132H and R132C IDH-1 mutants, Compound 1 inhibits the IDH-1 mutants R132L, R132G, and R132S. Notably, Compound 1 inhibits all five of these IDH-1 mutants (R132L, R132G, R132S, R132H, and R132C) with only a 7-fold range in potencies. Therefore, patients diagnosed with cancer possessing mutant IDH-1, e.g., having an IDH-1 R132X mutation selected from the group consisting of: R132L, R132G, and R132S (in addition to R132H and R132C IDH-1 mutations), can be treated with Compound 1 (see Example 3).

Blood Brain Barrier Permeability of Compound 1

IDH-1 mutations in brain cancers, such as glioma, can result in abnormal hypermethylation of histones and DNA and suppression of normal cellular differentiation. IDH-1 R132H mutations represent more than 90% of the IDH mutations present in low grade glioma and secondary glioblastoma multiforme (GBM) patients. In addition, IDH-1 mutations R132C and R132S are also reported in glioma patients. However, in order to be able to treat glioma, a small molecule inhibitor of mIDH-1 must be able to cross the blood brain barrier ("BBB") at a therapeutically effective concentration over time, presenting another challenge to selecting a compound suitable for the treatment of glioma.

The ability to cross the BBB is by no means an intrinsic property of mIDH-1 inhibitors. Referring to Table 13, many known mIDH-1 inhibitors have undesirably low CNS MPO values (e.g., Table 13, compounds GSK321 and Bay1436032). Therefore, even among these advanced drug candidates, there is no apparent reported correlation between mIDH-1 inhibitory activity and CNS MPO values.

In fact, selecting a compound that is both a potent inhibitor of mIDH-1 and possesses a desirably high MPO value is not straightforward. For example, of the compounds specifically exemplified in WO/2016044789 ("the '789 publication"), which include Compound 1, several compounds are reported as having greater in vitro potency than Compound 1 in at least one assay reported in Table 6 of the '789 publication (i.e., compounds I-20, I-22, I-23, I-25, I-26, I-27, and I-29). See Table 13, which reproduces these data from the '789 publication. However, none of these compounds has a CNS MPO score as great as Compound 1. In fact, one compound (I-26) does not even meet a desired minimum MPO threshold value of 3.8 desired as a predictor of BBB permeability. Conversely, of the six compounds with CNS MPO scores higher than Compound 1, five are less potent in vitro than Compound 1 in at least one biochemical assay of IDH inhibition (i.e., compounds I-2, I-3, I-5, I-6, and I-11), with one compound being "equipotent" (compound I-1).

The lack of correlation between mIDH-1 inhibition and CNS MPO scores in Table 13 highlights the unpredictability in selecting a single mIDH-1 inhibitor compound that inhibits multiple R132X forms of mIDH-1 with sufficiently similar potencies, and is also characterized by a sufficiently high MPO score (e.g., 3.8 or higher), both of which are desired in a therapy to treat a mIDH1 glioma. It is against this backdrop that the identification of Compound 1 as a compound having a MPO score of 3.8 or higher is unexpected. Indeed, rodent modeling showed a stark contrast between Compound 1 and two other reported mIDH-1 inhibitors, AG-120 and AG-881. As described in Example 6, Compound 1 partitions into the brain at a level 2-fold greater than that estimated to achieve a therapeutic benefit, whereas AG-120 and AG-881 partition into the brain at a level less than what is estimated to achieve a therapeutic benefit. Thus, even when compared to another compound also having a CNS MPO score suggestive of good BBB permeability, such as AG-881, these data indicate that Compound 1 possesses unexpectedly superior properties by combining desired comparative and selective in vitro potency and predicted drug exposure in the brain.

For instance, as described in Example 6, preclinical studies show that Compound 1 can cross the BBB in rodent models at desirable levels. Oral administration of Compound 1 showed high systemic bioavailability in multiple preclinical species. Permeability was excellent, with little evidence of efflux, and significant brain penetration was observed in mice (98% brain binding in murine animal model). Based on these assessments in rodents, Compound 1 is believed to cross the blood-brain barrier to an extent effective to reach free concentration levels in the brain consistent with pharmacological activity.

Dose and Administration of Compound 1

Upon identifying the unique characteristics of the mDH-1 inhibitor Compound 1 mentioned above, the next challenge was to determine a suitable dose of Compound 1 to be administered to human patients. A suitable dose should possess an appropriate therapeutic index (e.g., an observed in vivo efficacy against multiple forms of cancer harboring mIDH-1, but without unacceptable levels of toxic side effects). More specifically, a drug plasma concentration providing in vivo efficacy ("$C_{eff}$") in patients with tumors producing 2-HG has been defined in the literature as one that provides >90% inhibition of 2-HG production (Fan et al., 2014). Based upon mouse xenograft experiments described in Example 7 and plasma protein binding correlation in humans, Compound 1 was found to have a $C_{eff}$ of about 1,652 ng/mL. Therefore, preferred methods of administering Compound 1 to treat a patient having a cancer harboring mIDH-1 can achieve a plasma concentration of at least about 1,652 ng/mL.

In addition, preferred methods of administering Compound 1 avoid unacceptably high concentrations of Compound 1 in the patient. The discovery of the maximum preferred concentration of Compound 1 was based in part on the results from a 28-day oral toxicity study in monkeys (see Example 9), which found that the most significant adverse event was an increase in mean QTc interval duration, a type of cardiac event that may cause arrhythmia. The lowest $C_{max}$ plasma concentration of Compound 1 at which prolonged QTc interval duration was observed was about 7,840 ng/mL. Accordingly, Compound 1 is preferably dosed in a manner that achieves a drug plasma concentration of no greater than about 7,800 ng/mL ("$C_{tox}$").

Preferred methods of administering a therapeutically effective amount of Compound 1 provide a concentration of Compound 1 in the patient blood plasma within a therapeutic range of about 1,652-7,840 ng/mL.

The discovery of provided methods of administering Compound 1 is based on the evaluation of multiple doses of Compound 1 (100 mg, 150 mg and 300 mg) at multiple dose intervals (once daily and twice daily), both as a single agent and in combination with another therapeutic agent. Notably, the administration of Compound 1 at a total daily dose of 300 mg each day (preferably, 150 mg BID) ultimately demonstrated therapeutic benefits in patient treatment across multiple forms of mIDH1 cancer. As described in Example 10, a Phase 1/2 study of Compound 1 was initiated to evaluate Compound 1 alone or in combination with azacitidine ("AZA") in mIDH-1 AML/myelodysplastic syndrome (MDS) patients. The blood plasma concentration and other effects of administering Compound 1 were evaluated at multiple different dose of Compound 1 at different dose intervals: 100 mg QD (i.e., 100 mg once daily), 150 mg QD (i.e., 150 mg once daily), 300 mg QD (i.e., 300 mg once daily), and 150 mg BID (i.e., 150 mg twice daily), with Compound 1 administered both as a single agent and/or in combination with AZA. As shown in FIG. 19 and described in Example 10, as a single agent, median $C_{min}$ concentrations of Compound 1 at steady-state were below $C_{eff}$ in patients given doses of 100 mg or 150 mg once daily. When given at a dose of 300 mg once a day, Compound 1 achieved a median $C_{min}$ above $C_{eff}$, with a majority of patients reaching $C_{eff}$. However, 150 mg given twice daily achieved the highest median $C_{min}$ and also showed less inter-quartile variability in minimum concentrations as compared to 150 mg once daily.

Compound 1 was also administered in combination with azacitidine (AZA). As shown in FIG. 20, in this combination, dosing a total of 150 mg of Compound 1 once daily shows a median $C_{min}$ less than 1000 ng/mL, which is well below $C_{eff}$. In contrast, dosing a total of 150 mg of Compound 1 twice daily shows a median $C_{min}$ of over 3000 ng/mL, which is nearly twice $C_{eff}$.

Therefore, the present disclosure provides that a total daily dose of 300 mg of Compound 1, preferably administered in a divided daily dose of 150 mg BID, is preferred compared to other doses and dose intervals tested. Applicant selected 300 mg total daily dose, administered as a 150 mg dose form. A suitable dose can be Compound 1 administered in a 300 mg dose once daily. Preferably, a suitable dose can be Compound 1 administered in a 150 mg dose twice daily.

Durable Steady State Concentration of Compound 1

Despite having found that a 300 mg total daily dose of Compound 1 provides the desired efficacy, it was not clear whether this dosing would be able to deliver a continued patient benefit for at least a six month course of treatment (e.g., six four-week treatment cycles). More specifically, Applicant could not predict whether Compound 1 could maintain a steady state blood concentration ("$C_{ss}$", as measured by $C_{min}$ or trough concentration) without a substantial decline in concentration over six four-week treatment cycles.

Compound 1 provides an unexpectedly durable steady state drug plasma concentration throughout a desired course of treatment. After the initial 15 days of treatment with 150 mg twice daily of Compound 1, the median steady state blood concentration of Compound 1 was maintained above about 2,000 ng/mL throughout a course of treatment (e.g., up to about 36 weeks, including 12-32 weeks, as well as other intervals therein, all measured from initial administration of Compound 1). The median $C_{ss}$ was also well below the predicted threshold for QTc prolongation risk as discussed above. As shown in FIG. 8A, which shows data for Compound 1 dosed as a single agent at 150 mg twice daily, the median $C_{ss}$ achieved on day 15 of cycle 1 (i.e., "C1D15, or on the $15^{th}$ day of treatment with Compound 1) was maintained for at least six four-week treatment cycles, and in fact extended to beyond nine four-week cycles. While concentrations are somewhat variable across patients, the median $C_{ss}$ level is maintained and does not trend downward. Good retention of $C_{ss}$ levels were also observed in combination with AZA as shown in FIG. 8B.

The discovery of the unique and remarkable properties of Compound 1 as a selective inhibitor of mIDH-1 across multiple mIDH-1 cancers led to the development of a dosing regimen of Compound 1 that overcomes therapeutic obstacles encountered with prior mIDH-1 inhibitor compounds. Through the administration of Compound 1 at a total daily dose of 300 mg, the present disclosure provides sustained delivery of a mIDH-1 inhibitor at a desired drug plasma concentration for the treatment of cancer in patients harboring mIDH-1.

BRIEF DESCRIPTION OF THE DRAWINGS

FIG. 10A also illustrates steady state is achieved by Week 2; ($t_{1/2}$~60 hrs) and 150 mg BID steady state exposures >$IC_{90}$ and below levels are expected to increase QTcF potential.

FIG. 11A also illustrates that plasma exposures of Compound 1 are stable throughout treatment duration in patients. This can serve as basis for selecting a 150 mg BID dose for dose expansion and a recommended phase II dose.

FIG. 19 also illustrates steady state is achieved by Week 2; ($t_{1/2}$~60 hrs) and 150 mg BID and 300 mg QD steady state exposures are >$C_{eff}$.

FIG. 20 also illustrates steady state is achieved by Week 2; ($t_{1/2}$~60 hrs) and 150 mg BID QD steady state exposures are >$C_{eff}$.

DEFINITIONS

Figure 1A:
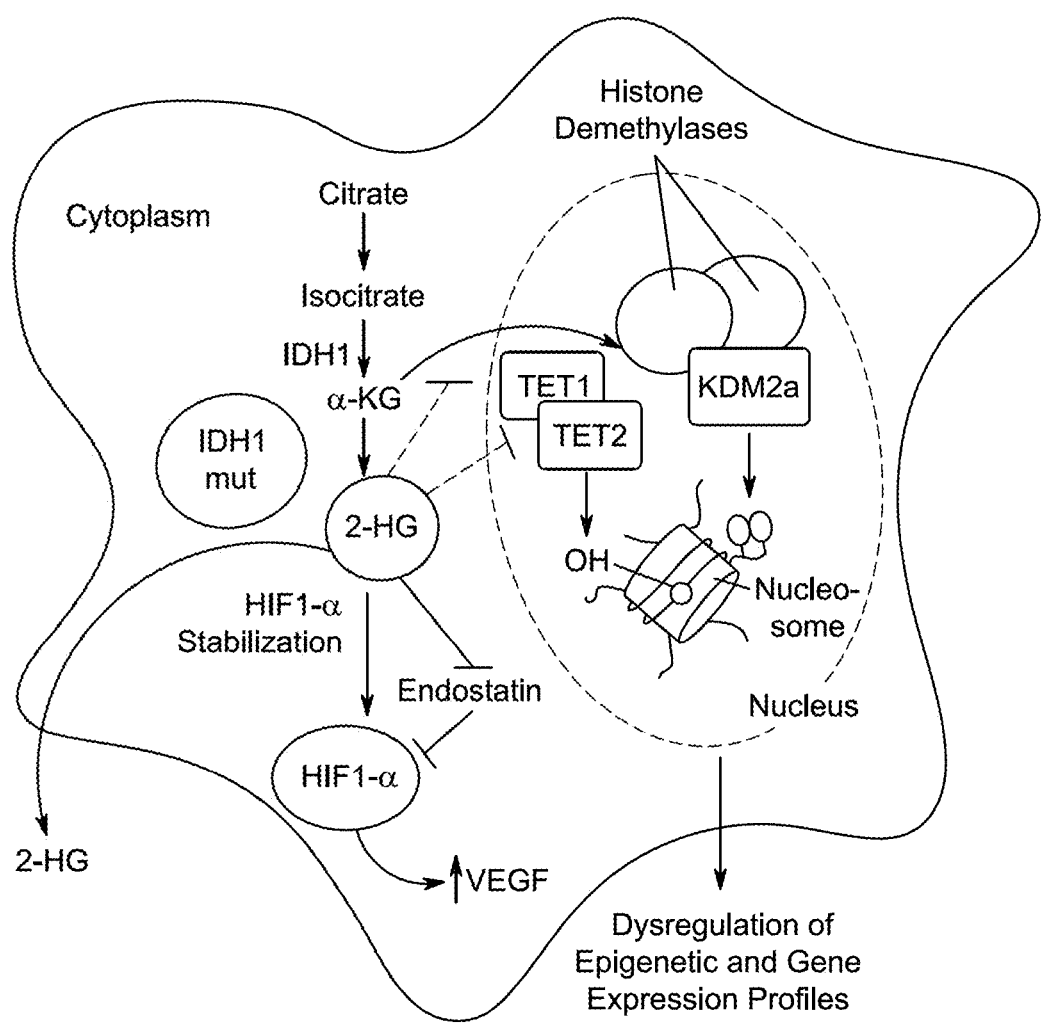
FIG. 1A and FIG. 1B are a schematic of the dysregulation of epigenetic and gene expression profiles associated with IDH mutants.
Figure 1B:
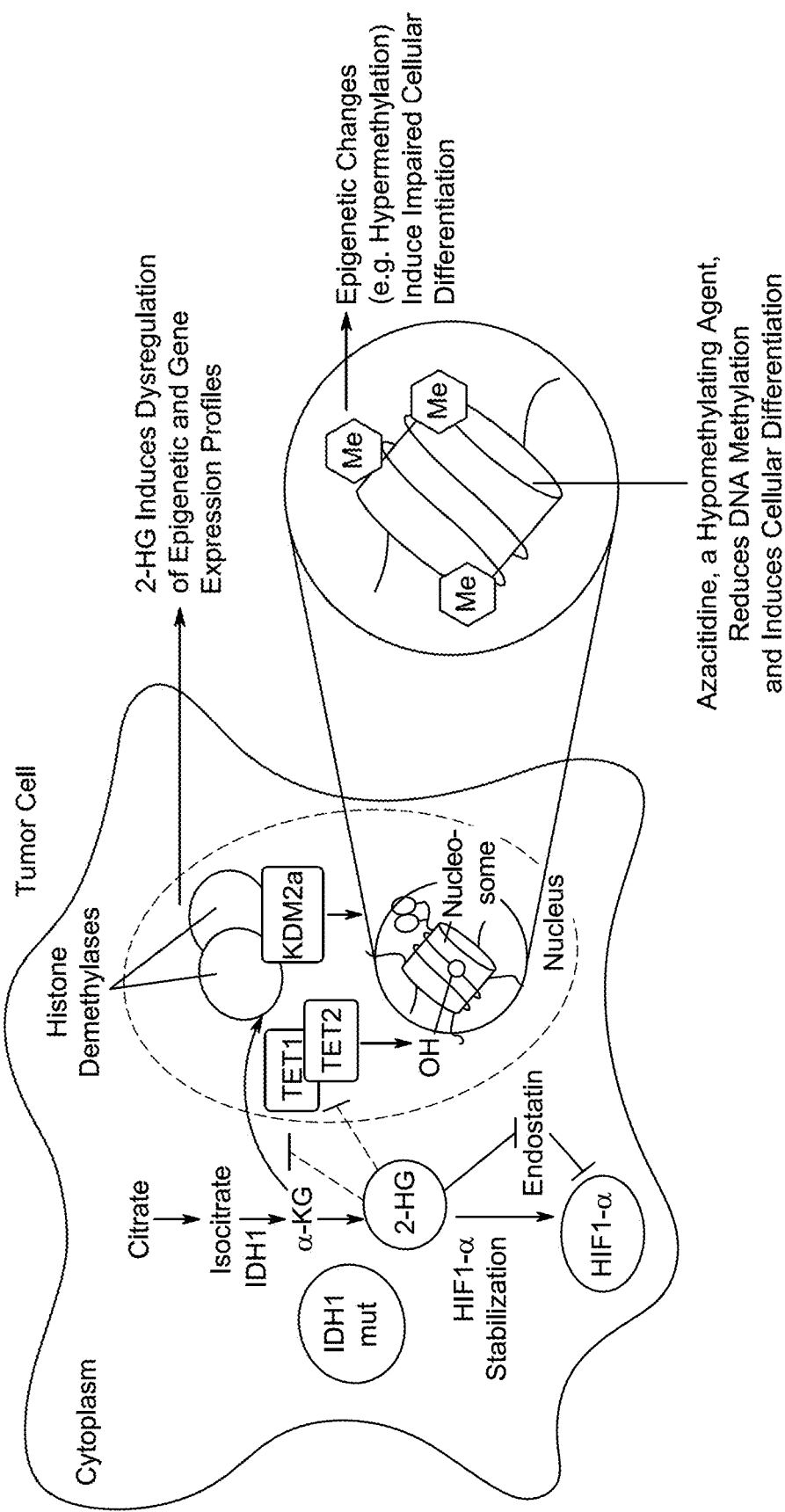
Figure 2:
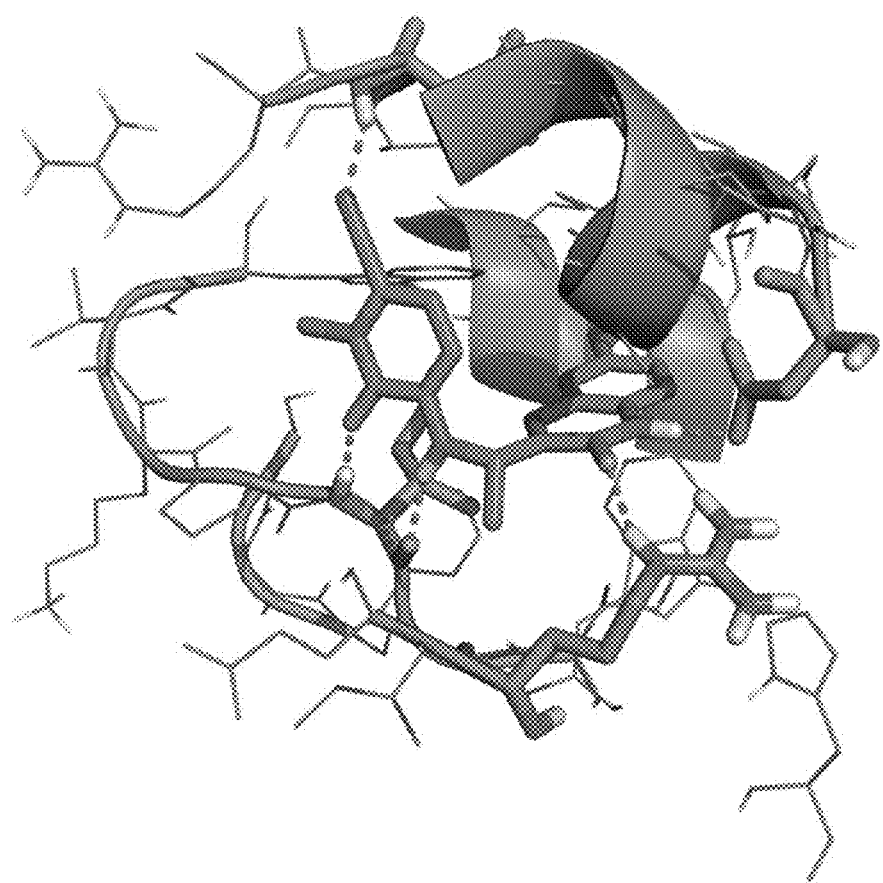
FIG. 2 illustrates Compound 1 binding with mIDH.
Figure 3A:
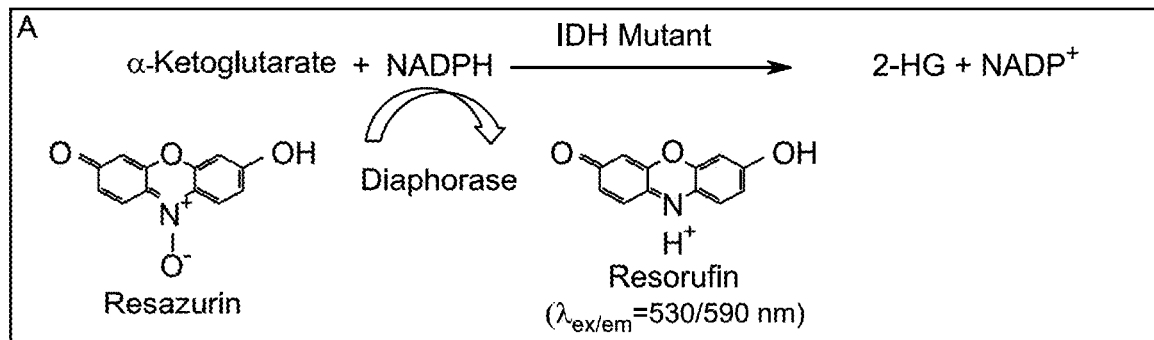
FIG. 3A and FIG. 3B are each a schematic of diaphorase-coupled assays used in Example 1, which measure activity by the determination of the level of remaining co-substrate NADPH after the enzymatic reaction is quenched.
Figure 3B:
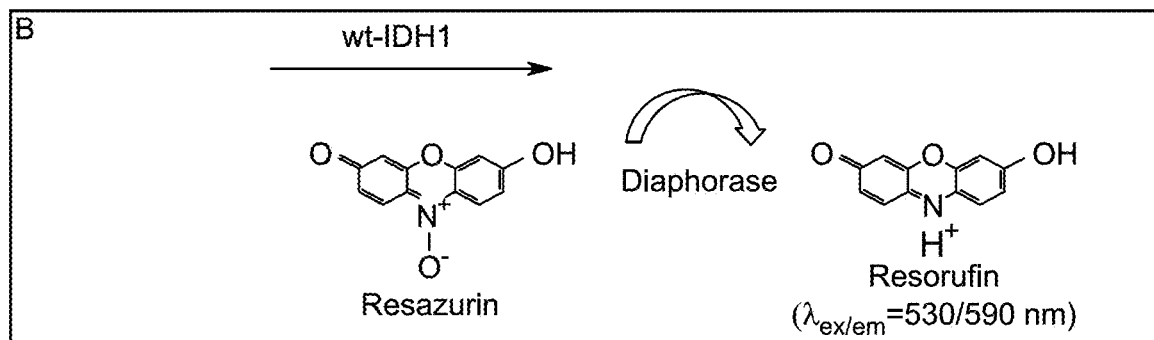

As used herein, the term "Course of Treatment" refers to the time period in which a patient is being administered an agent, including any administration holidays or recovery periods. A course of treatment can include a single treatment cycle or multiple treatment cycles. Additionally, a course of treatment can include a partial treatment cycle. The Course of Treatment can include the total time period during which a patient is on a treatment protocol for a disease, e.g. AML or MDS, with a therapy comprising the administration of a mIDH-1 inhibitor compound.

"Next-generation sequencing or NGS or NG sequencing" as used herein, refers to any sequencing method that determines the nucleotide sequence of either individual nucleic acid molecules (e.g., in single molecule sequencing) or clonally expanded proxies for individual nucleic acid molecules in a high-throughput fashion (e.g., greater than 103 or more molecules are sequenced simultaneously). Various next generation sequencing methods are known. In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) Nature Biotechnology Reviews 11:31-46, incorporated herein by reference. Next generation sequencing can detect a variant present in less than 5% of the nucleic acids in a sample.

As used herein, the term "R132X mIDH-1 mutation(s)" refers to a mutation at the IDH-1 arginine 132 that results in inhibitory activity of Compound 1 against the mutated IDH-1 form harboring the R132 mutation. Preferably, the R132X mutations have a 2-HG $IC_{50}$ value of less than 500 nM (most preferably less than 250 nM or less than 150 nM) using the in vitro assay of Example 2. Accordingly, preferred R132X mutations include R132H and R132C, as well as R132L, R132G, and R132S (or other R132X mutations having therapeutically relevant 2-HG $IC_{50}$ values obtained using the in vitro assay of Example 2). Patients having R132X mIDH-1 mutation(s) can be identified using a suitable diagnostic, such as a diagnostic analyzing patient tissue with next generation sequencing technology that identified the presence of the R132X mIDH-1 mutation in the patient tissue sample.

As used herein, the term "R132X mIDH-1 Selective Inhibitor Therapy" refers to a therapy administered to a patient to inhibit the activity of R132X mIDH-1 in the patient, where the therapy is known to have selective inhibitory activity against R132X mIDH-1 over wild type IDH-1. An R132X mIDH-a selective inhibitor therapy can be administration of Compound 1 as disclosed herein.

As used herein, "sequencing" can be Next Generation Sequencing (NGS), a high-throughput sequencing technology that performs thousands or millions of sequencing reactions in parallel. Although the different NGS platforms use varying assay chemistries, they preferably generate sequence data from a large number of sequencing reactions run simultaneously on a large number of templates. The sequence data can be collected using a scanner, and then assembled and analyzed bioinformatically. Thus, the sequencing reactions are performed, read, assembled, and analyzed in parallel.

The terms "subject" and "patient" are used interchangeably in the present disclosure.

Susceptible IDH1 mutations are defined as those leading to increased levels of 2-hydroxyglutarate (2-HG) in the specified mIDH1 cancer cells (e.g., mIDH1 leukemia cells or mIDH1 glioma cells) and where efficacy is predicted by 1) clinically meaningful remissions with the recommended dose of Compound 1 and/or 2) inhibition of mutant IDH1 enzymatic activity at concentrations of Compound 1 sustainable at the recommended dosage according to validated methods. Susceptible mutations include R132H and R132C mIDH1 substitution mutations.

DETAILED DESCRIPTION

Compound 1 is a small molecule mIDH-1 inhibitor useful for the treatment of patients harboring IDH-1 mutations. In some embodiments, Compound 1 is a small molecule mIDH-1 inhibitor useful for the treatment of solid tumors in the CNS (e.g., glioma), hematological malignancies (e.g., AML or MDS), or other solid tumors (e.g., chondrosarcoma, hepatobiliary, and intrahepatic cholangiocarcinoma).

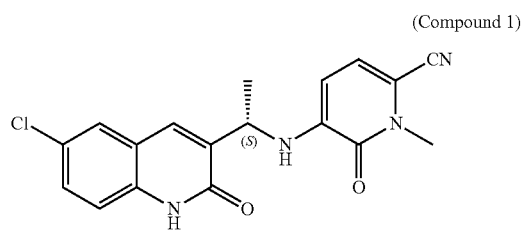

(Compound 1)

Compound 1 can also be referred to as olutasidenib, CAS No.: 1887014-12-1, (S)-5-((1-(6-chloro-2-oxo-1,2-dihydroquinolin-3-yl)ethyl)amino)-1-methyl-6-oxo-1,6-dihydropyridine-2-carbonitrile, 5-{[(1S)-1-(6-chloro-2-oxo-1,2-dihydroquinolin-3-yl)ethyl]amino}-1-methyl-6-oxo-1,6-dihydropyridine-2-carbonitrile, or a compound of Formula (I).

Compound 1 has potent and equivalent biochemical activity against a number of IDH-1 arginine 132 (R132) mutated forms, of which R132H and R132C are the most prevalent observed for human IDH-1. Compound 1 is a small molecule mIDH-1 (mutated isocitrate dehydrogenase 1) inhibitor. As shown in Example 3, it is a permeable, orally bioavailable compound, with an excellent preclinical profile in both in vitro and in vivo models. Compound 1 is a potent and highly selective inhibitor of mutated $IDH1^{R132}$ enzymes:

TABLE 2

| | IDH1 Mutation | | | | |
|---|---|---|---|---|---|
| | R132H | R132C | R132G | R132L | R132S |
| $IC_{50}$ (nM) | <10 | <50 | <50 | <10 | <10 |

Compound 1 exhibits robust (>90%) knockdown of 2-HG in animal and neurosphere PD models. Compound 1 shows no CYP3A4 inhibition. Compound 1 is blood brain barrier penetrant, showing total (bound) brain/plasma ratio of 30% in rats.

Compound 1 can be administered in combination with azacitidine. In some examples, patients have been treated with or are already being treated with azacitidine. In some embodiments, a combination therapy of Compound 1 and azacitidine can be administered for the treatment of patients with a cancer harboring IDH-1 mutations (e.g., mIDH1 forms of AML or glioma or other solid tumors). For example, patients can be administered Compound 1 daily (BID) in continuous 28-day cycles, in combination with azacitidine (administered at the dose of 75 mg/m² for 7 days IV/SC per every 28-day cycle).

Isocitrate dehydrogenase (IDH) is a class of enzymes that catalyze the oxidative decarboxylation of isocitrate to α-keto-glutarate (α-KG). There are three isoforms in human cells. IDH-1 resides in the cytosol and peroxisomes, whereas IDH-2 and IDH-3 are mitochondrial enzymes. IDH-1 is dimeric and uses NADP+ as an electron acceptor. IDH-3 is a tetrameric enzyme and, in contrast, uses NAD+ as an electron acceptor. IDH-3 is the primary IDH enzyme participating in the Krebs cycle. The presence of the IDH-1 mutations imparts a neomorphic activity to the enzyme, resulting in the production of (R)-2-hydroxyglutarate (2-HG) which has been termed an "oncometabolite", and has pleotropic roles in tumorigenesis.

Since IDH-1 mutations are only found in tumor tissue, the present invention is based in part on the discovery that the selective mIDH-1 inhibitor of Compound 1 can be developed as a targeted therapy for multiple mIDH-1 forms of cancer. A patient selection biomarker for the use of Compound 1 can be the existence of IDH-1 mutation in a patient diagnosed with a cancer harboring mIDH-1. Studies in genetically engineered mouse models and models derived from cancer patient samples both support the discovery that mIDH produces 2-HG, the downstream effects of which are believed to cause epigenetic changes that can consequently block the proper differentiation of progenitor cells and lead to cancer. In particular, IDH-1 mutations can lead to the loss of wild type enzymatic activity (conversion of isocitrate to α-KG). Instead, the mutated enzymes acquire the neomorphic activity of converting α-KG to 2-HG. In mIDH-1 harboring cancer cells, wild type and mutant IDH-1 form a heterodimeric complex that can produce very high 2-HG levels. IDH-1 mutations can result in the formation of the (R)-enantiomer of 2-HG, which is in contrast to the accumulation of (S)-enantiomer found in L2HG aciduria patients, who harbor homozygous loss-of-function mutations in 2-HG dehydrogenase. Given the structural similarity between 2-HG and α-KG, 2-HG has been shown to be a competitive inhibitor of a number of α-KG dependent histone and DNA demethylases. 2-HG can inhibit several KDM family histone demethylases in vitro, including H3K9/H3K36 demethylases KDM4A and KDM4C, and H3K36 demethylase KDM2A. Furthermore, elevated methylation levels of H3K4, H3K9, H3K27 and H3K79 have been observed in mIDH-1 containing patient-derived samples, as well as in cells expressing IDH mutations or treated with a cell-permeable ester of 2-HG. 2-HG can also inhibit the TET family of DNA demethylases, which in turn can result in the hypermethylation of DNA CpG islands. Mutations in IDH-1/2 and TET2 are thus far mutually exclusive, which supports the notion that 2-HG produced by mIDH can inhibit TET2 and impair hematopoietic cell differentiation. In addition, 2-HG has also been shown to block PHD activity, which is critical for regulation of hypoxia inducible factors and collagen hydroxylation and maturation. Hydroxylated collagen is important for the regulation of proliferation and proper differentiation of hematopoietic cells in bone marrow. Mutated IDH is also reported to block proper hepatocyte differentiation and promote cholangiocarcinoma.

Using in vitro cellular mechanistic assays monitoring levels of the errantly overproduced, tumorigenic metabolic byproduct 2-HG, inhibition of mIDH-1 results in a >90% reduction in levels of measured 2-HG, an effect that has also been shown to translate into similar levels of 2-HG suppression in in vivo PK-PD studies in HCT116 (IDH-1 R132H) and HCT116 (IDH-1 R132C) xenograft bearing mice. In both models, the free concentration of Compound 1 was comparable in plasma and xenograft tumors, and exposures were dose dependent. At the highest dose tested in these studies (50 mg/kg), Compound 1 inhibited 2-HG levels in tumor by >90% for up to 24 hours after the last dose in the HCT116 (IDH-1 R132H) xenograft model, and to similar levels for at least 12 hours in the HCT116 (IDH-1 R132C) model.

By far the most frequent IDH1 mutations occur at amino acid position R132, and include R132H, R132C, R132S, R132G, and R132L mutations. Given that Compound 1 is a potent inhibitor of a spectrum of different IDH1 R132 mutations, but is inactive against either wild type IDH1 or mutated IDH2, patients will be selected based on the occurrence of an IDH1 mutation at the R132 residue. Accordingly, Compound 1 is useful in methods of treating patients diagnosed with a cancer harboring an IDH-1 mutation such as, AML, MDS, glioma, hepatobiliary tumors, chondrosarcoma, cholangiocarcinoma or other solid tumors harboring an IDH1 mutation. For example, IDH-1 R132 mutations represent more than 90% of the IDH mutations present in low grade glioma and secondary GBM patients. The neomorphic enzymatic activity acquired as a result of IDH-1 mutation is believed to lead to the conversion of α-KG to 2-HG. In consequence, patients bearing IDH-1 mutations have elevated levels of 2-HG. Most IDH-1 mutations result in a single amino acid change at the R132 residue, whereas most IDH-2 mutations occur at either Arginine 140 (R140) or Arginine 172 (R172). The IDH mutation spectrum varies among different tumor types (Table 3).

TABLE 3

| Tumor Types | Total Mutation Frequency | IDH Mutation Identities |
|---|---|---|
| Glioma | 70-90% | $IDH1^{R132H}$, $IDH1^{R132C}$, $IDH1^{R132S}$, $IDH2^{R172K}$ |
| AML | 10-30% | $IDH2^{R140Q}$, $IDH1^{R132H}$, $IDH1^{R132C}$, $IDH2^{R172K}$, $IDH1^{R132G}$, $IDH1^{R132S}$ |
| Chondrosarcoma | 75% | $IDH1^{R132C}$, $IDH1^{R132H}$ |
| Intrahepatic Cholangiocarcinoma | 10-25% | $IDH1^{R132C}$, $IDH1^{R132L}$, $IDH1^{R132G}$, $IDH1^{R132H}$, $IDH2^{R172W}$ |

For example, IDH-1 R132 mutations represent more than 90% of the IDH mutations present in low grade glioma and secondary GBM patients. IDH-1 mutations have been reported in hematological malignancies such as acute myeloid leukemia (AML) and myelodysplastic syndrome (MDS), as well as many solid tumors types, including low grade glioma, secondary glioblastoma, intrahepatic cholangiocarcinoma (IHCC), chondrosarcoma, melanoma and hepatocellular carcinoma, specifically in cells which have R132 mutation (e.g., R132C).

Compound 1 is an isocitrate dehydrogenase-1 (IDH1) inhibitor useful for the treatment of acute myeloid leukemia (AML) with a susceptible IDH1 mutation as detected by an FDA-approved test. In some embodiments, pharmaceutical compositions comprising Compound 1 can be administered to adult patients with newly-diagnosed AML who are ≥75 years old or who have comorbidities that preclude use of intensive induction chemotherapy. In some embodiments, pharmaceutical compositions comprising Compound 1 can be administered to adult patients with relapsed or refractory AML.

Patients can be selected for the treatment of AML with Compound 1 based on the presence of IDH1 mutations in the blood or bone marrow. Patients without IDH1 mutations at diagnosis should be retested at relapse because a mutation in IDH1 may emerge during treatment and/or at relapse. Information on FDA-approved tests for the detection of IDH1 mutations in AML is available at http://www.fda.gov/CompanionDiagnostics.

The patient can be diagnosed as having an IDH-1 R132 mutation disclosed herein using sequencing methods, such as next-generation sequencing methods or a PCR based method. The diagnostic patient selection method can be a next-generation sequencing (NGS)-based tumor genotyping assay analyzing a patient tissue sample, such as a bone marrow sample. Useful techniques and technologies for diagnosing a patient as having a IDH-1 R132 mutation may include, without limitation, sequencing machines and/or strategies well known in the art, such as those developed by Illumina/Solexa (the Genome Analyzer; Bennett et al. (2005) Pharmacogenomics, 6:373-20 382), by Applied Biosystems, Inc. (the SOLiD Sequencer; solid.appliedbiosystems.com), by Roche (e.g., the 454 GS FLX sequencer; Margulies et al. (2005) Nature, 437:376-380), and by others.

Next generation sequencing methods are known in the art. "Next-generation sequencing or NGS or NG sequencing" as used herein, refers to any sequencing method that determines the nucleotide sequence of either individual nucleic acid molecules (e.g., in single molecule sequencing) or clonally expanded proxies for individual nucleic acid molecules in a high-throughput fashion (e.g., greater than 103 or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) Nature Biotechnology Reviews 11:31-46, incorporated herein by reference. Next generation sequencing can detect a variant present in less than 5% of the nucleic acids in a sample.

In some examples, patients treated with Compound 1 can have a mutant IDH-1 cancer that does not have a mIDH-2 mutation detected with a FDA approved mIDH-2 diagnostic (e.g, as provided at www.fda.gov/CompanionDiagnostics).

It will be appreciated that where the present disclosure refers to the treatment of a patient, such disclosure includes the treatment of a population of patients as well (e.g., a population of patients having a cancer harboring m-IDH1).

Pharmaceutical compositions comprising Compound 1 can be administered throughout a course of treatment. A course of treatment preferably comprises administration of Compound 1 to a patient in need thereof until the concentration of Compound 1 in the blood of the patient reaches steady state (e.g., 15 consecutive days), until a desired therapeutic response (e.g., 6 months or more) or until disease progression or unacceptable toxicity.

In some embodiments, Compound 1 can be formulated as a film-coated (e.g., 150 mg or 50 mg) tablet or capsule for oral administration. Each tablet or capsule can contain the following inactive ingredients: colloidal silicon dioxide, croscarmellose sodium, hypromellose acetate succinate, magnesium stearate, microcrystalline cellulose, and sodium lauryl sulfate. The tablet or capsule coating can include other components such as FD&C blue #2, hypromellose, lactose monohydrate, titanium dioxide, and triacetin.

Compound 1 is a Selective mIDH1 Inhibitor

Compound 1 was selected as a potent and selective mIDH1 inhibitor. The present disclosure provides methods for treating cancer. In particular, patients diagnosed with cancer harboring a mutant IDH-1 cancer cell, e.g., having a IDH-1 R132 mutation selected from the group consisting of: R132L, R132G, and R132S (in addition to R132H and R132C IDH-1 mutations), can be treated with a therapeutically effective amount of Compound 1. In some examples, patients treated with Compound 1 can have a mutant IDH-1 cancer that does not have a mIDH-2 mutation detected with a FDA approved mIDH-2 diagnostic (e.g., as provided at www.fda.gov/CompanionDiagnostics).

Studies in genetically engineered mouse models and models derived from cancer patient samples both support the discovery that mIDH produces 2-HG, the downstream effects of which cause epigenetic changes that consequently block the proper differentiation of progenitor cells and lead to cancer. In particular, IDH-1 mutations can lead to the loss of wild type enzymatic activity (conversion of isocitrate to alpha-KG (α-KG)). Instead, the mutated enzymes acquire the neomorphic activity of converting α-KG to 2-HG. In mIDH-1 harboring cancer cells, wild type and mutant IDH-1 form a heterodimeric complex that can produce very high 2-HG levels. All IDH-1 mutations result in the formation of the (R)-enantiomer of 2-HG, which is contrast to the accumulation of (S)-enantiomer found in L2-HG aciduria patients, who harbor homozygous loss-of-function mutations in 2-HG dehydrogenase. Given the structural similarity between 2-HG and α-KG, 2-HG has been shown to be a competitive inhibitor of a number of α-KG dependent histone and DNA demethylases. 2-HG inhibits several KDM family histone demethylases in vitro, including H3K9/H3K36 demethylases KDM4A and KDM4C, and H3K36 demethylase KDM2A. Furthermore, elevated methylation levels of H3K4, H3K9, H3K27, and H3K79 have been observed in mIDH-1 containing patient-derived samples, as well as in cells expressing IDH mutations or treated with a cell-permeable ester of 2-HG. 2-HG also inhibits the TET family of DNA demethylases, which in turn results in the hypermethylation of DNA CpG islands. Mutations in IDH-1/2 and TET2 are thus far mutually exclusive, which supports the notion that 2-HG produced by mIDH inhibits TET2 and impairs hematopoietic cell differentiation. In addition, 2-HG has also been shown to block PHD activity, which is critical for regulation of hypoxia inducible factors and collagen hydroxylation and maturation. Hydroxylated collagen is important for the regulation of proliferation and proper differentiation of hematopoietic cells in bone marrow. Mutated IDH is also reported to block proper hepatocyte differentiation and promote cholangiocarcinoma. Since IDH-1 mutations are only found in tumor tissue, the present invention is based in part on the discovery of that the selective mIDH-1 inhibitor of Compound 1 can be developed as a targeted therapy for cancer. The patient selection biomarker for the use of Compound 1 can be the existence of IDH-1 mutation in a patient diagnosed with a cancer harboring mIDH-1.

Using in vitro cellular mechanistic assays monitoring levels of the errantly overproduced, tumorigenic metabolic byproduct 2-hydroxy glutarate (2-HG), inhibition of mIDH-1 results in a >90% reduction in levels of measured 2-HG, an effect that has also been shown to translate into similar levels of 2-HG suppression in in vivo PK-PD studies in HCT116 (IDH-1 R132H) and HCT116 (IDH-1 R132C) xenograft bearing mice. In both models, the free concentration of Compound 1 was comparable in plasma and xenograft tumors, and exposures were dose dependent. At the highest dose tested in these studies (50 mg/kg), Compound 1 inhibited 2-HG levels in tumor by >90% for up to 24 hours after the last dose in the HCT116 (IDH-1 R132H) xenograft model, and to similar levels for at least 12 hours in the HCT116 (IDH-1 R132C) model.

Accordingly, Compound 1 is useful in methods of treating patients diagnosed with a cancer harboring an IDH-1 mutation. The neomorphic enzymatic activity acquired as a result of IDH-1 mutation is believed to lead to the conversion of α-ketoglutarate (alpha-KG) to 2-hydroxyglutarate (2-HG). In consequence, patients bearing IDH-1 mutations have elevated levels of 2-HG. Most IDH-1 mutations result in a single amino acid change at the R132 residue, whereas most IDH-2 mutations occur at either Arginine 140 (R140) or Arginine 172 (R172). The IDH mutation spectrum varies among different tumor types (Table 3 above).

For example, IDH-1 R132 mutations represent more than 90% of the IDH mutations present in low grade glioma and secondary GBM patients. IDH-1 mutations have been reported in hematological malignancies such as acute myeloid leukemia (AML) and myelodysplastic syndrome (MDS), as well as many solid tumors types, including low grade glioma, secondary glioblastoma, intrahepatic cholangiocarcinoma (IHCC), chondrosarcoma, and melanoma. By far the most frequent IDH-1 mutations occur at amino acid position R132, and include R132H, R132C, R132S, R132G, and R132L mutations. Given that Compound 1 is a potent inhibitor of a spectrum of different IDH-1 R132 mutations, but is inactive against either wild type IDH-1 or mutated IDH-2, patients will be selected based on the occurrence of an IDH-1 mutation at the R132 residue.

The patient can be diagnosed as having an IDH-1 R132 mutation disclosed herein using sequencing methods, such as next-generation sequencing methods. The diagnostic patient selection method can be a next-generation sequencing (NGS)-based tumor genotyping assay analyzing a patient tissue sample such as a bone marrow sample. Useful techniques and technologies for diagnosing a patient as having a IDH-1 R132 mutation may include, without limitation, sequencing machines and/or strategies well known in the art, such as those developed by Illumina/Solexa (the Genome Analyzer; Bennett et al. (2005) Pharmacogenomics, 6:373-20 382), by Applied Biosystems, Inc. (the SOLiD Sequencer; solid.appliedbiosystems.com), by Roche (e.g., the 454 GS FLX sequencer; Margulies et al. (2005) Nature, 437:376-380), and by others.

The invention is based in part on the discovery that Compound 1 selectively inhibits the production of 2-HG from mIDH-1 cancer cells harboring R132 mutations including R132S, R132G and R132L with clinically relevant comparative potencies, while remaining inactive at wild type IDH-1 cells. In addition, Applicants have discovered that Compound 1 is a targeted, selective small molecule inhibitor of 2-HG production from mIDH-1 cancer cells and is also inactive in mIDH-2 cancer cells that produce 2-HG (e.g., Compound 1 selectively inhibits the production of 2-HG from mIDH-1 cancer.

Solid Tumors

The invention is based in part on the discovery that Compound 1 selectively inhibits the production of 2-HG from mIDH1 cancer cells harboring R132 mutations including R132S, R132G and R132L with clinically relevant comparative potencies, while remaining inactive in wild type IDH1 cells. In addition, Applicants have discovered that Compound 1 decreases 2-HG production in mIDH1 cancer cells, is an inhibitor of mutant IDH1 in cancer cells and is also inactive in mIDH2 cancer cells that produce 2-HG (e.g., Compound 1 selectively inhibits the production of 2-HG from mIDH1 cancer).

In some examples, methods are provided for treating solid tumors in the CNS, including glioma cancer cells, harboring an IDH1 R132 mutation. For example, patients diagnosed with glioma harboring a mutant IDH1 cancer cell can be treated with a therapeutically effective amount of Compound 1 in combination with azacitidine.

Achieving Effective Blood Plasma Concentrations of Compound 1

The present disclosure provides methods for the treatment of AML or MDS comprising a step of administering to a subject a therapeutically effective amount of a pharmaceutically acceptable form of Compound 1. In some examples, the pharmaceutically acceptable form of Compound 1 is an oral dosage form (e.g., as provided in Example 1) administered to the patient as R132X mIDH-1 Selective Inhibitor Therapy consisting of the oral administration of an oral dosage form of Compound 1 administered either as a single agent inhibitor of mIDH-1, or in combination with azacitidine or cytarabine. When Compound 1 is administered in such combination therapy, the subject can be receiving or have previously received treatment with azacitidine or cytarabine.

Figure 22:
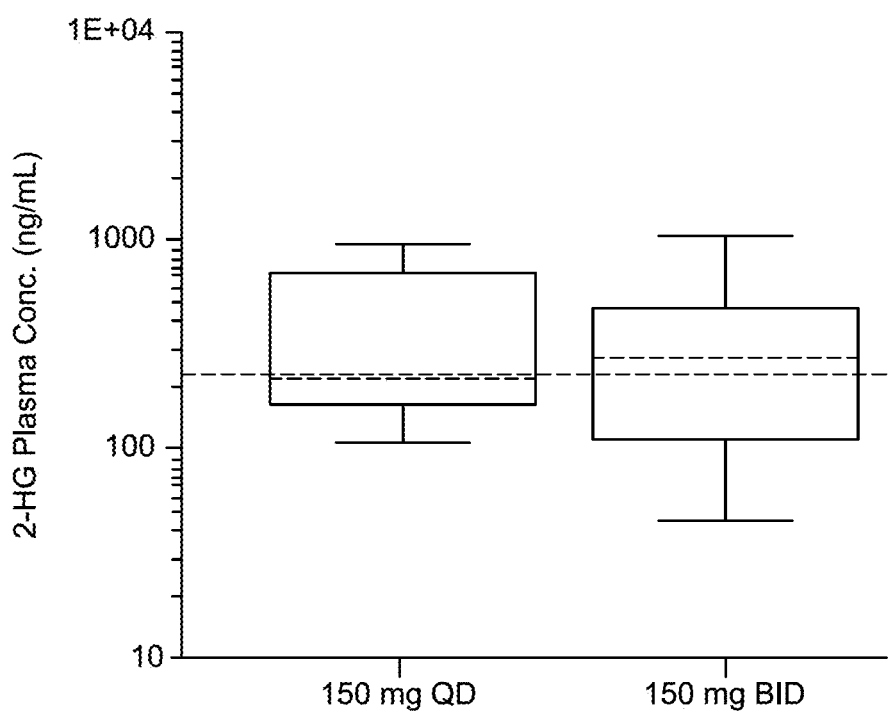
FIG. 22 illustrates a therapeutically reduced level of 2-HG in the patient plasma after consecutive treatment cycles of treatment with Compound 1 and azacitidine.

Post-therapy, 2-HG plasma levels less than 180 ng/mL are associated with better overall and disease-free survival in patients with IDH-1 and IDH-2 mutated AML (JANIN, M. et al., Serum 2-Hydroxyglutarate Production in IDH1- and IDH2-Mutated De Novo Acute Myeloid Leukemia: A Study by the Acute Leukemia French Association Group, Journal of Clinical Oncology, 32(4): 297-305 (2014)). FIG. 22 shows that 150 mg once daily dosing achieved a median 2-HG plasma concentration above 600 ng/mL. Meanwhile, 300 mg once daily achieved a median 2-HG plasma concentration slightly above 200 ng/mL, and 150 mg twice daily achieved a median 2-GH HG plasma concentration of approximately 100 ng/mL. This demonstrates the ability of 150 mg twice daily dosing to lower 2-HG levels below a literature established level as compared to 150 mg and 300 mg once daily.

The invention is based in part on the discovery that oral administration of Compound 1 (in the pharmaceutically acceptable oral dosage form resulting from the preparation method of Example 1) to humans having elevated blood 2-HG levels (i.e., above about 180 ng/mL) can provide a steady state (trough) blood concentrations above a therapeutically effective amount of Compound 1 (e.g., above the $IC_{90}$ concentration for R132H and/or R132C mIDH-1, and/or concentrations of greater than about 2,000 ng/mL or concentrations of greater than about 1652 ng/mL) throughout a course of treatment of 6 months from the initial administration of Compound 1, while simultaneously reducing and then maintaining the levels of 2-HG to below 200 ng/mL within about 15 days of daily treatment with Compound 1. Alternatively, the levels of 2-HG are maintained below 180 ng/mL within about 15 days of daily treatment with Compound 1. In these observations, Compound 1 was administered in an oral dosage form (obtainable from the method in Example 1) twice per day (150 mg BID) to AML or MDS adult patients harboring a R132X IDH-1 mutation. After the initial 15 days of treatment with 150 mg BID of this oral dosage form of Compound 1, the steady state (trough) blood concentration of Compound 1 (pre-dose) was maintained above about 2,000 ng/mL (and well below the predicted threshold for QTc risk) throughout a course of treatment (e.g., up to about 30 weeks, including 12-30 weeks, and 20 weeks as well as other intervals therein, all measured from initial administration of Compound 1).

Accordingly, the present disclosure provides methods of treating patients harboring isocitrate dehydrogenase 1 mutations (mIDH-1) (preferably including one or more R132X mIDH-1) diagnosed with AML or MDS. The method can comprise administering to the patient in need thereof a therapeutically effective amount of a R132X mIDH-1 Selective Inhibitor Therapy. The R132X mIDH-1 selective inhibitor can consist of Compound 1 as the only R132X mIDH-1 inhibitor compound administered to the patient (e.g., in an oral dosage form such as the solid form obtained from Example 1). Compound 1 can be administered to a patient harboring the R132X mIDH-1 identified in a tissue sample, and/or an elevated 2-HG blood concentration (e.g., above about 180 ng/mL) for a course of treatment of at least three consecutive treatment cycles of 28 consecutive days of administration for each cycle. The course of treatment can start with the initial administration of Compound 1 in the first of the at least three or more consecutive 28-day treatment cycles. The administration of the therapeutically effective amount of Compound 1 throughout a course of treatment (e.g., at least 15 consecutive days, preferably up to 30 weeks or more) to a patient having elevated 2-HG levels (e.g., 2-HG blood concentrations in plasma of 200-10,000 ng/mL) can result in a therapeutic effect on the patient evidenced by a durable therapeutically effective trough blood plasma concentration of Compound 1 in the patient throughout the course of treatment (e.g, above the $IC_{90}$ concentration for R132H and/or R132C mIDH-1, and/or concentrations of greater than about 2,000 ng/mL and less than about 7,200 ng/mL, or above the $IC_{90}$ concentration for R132H and/or R132C mIDH-1, and/or concentrations of greater than about 1652 ng/mL and less than about 7,840 ng/mL).

Compound 1 can be administered at a dose of 150 mg twice per day throughout the course of treatment. Compound 1 can be administered with food to improve bioavailability of Compound 1. The course of treatment can be at least 15 consecutive days starting with the initial dose of Compound 1 and longer (e.g., up to 30 weeks, 15 days to 30 weeks, 15 days to 12 weeks, at least 12 weeks, 12-30 weeks, 15 days to 6 months and other intermediate or longer durations or intervals apparent based on the present disclosure).

Some methods further comprise the administration of azacitidine to the patient throughout the course of treatment. Azacitidine can be subcutaneously or intravenously administered to the patient in an azacitidine treatment cycle consisting of the administration of a total dose of 75 mg/m² each day for 7 consecutive days beginning at the start of each treatment cycle, followed by 21 consecutive days without administration of the azacitidine to the patient. A 48-hour dose-interruption of azacitidine is allowed for weekends or holidays. If no response is seen after 2 treatment cycles, Azacitidine can be administered at a total dose of 100 mg/m² each day. Treatment with IDH1m inhibitor and azacitidine showed synergistic effects on releasing differentiation block in mIDH leukemia models in vitro.

The methods can further comprise the administration of cytarabine to the patient throughout the course of treatment. Cytarabine can be subcutaneously or intravenously administered to the patient in a cytarabine treatment cycle consisting of the administration of a total dose of 20 mg/day each day for 7 consecutive days beginning at the start of each treatment cycle, followed by 10 consecutive days without administration of the cytarabine to the patient. Cytarabine can also be administered 20 mg BID subcutaneously for 10 days beginning at the start of each treatment cycle. In the induction therapy of AML, the cytarabine dose administered in combination with other anticancer drugs can be 100 mg/m²/day by continuous IV infusion (Days 1 to 7) or 100 mg/m² IV every 12 hours (Days 1 to 7). Cytarabine injection can be used intrathecally in acute leukemia in doses ranging from 5 mg/m2 to 75 mg/m² of body surface area. The frequency of administration can vary from once a day for 4 days to once every 4 days. The dose can be 30 mg/m² every 4 days until cerebrospinal fluid findings are normal, followed by one additional treatment.

A patient can be identified as having a R132X mutation in mIDH-1 using a diagnostic method comprising a sequencing analysis (e.g., next generation sequencing (NGS)) of bone marrow or other tissue sample obtained from the patient prior to the administration of Compound 1 to the patient. The R132X gene mutation can be determined prior to administration of Compound 1 to the patient. Compound 1 can be administered to patients who have received prior anticancer therapy and/or other concomitant (non-anticancer) medications. In some examples, Compound 1 is administered to patient who has not received a prior mIDH-1 inhibitor therapy.

As provided herein, methods for the administration of an inhibitor of the R132X mutant IDH-1 (mIDH-1 Inhibitor) Compound 1 provide an unexpectedly durable steady state blood concentration of the mIDH-1 Inhibitor throughout a desired course of treatment. For example, the therapeutic methods provided herein can provide AML or MDS patients harboring a R132X mIDH-1 mutation with durable steady state blood concentrations of the mIDH-1 Inhibitor of Compound 1 at a therapeutically effective level (e.g., above the $IC_{90}$ concentration for a R312X mIDH-1) without a substantial decline (e.g., no more than 10% reduction) in initial Compound 1 mIDH-1 Inhibitor steady state blood concentration (e.g., blood concentration measured about 12 hours after an initial dose of the mIDH-1 Inhibitor) over a course of treatment of greater than about 12 consecutive weeks (e.g., 3 consecutive 28-day treatment cycles and preferably at least about 6 months). In addition, the mIDH-1 Inhibitor Compound 1 can be administered to AML or MDS patients harboring a R132X mIDH-1 mutation in a therapeutically effective manner that provides for the reduction of elevated 2-HG levels within about 15 days of initiating a course of treatment, preferably achieving and maintaining 2-HG levels in these patients at a level at or below about 180 ng/mL starting by day 15 in a course of treatment and continuing throughout a course of treatment lasting for at least 12 weeks or longer (e.g, 12-30 weeks).

Figure 8A:
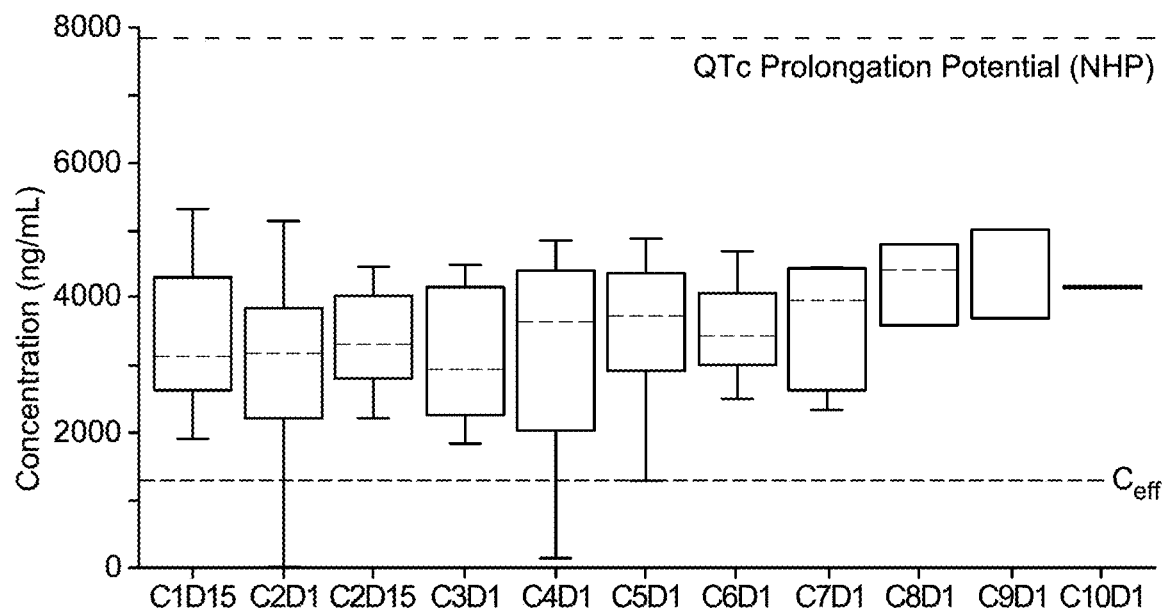
FIG. 8A is a graph of blood plasma concentration of Compound 1 measured in a group of human patients treated with Compound 1 as a single agent throughout a course of treatment. The dashed line labeled "$C_{eff}$" is lower than 1652 ng/mL.
Figure 8B:
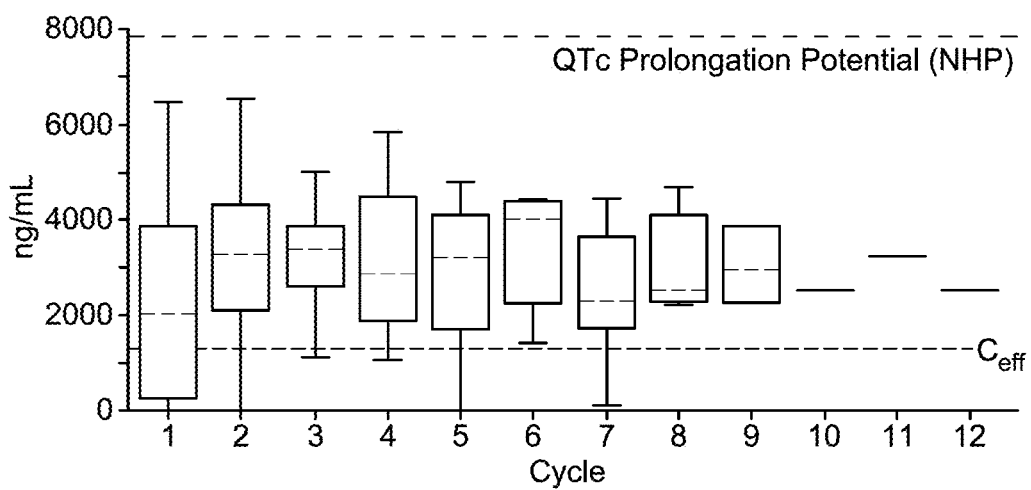
FIG. 8B is a graph of blood plasma concentration of Compound 1 measured in a group of human pateints treated with Compound 1 and azacitidine throughout a course of treatment. The dashed line labeled "$C_{eff}$" is lower than 1652 ng/mL.
Figure 8C:
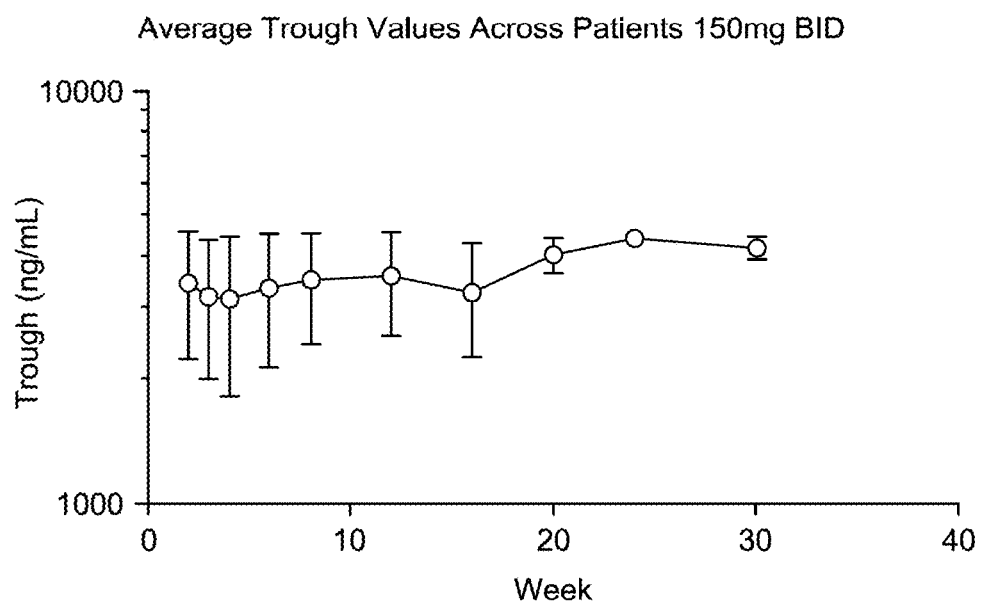
FIG. 8C is a graph of effective blood plasma concentration of Compound 1 measured in a group of human patients throughout a course of treatment.
Figure 8D:
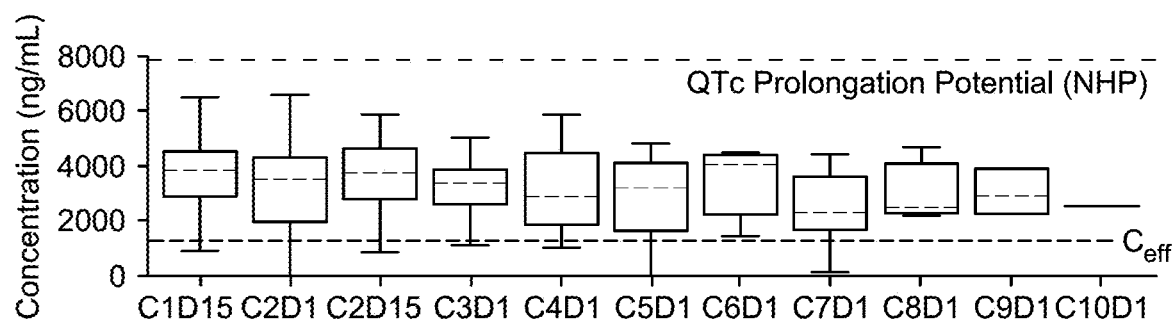
FIG. 8D is a graph of blood plasma concentration of Compound 1 measured in a group of human patients treated with Compound 1 and Azacitidine throughout a course of treatment. The dashed line labeled "$C_{eff}$" is lower than 1652 ng/mL.
Figure 8E:
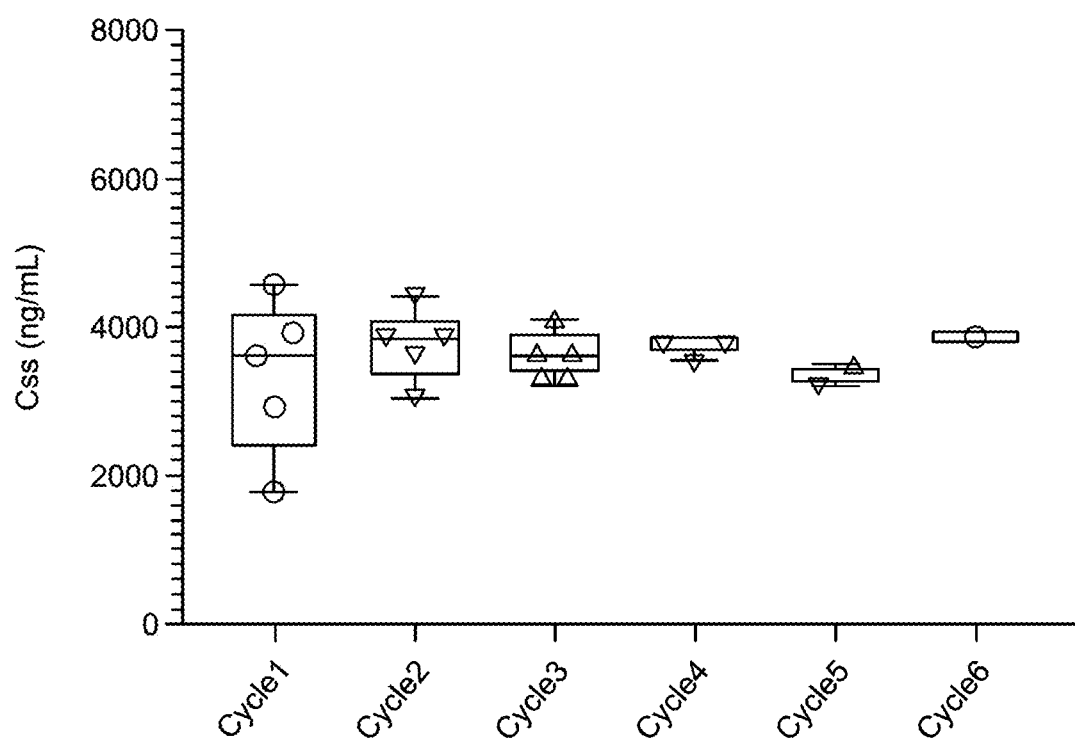
FIG. 8E is a graph of blood plasma concentration of Compound 1 measured in a group of human patients throughout a course of treatment.
Figure 11A:
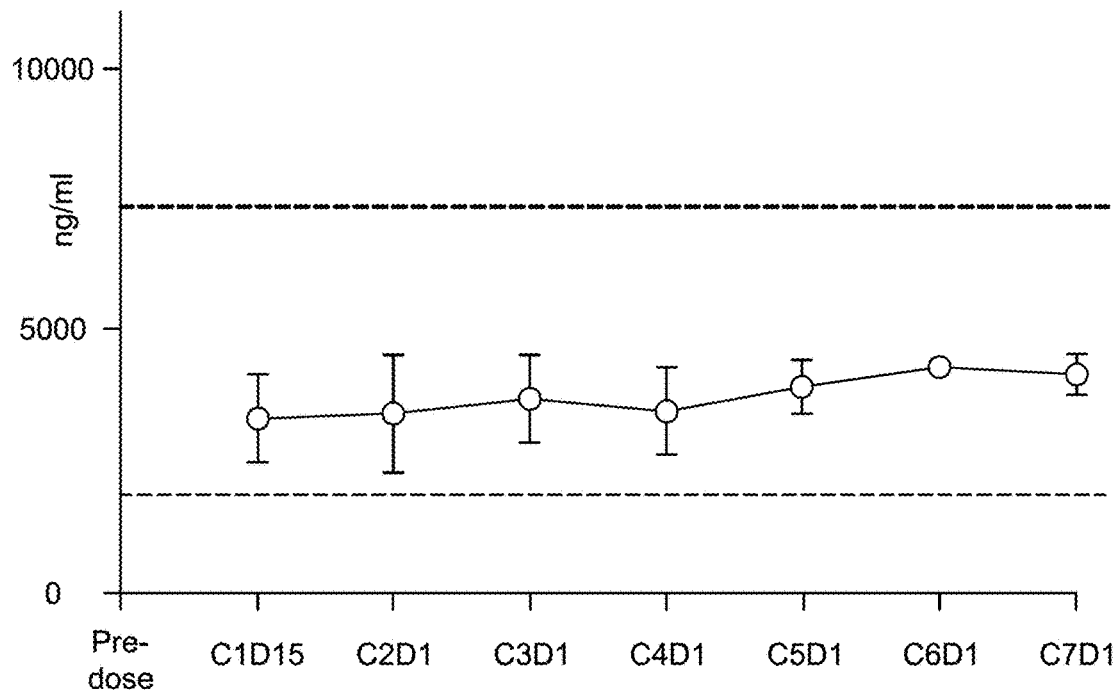
FIG. 11A is a graph $C_{ss}$ over time of patients treated with Compound 1 at 150 mg BID.
Figure 11B:
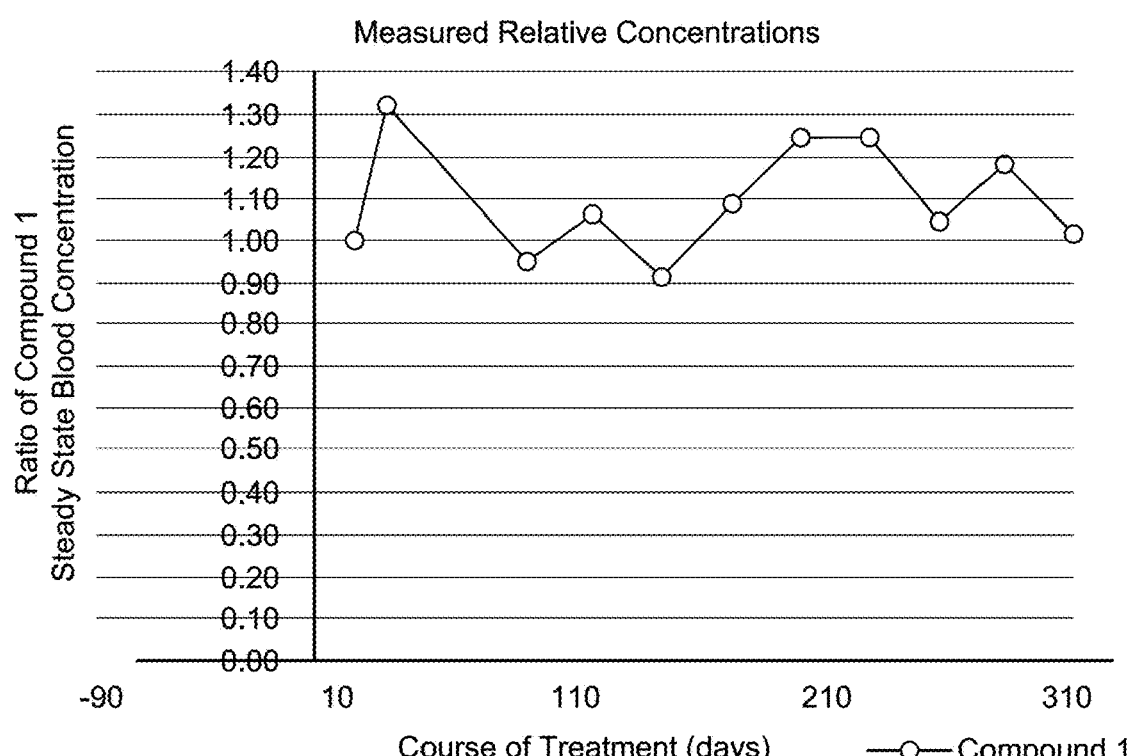
FIG. 11B is a graph plotting the ratio of steady state blood concentration of Compound 1 measured at different points during a Course of Treatment in a human patient during the administration of Compound 1 (150 mg BID). The Y-axis values are normalized to 1.0 using the concentration measured on day 15 of a Course of Treatment. The data for this graph were obtained from a single patient who received 150 mg BID of the solid form of Compound 1 obtainable from Example 1 throughout a Course of Treatment of over 300 days (i.e., greater than 6 months).

Referring to FIGS. 8A-8E the administration of Compound 1 in the oral dosage form described in Example 1 at 150 mg BID resulted in a sustained therapeutically effective trough blood plasma concentration above 2,000 ng/mL after cycle 3 of a 28-day treatment cycle. Simultaneously, referring to FIGS. 9A-9D, the administration of Compound 1 in the oral dosage form from Example 1 at 150 mg BID resulted in a sustained 2-HG level (e.g., under 200 ng/mL in plasma after cycle 3 day 1 of a 28-day treatment cycle). This effect is in contrast to other IDH1 inhibitors that have been advanced clinically. Accordingly, the invention is also based in part on the discovery that administration of Compound 1 at 150 mg BID results in a sustained ratio of greater than about 10 (preferably greater than about 20) of blood plasma concentration of Compound 1 (e.g., trough concentrations measured pre-dose at concentrations of about 2,000 ng/mL or greater) to 2-HG blood level (e.g, plasma concentrations of about 200 ng/mL or lower, including concentrations of about 100 ng/mL) after cycle 3 day 1 (i.e., after BID doses administered over the initial 15 consecutive days of treatment) of a 28-day treatment cycle. A plasma half-life of about 60 hours was estimated for Compound 1, with steady state achieved by week 2 of the course of treatment. The steady state blood concentrations of Compound 1 measured in the patients was above the $IC_{90}$ value for 2-HG inhibition in R132X mIDH-1 cells (described in the Examples). As shown in FIGS. 8A-8E, the plasma exposures (steady state blood plasma concentration) of Compound 1 were durable (i.e., sustained) throughout the 30-week treatment duration. As shown in FIGS. 9A-9D the plasma 2-HG concentrations were reduced to the normal range within 1 cycle (C2D1) and maintained throughout the treatment duration. No dose limiting toxicities of Compound 1 were observed during dose escalation studies, and the maximum tolerated dose (MTD) of Compound 1 was not reached. FIGS. 8A-8E are graphs of the data obtained from measuring the steady state concentrations from patients in the clinical trial receiving a 150 mg BID dose of Compound 1, either as a single agent or in combination with azacitidine as described in Example 10. As shown in FIG. 8D, azacitidine did not alter the pharmacokinetics of Compound 1, with consistent Compound 1 plasma concentrations observed over the treatment duration. FIG. 11A is a graph showing the steady state concentration of Compound 1 measured in patients at various points during the Course of Treatment described in the clinical trial of Example 10, with each point representing a cycle number and day number (each cycle is 28 consecutive days of administration of 150 mg BID Compound 1). The steady state concentration of Compound 1 remained above the minimum desired level (bottom dashed line) and the maximum desired level (upper dashed line).

Compound 1, with a plasma half-life of 60 hours, achieved steady-state concentration within 2 weeks of dosing and remained consistent over treatment duration. At 150 mg BID (RP2D) as a single agent, steady-state plasma concentrations are above the preclinical $C_{eff}$ resulting in ≥90% reduction in plasma 2-HG and below Compound 1 levels predicted, in NHP, to pose a QTc prolongation risk. At 150 mg BID as a single agent, a significant reduction (p<0.0009) in plasma 2-HG levels was achieved by end of Cycle 1 and was sustained over the treatment duration. Combination therapy of azacitidine plus Compound 1 150 mg BID achieved steady state concentrations of Compound 1 above the preclinical $C_{eff}$, resulting in ≥90% reduction in plasma 2-HG and below Compound 1 levels predicted to pose a QTc prolongation risk. A significant (p<0.0001) reduction in plasma 2-HG levels at the end of Cycle 1 was observed with the combination of Compound 1 (150 mg BID) and azacitidine and was sustained over the treatment duration. However, a slower rate of decline compared to the single agent Compound 1 has been observed.

Figure 12A:
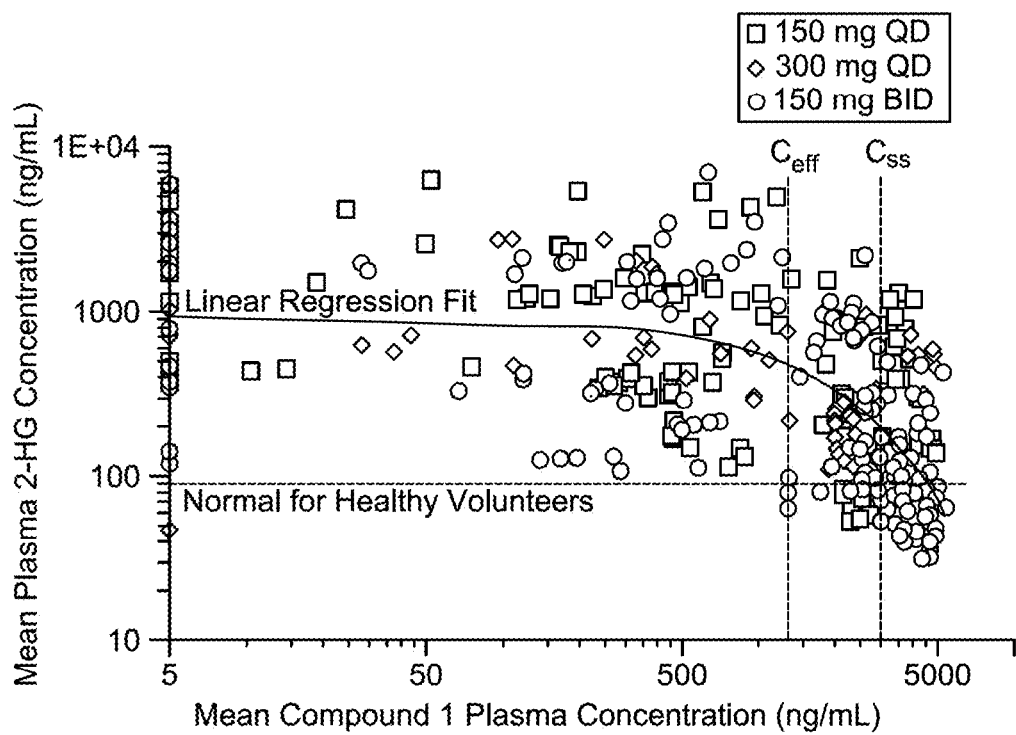
FIG. 12A is a graph showing the correlation between Compound 1 and 2-HG plasma levels in patients treated with Compound 1 as a single agent across treatment groups and irrespective of time on treatment.

The PK/PD relationship of individual subjects' plasma Compound 1 and 2-HG concentration across single agent treatment groups and irrespective of time on treatment is presented in FIG. 12A. Compound 1 concentrations <1,000 ng/mL correspond to early time point assessments (C1D0-C1D15). No correlation of exposure to 2-HG reduction is observed until Compound 1 concentrations crossed the $C_{eff}$ predicted by in vivo models to result in >90% reduction in plasma 2-HG levels. As shown in FIG. 12A, no correlation of exposure to 2-HG reduction is observed until Compound 1 concentrations crossed the $C_{eff}$ predicted by in vivo models to result in >90% reduction in plasma 2-HG levels. Maximum, most consistent exposure-response was observed at the median $C_{ss}$ of Compound 1 with 150 mg BID (RP2D).

Figure 12B:
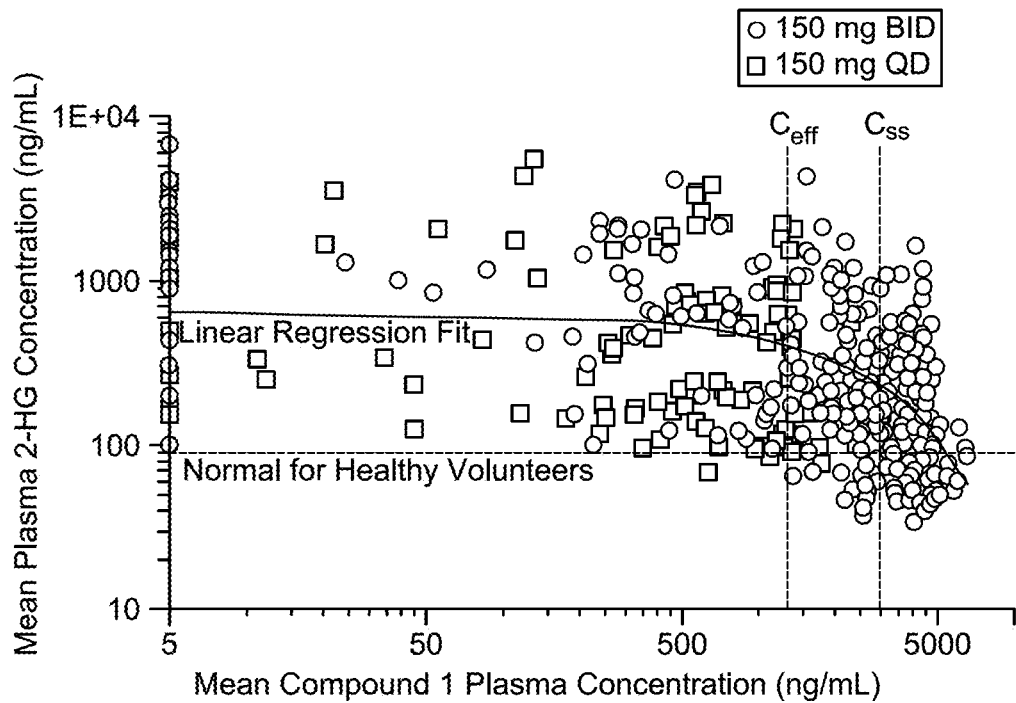
FIG. 12B is a graph showing the correlation between Compound 1 and 2-HG plasma levels in patients treated with Compound 1 and azacitidine in combination across treatment groups and irrespective of time on treatment.

The PK/PD relationship of individual subjects' plasma Compound 1 and 2-HG concentration across combination of Compound 1 and azacitidine treatment groups and irrespective of time on treatment is presented in FIG. 12B. Compound 1 concentrations <1,000 ng/mL correspond to early time point assessments (C1D0-C1D15). No correlation of exposure to 2-HG reduction is observed until Compound 1 concentrations crossed the $C_{eff}$ predicted by in vivo models to result in >90% reduction in plasma 2-HG levels. Maximum, most consistent exposure-response was observed at the median $C_{SS}$ of Compound 1 with 150 mg BID (RP2D).

Figure 13A:
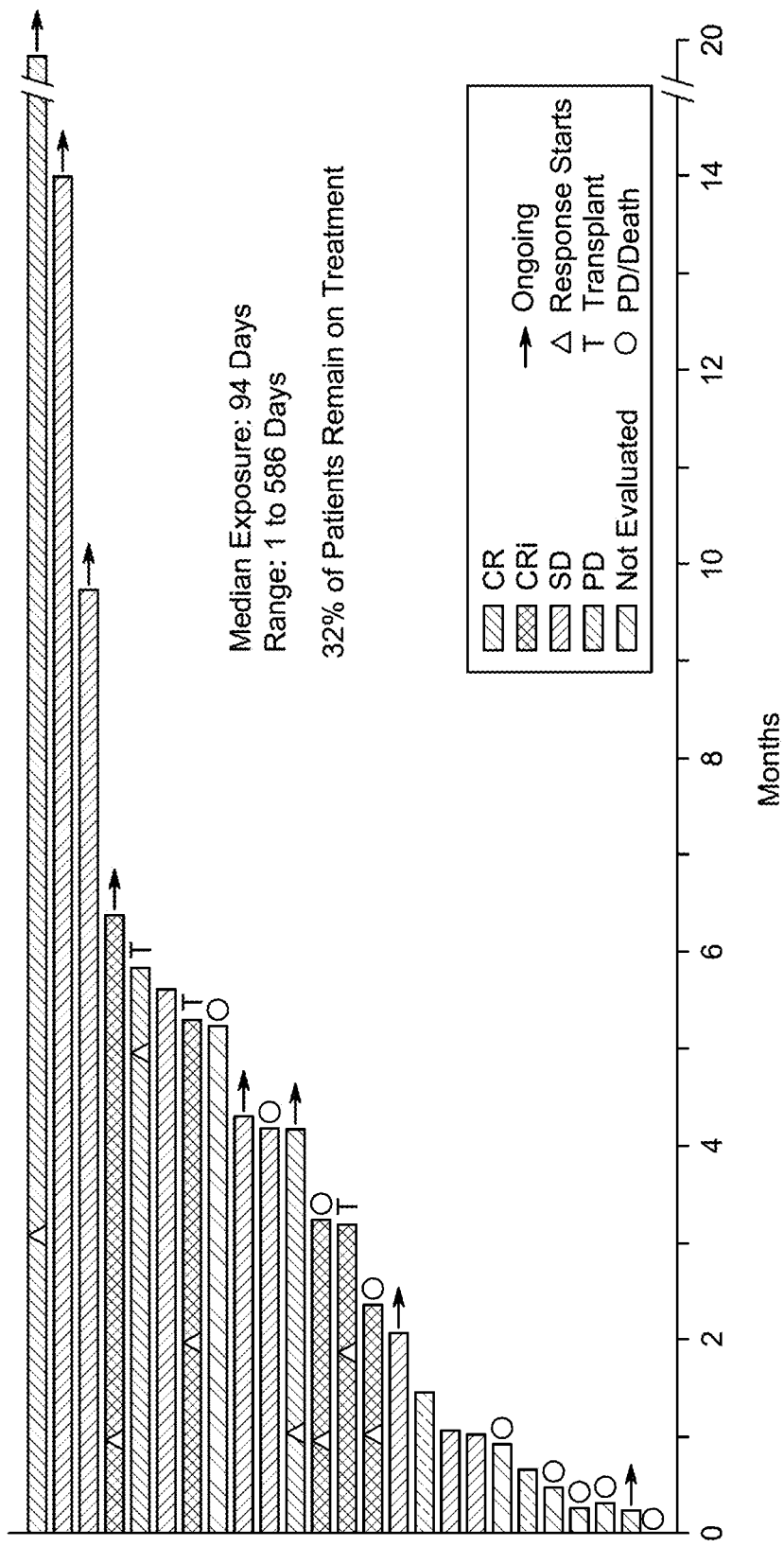
FIG. 13A, FIG. 13B, and FIG. 13C is a graph showing time on treatment of AML patients treated with a single agent (Compound 1).
Figure 13B:
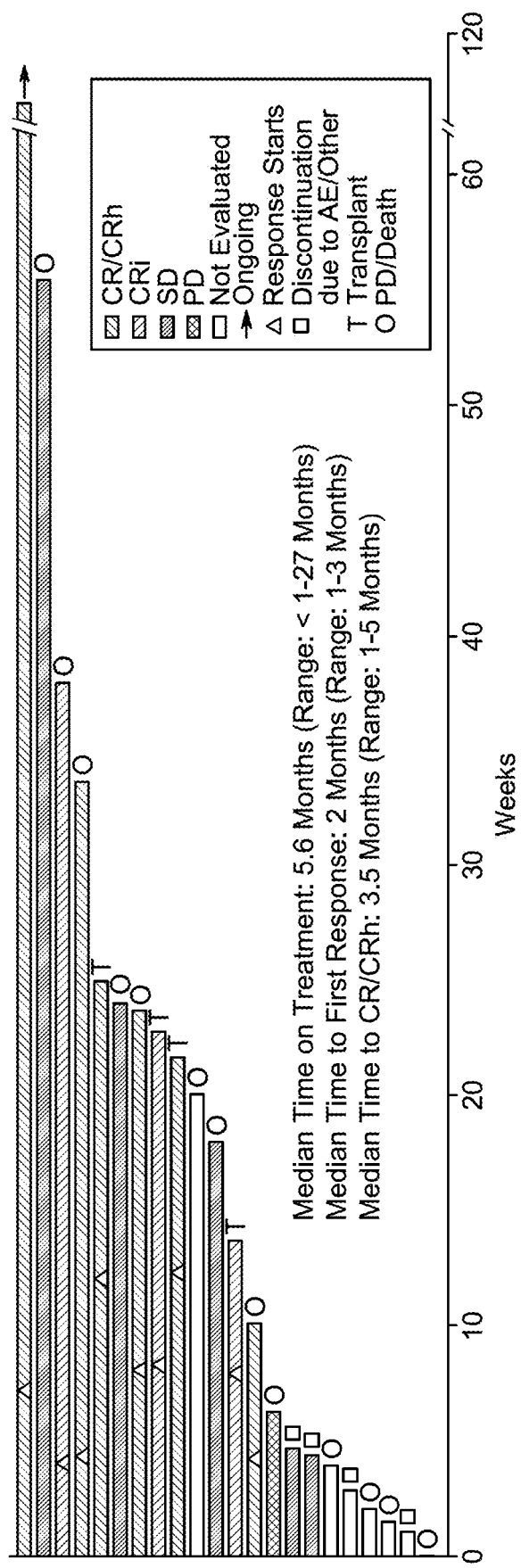
Figure 13C:
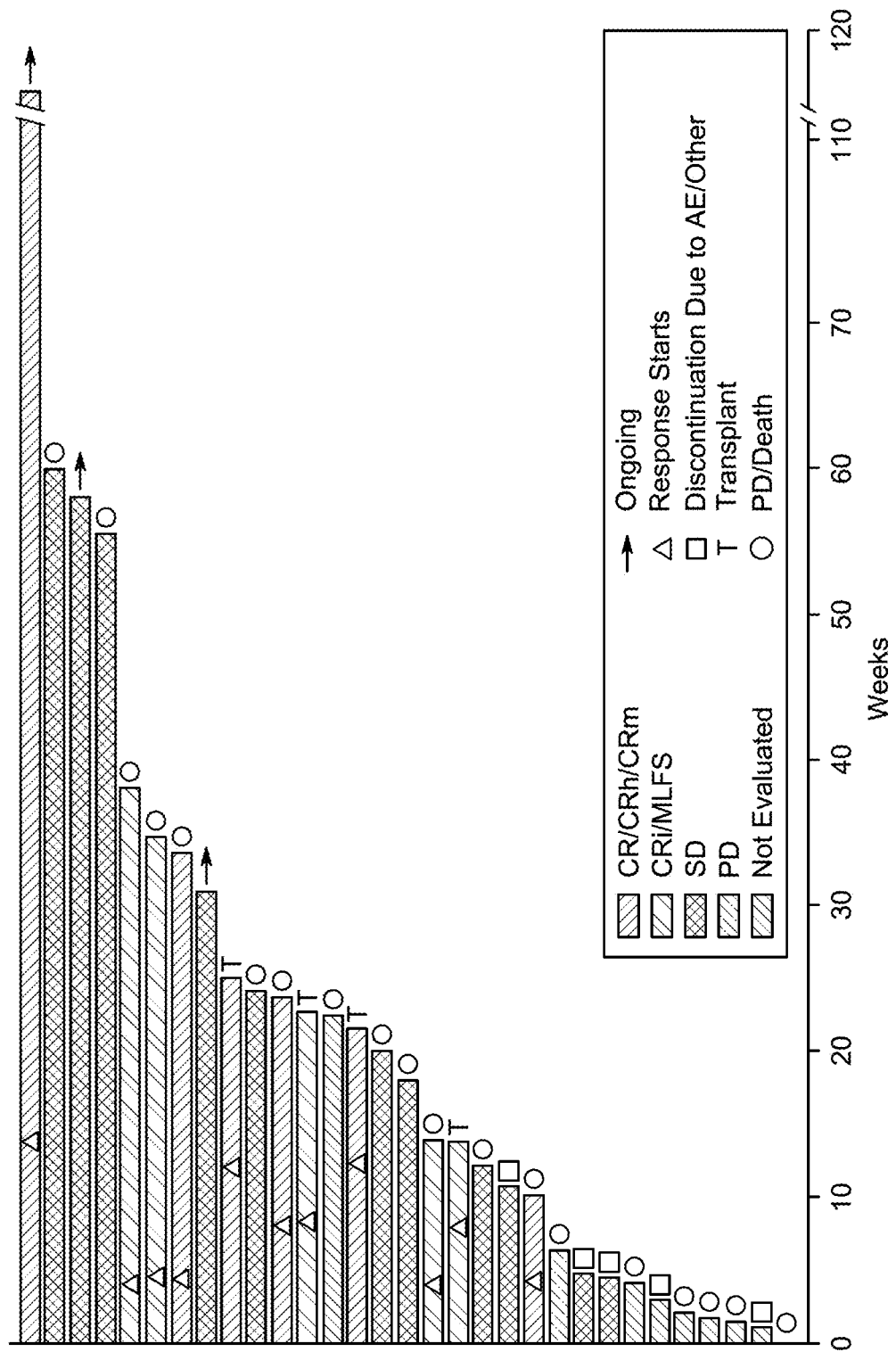

FIGS. 13A and 13C are graphs showing the results from the clinical trial in Example 10, showing the 150 mg BID administration Compound 1 (solid form obtainable from Example 1) was administered as a single agent to multiple patients over a Course of Treatment with times having a median of 94 days, and a range of 1 to 586 days. About 32% of the patients remain on treatment.

FIG. 13B depicts responses for relapsed or refractory (R/R) AML patients, and shows prolonged duration of treatment with Compound 1 was observed with a 1st response occurring within 2 months of treatment with Compound 1. Responses <CR/CRi were noted to deepen with continued treatment resulting in CR/CRh/CRi rate of 41% in R/R AML. Clinical benefit (SD≥8 weeks) was observed in subjects without an IWG defined response. 10% of patients (1 AML and 2 MDS) remained on treatment. Treatment Discontinuation: Progressive Disease (PD) (9), death (6), transplant (4), Adverse Events (AE) (3), investigator's decision (2), withdrawal of consent (1), and lack of response (3).

Summary of Response for Compound 1 as a Single Agent

TABLE 4

| Response | R/R AML N = 22 | All AML & MDS N = 31 |
|---|---|---|
| ORR, n (%)* | 9 (41) | 11 (35) |
| [95% CI] | [21, 64] | [19, 55] |
| CR, n (%) | 4 (18) | 5 (16) |
| CRh, n (%) | 2 (9) | 2 (6) |
| CRi, n (%) | 3 (14) | 4 (13) |
| SD, n (%) | 5 (23) | 11 (35) |
| PD, n (%) | 1 (5) | 1 (3) |
| NE, n (%) | 7 (32) | 8 (26) |

*ORR = overall response rate: CR + CRh + CRi + PR + MLFS. No PR/MLFS observed.

Administration of Compound 1 at 150 mg BID in the clinical trial of Example 10 reduced the measured levels of 2-HG in the blood of patients as shown in FIGS. 9A-9D and FIGS. 10B-10C. The 2-HG levels measured in the blood of patients during this clinical trial of Example 10 are shown in FIGS. 9A-9D, demonstrating reduction of 2-HG levels within about 1-2 28-day treatment cycles (150 mg Compound 1 is administered BID on each day for 28 consecutive days for each treatment cycle, as described in Example 10).

Figure 10A:
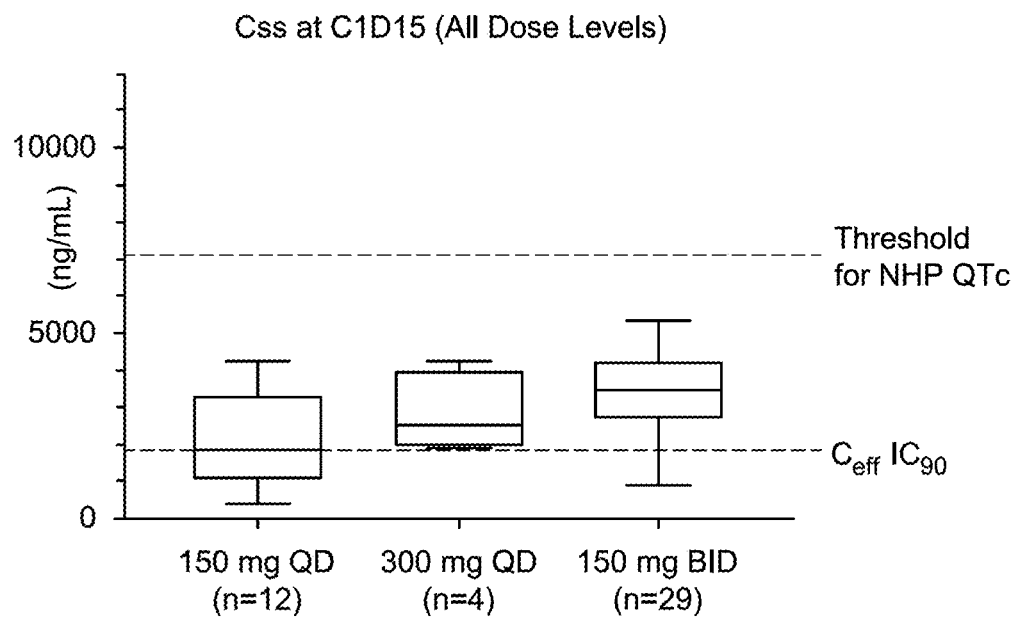
FIG. 10A is a graph showing the levels of steady-state concentration of Compound 1 measured in a group of human patients at the day 15 trough (ng/mL) of Compound 1 after administration to patients of 150 mg QD, 300 mg QD, and 150 mg BID of Compound 1.
Figure 10B:
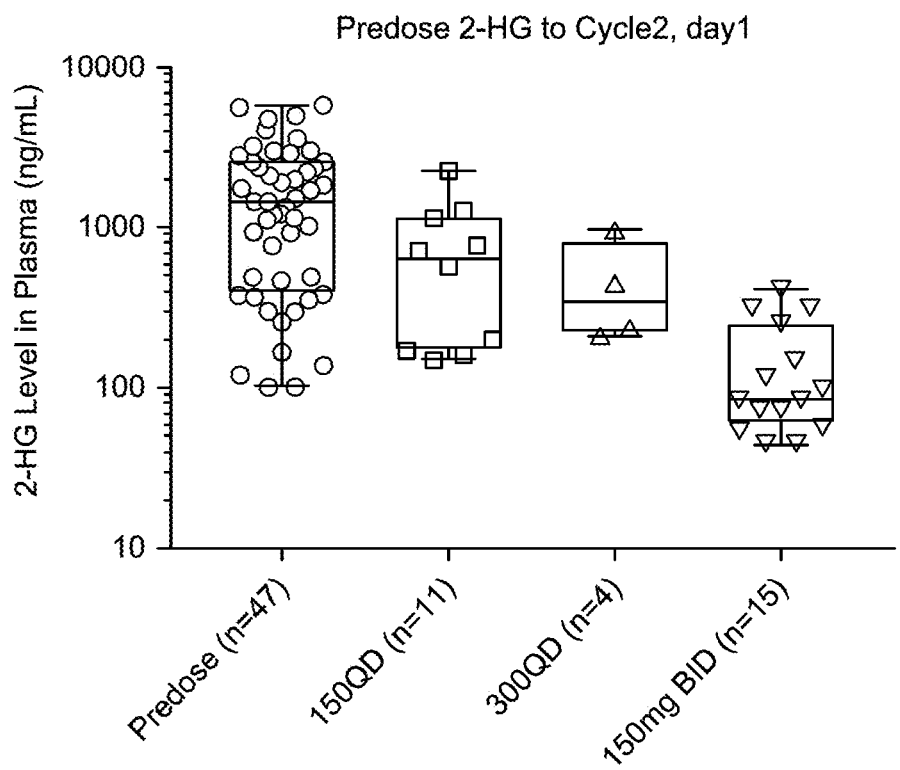
FIG. 10B is a graph showing the 2-HG level measured in plasma (ng/mL) in a group of human patients after administration of 150 mg QD, 300 mg QD, and 150 mg BID of Compound 1.
Figure 10C:
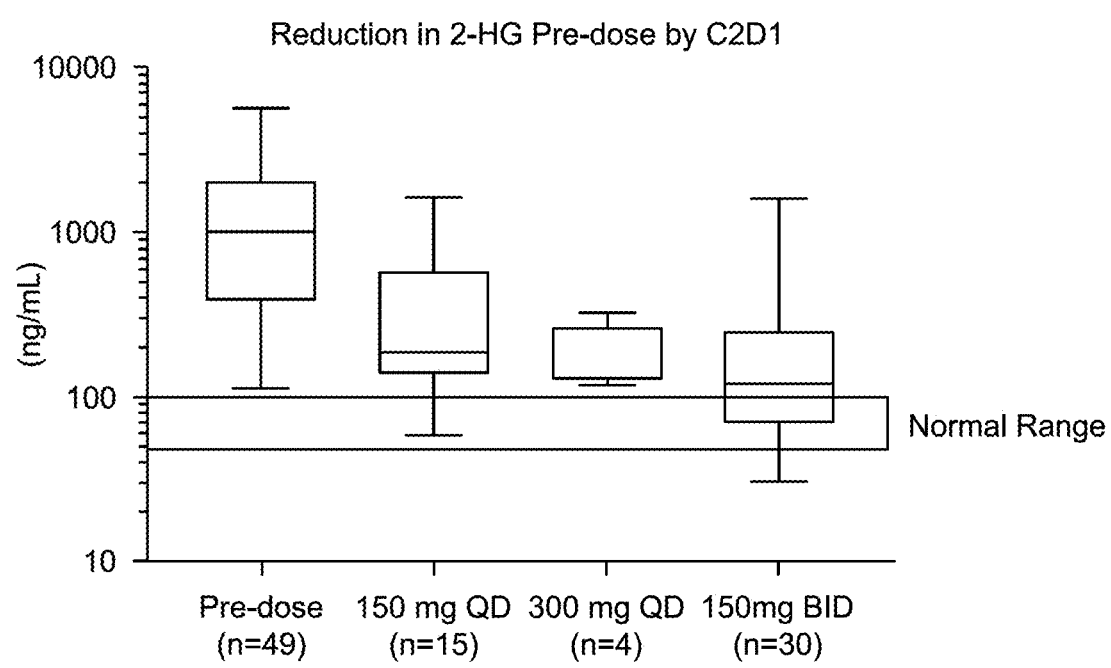
FIG. 10C is a graph showing the plasma 2-HG reduction observed in a human patient population at all doses and schedules by cycle 2, day 1 of administration of Compound 1 and that a preferred PD response was observed with 150 mg BID of Compound 1.

FIGS. 10B-10C are each a graph showing the concentration of 2-HG measured in the blood of patients receiving one of three different dose and dose intervals: 150 mg QD, 300 mg QD or 150 mg BID (either receiving Compound 1 as a single agent or in combination with azacitidine as described in the clinical trial of Example 10, in each category). The 2-HG levels are measured prior to administration of Compound 1, and then measured after administration of Compound 1 up to cycle 2, day 1 after first receiving Compound 1 (as the solid form obtained from Example 1).

The invention is based in part on the discovery that administration of Compound 1 at 150 mg BID resulted in a higher blood exposure level than either 150 mg QD or 300 mg BID at day 15. See, for example, FIG. 10A. Administration of Compound 1 at 150 mg QD BID resulted in a blood exposure level of <3000 ng/mL at day 15. Administration of Compound 1 at 300 mg QD BID did not result in improved blood levels at day 15. In contrast, administration of Compound 1 at 150 mg BID results in a blood exposure level of >3000 ng/mL at day 15. Additionally, the invention is based in part on the discovery that administration of Compound 1 at 150 mg BID resulted in a lower 2-HG level in plasma than either 150 mg QD or 300 mg BID at day 15. See, for example, FIG. 10B.

The oral dosage form of Compound 1 (Example 1) was administered to human patients as a single agent (150 mg QD, 300 mg QD, 150 mg BID and 100 mg QD until disease progression) in a human clinical trial treating AML/MDS in cancer patients harboring a mIDH1 mutation, as described in the Examples below. FIG. 10A is a graph showing the concentration of Compound 1 measured in the blood of patients after receiving Compound 1 (as the solid form obtained from Example 1) in one of three different dose and dose intervals: 150 mg QD, 300 mg QD or 150 mg BID (either receiving Compound 1 as a single agent or in combination with azacitidine as described in the clinical trial of Example 10, in each category).

The present disclosure includes methods for treating AML or MDS in patients having one or more R132X mIDH-1 mutations (e.g., as measured in a tissue sample obtained from the patient) and/or elevated 2-HG levels (e.g., 2-HG levels measured in a blood sample at above about 180 ng/mL), comprising administration of Compound 1 alone (e.g., as a single agent) or in combination with azacitidine or cytarabine. For methods where Compound 1 is administered as a combination, the subject being administered Compound 1 may be receiving or previously received treatment with azacitidine or cytarabine.

The methods of treatment can include the administration of Compound 1 such that on day 1 of cycle 4 of repeated 28-day treatment cycles (or day 1 of any subsequent cycle), the trough blood plasma concentration of Compound 1 has not decreased more than about 5-25%, about 5-20%, about 5-15%, about 5-10%, about 10-25%, about 10-20%, or about 10-15%, as compared to the trough blood plasma concentration on day 1 of cycle 2. Preferably, patients harboring a R132X mIDH-1 mutation can be administered 150 mg of Compound 1 twice daily (BID) every day on consecutive days (without holiday) for one or more continuous 28-day cycles.

Figure 14A:
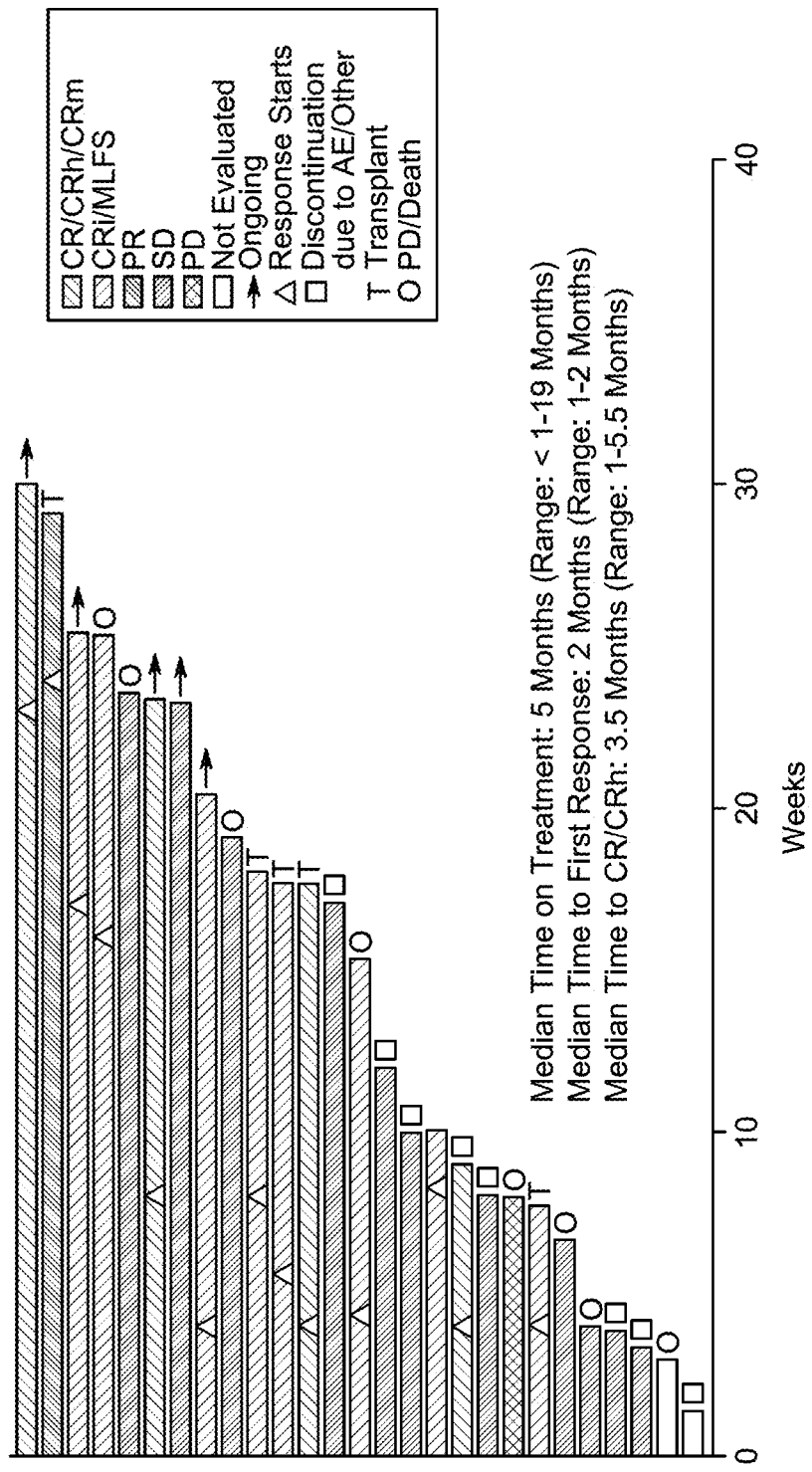
FIG. 14A and FIG. 14B is a graph showing time on treatment of AML patients treated with a combination of Compound 1 and azacitidine.
Figure 14B:
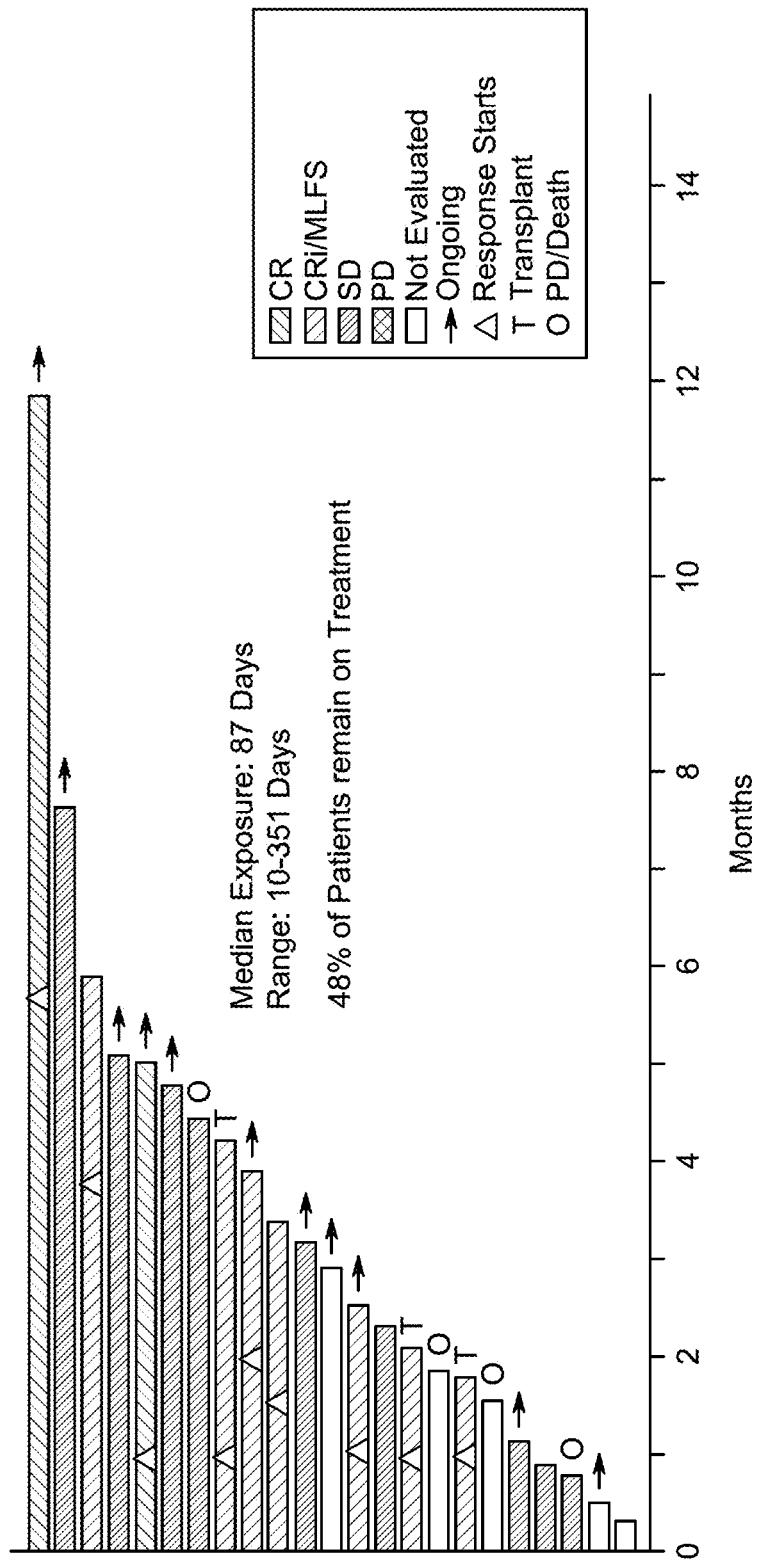

Compound 1 can be administered to certain patients in combination with a hypomethylating agent such as azacitidine. IDH1 mutations (e.g., in AML or MDS patients harboring a R132X mIDH-1 mutation) can result in abnormal hypermethylation of histones and DNA and suppression of normal cellular differentiation. The combination of Compound 1 and azacitidine can be administered for the treatment of patients with AML harboring IDH1 mutations. For example, patients can be administered the Compound 1 daily (BID) in continuous 28-day cycles, alone or in combination with azacitidine (administered at the dose of 75 mg/m$^2$ for 7 days IV/SC per every 28-day cycle). For example, Compound 1 can be administered at a dose of 150 mg QD or 150 mg BID in combination with azacitidine (azacitidine administered per standard of care for a patient). FIG. 14 is a graph showing the results from the clinical trial in Example 10, showing the 150 mg BID administration Compound 1 (solid form obtainable from Example 1) in combination with the administration of azacitidine (administered at the dose of 75 mg/m$^2$ for 7 days IV/SC per every 28-day cycle), administered to multiple patients over a Course of Treatment with times having a median of 87 days, and a range of 10 to 351 days. About 48% of the patients remain on treatment.

As shown in FIG. 13B, upon further duration of treatment, clinical responses observed in R/R or TN AML and MDS: cytopenias associated with azacitidine may influence depth of IWG response. An ORR of 46% was observed for the combination of Compound 1 with azacitidine in R/R AML and an ORR of 78% was observed in TN AML (CR/CRi of 66%). Treatment Discontinuation was caused by: PD (6), transplant (6), investigator's decision (5), death (4), AE (2), and others: treatment failure, hospice, other treatment (1 each). 37% of patients (AML and MDS) remain on treatment.

TABLE 5

Summary of Response for Compound 1 as a single agent

| Response | R/R AML N = 26 | TN AML N = 9 | All AML & MDS N = 41 |
|---|---|---|---|
| ORR, n (%)* | 12 (46) | 7 (78) | 22 (54) |
| [95% CI] | [27, 67] | [40, 97] | [37, 69] |
| CR, n (%) | 3 (12) | 2 (22) | 8 (20) |
| CRh, n (%) | 1 (4) | 0 | 1 (2) |
| CRi, n (%) | 5 (19) | 4 (44) | 9 (22) |
| PR, n (%) | 1 (4) | 1 (11) | 2 (5) |
| MLFS, n (%) | 2 (8) | 0 | 2 (5) |

TABLE 5-continued

Summary of Response for Compound 1 as a single agent

| Response | R/R AML N = 26 | TN AML N = 9 | All AML & MDS N = 41 |
|---|---|---|---|
| SD, n (%) | 11 (42) | 1 (11) | 14 (34) |
| PD, n (%) | 1 (4) | 0 | 1 (2) |
| NE, n (%) | 2 (8) | 1 (11) | 4 (10) |

*ORR = CR + CRh + Cri + PR + MLFS

In some methods, Compound 1 can be administered with cytarabine. Low dose cytarabine (LDAC) can be administered to certain AML patients (e.g., AML patients at or above about 60 years of age who are not candidates for intensive therapy, and harboring a R132X mIDH-1 mutation). The therapeutically effective combination of Compound 1 with LDAC can be administered to AML patients harboring IDH1 mutation. For example, patients can be administered the Compound 1 daily (BID) in continuous 28-day cycles, alone or in combination with LDAC (administered at the dose of 20 mg BID SC for 10 days every 28-day cycle) until treatment discontinuation.

Subjects that are treated according to provided methods and combination therapies can have relapsed or refractory AML or MDS, or "high risk" MDS, and may have been previously treated with a mIDH1 inhibitor. Such refractory AML or MDS (i) can be naïve to prior hypomethylating therapy and IDH1 inhibitor therapy and/or (ii) may have shown inadequate response or progressed immediately preceding hypomethylating therapy. The provided methods and combination therapies can be used to treat subjects with residual IDH-R132 mutations. The provided methods and combination therapies can also be used to treat subjects with AML or MDS in morphologic complete remission or complete remission with incomplete blood count recovery (CR/CRi) after cytotoxic-containing induction therapy.

The methods of treatment are based in part on a human clinical study of administration of Compound 1 in 3 stages: a phase 1 dose-escalation stage, a phase 1 dose-expansion stage and a phase 2 stage, as further described in the Examples. Single agent Compound 1 dose escalation was administered in once-daily (QD) doses of 150 and 300 mg, a twice-daily (BID) dose of 150 mg or a once daily dose of 100 and 150 mg with food to potentially improve bioavailability. During the course of single agent dose escalation, a parallel escalation arm can be initiated for Compound 1 in combination with azacitidine. This combination can be initiated once the first dose level cohort of Compound 1 in the single agent schedule (150 mg QD) is complete. Once the maximum tolerated dose or the maximum evaluated dose is identified for the single-agent and combination cohorts, select populations of patients can be enrolled into phase 1 dose expansion cohorts at the selected single agent or combination doses, to further characterize the safety profile and confirm the recommended phase 2 dose. After the recommended phase 2 dose in combination with azacitidine is selected, a cohort of 6 patients are treated with Compound 1, at that dose, in combination with low dose cytarabine. In the Phase 2 portion, specific populations of patients with AML/MDS harboring IDH1-R132 mutations are enrolled to receive Compound 1 either as a single agent or in combination with azacitidine at the recommended phase 2 doses.

Figure 7A:
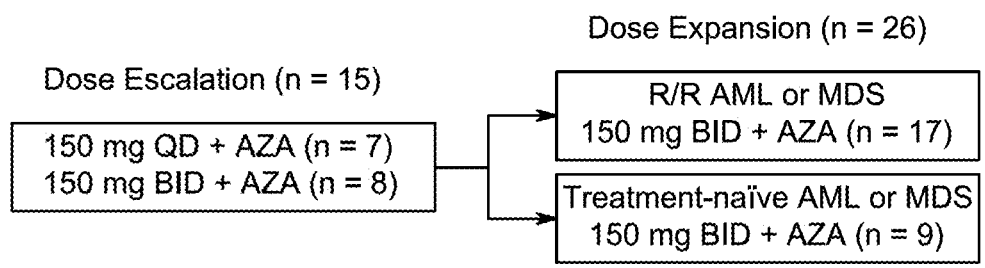
FIG. 7A illustrates the summary of cohorts from a phase 1 study in mIDH1 AML.
Figure 7B:
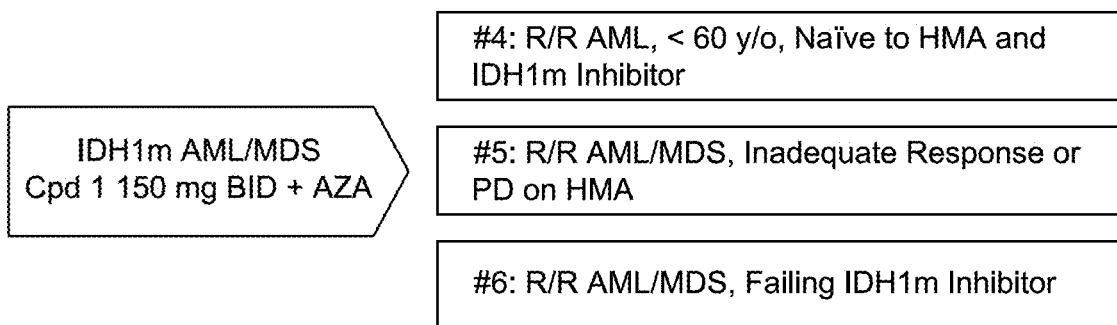
FIG. 7B illustrates use of Compound 1 in a phase 2 study in mIDH1 AML and MDS.
Figure 7C:
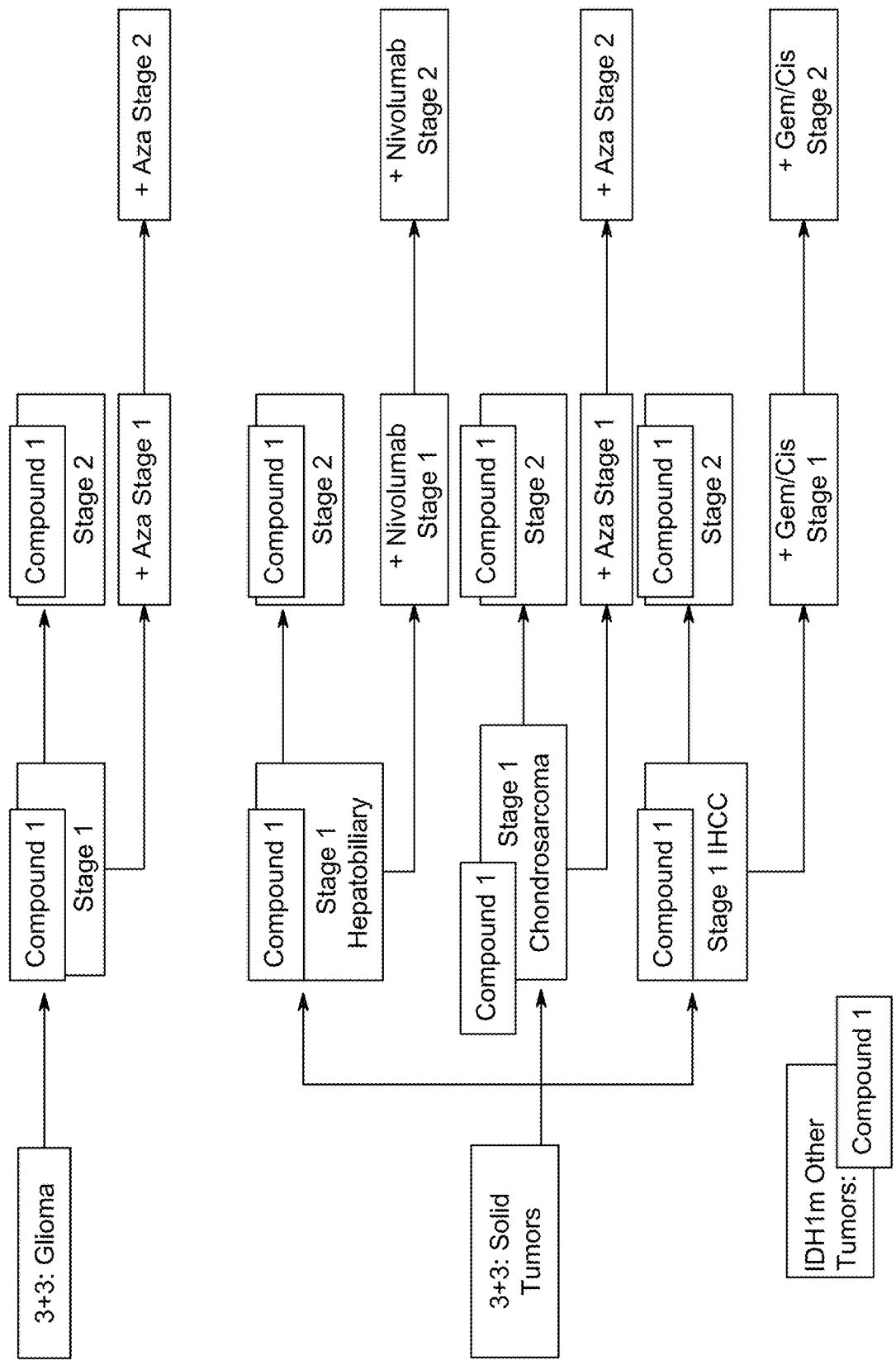
FIG. 7C is a flow chart of human clinical trials of Compound 1, as described in Example 10.

As outlined in Examples 10 and 12, Compound 1 demonstrates clinical activity as single agent in a high-risk Phase 1 population of AML/MDS patients with IDH1 mutation. 41% CR/CRh/CRi in R/R AML (35% in all AML/MDS) was observed in patients treated with Compound 1 as a single agent. Transfusion independence was observed in both IWG responders/non-responders. Durable disease control or stable disease 4-12+ months was observed in R/R AML. An observed reduction in bone marrow blasts is supportive of clinical benefit to patients. Compound 1 was well tolerated with patients maintained in treatment for a median of 5.6 months, likely contributing to rate and depth (CR/CRh) of response. Compound 1 plasma exposure correlates with 2-HG response. Compound 1 $C_{ss}$ reduction of 2-HG supports 150 mg BID as the dose and schedule selected for evaluation in global Phase 2 trial outlined in FIG. 7B.

As outlined in Examples 10 and 12, the combination of Compound 1 and azacitidine demonstrates clinical activity in a high-risk Phase 1 population of AML/MDS patients with IDH1 mutation. Patients maintained treatment for a median of 5 months. Durable disease control (>6 months) was observed in the absence of IWG response. 46% ORR and 35% CR/CRh/CRi in R/R AML, 78% ORR in TN AML was observed. Compound 1 is well tolerated in combination with azacitidine and possesses low risk of QT prolongation (2 AEs reported). Azacitidine combination modestly increased metabolic and gastrointestinal treatment emergent adverse events (TEAEs). Higher rates of neutropenia compared to SA treatment (Grade 3/4 17% vs 6%) were observed which may be impacting the depth (CR/CRh) response. Compound 1 plasma exposure was shown to correlate with 2-HG response. Compound 1 $C_{ss}$ reduction of 2-HG supports selection of 150 mg BID as RP2D.

In some embodiments, the present disclosure additionally provides methods of treating AML or MDS in a patient harboring isocitrate dehydrogenase 1 mutations (mIDH1), which can comprise administering to a patient in need thereof a therapeutically effective amount of Compound 1 each day for at least three consecutive treatment cycles of 28 consecutive days each. The administration of a therapeutically effective amount of Compound 1 can result in the patient having a durable therapeutically effective trough blood plasma concentration of Compound 1 in the patient throughout the course of treatment.

In some embodiments, the administration of a therapeutically effective amount of Compound 1 can result in the level of 2-HG in the patient's plasma being maintained at or below about 200 ng/mL at the start of the third consecutive treatment cycle (e.g., prior to dosing on day 15 or Cycle 3, Day 1), and the steady state blood plasma concentration of Compound 1 in the patient being maintained at or above about 2,000 ng/mL and below about 7,500 ng/mL (preferably, below about 7,200 ng/mL) throughout the course of treatment. In some embodiments, the steady state blood plasma concentration of Compound 1 in the patient is maintained at or above about 1652 ng/mL and below about 7,840 ng/mL throughout the course of treatment.

Maintaining Therapeutically Effective Blood Plasma Concentrations of Compound 1 Throughout a Course of Treatment The invention is based in part on the discovery that oral administration of Compound 1 (in the pharmaceutically acceptable oral dosage form resulting from the preparation method of Example 1) to humans can provide steady state (trough) blood concentrations above a therapeutically effective amount (e.g., above the $IC_{90}$ concentration for R132H and/or R132C mIDH-1, and/or concentrations of greater than about 2,000 ng/mL) throughout a course of treatment of at least up to 30 weeks and beyond starting from the initial administration of Compound 1. Compound 1 can be administered to patients having elevated blood 2-HG levels (i.e., above about 180 ng/mL), leading to a reduction in 2-HG levels in the blood within 15 consecutive days starting with the first day of the administration of Compound 1, followed by maintaining the levels of 2-HG to below 200 ng/mL throughout the ensuing course of treatment. Alternatively, Compound 1 can be administered to patients having elevated blood 2-HG levels (i.e., above about 180 ng/mL), leading to a reduction in 2-HG levels in the blood within 15 consecutive days starting with the first day of the administration of Compound 1, followed by maintaining the levels of 2-HG to below 180 ng/mL throughout the ensuing course of treatment. Compound 1 was administered in an oral dosage form (obtainable from the method in Example 1) twice per day (150 mg BID). After the initial 15 days of treatment with 150 mg BID of this oral dosage form of Compound 1, the steady state (trough) blood concentration of Compound 1 (pre-dose) was maintained above about 2,000 ng/mL and well below the predicted threshold for QTc risk (e.g., below about 7,200 ng/mL) throughout a course of treatment (e.g., at least up to about 30 weeks or longer, including 12-30 weeks or up to 6 months or longer, from initial administration of Compound 1). Alternatively, after the initial 15 days of treatment with 150 mg BID of this oral dosage form of Compound 1, the steady state (trough) blood concentration of Compound 1 (pre-dose) was maintained above about 1652 ng/mL and well below the predicted threshold for QTc risk (e.g., below about 7840 ng/mL) throughout a course of treatment (e.g., at least up to about 30 weeks or longer, including 12-30 weeks or up to 6 months or longer, from initial administration of Compound 1). In some embodiments of the methods of treatment disclosed herein, the steady state blood concentration of Compound 1 after day 15 is maintained at greater than about 10-times the measured blood concentrations of 2-HG in the patient (e.g., at or below about 200 ng/mL). A R132X mIDH-1 Selective Inhibitor Therapy provides administering to a patient in need thereof a total dose of 150 mg BID of a pharmaceutically acceptable form of Compound 1 provided in Example 1 in an oral dosage form, on consecutive days throughout a Course of Treatment. Compound 1 is preferably the only inhibitor of mutant IDH-1 (mIDH-1) having one or more R132X mIDH-1 Mutation(s) administered to the patient throughout the Course of Treatment of the R132X mIDH-1 Selective Inhibitor Therapy. Unless otherwise indicated, the mIDH-1 selective inhibitor (e.g. Compound 1) can be administered as a single agent as the R132X mIDH-1 Selective Inhibitor Therapy, or in combination with other therapeutic agents that are not mIDH-1 inhibitors as a combination for the R132X mIDH-1 Selective Inhibitor Therapy.

Compound 1 is a potent and selective small molecule inhibitor of certain mutated forms of the isocitrate dehydrogenase 1 (IDH-1) enzyme. Compound 1 selectively inhibits mutant IDH-1 enzymes compared to the wild type IDH-1 enzyme, targeting the mutant IDH-1 variants defined herein as R132X mIDH-1 Mutation(s). Example 2 provides in vitro data demonstrating inhibition of various R132X mutations of mIDH-1 enzyme. For example, Compound 1 targets the mutant IDH-1 variants R132H, R132C, R132L, R132G, and R132S using assays described in Example 2 with $IC_{50}$ concentrations that are approximately at least 180-fold lower than the wild-type IDH-1 enzyme in vitro. In addition, Compound 1 targets the R132H and R132C mutations of IDH-1 at $IC_{50}$ concentrations demonstrating selectivity over wild-type IDH-1 enzyme in vitro (based on $IC_{50}$ measurements as determined in Example 2 based on average+/− SEM, nM). Accordingly, preferred R132X mutations include R132H and R132C, as well as R132L, R132G, and R132S (or other R132X mutations having therapeutically relevant 2-HG $IC_{50}$ values obtained using the in vitro assay of Example 2). In addition, Compound 1 selectively inhibits mutant IDH-1 compared to mutant IDH-2 forms. The selectivity of Compound 1 against other IDH isozymes was tested using diaphorase coupled assays employing either wild-type IDH-1 or one of 2 alternative mutated forms of IDH-2 (R140Q and R172K). Compound 1 had very weak activity against either wild type IDH-1 or R172K IDH-2 mutation (with enzymatic $IC_{50}$ measurements obtained according to Example 2 of about 20-25 micromolar, compared with $IC_{50}$ values of less than about 150 nanomolar obtained for the R132X m-IDH-1 Mutations). In addition, Compound 1 did not show any inhibition of R140Q IDH-2 up to a concentration of 100 micromolar. These selectivity data demonstrate that Compound 1 is a potent and selective inhibitor of enzymes harboring R132X mIDH-1 Mutation(s).

The R132X mIDH-1 Selective Inhibitor Therapy (single agent or combination) can be administered to adult patients with an IDH-1 mutation as detected by a medically appropriate (e.g., FDA-approved) test for mIDH-1 mutation(s). Preferably, the test is a diagnostic that identifies an R132X mIDH-1 Mutation(s) in the patient prior to the administration of Compound 1. Preferably, the patient is identified as harboring one or more R132X mIDH-1 Mutation(s) based on Next Generation Sequencing (NGS) detection on a tissue sample obtained from the patient prior to the administration of Compound 1 and/or administration of any R132X mIDH-1 Selective Inhibitor Therapy.

A patient in need of R132X mIDH-1 Selective Inhibitor Therapy can have an elevated level of 2-HG measured in the patient (e.g., in the blood plasma of the patient) prior to initiating any R132X mIDH-1 Selective Inhibitor Therapy. Preferably, the level of 2-HG measured in the blood of the patient declines during the first 2 weeks of the Course of Treatment of a R132X mIDH-1 Selective Inhibitor Therapy. For example, a patient may have a measured blood concentration level of 2-HG that is greater than about 200 ng/mL of 2-HG prior to the administration of Compound 1 pursuant to administration of a R132X mIDH-1 Selective Inhibitor Therapy to the patient in need thereof, and a measured blood concentration level of 2-HG of less than about 200 ng/mL during a Course of Treatment with a R132X mIDH-1 Selective Inhibitor Therapy. For example, in the human clinical trial disclosed in Example 3, all IDH-1m+ patients had elevated 2-HG, which was reduced upon treatment with Compound 1 by day 15 of the Course of Treatment, with about 30% demonstrating a response to the administration of Compound 1 at some point during the Course of Treatment. In this patient population, the normal 2-HG measured in patient blood at CRL was about 70±17 ng/mL; the observed highest was about 91 ng/mL and the lowest was about 43 ng/mL. Preferably, the R132X mIDH-1 Selective Inhibitor Therapy consists of the administration of Compound 1 (i.e., Compound 1 is the only mIDH-1 inhibitor administered to the patient throughout the Course of Treatment).

Compound 1 is administered over a therapeutically effective Course of Treatment, which is preferably long enough to provide and sustain an intended therapeutic effect. For example, the Course of Treatment can be long enough to therapeutically reduce elevated 2-HG levels in a patient (e.g., reduce 2-HG levels measured in patient blood plasma to below about 200 ng/mL), with continued administration of Compound 1 to the patient in a manner that provides therapeutically effective steady state blood plasma concentration levels of Compound 1 (e.g., trough blood plasma concentrations greater than the $IC_{90}$ concentration value for 2HG production measured for a R132X IDH-1 mutation identified in cells obtained from the patient). When treating patients with elevated 2-HG levels measured in the patient's blood prior to administration of Compound 1, the Course of Treatment can be at least a number of consecutive days starting from the initial administration of Compound 1 to the patient with elevated 2-HG levels, and continuing with daily administration of Compound 1 (e.g., 150 mg BID) for at least a number of days effective to reduce the 2-HG levels measured in the blood of the patient to less than about 200 ng/mL (preferably less than 180 ng/mL) and/or a level considered medically appropriate for the patient (e.g., to a range determined to be medically normal for that patient in the treatment paradigm). Preferably, the Course of Treatment is at least 15 consecutive days starting with the day of the initial administration of Compound 1 to the patient and comprises 150 mg of the solid oral dosage form of Compound 1 (e.g., Example 1) administered to the patient twice per day (e.g., every 12 hours) every day for at least 15 days. The Course of Treatment can be one or more 28-day treatment cycles of daily BID administration of 150 mg of Compound 1 in the solid oral dosage form obtained from Example 1. The Course of Treatment can continue throughout a medically appropriate number of days for a patient. For example, the Course of Treatment can last for any medically appropriate number of consecutive 28-day treatment cycles, including a Course of Treatment lasting for 1, 2, 3, 4, 5, 6 consecutive treatment cycles of 28-days each, and/or a Course of Treatment of 20 weeks, and/or a Course of Treatment of 6 months or more. In some methods, the Course of Treatment is at least 6 months, or between at least 15 consecutive days and 6 months of consecutive days of treatment comprising administration of 150 mg BID of Compound 1 in a pharmaceutical form obtained from Example 1.

The R132X mIDH-1 Selective Inhibitor Therapy (e.g., oral administration of 150 mg BID of Compound 1 throughout a Course of Treatment) provided unexpectedly durable blood concentration levels throughout the Course of Treatment exceeding 6 months. The level of steady state blood concentration during the Course of Treatment was durable, meaning that the steady state blood concentration of Compound 1 did not decrease by more than 10% throughout a Course of Treatment with continued administration of Compound 1 at a dose of 150 mg BID each day, while remaining within a therapeutic concentration window defined by a minimum concentration above the $IC_{90}$ determined in vitro for the 2-HG production of a R132X mIDH-1 mutation harbored by the patient (e.g., above about 2,000 ng/mL or above about 1652 ng/mL), and a maximum concentration value below the concentration associated with medically unacceptable risk of QTc prolongation (e.g., about 7,200 ng/mL or about 7840 ng/mL).

In addition, the R132X mIDH-1 Selective Inhibitor Therapy can reduce 2-HG levels in the blood of the patient, although this reduction did not correlate with disease response in the patients during the Course of Treatment. As shown in FIGS. 9A-9D, the R132X mIDH-1 Selective Inhibitor Therapy provided a sustained reduction in 2HG levels, meaning that elevated levels of the blood concentration of 2-HG in patient blood plasma were reduced relative to pre-dose levels during the initial portion of a Course of Treatment (e.g., within the first 15 days) and then sustained at or below about the pre-dose level throughout the rest of the Course of Treatment (e.g., at or below about 200 ng/mL for 6 consecutive 28-day treatment cycles or at or below about 180 ng/mL for 6 consecutive 28-day treatment cycles).

FIGS. 8A-8E is a graph showing the steady state (trough) blood concentration measured in patients after administration of 150 mg of Compound 1 BID, as described in the human clinical trial of Example 10. FIGS. 8A-8E are different graphs each showing the steady state blood concentration of Compound 1 measured in patient blood for a collection of patients in the human clinical trial described in Example 10. FIGS. 8A-8E are each graphs showing the measured steady state blood concentrations measured in each of individual patients included in the population, at the indicated time points, in the human clinical trial of Example 10. Notably, the steady state blood concentration of Compound 1 remained above a therapeutic minimum value (e.g., the $IC_{90}$ value for 2-HG production by at least one of the R132X mutation(s) identified in patient's tissue prior to administration of Compound 1) throughout the Course of Treatment (e.g., 30 weeks). In particular, the administration of Compound 1 in the oral dosage form described in Example 1 at 150 mg BID resulted in a sustained therapeutically effective trough blood plasma concentration above 2,000 ng/mL throughout a 30-week Course of Treatment as shown in FIGS. 8A-8E (e.g., including after cycle 3 of a 28-day treatment cycle, after week 20 and continuing to week 30). The trough concentration measurements of Compound 1 in patient blood did not decline below a therapeutically effective level at each point measured during the Course of Treatment. Referring to FIGS. 9A-9D, the administration of Compound 1 in the oral dosage form from Example 1 at 150 mg BID in the human clinical trial of Example 10 resulted in a sustained 2-HG level under 200 ng/mL in plasma throughout the Course of Treatment ranging from cycle 2, day 1 through cycle 8, day 1 (each cycle represents 28 consecutive days of oral administration of 150 mg BID of the solid form of Compound 1 obtainable from the production method of Example 1).

The invention is based in part on the discovery that a R132X mIDH-1 Selective Inhibitor Therapy where Compound 1 is the only mIDH-1 inhibitor administered (administration of Compound 1 at 150 mg BID) unexpectedly resulted in a steady state blood concentration that was durable (e.g., blood plasma steady state concentration of Compound 1 remains within about 20% (or does not decrease by more than about 20%), and preferably remains within 10% (or does not decrease by more than 10%) of the concentration measured the day after the initial 28-day cycle in a Course of Treatment). In addition, the administration of Compound 1 as described in Example 10 reduced elevated 2-HG concentrations in the blood of the patients within about 15 days and then sustained patient blood concentrations of 2-HG at less than about 200 ng/mL after about 15 days of a Course of Treatment.

The R132X mIDH-1 Selective Inhibitor Therapy can provide a sustained ratio of greater than about 10 (preferably greater than about 20) of blood plasma concentration of Compound 1 (e.g., trough concentrations measured pre-dose at concentrations of about 2,000 ng/mL or greater) to 2-HG blood level (e.g, concentrations of plasma concentrations of about 200 ng/mL or lower, including concentrations of about 100 ng/mL) after cycle 3 day 1 (i.e., after BID doses administered over the initial 15 consecutive days of treatment) of a 28-day treatment cycle. A plasma half-life of about 60 hours was estimated for Compound 1, with steady state achieved by week 2 of the course of treatment. The steady state blood concentrations of Compound 1 measured in the patients was above the $IC_{90}$ value for 2-HG inhibition in R132X mIDH-1 cells (described in the Examples). As shown in FIGS. 8A-8E, the plasma exposures (steady state blood plasma concentration) of Compound 1 were durable (i.e., sustained) throughout the 30-week treatment duration. As shown in FIGS. 9A-9D, the plasma 2-HG concentrations were reduced to the normal range within 1 cycle (C2D1) and maintained throughout the treatment duration. No dose limiting toxicities of Compound 1 were observed during dose escalation studies, and the maximum tolerated dose (MTD) of Compound 1 was not reached. Preferably, the R132X mIDH-1 Selective Inhibitor Therapy can be administered to a patient that has not received any other R132X mIDH-1 inhibitor compound.

As described in Example 10, FIG. 11A shows the ratio of the steady state blood concentration of Compound 1, normalized to 1.0 using the concentration measured on day 15 of a Course of Treatment, for a single patient who received 150 mg BID of the solid form of Compound 1 obtainable from Example 1 throughout a Course of Treatment of over 300 days (i.e., greater than 6 months). The steady state blood exposure (concentration) of Compound 1 varied from about 90-133% of the concentration of Compound 1 measured in the patient at cycle 1, day 15, throughout the subsequent remainder of this Course of Treatment.

Optionally, a hypomethylating agent and/or a nucleic acid synthesis inhibitor can also be administered to the patient during the Course of Treatment. Suitable agents that can also be administered during the Course of Treatment include azacitabine and/or decitabine.

In some embodiments, a combination therapy of Compound 1 and azacitidine can be administered for the treatment of patients with certain forms of cancer (e.g., glioma) harboring IDH-1 mutations. For example, patients can be administered Compound 1 daily (BID) in continuous 28-day cycles, in combination with azacitidine (administered at the dose of 75 mg/m$^2$ for 7 days IV/SC per every 28-day cycle). Azacitidine (also, azacytidine or AZA herein) is believed to exert its antineoplastic effects by causing hypomethylation of DNA and direct cytotoxicity on abnormal hematopoietic cells in the bone marrow. Azacitidine can be administered during a Course of Treatment at a subcutaneous dose of 75 mg/m$^2$ daily for 7 days every 4 weeks. The azacitidine dose can be increased to 100 mg/m$^2$ if no beneficial effect was seen after 2 treatment cycles. The dose of azacitidine can be decreased and/or delayed based on hematologic response or evidence of renal toxicity. Azacitidine is indicated for treatment of patients with the following myelodysplastic syndrome subtypes: refractory anemia or refractory anemia with ringed sideroblasts (if accompanied by neutropenia or thrombocytopenia or requiring transfusions), refractory anemia with excess blasts, refractory anemia with excess blasts in transformation, and chronic myelomonocytic leukemia. In some embodiments, a method of treatment comprises (a) the (e.g., oral) administration of a total of 150 mg of Compound 1 BID to a patient throughout a Course of Treatment; and (b) administering a therapeutically effective amount of azacitidine to the patient (e.g, administering azacitidine at a dose of 75 mg/m$^2$ daily for 7 days every 4 weeks, wherein the azacitidine dose can be increased to 100 mg/m$^2$ if no beneficial effect was seen after 2 treatment cycles and the dose of azacitidine can be decreased and/or delayed based on hematologic response or evidence of renal toxicity).

Decacitabine (5-aza-2'-deoxycytidine) is a nucleoside metabolic inhibitor indicated for treatment of patients with myelodysplastic syndromes (MDS) including previously treated and untreated, de novo and secondary MDS of all French-American-British subtypes (refractory anemia, refractory anemia with ringed sideroblasts, refractory anemia with excess blasts, refractory anemia with excess blasts in transformation, and chronic myelomonocytic leukemia) and intermediate-1, intermediate-2, and high-risk International Prognostic Scoring System groups. In some embodiments, a method of treatment comprises the (e.g., oral) administration of a total of 150 mg of Compound 1 BID to a patient throughout a Course of Treatment; and (b) administering a therapeutically effective amount of decacitabine to the patient (e.g, administering decacitabine at a dose of 15 mg/m$^2$ by continuous intravenous infusion over 3 hours repeated every 8 hours for 3 days and repeating this cycle every 6 weeks; or administering the decacitabine at a dose of 20 mg/m$^2$ by continuous intravenous infusion over 1 hour repeated daily for 5 days. Repeat cycle every 4 weeks).

Glioma

The present disclosure provides methods for treating solid tumors in the CNS, including a brain cancer tumor, harboring a R132 IDH-1 mutation. For example, patients diagnosed with brain cancer harboring a mutant IDH-1 cancer cell can be treated with a therapeutically effective amount of Compound 1 in combination with azacitidine.

Compound 1 is a small molecule inhibitor of mutated forms of isocitrate dehydrogenase 1 (IDH-1) enzyme, and is useful for the treatment of adult patients diagnosed with cancer having an IDH-1 mutation as detected by an FDA-approved test. Compound 1 can be administered to patients in need thereof in a therapeutically effective amount (e.g., 150 mg orally twice daily until disease progression or unacceptable toxicity). Patients for the treatment of cancer with Compound 1 can be selected based on the presence of IDH-1 mutations in the blood or bone marrow. In one embodiment, the recommended starting dose of Compound 1 is 150 mg taken orally twice daily with or without food until disease progression or unacceptable toxicity. For patients without disease progression or unacceptable toxicity, the patient can receive the therapeutically effective amount of Compound 1 for a minimum of 6 months to allow time for clinical response.

The invention is based in part on preclinical studies showing that Compound 1 can cross the blood brain barrier (BBB) in mouse models. Oral administration of Compound 1 showed high systemic bioavailability in multiple preclinical species. Permeability was excellent, with little evidence of efflux, and significant brain penetration was observed in mice (98% brain binding in murine animal model).

Preferably, patients diagnosed with glioma harboring a R132 IDH-1 mutation can be treated with a therapeutically effective combination of a pharmaceutical composition of Compound 1 (e.g., an oral dosage form providing 150 mg of Compound 1 administered twice per day on consecutive days for a course of treatment comprising multiple treatment cycles totaling at least 6 months) and azacitidine. The azacitidine can be subcutaneously or intravenously administered to the patient in an azacitidine treatment cycle consisting of the administration of a total dose of 75 mg/m$^2$ each day for 7 consecutive days beginning at the start of each treatment cycle, followed by 21 consecutive days without administration of the azacitidine to the patient. A 48-hour dose-interruption of azacitidine is allowed for weekends or holidays. If no response is seen after 2 treatment cycles, azacitidine can be administered at a total dose of 100 mg/m$^2$ each day.

Compound 1 is preferably administered on consecutive days throughout a Course of Treatment. As used herein, the term "Course of Treatment" refers to the time period in which a patient is being administered Compound 1 (e.g., as a single agent, or in combination with another therapeutic agent), including any administration holidays or recovery periods. A course of treatment can include a single treatment cycle or multiple treatment cycles. For example, a Course of Treatment can comprise one or more 28-day treatment cycles. Additionally, a course of treatment can include a partial treatment cycle. The Course of Treatment can include the total time period during which a patient is on a treatment protocol for a therapy comprising the administration of a mIDH-1 inhibitor compound. Preferably, the Course of Treatment is at least about 15 consecutive days, at least about a 28-consecutive day treatment cycle, or at least about four, five, six or more consecutive 28-day treatment cycles and more preferably, at least about 4 months or longer (e.g., 6 months or longer). Preferably, Compound 1 is administered twice per day (e.g., about every 12 hours) every day throughout a Course of Treatment.

In some embodiments, patients can be treated with Compound 1 in combination with a hypomethylating agent such as azacitidine or decitabine. The recommended starting dose for azacitidine in the first treatment cycle, for all patients regardless of baseline hematology laboratory values, is 75 mg/m² of body surface area, injected subcutaneously, daily for 7 days, followed by a rest period of 21 days (28-day treatment cycle). It is recommended that patients be treated for a minimum of 6 cycles. Treatment should be continued as long as the patient continues to benefit or until disease progression. In some methods, azacitidine is administered to the patient in need thereof at a dose of 75 mg/m², SC, d1-7, q4 wk throughout a course of treatment, while receiving Compound 1 at a dose of 150 mg BID. In other methods, decitabine is administered to the patient in need thereof at a dose of 20 mg/m², IV, d1-5, q4 wk, while receiving Compound 1 at a dose of 150 mg BID.

In one embodiment, patients diagnosed with glioma harboring a mIDH1 can be treated with a mIDH1 Inhibitor Therapy consisting of Compound 1 and azacitidine. Treatment with the hypomethylating agent azacitidine can cause tumor growth inhibition in a patient-derived IDH1-mutated glioma model by reducing DNA methylation and inducing glial differentiation. IDH1 R132H mutations represent more than 90% of the IDH mutations present in low grade glioma and secondary GBM patients. The IDH1 mutations R132C and R132S are also reported in glioma patients. At least in mIDH1 harboring cancer cells, wild type and mutant IDH1 form a heterodimeric complex that can produce very high 2-HG levels (up to 3-35 mM in glioma cells). For example, patients bearing IDH1 mutations have elevated levels of 2-HG, which in some cases reach tumor concentrations >10 mM (glioma).

In another embodiment, patients diagnosed with chondrosarcoma harboring a mutant IDH1 cancer cell can be treated with a therapeutically effective amount of Compound 1 alone or in combination with azacitidine. In some embodiments, a combination therapy comprising Compound 1 and azacitidine can be administered for the treatment of patients with chondrosarcoma harboring IDH1 mutations. For example, patients can be administered Compound 1 daily (BID) in continuous 28-day cycles, in combination with azacitidine (administered at the daily dose of 75 mg/m² for 7 days IV/SC per every 28-day cycle).

Preferably, patients treated with a combination of Compound 1 and azacitidine receive a therapeutically effective amount of a mIDH1 Inhibitor Therapy selected from a dose level indicated in Table 6 below.

TABLE 6

Preferred Dose Levels for mIDH1 Inhibitor Therapy with Azacitidine

| Dose Level | Compound 1 | Azacitidine |
|---|---|---|
| 1 (Starting Dose) | 150 mg BID continuously for 28 consecutive days | 75 mg/m²/day × 7 days every 28 days |
| −1 (Hematologic Dose-Limiting Toxicity (DLT)) | 150 mg BID continuously for 28 consecutive days | 37 mg/m²/day × 7 days every 28 days |
| −1 (non-Hematologic DLT) | 150 mg BID continuously for 28 consecutive days | 75 mg/m²/day × 7 days every 28 days |

Patients diagnosed with hepatobiliary carcinoma (HBC) harboring a mutant IDH1 cancer cell can be treated with a therapeutically effective amount of Compound 1 alone or in combination with a PD-1 inhibitor (e.g., Pembrolizumab (Keytruda) or Nivolumab (Opdivo)). In some embodiments, a combination therapy of Compound 1 and the PD-1 inhibitor can be administered for the treatment of patients with a HBC cancer harboring IDH1 mutations. For example, patients can be administered compound 1 daily (BID) in continuous 28-day cycles, in combination with Pembrolizumab (e.g., administered at the dose of 200 mg every 3 weeks). For example, patients can be administered compound 1 daily (BID) in continuous 28-day cycles, in combination with Nivolumab (e.g., administered at the dose of 240 mg every 2 weeks or 480 mg every 4 weeks). Preferably, patients treated with a combination comprising Compound 1 and Nivolumab receive a therapeutically effective amount of a mIDH1 Inhibitor Therapy selected from a dose level indicated in Table 7 below.

TABLE 7

Preferred Dose Levels for mIDH1 Inhibitor Therapy with Nivolumab

| Dose Level | Compound 1 | Nivolumab |
|---|---|---|
| 1 (Starting Dose) | 150 mg BID continuously for 28 consecutive days | 240 mg intravenous every 2 weeks |
| −1 (any DLT) | 150 mg once daily continuously for 28 consecutive days | 240 mg intravenous every 2 weeks |

Patients diagnosed with IHCC harboring a mutant IDH1 cancer cell can be treated with a therapeutically effective amount of Compound 1 alone or in combination with a chemotherapy (e.g., gemcitabine and cisplatin). Preferably, patients treated with a combination of Compound 1 and gemcitabine and cisplatin chemotherapy receive a therapeutically effective amount of a mIDH1 Inhibitor Therapy selected from a dose level indicated in Table 8 below.

TABLE 8

Preferred Dose Levels for mIDH1 Inhibitor Therapy with Gemcitabine/Cisplatin

| Dose Level | Compound 1 | Gemcitabine/Cisplatin |
|---|---|---|
| 1 (Starting Dose) | 150 mg BID continuously for 28 consecutive days | Cisplatin 25 mg/m² followed by gemcitabine 1,000 mg/m² on Day 1 and Day 8 |
| −1 (any DLT) | 150 mg once daily continuously for 28 consecutive days | Cisplatin 25 mg/m² followed by gemcitabine 1,000 mg/m² on Day 1 and Day 8 |

It will be appreciated that use of headers in the present disclosure are provided for the convenience of the reader. The presence and/or placement of a header is not intended to limit the scope of the subject matter described herein.

The present disclosure contemplates, among other things, the following numbered embodiments:

1. A method of treating AML or MDS in a patient harboring isocitrate dehydrogenase 1 mutations (mIDH-1), the method comprising administering to a patient in need thereof a therapeutically effective amount of a R132X mIDH-1 Selective Inhibitor Therapy consisting of Compound 1 in an oral dosage form for a course of treatment starting with the initial administration of Compound 1 and continuing on consecutive days for at least 15 days, wherein the administration of the therapeutically effective amount of Compound 1 results in the patient having a durable therapeutically effective trough blood plasma concentration of Compound 1 in the patient throughout the course of treatment.
2. A method of treating AML or MDS in a patient harboring isocitrate dehydrogenase 1 mutations (mIDH-1), the method comprising administering to a patient in need thereof a therapeutically effective amount of Compound 1 for at least three consecutive treatment cycles of 28 consecutive days each, wherein the administration of the therapeutically effective amount of Compound 1 results in the patient having both:
   a. a durable sustained therapeutically effective trough blood plasma concentration of Compound 1 in the patient throughout the course of treatment, and
   b. a reduced level of 2-HG in the patient's plasma after the first two consecutive treatment cycles.
3. The method of any one of embodiments 1 or 2, wherein
   a. the steady state blood plasma concentration of Compound 1 in the patient is maintained at or above about 2,000 ng/mL throughout the course of treatment, and
   b. the level of 2-HG in the patient plasma is maintained at or below about 200 ng/mL after the start of the third consecutive treatment cycle of the course of treatment on day 15 after the initial dose of Compound 1.
4. The method of any one of embodiments 1-3, wherein the Compound 1 is administered in a dose of 150 mg/day twice per day throughout the course of treatment.
5. The method of any one of embodiments 1-4, wherein the Compound 1 is administered with food to improve bioavailability of Compound 1.
6. The method of any one of embodiments 1-5, wherein the course of treatment is 12-30 weeks.
7. The method of any one of embodiments 1-6, wherein the method further comprises the administration of azacitidine to the patient throughout the course of treatment.
8. The method of any one of embodiments 1-6, wherein the patient is receiving or previously received treatment with azacitidine.
9. The method of embodiment 7 or 8, wherein the azacitidine is subcutaneously or intravenously administered to the patient in an azacitidine treatment cycle consisting of the administration of a total dose of 75 mg/m$^2$ each day for 7 consecutive days beginning at the start of each treatment cycle, followed 21 consecutive days without administration of the azacitidine to the patient.
10. The method of any one of embodiments 1-6, wherein the method further comprises the administration of cytarabine to the patient throughout the course of treatment.
11. The method of any one of embodiments 1-6, wherein the patient is receiving or previously received treatment with cytarabine.
12. The method of embodiment 10 or 11, wherein the cytarabine is subcutaneously or intravenously administered to the patient in a cytarabine treatment cycle consisting of the administration of a total dose of 20 mg/day each day for 7 consecutive days beginning at the start of each treatment cycle, followed 10 consecutive days without administration of the cytarabine to the patient.
13. The method of any one of embodiment 1-12, wherein the patient has been identified as having a R132X mutation in mIDH-1 using a diagnostic method comprising a next generation sequencing (NGS) analysis of a bone marrow or other tissue sample from the patient obtained prior to the administration of Compound 1 to the patient.
14. The method of any one of embodiments 1-13, wherein the subject has relapsed or refractory (R/R) AML.
15. The method of any one of embodiments 1-13, wherein the subject has AML or MDS with residual R132X mIDH-1 in morphologic complete remission or complete remission with incomplete blood count recovery (CR/CRi) after cytotoxic-containing induction therapy with residual IDH-R132X mutation.
16. The method of any one of embodiments 1-13, wherein the subject has relapsed or refractory AML or MDS previously treated with an IDH1 inhibitor.
17. The method of any one of embodiments 1-13, wherein the subject has relapsed or refractory AML or MDS that are naïve to prior hypomethylating therapy and IDH1 inhibitor therapy
18. The method of any one of embodiments 1-13, wherein the subject has relapsed or refractory AML or MDS that has inadequately responded or has progressed immediately preceding hypomethylating therapy.
19. The method of any one of embodiments 1-13, wherein the subject is a subject with relapsed or refractory AML or MDS that have been previously treated with single-agent IDH1 inhibitor therapy as their last therapy prior to study enrollment.
20. The method of any one of embodiments 1-19, wherein the subject has been diagnosed with AML with a R132X mIDH-1.
21. The method of any one of embodiments 1-19, wherein the subject has MDS with AML with a R132X mIDH-1.
22. The method of any one of embodiments 1-21, wherein the subject has been diagnosed with a R132X mIDH-1 selected from the group consisting of R132H, R132C or both R132H and R132C.
23. A method of treating AML or MDS in a patient harboring at least one R132X isocitrate dehydrogenase 1 mutation (mIDH-1), the method comprising administering to the patient in need thereof a R132X mIDH-1 Selective Inhibitor Therapy consisting of 150 mg BID of Compound 1 in an pharmaceutically acceptable oral dosage form for a course of treatment starting with the initial administration of Compound 1 and continuing on consecutive days for at least 15 days.
24. The method of embodiment 23, wherein the course of treatment comprises at least 4 consecutive treatment cycles each consisting of 28 consecutive days of administering Compound 1 to the patient twice per day.
25. The method of embodiment 23, wherein the course of treatment comprises 12-30 weeks of consecutive days of administering Compound 1 to the patient twice per day.
26. A method of treating AML or MDS in a patient harboring at least one R132X isocitrate dehydrogenase 1 mutation (mIDH-1), the method comprising administering to the patient 150 mg BID of Compound 1 in a pharmaceutically acceptable oral dosage form for a course of treatment starting with the initial administration of Compound 1 and continuing on consecutive days for at least 15 days.

27. A method of treating AML or MDS in a patient harboring at least one R132X isocitrate dehydrogenase 1 mutation (mIDH-1), the method comprising administering to the patient 150 mg BID of Compound 1 in a pharmaceutically acceptable oral dosage form for a course of treatment starting with the initial administration of Compound 1 and continuing on consecutive days for at least 12 weeks.

28. A method of treating AML or MDS in a patient harboring at least one R132X isocitrate dehydrogenase 1 mutation (mIDH-1), the method comprising administering to the patient 150 mg BID of Compound 1 in a pharmaceutically acceptable oral dosage form for a course of treatment starting with the initial administration of Compound 1 and continuing on consecutive days for at least 30 weeks.

29. A method of treating AML or MDS in a patient harboring one or more R132X isocitrate dehydrogenase 1 mutations (mIDH-1), the method comprising administering to a patient in need thereof a therapeutically effective amount of a R132X mIDH-1 Selective Inhibitor Therapy consisting of Compound 1 in an oral dosage form for a course of treatment starting with the initial administration of Compound 1 and continuing on consecutive days for at least 15 days, wherein the administration of the therapeutically effective amount of Compound 1 results in the patient having both:
   a. a durable trough blood plasma concentration of Compound 1 in the patient measured at or above the IC90 concentration of Compound 1 for 2-HG suppression of the R132X mIDH-1 throughout the course of treatment, and
   b. a level of 2-HG in the patient's plasma of less than about 200 ng/mL within two initial consecutive treatment cycles that is maintained throughout the course of treatment.

30. The method of embodiment 29, wherein course of treatment is at least 3 consecutive 28-day treatment cycles.

31. The method of embodiments 29 or 30, wherein the trough blood plasma concentration of Compound 1 in the patient is measured between 2,000 ng/mL-7,200 ng/mL.

32. The method of any one of embodiments 29-31, wherein the level of 2-HG is maintained at about 180 ng/mL in the blood plasma of the patient throughout the course of treatment after the first 15 consecutive days of administering Compound 1 to the patient.

33. The method of any one of embodiments 1-32, wherein the concentration of Compound 1 measured in the blood of the patient does not decline more than 20% throughout the course of treatment compared to the steady state blood concentration of Compound 1 measured prior to administration of Compound 1 at cycle 2, day 1 (day 29).

34. The method of any one of embodiments 1-32, wherein the concentration of Compound 1 measured in the blood of the patient does not decline more than 10% throughout the course of treatment compared to the steady state blood concentration of Compound 1 measured prior to administration of Compound 1 at cycle 2, day 1 (day 29).

35. The method of any one of embodiments 33 and 34, wherein the course of treatment is a total of 12 weeks.

36. The method of any one of embodiments 33 and 34, wherein the course of treatment is a total of 30 weeks.

37. The method of any one of embodiments 22-36, wherein the subject has been diagnosed with a R132X mIDH-1 selected from the group consisting of R132H, R132C or both R132H and R132C.

38. The method of any one of embodiments 1-37, wherein Compound 1 is administered in the pharmaceutically acceptable dosage form obtainable from Step 6 of Example 1.

39. A method of treating AML in a patient harboring at least one R132X isocitrate dehydrogenase 1 mutation (mIDH-1) selected from the group consisting of: R132C, R132H, R132S, R132G, and R132L, wherein the method comprises administering to the patient 150 mg BID of Compound 1 in a pharmaceutically acceptable oral dosage form for a course of treatment starting with the initial administration of Compound 1 and continuing for at least 28 consecutive days.

40. A method of treating AML in a patient harboring one or more R132X isocitrate dehydrogenase 1 mutations (mIDH-1) selected from the group consisting of: R132C, R132H, R132S, R132G, and R132L, wherein the method comprises administering to a patient in need thereof a therapeutically effective amount of a R132X mIDH-1 Selective Inhibitor Therapy consisting of Compound 1 in an oral dosage form for a course of treatment starting with the initial administration of Compound 1 and continuing for at least 15 consecutive days, wherein the administration of the therapeutically effective amount of Compound 1 results in the patient having a durable trough blood plasma concentration of Compound 1 in the patient measured at or above the $IC_{90}$ concentration of Compound 1 for 2-HG suppression of the R132X mIDH-1 throughout the course of treatment.

41. The method of embodiment 40, wherein the administration of the therapeutically effective amount of Compound 1 results in the patient having a level of 2-HG in the patient's plasma of less than about 200 ng/mL within two initial consecutive treatment cycles that is maintained throughout the course of treatment.

42. A method of treating AML in a patient harboring one or more R132X isocitrate dehydrogenase 1 mutations (mIDH-1) selected from the group consisting of: R132C, R132H, R132S, R132G, and R132L, wherein the method comprises administering to a patient in need thereof a therapeutically effective amount of a R132X mIDH-1 Selective Inhibitor Therapy consisting of Compound 1 in an oral dosage form for a course of treatment starting with the initial administration of Compound 1 and continuing for at least 15 consecutive days, wherein the administration of the therapeutically effective amount of Compound 1 results in the patient having a level of 2-HG in the patient's plasma of less than about 200 ng/mL within two initial consecutive treatment cycles that is maintained throughout the course of treatment.

43. The method of embodiment 42, wherein the administration of the therapeutically effective amount of Compound 1 results in the patient having a durable trough blood plasma concentration of Compound 1 in the patient measured at or above the $IC_{90}$ concentration of Compound 1 for 2-HG suppression of the R132X mIDH-1 throughout the course of treatment.

44. A method of treating AML in a patient harboring one or more R132X isocitrate dehydrogenase 1 mutations (mIDH-1) selected from the group consisting of: R132C, R132H, R132S, R132G, and R132L, the method comprising administering to a patient in need thereof a therapeutically effective amount of a R132X mIDH-1 Selective Inhibitor Therapy consisting of Compound 1 in an oral dosage form for a course of treatment starting with the initial administration of Compound 1 and continuing for at least 15 consecutive days, wherein the administration of the therapeutically effective amount of Compound 1 results in the patient having a durable trough blood plasma concentration of Compound 1 in the patient measured at or above 2,000 ng/mL throughout the course of treatment of at least 6 months.

45. The method of embodiment 44, wherein the administration of the therapeutically effective amount of Compound 1 results in the patient having a level of 2-HG in the patient's plasma of less than about 200 ng/mL within two initial consecutive 28-day treatment cycles and is maintained throughout the course of treatment.

44. A method of treating AML in a patient harboring one or more R132X isocitrate dehydrogenase 1 mutations (mIDH-1) selected from the group consisting of: R132C, R132H, R132S, R132G, and R132L, wherein the method comprises administering to a patient in need thereof:
  a. a therapeutically effective amount of Compound 1 in an oral dosage form for a Course of Treatment starting with the initial administration of Compound 1 and continuing for at least 15 consecutive days for one or more consecutive R132X mIDH-1 Selective Inhibitor 28-day Treatment Cycles, wherein Compound 1 is the only R132X mIDH-1 selective inhibitor administered to the patient during the Course of Treatment; and
  b. azacitidine subcutaneously or intravenously administered to the patient throughout the one or more R132X mIDH-1 Selective Inhibitor 28-day Treatment Cycle(s), in an azacitidine treatment cycle consisting of the administration of a total dose of 75 mg/m$^2$ each day for 7 consecutive days beginning at the start of each treatment cycle, followed 21 consecutive days without administration of the azacitidine to the patient;
  wherein the administration of the therapeutically effective amount of Compound 1 results in the patient having a durable trough blood plasma concentration of Compound 1 in the patient that is no less than about 90% of the concentration of Compound 1 measured after the first 15 days of the first R132X mIDH-1 Selective Inhibitor 28-day Treatment Cycle, throughout the Course of Treatment of at least 6 months.

45. A method of treating an adult patient diagnosed with a mutant IDH-1 form of AML, comprising administering to the patient in need thereof a combination therapy throughout a Course of Treatment lasting at least 6 months, wherein the combination therapy comprises a combination of:
  a. 150 mg BID of Compound 1 each day throughout a Course of Treatment of at least 6 months, wherein the Compound 1 is the only mutant IDH-1 inhibitor administered to the patient during the Course of Treatment;
  b. azacitidine subcutaneously or intravenously administered to the patient throughout the Course of Treatment at a total dose of 75 mg/m$^2$ each day for 7 consecutive days beginning at the start of each treatment cycle, followed 21 consecutive days without administration of the azacitidine to the patient.

46. A method of treating an adult patient diagnosed with a mutant IDH-1 form of AML, comprising administering to the patient in need thereof 150 mg BID of Compound 1 each day throughout a Course of Treatment of at least 6 months, in combination with azacitidine for the treatment of the AML in the adult patient, wherein Compound 1 is the only mutant IDH-1 inhibitor targeting R132C, R132H, R132S, R132G, or R132L variants of IDH-1 that is administered to the patient during the Course of Treatment.

47. The method of embodiment 46, wherein the azacitidine is administered subcutaneously or intravenously to the patient throughout the Course of Treatment at a total dose of 75 mg/m$^2$ each day for 7 consecutive days beginning at the start of each treatment cycle, followed 21 consecutive days without administration of the azacitidine to the patient.

The present disclosure also contemplates, among other things, the following numbered embodiments:

1. A method of treating a patient harboring one or more R132X isocitrate dehydrogenase 1 mutations (mIDH-1), the method comprising administering to the patient in need thereof a R132X mIDH-1 Selective Inhibitor Therapy consisting of the oral administration of Compound 1 to the patient at a dose of 150 mg twice per day (BID) for a Course of Treatment starting with the initial administration of Compound 1 and continuing on consecutive days for at least 15 days.
2. The method of embodiment 1, wherein Compound 1 is administered with food to improve bioavailability of Compound 1.
3. The method of any one of embodiments 1-2, wherein the Course of Treatment is at least 12 weeks.
4. The method of any one of embodiments 1-2, wherein the Course of Treatment is at least 20 weeks.
5. The method of any one of embodiments 1-2, wherein the Course of Treatment is at least 30 weeks.
6. The method of any one of embodiments 1-2, wherein the Course of Treatment is at least 6 months.
7. The method of any one of embodiments 1-6, wherein the subject has a R132X mIDH-1 selected from the group consisting of R132H, R132C or both R132H and R132C.
8. The method of any one of embodiments 1-7, wherein Compound 1 is administered in the solid form obtained from Example 1.
9. A method of treatment of a disease in a patient harboring a mIDH-1 mutation, the method comprising the steps of:
  a. selecting a patient for treatment based on the presence of an IDH-1 mutation detected in cells obtained from the patient;
  b. administering Compound 1 to the selected patient from step (a) at a starting dose of 150 mg taken orally twice daily until disease progression or unacceptable toxicity.
10. The method of embodiment 9, further comprising administering Compound 1 to the selected patient for at least 6 months.
11. The method of any one of embodiments 9-10, wherein Compound 1 is administered to the patient as a single agent or in combination with other therapeutic agents.
12. The method of any one of embodiments 9-11, further comprising assessing blood counts and blood chemistries of the selected patient for leukocytosis and tumor lysis syndrome prior to the initiation of Compound 1 in step (b).
13. The method of any one of embodiments 9-12, further comprising the step (c) of monitoring a selected patient at a minimum of every 2 weeks for at least the first 3 months during treatment of the patient with compound 1 according to step (b).
14. The method of any one of embodiments 9-13, wherein Compound 1 is administered in the solid form obtained from Example 1 in a pharmaceutically acceptable oral dosage form.
15. The method of any one of embodiments 9-14 wherein the patient is selected for treatment based on the detection of one or more R132X IDH-1 mutations in cells obtained from the patient.

16. The method of embodiment 15, wherein the R132X IDH-1 mutation is detected using next generation sequencing of patient bone marrow tissue.
17. The method of any one of embodiments 15-16, wherein the R132X mutation is selected from the group consisting of R132H and R132C.
18. The method of any one of embodiments 16-17, wherein the R132X IDH-1 mutation is detected prior to the administration of Compound 1.
19. A method of treating a patient harboring one or more R132X isocitrate dehydrogenase 1 mutations (mIDH-1), the method comprising orally administering to the patient 150 mg of an oral pharmaceutical dosage form of the compound 5-{[(1S)-1-(6-chloro-2-oxo-1,2-dihydroquinolin-3-yl)ethyl]amino}-1-methyl-6-oxo-1,6-dihydropyridine-2-carbonitrile twice per day (BID) on consecutive days for at least 15 days.
20. The method of embodiment 19, wherein the oral pharmaceutical dosage form is the solid form of Compound 1 obtained by the process of Example 1.
21. The method of any one of embodiments 19-20, wherein the R132X mutation is selected from the group consisting of R132H and R132C.
22. The method of any one of embodiments 19-21, wherein the compound is administered to the patient on consecutive days for at least 20 weeks.
23. The method of any one of embodiments 19-22, wherein the compound is administered to the patient on consecutive days for at least 30 weeks.
24. The method of any one of embodiments 19-23, further comprising detection of the R132X IDH-1 mutation in the patient using next generation sequencing of patient bone marrow tissue prior to the administration of the compound to the patient.
25. A method of treatment comprising orally administering to a patient harboring a R132X mIDH-1 arginine mutation a dose of 150 mg BID of a pharmaceutically acceptable solid form of compound of formula (I) as obtained from Example 1

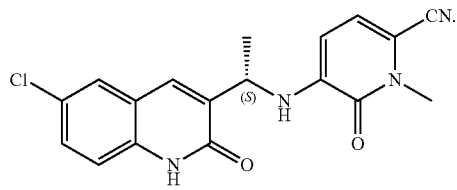

26. The method of embodiment 25, wherein the pharmaceutically acceptable solid form of Compound 1 is administered to the patient on consecutive days for at least 20 weeks.
27. The method of embodiment 25, wherein the pharmaceutically acceptable solid form of Compound 1 is administered to the patient on consecutive days for at least 30 weeks.
28. The method of embodiment 25, wherein the pharmaceutically acceptable solid form of Compound 1 is administered to the patient on consecutive days for at least 6 months.
29. The method of any one of embodiments 25-28, wherein Compound 1 is administered to the patient as a single agent or in combination with other therapeutic agents.
30. The method of any one of embodiments 25-29, wherein the R132X mIDH-1 arginine mutation is selected from the group consisting of: R132H, R132C, R132G, R132L, and R132S.
31. The method of any one of embodiments 25-30, further comprising detection of the R132X IDH-1 arginine mutation in the patient using next generation sequencing of patient bone marrow tissue prior to the administration of Compound 1 to the patient.
32. The method of any one of embodiments 1-31, wherein the patient has not received another mIDH-1 inhibitor compound.
33. The method of any one of embodiments 1-8, wherein the patient has greater than 200 ng/mL of 2-HG prior to initiating the R132X mIDH-1 Selective Inhibitor Therapy.
34. The method of any one of embodiments 9-18, wherein the patient selected in step (a) has greater than 200 ng/mL of 2-HG prior to administering Compound 1 in step (b).
35. The method of any one of embodiments 19-24, wherein the patient has greater than 200 ng/mL of 2-HG prior to administration of the oral pharmaceutical dosage form of the compound to the patient.
36. The method of any one of embodiments 25-31, wherein the patient has greater than 200 ng/mL of 2-HG prior to administration of the compound of formula (I) to the patient.
37. A method of treatment comprising orally administering to a patient having elevated blood levels of 2-HG greater than about 200 ng/mL and harboring at least one of a R132H, R132C, R132G, R132L, and R132S IDH-1 mutation, a dose of 150 mg BID each day of a pharmaceutically acceptable solid form of compound of formula (I) as obtained from Example 1

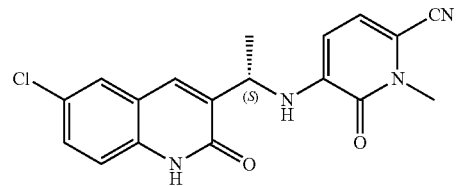

on consecutive days for at least 15 days.
38. The method of embodiment 37, wherein the pharmaceutically acceptable solid form of Compound 1 is administered to the patient on consecutive days for at least 20 weeks.
39. The method of embodiment 37, wherein the pharmaceutically acceptable solid form of Compound 1 is administered to the patient on consecutive days for at least 30 weeks.
40. The method of embodiment 37, wherein the pharmaceutically acceptable solid form of Compound 1 is administered to the patient on consecutive days for at least 6 months.
41. A method of treating a patient diagnosed with a cancer harboring one or more R132X isocitrate dehydrogenase 1 mutations (mIDH-1) selected from the group consisting of R132C, R132H, R132L, R132G, and R132S, the method comprising the oral administration of Compound 1 as the only inhibitor of mIDH-1 to the patient, at a total dose of 150 mg twice per day (BID) throughout a Course of Treatment starting with the initial administration of Compound 1 and continuing on consecutive days for at least 6 months.

42. A method of treating an adult patient diagnosed with a cancer harboring one or more R132X isocitrate dehydrogenase 1 mutations (mIDH-1) selected from the group consisting of R132C, R132H, R132L, R132G, and R132S, the method comprising the oral administration of a total dose of 150 mg twice per day (BID) of Compound 1 in the solid form obtained from Example 1, on consecutive days throughout a Course of Treatment starting with the initial administration of Compound 1 and continuing on consecutive days for at least 6 months, wherein Compound 1 is the only inhibitor of mIDH-1 administered to the patient during a Course of Treatment.

43. The method of any one of embodiments 41-42, further comprising the administration of an hypomethylating agent to the patient during the Course of Treatment.

The present disclosure also contemplates, among other things, the following numbered embodiments:

1. A method of treating a patient diagnosed with a glioma cancer harboring a cancer cell with an IDH-1 R132 mutation, the method comprising administering to the patient in need thereof a therapeutically effective amount of Compound 1 and a hypomethylating agent over a course of treatment comprising multiple 28-day treatment cycles.

2. A method of treatment comprising the steps of:
   a. selecting a patient diagnosed with a glioma cancer harboring an IDH-1 mutation;
   b. administering Compound 1 to the selected patient from step (a) at a starting dose of 150 mg taken orally twice daily for a treatment cycle of 28 consecutive days; and
   c. administering azacitidine subcutaneously or intravenously to the patient during the same treatment cycle as step (b), in a total dose of 75 mg/m2 each day for the first 7 consecutive days of the treatment cycle followed by 21 consecutive days without the administration of azacitidine until the end of the treatment cycle, with the exception of optionally permitting a 48-hour dose interruption of azacitidine on a weekend of holiday during the treatment cycle.

3. The method of any one of embodiments 1-2, wherein the cancer does not harbor a IDH-2 mutation.

4. The method of any one of embodiments 1-3, wherein the patient has been diagnosed as having a R132 mutation based on a patient diagnostic.

5. The method of embodiment 4, wherein the patient diagnostic comprises detecting the R132 mutation in a biological sample obtained from the patient.

6. The method of embodiment 5, wherein the tissue sample is obtained from the CNS of the patient.

7. The method of any one of embodiments 4-6, wherein the R132 mutation is detected using next generation sequencing (NGS) without the use of PCR.

8. The method of any one of embodiments 1-7, wherein the method comprises administering 150 mg of Compound 1 to the patient in the solid form obtained from the method of Example 1.

9. The method of any one of embodiments 1-8, wherein Compound 1 is administered to the patient once every 12 hours on consecutive days throughout a course of treatment.

10. The method of any one of embodiments 1-9, wherein Compound 1 is administered to the patient throughout a course of treatment of at least 6 months.

11. The method of any one of embodiments 2-9, wherein Compound 1 is administered to the patient throughout a course of treatment of at least 6 consecutive treatment cycles.

12. A method of treating a glioma cancer having an IDH-1 mutation in an adult patient, the method comprising administering to the patient in need thereof
   a. a pharmaceutical composition comprising a total of 150 mg of a pharmaceutically acceptable solid form of 5-{[(1S)-1-(6-chloro-2-oxo-1,2-dihydroquinolin-3-yl)ethyl]amino}-1-methyl-6-oxo-1,6-dihydropyridine-2-carbonitrile obtained from Example 1, twice per day on consecutive days for a 28 day treatment cycle; and
   b. administering azacitidine subcutaneously or intravenously to the patient during the same treatment cycle as step (a), in a total dose of 75 mg/m² each day for the first 7 consecutive days of the treatment cycle followed by 21 consecutive days without the administration of azacitidine until the end of the treatment cycle, with the exception of optionally permitting a 48-hour dose interruption of azacitidine on a weekend of holiday during the treatment cycle.

13. A method of treating a glioma cancer having an IDH-1 mutation in an adult patient, the method comprising administering to the patient in need thereof
   a. a pharmaceutical composition comprising a total of 150 mg of a Compound 1 in a pharmaceutically acceptable solid form (e.g. that obtainable from Example 1), twice per day on consecutive days for a 28 day treatment cycle; and
   b. administering azacitidine subcutaneously or intravenously to the patient during the same treatment cycle as step (a), in a total dose of 75 mg/m² each day for the first 7 consecutive days of the treatment cycle followed by 21 consecutive days without the administration of azacitidine until the end of the treatment cycle, with the exception of optionally permitting a 48-hour dose interruption of azacitidine on a weekend of holiday during the treatment cycle.

14. The method of any one of embodiments 1-13, wherein the patient is diagnosed with glioblastoma multiforme prior to the administration of Compound 1.

15. The method of any one of embodiments 1-14, wherein the patient has elevated 2HG blood levels prior to the administration of Compound 1.

16. The method of embodiment 15, wherein the level of 2HG measured in the blood of the patient is greater than about 200 ng/mL prior to the administration of Compound 1.

17. The method of any one of embodiments 1-16, wherein the level of 2HG measured in the blood of the patient is less than about 100 ng/mL measured on day 15 after the administration of Compound 1 for the first 14 consecutive days of the first treatment cycle.

The present disclosure also contemplates, among other things, the following numbered embodiments:

1. A method of treating a patient diagnosed with a cancer harboring a cancer cell with an IDH-1 R132 mutation selected from the group consisting of: R132L, R132G, and R132S, the method comprising administering to the patient in need thereof a therapeutically effective amount of Compound 1.
2. The method of embodiment 1, wherein the cancer does not harbor a IDH-2 mutation.
3. The method of embodiment 1, wherein the cancer does not harbor a IDH-2 mutation selected from the group consisting of: IDH-2 R172K and IDH-2 R140Q.
4. The method of embodiment 1, wherein the patient is diagnosed as having a R132 mutation based on a patient diagnostic.
5. The method of embodiment 4, wherein the patient diagnostic comprises detecting the R132 mutation in a tissue sample obtained from the patient.
6. The method of embodiment 5, wherein the tissue sample is obtained from the bone marrow of the patient.
7. The method of any one of embodiments 4-6, wherein the R132 mutation is detected using next generation sequencing (NGS) without the use of PCR.
8. A method of treatment comprising the steps of:
    a. selecting a patient for treatment based on the presence of one or more IDH-1 mutations selected from the group consisting of: R132L, R132G, and R132S;
    b. administering Compound 1 to the selected patient from step (a) at a starting dose of 150 mg taken orally twice daily until disease progression or unacceptable toxicity.
9. The method of embodiment 8, where the IDH-1 mutation is detected in cancer cells obtained from the blood or bone marrow of the patient.
10. The method of embodiment 9, wherein the IDH-1 mutation is detected prior to administering Compound 1 to the patient.
11. The method of any one of embodiments 1-10, comprising the step of detecting the IDH-1 mutation in a cell from the patient using a next-generation sequencing (NGS)-based tumor genotyping assay.
12. The method of any one of embodiments 1-11, wherein administration of Compound 1 to the patient results in a decreased 2-hydroxyglutarate (2-HG) levels in the blood of the patient within the first 15 consecutive days of treatment of the patient with Compound 1.
13. The method of any one of embodiments 1-12, wherein the method comprises administering 150 mg of Compound 1 to the patient in the solid form obtained from the method of Example 1.
14. The method of any one of embodiments 1-12, wherein the method comprises administering 150 mg of Compound 1 to the patient twice daily throughout a course of treatment.
15. The method of embodiment 14, wherein the course of treatment is at least 15 consecutive days.
16. The method of any one of embodiments 1-15, wherein Compound 1 is administered to the patient once every 12 hours on consecutive days throughout a course of treatment.
17. The method of any one of embodiments 1-16, wherein Compound 1 is administered to the patient throughout a course of treatment of at least 6 months.
18. A method of inhibiting the production of 2-HG from a cell harboring a IHD-1 mutation selected from the group consisting of: R132L, R132G and R132S, the method comprising contacting the cell with Compound 1 in an amount, under conditions, and for a time sufficient to inhibit the production of 2-HG from the cell.
19. A method of treating a patient diagnosed with a cancer harboring a cancer cell with an IDH-1 R132 mutation, the method comprising administering to the patient in need thereof a therapeutically effective amount of Compound 1.
20. The method of embodiment 19, wherein the patient is diagnosed with a cancer harboring an IDH-1 R132 mutation in a cell obtained from the patient, prior to the administration of Compound 1.
21. A method of treating a patient diagnosed with a cancer harboring a cancer cell with an IDH-1 R132 mutation, the method comprising administering to the patient in need thereof a therapeutically effective amount of Compound 1.
22. The method of embodiment 21, wherein the patient is diagnosed with a cancer harboring an IDH-1 R132 mutation in a cell obtained from the patient, prior to the administration of Compound 1.
23. A method of treating a patient diagnosed with a cancer, the method comprising
    a. diagnosing the patient as having a mutant IDH-1 mutation in a cell obtained from the patient; and
    b. administering a therapeutically effective amount of a pharmaceutical composition comprising Compound 1 to the patient in need of an inhibitor of the mutant IDH-1 enzyme that targets the mutant IDH-1 variants R132C at no greater than about 5 times the level of R132H; and
    c. continuing to administer the pharmaceutical composition to the patient throughout a course of treatment of at least 6 months.
24. The method of embodiment 23, wherein the patient is in need of an inhibitor of mIDH-1 variants selected from the group consisting of R132L, R132G, and R132S;
25. The method of any one of embodiments 23-24, wherein the relative targeting of R132C and R132H variants of mIDH-1 is measured by the ratio of $IC_{50}$ values obtained using the assay of Example 2.
26. The method of any one of embodiments 23-25, wherein the patient is diagnosed as having an IDH-1 mutation in a cell from the patient using a next-generation sequencing (NGS)-based tumor genotyping assay.
27. The method of any one of embodiments 23-26, wherein the pharmaceutical composition is administered to the patient twice per day.
28. The method of any one of embodiments 23-27, wherein the pharmaceutical composition is administered to the patient in a dose of 150 mg BID on consecutive days throughout the course of treatment.
29. The method of any one of embodiments 23-28, wherein Compound 1 in the pharmaceutical composition has the solid form obtained from Example 1.
30. A method of inhibiting the production of inhibiting the production of 2-HG in a R132C mutated IDH-1 enzyme at no more than about 5 times the inhibition of 2-HG production in a R132H mutated IDH-1 enzyme, the method comprising contacting an IDH-1 enzyme not having arginine at position 132 with a composition comprising Compound 1 under conditions and for a time effective to inhibit 2-HG production in either an IDH-1 R132C or an IDH-1 R132H mutation in the mIDH-1 enzyme.
31. A method of treating a cancer in an adult patient, the cancer having a known mIDH-1 frequency of about 10-90%, the method comprising administering to a patient diagnosed with an IDH-1 mutation comprising an IDH-1 mutation selected from the group consisting of R132C, R132H, R132L, R132G, and R132S, the method comprising administering to the patient in need thereof a pharmaceutical composition comprising a total of 150 mg of a pharmaceutically acceptable solid form of 5-{[(1S)-1-(6-chloro-2-oxo-1,2-dihydroquinolin-3-yl)ethyl]amino}-1-methyl-6-oxo-1,6-dihydropyridine-2-carbonitrile, twice per day on consecutive days for a course of treatment comprising 6 months.

32. The method of embodiment 31, wherein the patient is diagnosed as having an IDH-1 mutation in a cell from the patient using a next-generation sequencing (NGS)-based tumor genotyping assay.

33. The method of any one of embodiments 31-32, wherein the pharmaceutical composition is administered to the patient every 12 hours.

34. The method of any one of embodiments 31-33, wherein Compound 1 in the pharmaceutical composition has the solid form obtained from Example 1.

35. A method of treating a chrondrosarcoma cancer having an IDH-1 mutation in an adult patient, the method comprising administering to the patient in need thereof a pharmaceutical composition comprising a total of 150 mg of a pharmaceutically acceptable solid form of 5-{[(1S)-1-(6-chloro-2-oxo-1,2-dihydroquinolin-3-yl)ethyl]amino}-1-methyl-6-oxo-1,6-dihydropyridine-2-carbonitrile, twice per day on consecutive days for a course of treatment comprising 6 months.

36. The method of embodiment 35, wherein the patient is diagnosed as having an IDH-1 mutation in a cell from the patient using a next-generation sequencing (NGS)-based tumor genotyping assay.

37. The method of any one of embodiments 35-36, wherein the pharmaceutical composition is administered to the patient every 12 hours.

38. The method of any one of embodiments 35-37, wherein Compound 1 in the pharmaceutical composition has the solid form obtained from Example 1.

The present disclosure also contemplates, among other things, the following numbered embodiments:

1. A method of treating a patient diagnosed with a non-CNS solid tumor harboring a cancer cell with an IDH1 R132 mutation, the method comprising administering to the patient in need thereof a therapeutically effective amount of Compound 1 as a single agent.

2. A method of treating a patient diagnosed with glioma harboring a cancer cell with an IDH1 R132 mutation, the method comprising administering to the patient in need thereof a therapeutically effective amount Compound 1 in combination with a therapeutically effective amount of azacitidine.

3. A method of treating a patient diagnosed with a chondrosarcoma cancer harboring a cancer cell with an IDH1 R132 mutation, the method comprising administering to the patient in need thereof a therapeutically effective amount of Compound 1 in combination with a therapeutically effective amount of azacitidine.

4. A method of treating a patient diagnosed with a hepatobiliary cancer harboring a cancer cell with an IDH1 R132 mutation, the method comprising administering to the patient in need thereof a therapeutically effective amount of Compound 1 in combination with a therapeutically effective amount of a PD-1 inhibitor.

5. A method of treating a patient diagnosed with an intrahepatic cholangiocarcinoma cancer harboring a cancer cell with an IDH1 R132 mutation, the method comprising administering to the patient in need thereof a therapeutically effective amount of Compound 1 in combination with a therapeutically effective amount of a gemcitabine and cisplatin chemotherapy.

6. The method of any one of embodiments 1-5, wherein Compound 1 is administered at a dose of 150 mg taken orally twice daily.

7. The method of any one of embodiments 1-6, wherein Compound 1 is orally administered as the solid form obtained from Example 1.

8. The method of any one of embodiments 1-7, further comprising the steps of:
   a. selecting a patient diagnosed with the cancer harboring an IDH1 mutation;
   b. administering Compound 1 to the selected patient from step (a) at a starting dose of 150 mg taken orally twice daily for a treatment cycle of 28 consecutive days.

9. A method of treating a solid tumor or CNS cancer having an IDH1 mutation in an adult patient, the method comprising administering to the patient in need thereof a pharmaceutical composition comprising a total of 150 mg of a pharmaceutically acceptable solid form of 5-{[(1S)-1-(6-chloro-2-oxo-1,2-dihydroquinolin-3-yl)ethyl]amino}-1-methyl-6-oxo-1,6-dihydropyridine-2-carbonitrile obtained from Example 1, twice per day on consecutive days for a 28 day treatment cycle.

10. The method of any one of embodiments 1-9, wherein the cancer does not harbor a IDH2 mutation.

11. The method of any one of embodiments 1-10, wherein the cancer does not harbor a IDH2 mutation selected from the group consisting of: IDH2 R172K and IDH2 R140Q.

12. The method of any one of embodiments 1-11, comprising the step of detecting the IDH1 mutation in a cell from the patient using a next-generation sequencing (NGS)-based tumor genotyping assay.

13. The method of any one of embodiments 1-12, wherein administration of Compound 1 to the patient results in a decreased 2-hydroxyglutarate (2-HG) levels in the blood of the patient after the first 15 consecutive days of treatment of the patient with Compound 1.

14. The method of any one of embodiments 1-13, wherein the method comprises administering 150 mg of Compound 1 to the patient in the solid form obtained from the method of Example 1.

15. The method of any one of embodiments 1-14, wherein the method comprises administering 150 mg of Compound 1 to the patient twice daily throughout a course of treatment.

16. The method of embodiment 15, wherein the course of treatment is at least 15 consecutive days.

17. The method of any one of embodiments 1-16, wherein the Compound 1 is administered to the patient once every 12 hours on consecutive days throughout a course of treatment.

18. The method of any one of embodiments 1-17, wherein the Compound 1 is administered to the patient throughout a course of treatment of at least 4 months.

19. The method of any one of embodiments 1-17, wherein the Compound 1 is administered to the patient throughout a course of treatment of at least 6 months.

20. A method of treating a patient diagnosed with a cancer selected from the group consisting of: glioma, chondrosarcoma, hepatobiliary, and intrahepatic cholangiocarcinoma, the cancer harboring an IDH1 R132 mutation, the method comprising administering to the patient in need thereof a therapeutically effective amount of a mIDH1 Inhibitor Therapy throughout a Course of Treatment of at least one 28-day treatment cycle, the mIDH1 Inhibitor Therapy consisting of a. Compound 1 in combination with azacitidine for the patient diagnosed with glioma or chondrosarcoma cancer; or
b. Compound 1 in combination with a PD-1 inhibitor for the patient diagnosed with hepatobiliary cancer; or
c. Compound 1 in combination with gemcitabine and cisplatin chemotherapy for the patient diagnosed with intrahepatic cholangiocarcinoma.
21. The method of embodiment 20, wherein Compound 1 is administered at a dose of 150 mg BID.
22. The method of any one of embodiments 20-21, wherein the PD-1 inhibitor is nivolumab.
23. The method of any one of embodiments 20-22, wherein the nivolumab is administered at a dose of 240 mg every 2 weeks or 480 mg every 4 weeks.
24. The method of any one of embodiments 20-23, wherein the azacitidine is administered at a dose of 75 mg/m$^2$, SC, d1-7, q4 wk throughout the Course of Treatment.
25. The method of any one of embodiments 20-24, wherein the Course of Treatment is at least 4 months.
26. The method of any one of embodiments 20-25, wherein the Course of Treatment is at least 6 months.
27. The method of any one of embodiments 1-26, wherein the Compound 1 is administered as an oral dosage form obtained from Example 1.

The present disclosure also contemplates, among other things, the following numbered embodiments:
1. A method of treating a patient diagnosed with a chondrosarcoma cancer harboring a cancer cell with an IDH1 R132 mutation, the method comprising administering to the patient in need thereof a therapeutically effective amount of Compound 1 in combination with a therapeutically effective amount of azacitidine.
2. The method of embodiment 1, wherein Compound 1 is administered at a dose of 150 mg taken orally twice daily.
3. The method of any one of embodiments 1-2, wherein Compound 1 is orally administered as the solid form obtained from Example 1.
4. The method of any one of embodiments 1-3, further comprising the steps of:
a. selecting a patient diagnosed with the cancer harboring an IDH1 mutation;
b. administering Compound 1 to the selected patient from step (a) at a starting dose of 150 mg taken orally twice daily for a treatment cycle of 28 consecutive days.
5. The method of any one of embodiments 1-4, wherein the cancer does not harbor a IDH2 mutation.
6. The method of any one of embodiments 1-5, wherein the cancer does not harbor a IDH2 mutation selected from the group consisting of: IDH2 R172K and IDH2 R140Q.
7. The method of any one of embodiments 1-6, comprising the step of detecting the IDH1 mutation in a cell from the patient using a next-generation sequencing (NGS)-based tumor genotyping assay.
8. The method of any one of embodiments 1-7, wherein administration of Compound 1 to the patient results in a decreased 2-hydroxyglutarate (2-HG) levels in the blood of the patient after the first 15 consecutive days of treatment of the patient with Compound 1.
9. The method of any one of embodiments 1-8, wherein the method comprises administering 150 mg of Compound 1 to the patient in the solid form obtained from the method of Example 1.
10. The method of any one of embodiments 1-9, wherein the method comprises administering 150 mg of Compound 1 to the patient twice daily throughout a course of treatment.
11. The method of embodiment 10, wherein the course of treatment is at least 15 consecutive days.
12. The method of any one of embodiments 1-11, wherein the Compound 1 is administered to the patient once every 12 hours on consecutive days throughout a course of treatment.
13. The method of any one of embodiments 1-12, wherein the Compound 1 is administered to the patient throughout a course of treatment of at least 4 months.
14. The method of any one of embodiments 1-12, wherein the Compound 1 is administered to the patient throughout a course of treatment of at least 6 months.
15. A method of treating a patient diagnosed with a cancer, wherein the cancer is chondrosarcoma, the cancer harboring an IDH1 R132 mutation, the method comprising administering to the patient in need thereof a therapeutically effective amount of a mIDH1 Inhibitor Therapy throughout a Course of Treatment of at least one 28-day treatment cycle, the mIDH1 Inhibitor Therapy consisting of Compound 1 in combination with azacitidine for the patient diagnosed with glioma or chondrosarcoma cancer.
16. The method of embodiment 15, wherein Compound 1 is administered at a dose of 150 mg BID.
17. The method of any one of embodiments 15-16, wherein the azacitidine is administered at a dose of 75 mg/m$^2$, SC, d1-7, q4 wk throughout the Course of Treatment.
18. The method of any one of embodiments 15-17, wherein the Course of Treatment is at least 4 months.
19. The method of any one of embodiments 15-18, wherein the Course of Treatment is at least 6 months.
20. The method of any one of embodiments 1-19, wherein the Compound 1 is administered as an oral dosage form obtained from Example 1.

The present disclosure also contemplates, among other things, the following numbered embodiments:
1. A method of treating a patient diagnosed with an intrahepatic cholangiocarcinoma cancer harboring a cancer cell with an IDH1 R132 mutation, the method comprising administering to the patient in need thereof a therapeutically effective amount of Compound 1 in combination with a therapeutically effective amount of a gemcitabine and cisplatin chemotherapy.
2. The method of embodiment 1, wherein Compound 1 is administered at a dose of 150 mg taken orally twice daily.
3. The method of any one of embodiments 1-2, wherein Compound 1 is orally administered as the solid form obtained from Example 1.
4. The method of any one of embodiments 1-3, further comprising the steps of:
a. selecting a patient diagnosed with the cancer harboring an IDH1 mutation;
b. administering Compound 1 to the selected patient from step (a) at a starting dose of 150 mg taken orally twice daily for a treatment cycle of 28 consecutive days.
5. The method of any one of embodiments 1-4, wherein the cancer does not harbor a IDH2 mutation.
6. The method of any one of embodiments 1-5, wherein the cancer does not harbor a IDH2 mutation selected from the group consisting of: IDH2 R172K and IDH2 R140Q.
7. The method of any one of embodiments 1-6, comprising the step of detecting the IDH1 mutation in a cell from the patient using a next-generation sequencing (NGS)-based tumor genotyping assay.
8. The method of any one of embodiments 1-7, wherein administration of Compound 1 to the patient results in a decreased 2-hydroxyglutarate (2-HG) levels in the blood of the patient after the first 15 consecutive days of treatment of the patient with Compound 1.
9. The method of any one of embodiments 1-8, wherein the method comprises administering 150 mg of Compound 1 to the patient in the solid form obtained from the method of Example 1.
10. The method of any one of embodiments 1-9, wherein the method comprises administering 150 mg of Compound 1 to the patient twice daily throughout a course of treatment.
11. The method of embodiment 10, wherein the course of treatment is at least 15 consecutive days.
12. The method of any one of embodiments 1-11, wherein the Compound 1 is administered to the patient once every 12 hours on consecutive days throughout a course of treatment.
13. The method of any one of embodiments 1-12, wherein the Compound 1 is administered to the patient throughout a course of treatment of at least 4 months.
14. The method of any one of embodiments 1-12, wherein the Compound 1 is administered to the patient throughout a course of treatment of at least 6 months.
15. A method of treating a patient diagnosed with a cancer, wherein the cancer is intrahepatic cholangiocarcinoma, the cancer harboring an IDH1 R132 mutation, the method comprising administering to the patient in need thereof a therapeutically effective amount of a mIDH1 Inhibitor Therapy throughout a Course of Treatment of at least one 28-day treatment cycle, the mIDH1 Inhibitor Therapy consisting of Compound 1 in combination with gemcitabine and cisplatin chemotherapy for the patient diagnosed with intrahepatic cholangiocarcinoma.
16. The method of embodiment 15, wherein Compound 1 is administered at a dose of 150 mg BID.
17. The method of any one of embodiments 15-16, wherein the Course of Treatment is at least 4 months.
18. The method of any one of embodiments 15-17, wherein the Course of Treatment is at least 6 months.
19. The method of any one of embodiments 1-18, wherein the Compound 1 is administered as an oral dosage form obtained from Example 1.

The present disclosure also contemplates, among other things, the following numbered embodiments:
1. A method of treating a patient diagnosed with a hepatobiliary cancer harboring a cancer cell with an IDH1 R132 mutation, the method comprising administering to the patient in need thereof a therapeutically effective amount of Compound 1 in combination with a therapeutically effective amount of a PD-1 inhibitor.
2. The method of embodiment 1, wherein Compound 1 is administered at a dose of 150 mg taken orally twice daily.
3. The method of any one of embodiments 1-2, wherein Compound 1 is orally administered as the solid form obtained from Example 1.
4. The method of any one of embodiments 1-3, further comprising the steps of:
   a. selecting a patient diagnosed with the cancer harboring an IDH1 mutation;
   b. administering Compound 1 to the selected patient from step (a) at a starting dose of 150 mg taken orally twice daily for a treatment cycle of 28 consecutive days.
5. The method of any one of embodiments 1-4, wherein the cancer does not harbor a IDH2 mutation.
6. The method of any one of embodiments 1-5, wherein the cancer does not harbor a IDH2 mutation selected from the group consisting of: IDH2 R172K and IDH2 R140Q.
7. The method of any one of embodiments 1-6, comprising the step of detecting the IDH1 mutation in a cell from the patient using a next-generation sequencing (NGS)-based tumor genotyping assay.
8. The method of any one of embodiments 1-7, wherein administration of Compound 1 to the patient results in a decreased 2-hydroxyglutarate (2-HG) levels in the blood of the patient after the first 15 consecutive days of treatment of the patient with Compound 1.
9. The method of any one of embodiments 1-8, wherein the method comprises administering 150 mg of Compound 1 to the patient in the solid form obtained from the method of Example 1.
10. The method of any one of embodiments 1-9, wherein the method comprises administering 150 mg of Compound 1 to the patient twice daily throughout a course of treatment.
11. The method of embodiment 10, wherein the course of treatment is at least 15 consecutive days.
12. The method of any one of embodiments 1-11, wherein the Compound 1 is administered to the patient once every 12 hours on consecutive days throughout a course of treatment.
13. The method of any one of embodiments 1-12, wherein the Compound 1 is administered to the patient throughout a course of treatment of at least 4 months.
14. The method of any one of embodiments 1-12, wherein the Compound 1 is administered to the patient throughout a course of treatment of at least 6 months.
15. A method of treating a patient diagnosed with a cancer, wherein the cancer is hepatobiliary cancer, the cancer harboring an IDH1 R132 mutation, the method comprising administering to the patient in need thereof a therapeutically effective amount of a mIDH1 Inhibitor Therapy throughout a Course of Treatment of at least one 28-day treatment cycle, the mIDH1 Inhibitor Therapy consisting of Compound 1 in combination with a PD-1 inhibitor for the patient diagnosed with hepatobiliary cancer.
16. The method of embodiment 15, wherein Compound 1 is administered at a dose of 150 mg BID.
17. The method of any one of embodiments 15-16, wherein the PD-1 inhibitor is nivolumab.
18. The method of any one of embodiments 15-17, wherein the nivolumab is administered at a dose of 240 mg every 2 weeks or 480 mg every 4 weeks.
19. The method of any one of embodiments 15-18, wherein the Course of Treatment is at least 4 months.
20. The method of any one of embodiments 15-19, wherein the Course of Treatment is at least 6 months.
21. The method of any one of embodiments 1-20, wherein the Compound 1 is administered as an oral dosage form obtained from Example 1.

The present disclosure also contemplates, among other things, the following numbered embodiments:
1. Use of a pharmaceutical composition comprising Compound 1, or pharmaceutically acceptable salt thereof,

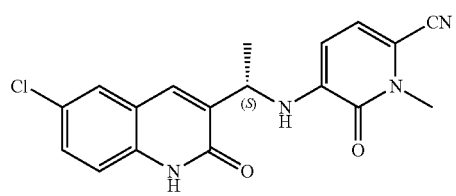

in treating a cancer harboring an isocitrate dehydrogenase-1 (IDH-1) mutation (mIDH-1) in a patient by administering a total of 300 mg of Compound 1 (or a corresponding amount in the form of a pharmaceutically acceptable salt thereof) to a patient each day during a course of treatment.

2. The use of embodiment 1, wherein a 150 mg amount of Compound 1 (or a corresponding amount in the form of a pharmaceutically acceptable salt thereof) is administered to the patient twice per day (BID) throughout the course of treatment.
3. The use of embodiment 1, wherein the cancer is a mIDH-1 form of acute myeloid leukemia.
4. The use of embodiment 3, wherein the acute myeloid leukemia is relapsed or refractory or is drug-resistant.
5. The use of embodiment 1, wherein the cancer is a mIDH-1 solid tumor.
6. The use of embodiment 1, wherein the cancer is of a mIDH-1 glioma.
7. The use of embodiment 6, wherein the mIDH-1 glioma is an advanced glioma that has recurred or progressed prior to the administration of Compound 1.
8. The use of any one of the preceding embodiments, wherein the mIDH1 is a R132X mutation.
9. The use of embodiment 8, wherein the R132X mIDH-1 mutation is selected from R132L, R132G and R132S.
10. The use of any one of the preceding embodiments, wherein the pharmaceutical composition comprising Compound 1 or a pharmaceutically acceptable salt thereof is orally administered to the patient.
11. The use of any one of the preceding embodiments, wherein Compound 1, (or a corresponding amount in the form of a pharmaceutically acceptable salt thereof) is administered as a single agent for the treatment of the cancer harboring the IDH-1 mutation.
12. The use of any of the preceding embodiments, wherein the course of treatment is at least 15 consecutive days to reach a steady state blood concentration of Compound 1 (or a corresponding amount in the form of a pharmaceutically acceptable salt thereof) in the patient.
13. The use of any one of the preceding embodiments, wherein the course of treatment is at least 6 months.
14. The use of any one of the preceding embodiments, wherein the pharmaceutical composition comprises Compound 1 in a Type A solid form characterized by a reflection X-ray powder diffraction (XRPD) pattern comprising characteristic peaks at 6.3, 12.8, 13.8, 23.6, and 27.8 degrees ±0.2° 2θ.
15. The use of any one of the preceding embodiments, wherein the pharmaceutical composition comprises the following formulation for oral administration: (a) Type A solid form of Compound 1 in a relative weight of about 33, (b) a microcrystalline cellulose in a relative weight of about 61, (c) a croscarmellose sodium in a relative weight of about 5 and a magnesium stearate in a relative weight of about 1;
wherein the Type A solid form of Compound 1 is characterized by a reflection X-ray powder diffraction (XRPD) pattern comprising characteristic peaks at 6.3, 12.8, 13.8, 23.6, and 27.8 degrees ±0.2° 2θ.

The present disclosure also contemplates, among other things, the following numbered embodiments:
1. A pharmaceutical composition comprising Compound 1:

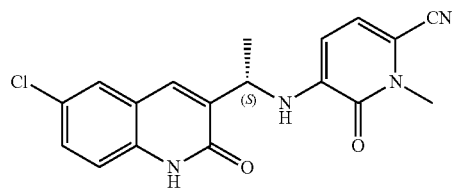

or pharmaceutically acceptable salt thereof, for use in treating a patient diagnosed with a form of cancer harboring an isocitrate dehydrogenase-1 (IDH-1) mutation (mIDH-1) by administering a total of 300 mg of Compound 1 (or a corresponding amount in the form of a pharmaceutically acceptable salt thereof) to the patient each day during a course of treatment.
2. The pharmaceutical composition of embodiment 1, wherein a 150 mg amount of Compound 1 (or a corresponding amount in the form of a pharmaceutically acceptable salt thereof) is administered to the patient twice per day (BID) throughout the course of treatment.
3. The pharmaceutical composition of embodiment 1, wherein the cancer is a mIDH-1 form of acute myeloid leukemia.
4. The pharmaceutical composition of embodiment 3, wherein the acute myeloid leukemia is relapsed or refractory or is drug-resistant.
5. The pharmaceutical composition of embodiment 1, wherein the cancer is a mIDH-1 solid tumor.
6. The pharmaceutical composition of embodiment 1, wherein the cancer is of a mIDH-1 glioma.
7. The pharmaceutical composition of embodiment 6, wherein the mIDH-1 glioma is an advanced glioma that has recurred or progressed prior to the administration of Compound 1.
8. The pharmaceutical composition of any one of the preceding embodiments, wherein the mIDH1 is a R132X mutation.
9. The pharmaceutical composition of embodiment 8, wherein the R132X mIDH-1 mutation is selected from R132L, R132G and R132S.
10. The pharmaceutical composition of any one of the preceding embodiments, wherein the pharmaceutical composition comprising Compound 1 or a pharmaceutically acceptable salt thereof is orally administered to the patient.
11. The pharmaceutical composition of any one of the preceding embodiments, wherein Compound 1, (or a corresponding amount in the form of a pharmaceutically acceptable salt thereof) is administered as a single agent for the treatment of the cancer harboring the IDH-1 mutation.
12. The pharmaceutical composition of any of the preceding embodiments, wherein the course of treatment is at least 15 consecutive days to reach a steady state blood concentration of Compound 1 (or a corresponding amount in the form of a pharmaceutically acceptable salt thereof) in the patient.
13. The pharmaceutical composition of any one of the preceding embodiments, wherein the course of treatment is at least 6 months.

14. The pharmaceutical composition of any one of the preceding embodiments, wherein the pharmaceutical composition comprises Compound 1 in a Type A solid form characterized by a reflection X-ray powder diffraction (XRPD) pattern comprising characteristic peaks at 6.3, 12.8, 13.8, 23.6, and 27.8 degrees ±0.2° 2θ.
15. The pharmaceutical composition of any one of the preceding embodiments, wherein the pharmaceutical composition comprises the following formulation for oral administration: (a) Type A solid form of Compound 1 in a relative weight of about 33, (b) a microcrystalline cellulose in a relative weight of about 61, (c) a croscarmellose sodium in a relative weight of about 5 and a magnesium stearate in a relative weight of about 1; wherein the Type A solid form of Compound 1 is characterized by a reflection X-ray powder diffraction (XRPD) pattern comprising characteristic peaks at 6.3, 12.8, 13.8, 23.6, and 27.8 degrees ±0.2° 2θ.

The present disclosure also contemplates, among other things, the following numbered embodiments:

1. A method of treating a patient diagnosed with a form of cancer harboring a R132X IDH1 mutation, the method comprising administering to the patient in need thereof a total of 150 mg of the compound of Formula (1) twice per day (BID)

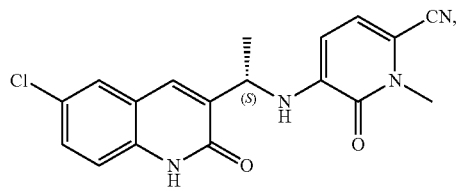

2. The method of embodiment 1 above, wherein the R132X IDH1 mutation is selected from the group consisting of: R132H and R132C IDH1 mutations.
3. The method of embodiment 1 above, wherein the R132X IDH1 mutation is selected from the group consisting of: R132S, R132G, and R132L IDH1 mutations.
4. The method of any one of the enumerated embodiments above, wherein the compound of Formula (1) is orally administered to the patient.
5. The method of any one of the enumerated embodiments above, further comprising administering a total of 150 mg BID of the compound of Formula (1) to the patient throughout a course of treatment of at least 15 consecutive days.
6. The method of embodiment 5 above, further comprising administering a total of 150 mg BID of the compound of Formula (1) to the patient on consecutive days throughout a course of treatment of between 15 days and 6 months.
7. The method of embodiment 5 above, further comprising administering a total of 150 mg BID of the compound of Formula (1) to the patient on consecutive days throughout a 6 month course of treatment.
8. The method of any one of the enumerated embodiments 1-7 above, wherein the compound of Formula (1) is administered to the patient in an oral unit dosage form.
9. A method of treating a patient diagnosed with acute myeloid leukemia (AML) having an IDH1 mutation, the method comprising administering to the patient in need thereof a combination of azacitidine and the compound of Formula (1),

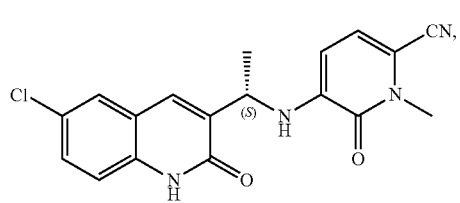

wherein a total of 150 mg of the compound of Formula (1) is administered to the patient twice per day (BID) each day, and the azacitidine is administered to the patient at a total dose of 75 mg/m² each day for 7 consecutive days beginning at the start of each treatment cycle, followed 21 consecutive days without administration of the azacitidine to the patient.

10. The method of embodiment 9 above, wherein the acute myeloid leukemia is relapsed or refractory or is drug-resistant.
11. The method of any one of the embodiments 9-10 above, wherein the IDH1 mutation is a R132X IDH1 mutation.
12. The method of any one of the embodiments 9-11 above, wherein the R132X IDH1 mutation is selected from the group consisting of: R132H and R132C IDH1 mutations.
13. The method of any one of the embodiments 9-11 above, wherein the R132X IDH1 mutation is selected from the group consisting of: R132S, R132G, and R132L IDH1 mutations.
14. The method of any one of the embodiments 9-13 above, further comprising administering a total of 150 mg BID of the compound of Formula (1) to the patient on consecutive days throughout a course of treatment of between 15 days and 6 months.
15. The method of any one of the embodiments 9-13 above, further comprising administering a total of 150 mg BID of the compound of Formula (1) to the patient on consecutive days throughout a course of treatment of at least 15 days.
16. The method of any one of the embodiments 9-13 above, further comprising administering a total of 150 mg BID of the compound of Formula (1) to the patient on consecutive days throughout a course of treatment of at least 6 months.
17. A method of treating a patient diagnosed with myelodysplastic syndrome (MDS) having an IDH1 mutation, the method comprising administering to the patient in need thereof a combination of azacitidine and the compound of Formula (1),

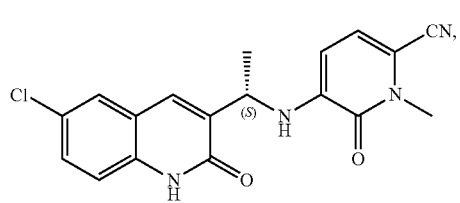

wherein a total of 150 mg of the compound of Formula (1) is administered to the patient twice per day (BID) each day, and the azacitidine is administered to the patient at a total dose of 75 mg/m² each day for 7 consecutive days beginning at the start of each treatment cycle, followed 21 consecutive days without administration of the azacitidine to the patient.
18. The method of embodiment 17 above, wherein the IDH1 mutation is a R132X IDH1 mutation.
19. The method of embodiment 18 above, wherein the R132X IDH1 mutation is selected from the group consisting of: R132H and R132C IDH1 mutations.
20. The method of embodiment 18 above, wherein the R132X IDH1 mutation is selected from the group consisting of: R132S, R132G, and R132L IDH1 mutations.
21. The method of any one of the embodiments 17-20 above, further comprising administering a total of 150 mg BID of the compound of Formula (1) to the patient on consecutive days throughout a course of treatment of between 15 days and 6 months.
22. The method of any one of the embodiments 17-20 above, further comprising administering a total of 150 mg BID of the compound of Formula (1) to the patient on consecutive days throughout a course of treatment of at least 15 days.
23. The method of any one of the embodiments 17-20 above, further comprising administering a total of 150 mg BID of the compound of Formula (1) to the patient on consecutive days throughout a course of treatment of at least 6 months.
24. A method of treating a patient diagnosed with myelodysplastic syndrome (MDS) having an IDH1 mutation, the method comprising administering to the patient in need thereof the compound of Formula (1),

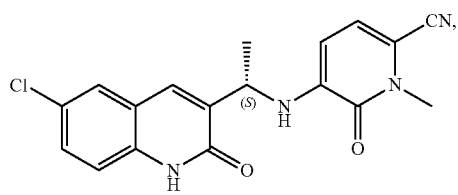

wherein a total of 150 mg of the compound of Formula (1) is administered to the patient twice per day (BID) each day.
25. The method of embodiment 24 above, wherein the acute myeloid leukemia is relapsed or refractory or is drug-resistant.
26. The method of any one of the embodiments 24-25 above, wherein the IDH1 mutation is a R132X IDH1 mutation.
27. The method of embodiment 26 above, wherein the R132X IDH1 mutation is selected from the group consisting of: R132H and R132C IDH1 mutations.
28. The method of embodiment 26 above, wherein the R132X IDH1 mutation is selected from the group consisting of: R132S, R132G, and R132L IDH1 mutations.
29. The method of any one of the embodiments 24-28 above, further comprising administering a total of 150 mg BID of the compound of Formula (1) to the patient on consecutive days throughout a course of treatment of between 15 days and 6 months.
30. The method of any one of the embodiments 24-28 above, further comprising administering a total of 150 mg BID of the compound of Formula (1) to the patient on consecutive days throughout a course of treatment of at least 15 days.
31. The method of any one of the embodiments 24-28 above, further comprising administering a total of 150 mg BID of the compound of Formula (1) to the patient on consecutive days throughout a course of treatment of at least 6 months.
32. A method of treating a patient diagnosed with glioma having an IDH1 mutation, wherein the method comprises administering to the patient in need thereof the compound of Formula (1),

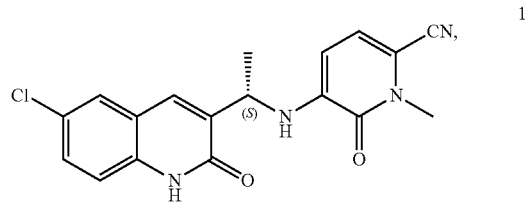

wherein a total of 150 mg of the compound of Formula (1) is administered to the patient twice per day (BID) each day.
33. The method of any one of the embodiments 32 above, wherein the IDH1 mutation is a R132X IDH1 mutation.
34. The method of embodiment 33 above, wherein the R132X IDH1 mutation is selected from the group consisting of: R132H and R132C IDH1 mutations.
35. The method of embodiment 34 above, wherein the R132X IDH1 mutation is selected from the group consisting of: R132S, R132G, and R132L IDH1 mutations.
36. The method of any one of the embodiments 32-35 above, further comprising administering a total of 150 mg BID of the compound of Formula (1) to the patient on consecutive days throughout a course of treatment of between 15 days and 6 months.
37. The method of any one of the embodiments 32-35 above, further comprising administering a total of 150 mg BID of the compound of Formula (1) to the patient on consecutive days throughout a course of treatment of at least 15 days.
38. The method of any one of the embodiments 32-35 above, further comprising administering a total of 150 mg BID of the compound of Formula (1) to the patient on consecutive days throughout a course of treatment of at least 6 months.
39. A method of treating a patient diagnosed with chondrosarcoma having an IDH1 mutation, wherein the method comprises administering to the patient in need thereof the compound of Formula (1),

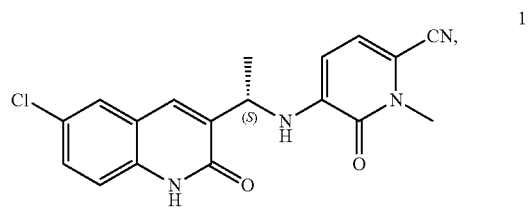

wherein a total of 150 mg of the compound of Formula (1) is administered to the patient twice per day (BID) each day.
40. The method of any one of the embodiments 39 above, wherein the IDH1 mutation is a R132X IDH1 mutation.
41. The method of embodiment 40 above, wherein the R132X IDH1 mutation is selected from the group consisting of: R132H and R132C IDH1 mutations.

42. The method of embodiment 40 above, wherein the R132X IDH1 mutation is selected from the group consisting of: R132S, R132G, and R132L IDH1 mutations.

43. The method of any one of the embodiments 39-42 above, further comprising administering a total of 150 mg BID of the compound of Formula (1) to the patient on consecutive days throughout a course of treatment of between 15 days and 6 months.

44. The method of any one of the embodiments 39-42 above, further comprising administering a total of 150 mg BID of the compound of Formula (1) to the patient on consecutive days throughout a course of treatment of at least 15 days.

45. The method of any one of the embodiments 39-42 above, further comprising administering a total of 150 mg BID of the compound of Formula (1) to the patient on consecutive days throughout a course of treatment of at least 6 months.

46. A method of treating a patient diagnosed with hepatobiliary cholangiocarcinoma having an IDH1 mutation, wherein the method comprises administering to the patient in need thereof the compound of Formula (1),

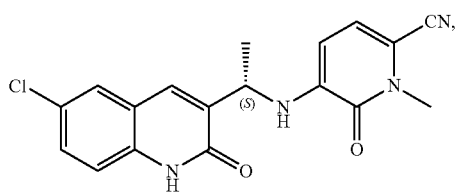

wherein a total of 150 mg of the compound of Formula (1) is administered to the patient twice per day (BID) each day.

47. The method of embodiment 46 above, wherein the IDH1 mutation is a R132X IDH1 mutation.

48. The method of embodiment 47 above, wherein the R132X IDH1 mutation is selected from the group consisting of: R132H and R132C IDH1 mutations.

49. The method of embodiment 47 above, wherein the R132X IDH1 mutation is selected from the group consisting of: R132S, R132G, and R132L IDH1 mutations.

50. The method of any one of the embodiments 46-49 above, further comprising administering a total of 150 mg BID of the compound of Formula (1) to the patient on consecutive days throughout a course of treatment of between 15 days and 6 months.

51. The method of any one of the embodiments 46-49 above, further comprising administering a total of 150 mg BID of the compound of Formula (1) to the patient on consecutive days throughout a course of treatment of at least 15 days.

52. The method of any one of the embodiments 46-49 above, further comprising administering a total of 150 mg BID of the compound of Formula (1) to the patient on consecutive days throughout a course of treatment of at least 6 months.

53. A method of treating a patient diagnosed with intrahepatic cholangiocarcinoma having an IDH1 mutation, wherein the method comprises administering to the patient in need thereof the compound of Formula (1),

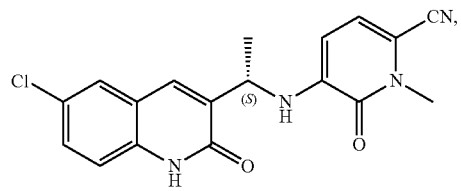

wherein a total of 150 mg of the compound of Formula (1) is administered to the patient twice per day (BID) each day.

54. The method of embodiment 53 above, wherein the IDH1 mutation is a R132X IDH1 mutation.

55. The method of embodiment 54 above, wherein the R132X IDH1 mutation is selected from the group consisting of: R132H and R132C IDH1 mutations.

56. The method of embodiment 54 above, wherein the R132X IDH1 mutation is selected from the group consisting of: R132S, R132G, and R132L IDH1 mutations.

57. The method of any one of the embodiments 53-56 above, further comprising administering a total of 150 mg BID of the compound of Formula (1) to the patient on consecutive days throughout a course of treatment of between 15 days and 6 months.

58. The method of any one of the embodiments 53-56 above, further comprising administering a total of 150 mg BID of the compound of Formula (1) to the patient on consecutive days throughout a course of treatment of at least 15 days.

59. The method of any one of the embodiments 53-56 above, further comprising administering a total of 150 mg BID of the compound of Formula (1) to the patient on consecutive days throughout a course of treatment of at least 6 months.

60. A method of treating a patient diagnosed with glioma having an IDH1 mutation, wherein the method comprises administering to the patient in need thereof a combination of azacitidine and the compound of Formula (1),

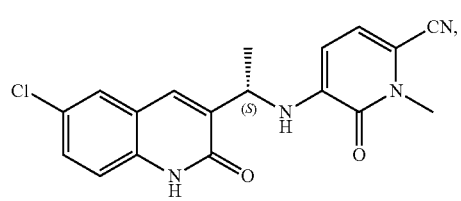

wherein a total of 150 mg of the compound of Formula (1) is administered to the patient twice per day (BID) each day, and the azacitidine is administered to the patient at a total dose of 75 mg/m$^2$ each day for 7 consecutive days beginning at the start of each treatment cycle, followed 21 consecutive days without administration of the azacitidine to the patient.

61. The method of embodiment 60 above, wherein the IDH1 mutation is a R132X IDH1 mutation.

62. The method of embodiment 61 above, wherein the R132X IDH1 mutation is selected from the group consisting of: R132H and R132C IDH1 mutations.

63. The method of embodiment 61 above, wherein the R132X IDH1 mutation is selected from the group consisting of: R132S, R132G, and R132L IDH1 mutations.

64. The method of any one of the embodiments 60-63 above, further comprising administering a total of 150 mg BID of the compound of Formula (1) to the patient on consecutive days throughout a course of treatment of between 15 days and 6 months.
65. The method of any one of the embodiments 60-63 above, further comprising administering a total of 150 mg BID of the compound of Formula (1) to the patient on consecutive days throughout a course of treatment of at least 15 days.
66. The method of any one of the embodiments 60-63 above, further comprising administering a total of 150 mg BID of the compound of Formula (1) to the patient on consecutive days throughout a course of treatment of at least 6 months.
67. A method of treating a patient diagnosed with chondrosarcoma having an IDH1 mutation, wherein the method comprises administering to the patient in need thereof a combination of azacitidine and the compound of Formula (1),

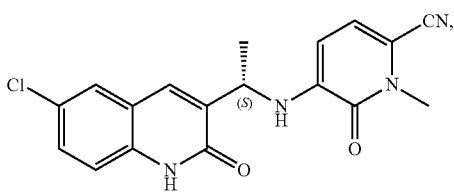

wherein a total of 150 mg of the compound of Formula (1) is administered to the patient twice per day (BID) each day, and the azacitidine is administered to the patient at a total dose of 75 mg/m² each day for 7 consecutive days beginning at the start of each treatment cycle, followed 21 consecutive days without administration of the azacitidine to the patient.
68. The method of embodiment 67 above, wherein the IDH1 mutation is a R132X IDH1 mutation.
69. The method of embodiment 68 above, wherein the R132X IDH1 mutation is selected from the group consisting of: R132H and R132C IDH1 mutations.
70. The method of embodiment 68 above, wherein the R132X IDH1 mutation is selected from the group consisting of: R132S, R132G, and R132L IDH1 mutations.
71. The method of any one of the embodiments 67-70 above, further comprising administering a total of 150 mg BID of the compound of Formula (1) to the patient on consecutive days throughout a course of treatment of between 15 days and 6 months.
72. The method of any one of the embodiments 67-70 above, further comprising administering a total of 150 mg BID of the compound of Formula (1) to the patient on consecutive days throughout a course of treatment of at least 15 days.
73. The method of any one of the embodiments 67-70 above, further comprising administering a total of 150 mg BID of the compound of Formula (1) to the patient on consecutive days throughout a course of treatment of at least 6 months.
74. A method of treating a patient diagnosed with hepatobiliary cholangiocarcinoma having an IDH1 mutation, wherein the method comprises administering to the patient in need thereof a combination of azacitidine and the compound of Formula (1),

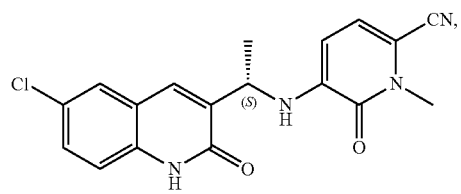

wherein a total of 150 mg of the compound of Formula (1) is administered to the patient twice per day (BID) each day, and the azacitidine is administered to the patient at a total dose of 75 mg/m² each day for 7 consecutive days beginning at the start of each treatment cycle, followed 21 consecutive days without administration of the azacitidine to the patient.
75. The method of embodiment 74 above, wherein the IDH1 mutation is a R132X IDH1 mutation.
76. The method of embodiment 75 above, wherein the R132X IDH1 mutation is selected from the group consisting of: R132H and R132C IDH1 mutations.
77. The method of embodiment 75 above, wherein the R132X IDH1 mutation is selected from the group consisting of: R132S, R132G, and R132L IDH1 mutations.
78. The method of any one of the embodiments 74-77 above, further comprising administering a total of 150 mg BID of the compound of Formula (1) to the patient on consecutive days throughout a course of treatment of between 15 days and 6 months.
79. The method of any one of the embodiments 74-77 above, further comprising administering a total of 150 mg BID of the compound of Formula (1) to the patient on consecutive days throughout a course of treatment of at least 15 days.
80. The method of any one of the embodiments 74-77 above, further comprising administering a total of 150 mg BID of the compound of Formula (1) to the patient on consecutive days throughout a course of treatment of at least 6 months.
81. A method of treating a patient diagnosed with intrahepatic cholangiocarcinoma having an IDH1 mutation, wherein the method comprises administering to the patient in need thereof a combination of azacitidine and the compound of Formula (1),

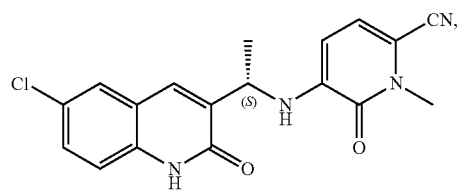

wherein a total of 150 mg of the compound of Formula (1) is administered to the patient twice per day (BID) each day, and the azacitidine is administered to the patient at a total dose of 75 mg/m² each day for 7 consecutive days beginning at the start of each treatment cycle, followed 21 consecutive days without administration of the azacitidine to the patient.
82. The method of embodiment 81 above, wherein the IDH1 mutation is a R132X IDH1 mutation.

83. The method of embodiment 82 above, wherein the R132X IDH1 mutation is selected from the group consisting of: R132H and R132C IDH1 mutations.
84. The method of embodiment 82 above, wherein the R132X IDH1 mutation is selected from the group consisting of: R132S, R132G, and R132L IDH1 mutations.
85. The method of any one of the embodiments 81-84 above, further comprising administering a total of 150 mg BID of the compound of Formula (1) to the patient on consecutive days throughout a course of treatment of between 15 days and 6 months.
86. The method of any one of the embodiments 81-84 above, further comprising administering a total of 150 mg BID of the compound of Formula (1) to the patient on consecutive days throughout a course of treatment of at least 15 days.
87. The method of any one of the embodiments 81-84 above, further comprising administering a total of 150 mg BID of the compound of Formula (1) to the patient on consecutive days throughout a course of treatment of at least 6 months.
88. The method of any one of the embodiments 1-87 above, wherein the compound of Formula (1) is administered in a crystalline form.
89. The method of any one of the embodiments 1-88 above, wherein the compound of Formula (1) is administered as a Type A crystalline form.
90. The method of any one of the embodiments 1-89 above, wherein the compound of Formula (1) is orally administered in a capsule comprising a total of 150 mg of the compound of Formula (1).
91. The method of any one of the embodiments 1-90 above, wherein the compound of Formula (1) is orally administered in multiple capsules each comprising a total of 50 mg of the compound of Formula (1).

The present disclosure enables one of skill in the relevant art to make and use the inventions provided herein in accordance with multiple and varied embodiments. Various alterations, modifications, and improvements of the present disclosure that readily occur to those skilled in the art, including certain alterations, modifications, substitutions, and improvements are also part of this disclosure. Accordingly, the foregoing description are by way of example to illustrate the discoveries provided herein.

EXAMPLES

Example 1—Synthesis of (S)-5-((1-(6-chloro-2-oxo-1,2-dihydroquinolin-3-yl)ethyl)amino)-1-methyl-6-oxo-1,6-dihydropyridine-2-carbonitrile (Compound 1)

Figure 23:
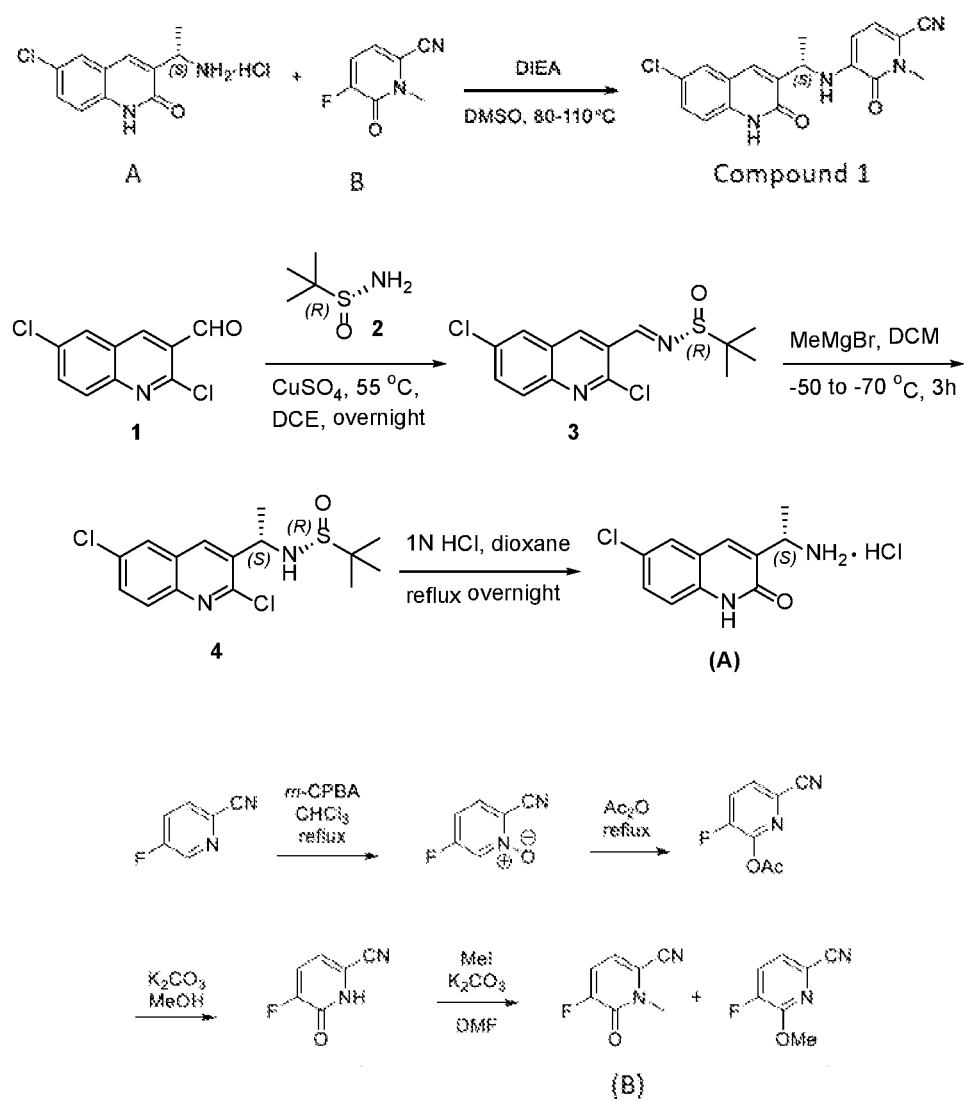
FIG. 23 is a synthetic reaction scheme for the preparation of Compound 1.

Compound 1 can be prepared in a convergent synthesis from Intermediate A and Intermediate B as shown in FIG. 23 via the nucleophilic displacement reaction under basic conditions of (S)-3-(1-aminoethyl)-6-chloroquinolin-2(1H)-one (Intermediate A) and the fluoropyridone (Intermediate B). $^1$H, $^{13}$C NMR and mass spectral data are consistent with the assigned structure. The asymmetric synthesis of Intermediate A started with the condensation of the commercially available quinoline aldehyde (1) with (R)-tert-butanesulfinamide (2) to form the chiral (R)—N-tert-butanesulfinimine (3), followed by addition of methyl magnesium bromide in dichloromethane to yield the desired product (4) as the major diastereoisomer (dr: 98:2). Cleavage of the chiral auxiliary and simultaneous hydrolysis of 2-chloroquinoline moiety under mildly acidic conditions using 1N HCl in dioxane gave Intermediate A in quantitative yield. The structure of Intermediate A was confirmed by NMR and mass spectroscopy, and the enantiomeric purity was determined by chiral SFC analysis. The (S)-stereochemistry was confirmed by X-ray co-crystal structures of several inhibitor analogs prepared from the same chiral amine intermediate bound to mIDH-1 R132H. Intermediate (B) was prepared from commercially available 5-fluoropicolinonitrile in four steps. N-oxidation of 5-fluoropicolinonitrile followed by reflux of the N-oxide in acetic anhydride gave the acetate, following work-up and purification. Solvolysis of the acetate group followed by N-methylation under standard conditions gave a mixture of N-methylated and O-methylated products (4:1). The minor O-methylated product was removed by column chromatography. NMR and mass spectral data are consistent with the structure of Intermediate Compound (B). Compound 1 (5-{[(1S)-1-(6-chloro-2-oxo-1,2-dihydroquinolin-3-yl)ethyl]amino}-1-methyl-6-oxo-1,6-dihydropyridine-2-carbonitrile) has a molecular weight of 355 with a melting point onset temperature of 251.3° C. (DSC) and peak maximum 254.1° C.

Intermediate 1: (S)-3-(1-aminoethyl)-6-chloroquinolin-2(1H)-one Hydrochloride

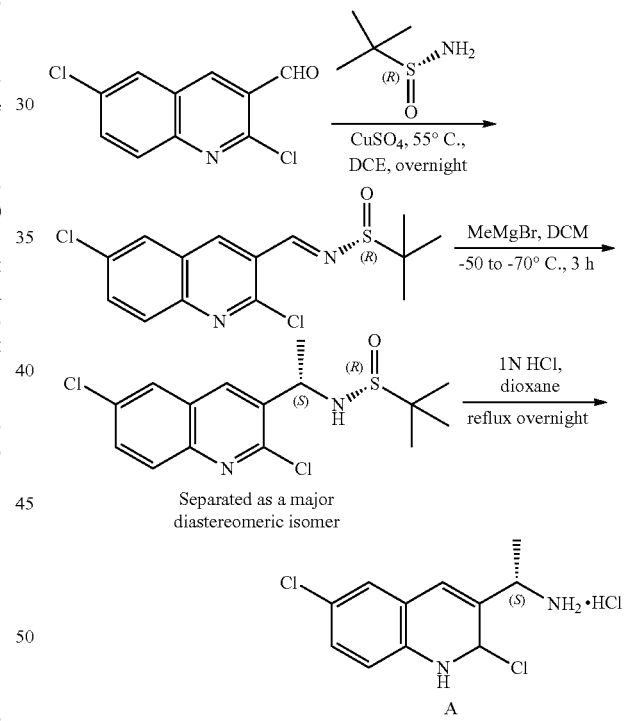

Step-1: (R,E)-N-((2,6-dichloroquinolin-3-yl)methylene)-2-methylpropane-2-sulfinamide

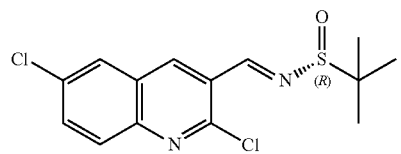

To a mixture of 2,6-dichloroquinoline-3-carbaldehyde (15.0 g, 66.37 mmol) and (R)-2-methylpropane-2-sulfinamide (8.85 g, 73.14 mmol) in 1,2-dichloroethane (150 mL) was added CuSO₄ (16.0 g, 100.25 mmol). The resulting mixture was heated to 55° C. and stirred at 55° C. overnight. After TLC and MS showed complete disappearance of starting materials, the mixture was cooled to room temperature and filtered through a pad of Celite®. The pad of Celite® was then rinsed with CH₂Cl₂. The filtrate was evaporated to dryness in vacuo and purified by SiO₂ column chromatography (0 to 25% hexanes/EtOAc) to afford the title compound, (R,E)-N-((2,6-dichloroquinolin-3-yl)methylene)-2-methylpropane-2-sulfinamide, as a yellow solid (17.7 g, 81% yield).

Step-2: (R)—N—((S)-1-(2,6-dichloroquinolin-3-yl)ethyl)-2-methylpropane-2-sulfinamide

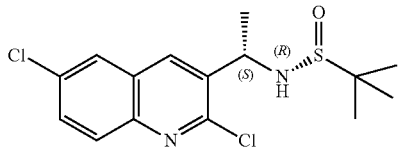

To a solution of (R,E)-N-((2,6-dichloroquinolin-3-yl)methylene)-2-methylpropane-2-sulfinamide (8.85 g, 26.88 mmol) in anhydrous CH₂Cl₂ (200 mL) at −60° C. was added dropwise MeMgBr (3M solution in diethyl ether, 13.5 mL, 40.54 mmol). The resulting reaction mixture was stirred at about −60 to −50° C. for 3 hours and then stirred at −20° C. overnight under an atmosphere of N₂. After TLC and MS showed complete disappearance of starting materials, saturated NH₄Cl (163 mL) was added at −20° C. and the resulting mixture was stirred for 10 minutes. The aqueous phase was extracted with CH₂Cl₂ (100 mL×3), dried over anhydrous Na₂SO₄, filtered, and evaporated. The residue was purified by column chromatography on an ISCO® chromatography system (SiO₂: Gold column; gradient; hexanes to 100% EtOAc) to provide the title compound, (R)—N—((S)-1-(2,6-dichloroquinolin-3-yl)ethyl)-2-methylpropane-2-sulfinamide, as a yellow solid (5.8 g, 63% yield).

Step-3: (S)-3-(1-aminoethyl)-6-chloroquinolin-2(1H)-one Hydrochloride (A)

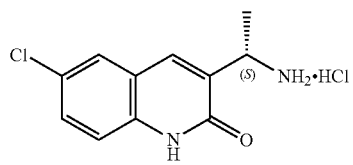

A mixture of (R)—N—((S)-1-(2,6-dichloroquinolin-3-yl)ethyl)-2-methylpropane-2-sulfinamide (6.6 g, 19.13 mmol) in 1,4-dioxane (41 mL) and 1N HCl (41 mL) was heated at reflux overnight. The solvents were evaporated in vacuo and the resulting residue was dissolved in hot water and lyophilized. The crude product was triturated with diethyl ether to afford the title compound A as a yellow solid (9.0 g, ee: 98.4%). ¹H NMR (300 MHz, DMSO-d₆): δ ppm 12.4 (br s, 1H), 8.32 (br s, 2H), 8.07 (s, 1H), 7.85 (d, J=2.2 Hz, 1H), 7.63 (dd, J1=8.8 Hz, J2=2.5 Hz, 1H), 7.40 (d, J=8.8 Hz, 1H), 4.40-4.45 (m, 1H), 1.53 (d, J=8.5 Hz, 3H). LCMS (Method 2): Rt 3.42 min, m/z 223.1 [M+H]⁺.

Intermediate 2: 5-fluoro-1-methyl-6-oxo-1,6-dihydropyridine-2-carbonitrile

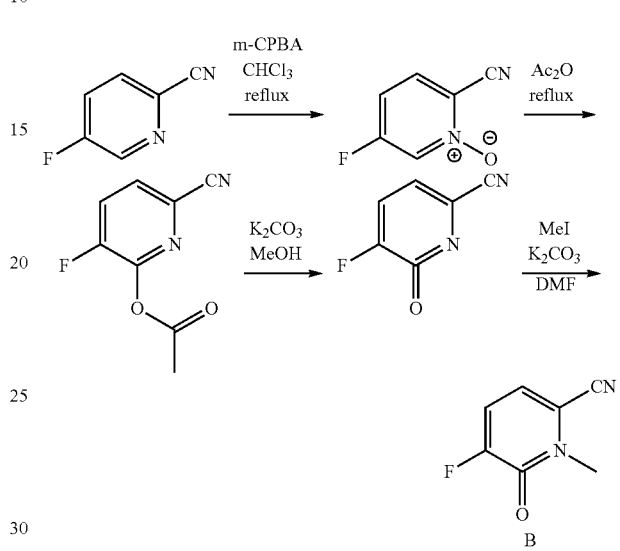

Step-1: 2-cyano-5-fluoropyridine 1-oxide

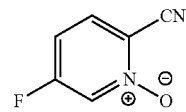

A solution of 5-fluoropicolinonitrile (7.27 g, 59.5 mmol) in CHCl₃ (60 mL) was added dropwise by addition funnel to a solution of m-CPBA (<77%, 22.00 g, 98 mmol) in CHCl₃ 160 mL). The solution was stirred at reflux for 4 days, at which time LCMS showed ~85% conversion. The sample was allowed to cool, then sodium sulfite (12.4 g, 98 mmol) was added and the sample was stirred at room temperature three hours, during which time the solution became thick with a white precipitate. The sample was diluted with DCM (300 mL) and filtered on a Buchner funnel, and the filter cake was washed with DCM (~400 mL). A white material precipitated in the filtrate. The filtrate mixture was washed with saturated aqueous NaHCO₃ (400 mL), during which the solids went into solution. The organic layer was washed with water (300 mL), then dried (MgSO₄) and filtered. Silica gel was added and the mixture was evaporated under reduced pressure. The material was chromatographed by Biotage MPLC (340 g silica gel column) with 0 to 100% EtOAc in hexanes, with isocratic elution when peaks came off to provide 2-cyano-5-fluoropyridine 1-oxide (4.28 g, 31.0 mmol, 52% yield) as a white solid. ¹H NMR (300 MHz, DMSO-d₆): δ ppm 8.85-8.93 (m, 1H), 8.23 (dd, J=9.09, 6.74 Hz, 1H), 7.53-7.64 (m, 1H). LCMS (Method 1): Rt 0.57 min., m/z 138.9 [M+H]⁺.

Step 2: 6-cyano-3-fluoropyridin-2-yl Acetate

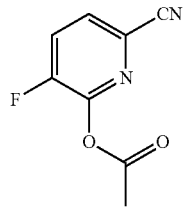

A solution of 2-cyano-5-fluoropyridine 1-oxide (4.28 g, 31.0 mmol) in acetic anhydride (40 ml, 424 mmol) was heated at reflux (150° C. bath) three days, during which the clear solution turned dark. The sample was concentrated under reduced pressure. The residue was dissolved in MeOH (30 mL) and stirred 1 hour. Silica gel was added and the solvent was evaporated under reduced pressure. The material was chromatographed by Biotage MPLC (100 g silica gel column) with 0 to 23% EtOAc in hexanes to provide 6-cyano-3-fluoropyridin-2-yl acetate (3.32 g, 18.43 mmol, 60% yield) as a clear liquid that solidified on cooling. $^1$H NMR (300 MHz, CHLOROFORM-d): δ ppm 7.65-7.75 (m, 2H), 2.42 (s, 3H). LCMS (Method 1): Rt 1.54 min., m/z 138.8 (loss of acetate).

Step 3: 5-fluoro-6-oxo-1,6-dihydropyridine-2-carbonitrile

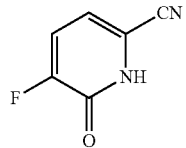

A solution of 6-cyano-3-fluoropyridin-2-yl acetate (3.32 g, 18.43 mmol) in MeOH (40 ml) was treated with potassium carbonate (5.10 g, 36.9 mmol) and stirred at room temperature for four hours. LCMS at 2 hours showed the reaction had gone to completion. The solvent was evaporated under reduced pressure. The residue was dissolved in water (100 mL) and acidified to pH ≤1 with 1M HCl. The solution was extracted with EtOAc (3×100 mL). The combined organic extracts were dried (Na$_2$SO$_4$), filtered, and evaporated under reduced pressure to provide 5-fluoro-6-oxo-1,6-dihydropyridine-2-carbonitrile (2.34 g, 16.94 mmol, 92% yield) as a white solid. $^1$H NMR (300 MHz, DMSO-d$_6$): δ ppm 12.92 (br s, 1H), 7.73 (br s, 1H), 7.43 (br s, 1H). LCMS (Method 1): Rt 0.70 min., m/z 138.9 [M+H]$^+$.

Step 4: 5-fluoro-1-methyl-6-oxo-1,6-dihydropyridine-2-carbonitrile (B)

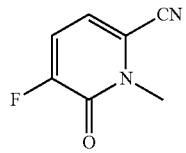

A mixture of 5-fluoro-6-oxo-1,6-dihydropyridine-2-carbonitrile (2.31 g, 16.73 mmol) and potassium carbonate (4.86 g, 35.2 mmol) in a 200 mL round bottom flask was treated with DMF (46 mL) and stirred 15 minutes. MeI (1.2 mL, 19.19 mmol) was added and the mixture was stirred at room temperature 45 minutes. The solvent was evaporated under reduced pressure. The residue was mixed with water (150 mL) and extracted with DCM (2×150 mL). The combined organic extracts were dried (MgSO$_4$), filtered, treated with silica gel, and evaporated under reduced pressure, then evaporated further at 60° C. under high vacuum. The material was chromatographed by Biotage MPLC with 0 to 35% EtOAc in hexanes, with isocratic elution at 16% EtOAc and 35% EtOAc while peaks came off. The peak that came off with 16% EtOAc was O-methylated material and was discarded. The peak that came off with 35% EtOAc provided the title compound B (1.70 g, 11.17 mmol, 67% yield) as a solid. $^1$H NMR (300 MHz, DMSO-d$_6$): δ ppm 7.53 (dd, J=9.38, 7.62 Hz, 1H), 7.18 (dd, J=7.77, 4.84 Hz, 1H), 3.60 (s, 3H). LCMS (Method 1): Rt 0.94 min., m/z 152.9 [M+H]$^+$.

Step 5: (S)-5-((1-(6-chloro-2-oxo-1,2-dihydroquinolin-3-yl)ethyl)amino)-1-methyl-6-oxo-1,6-dihydropyridine-2-carbonitrile (Compound 1)

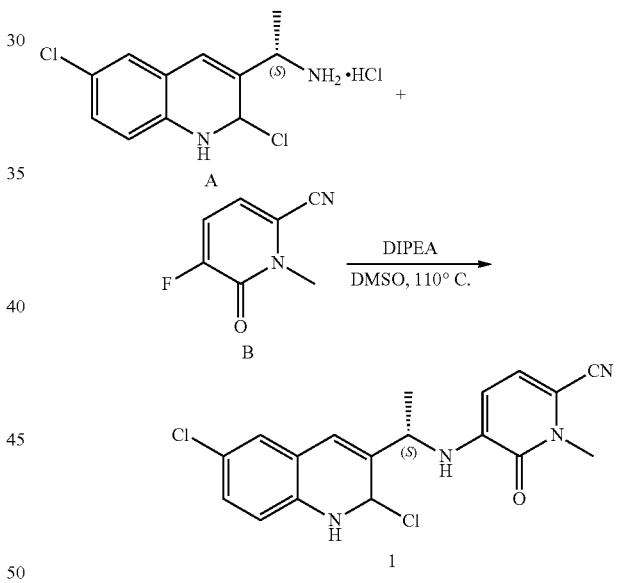

A mixture of 5-fluoro-1-methyl-6-oxo-1,6-dihydropyridine-2-carbonitrile B (1.23 g, 8.09 mmol), (S)-3-(1-aminoethyl)-6-chloroquinolin-2(1H)-one hydrochloride A (1.91 g, 7.37 mmol) and N,N-diisopropylethylamine (3.8 mL, 21.8 mmol) in anhydrous dimethyl sulfoxide (57 mL) under N$_2$ was heated to 110° C. and stirred for 6 hours. After cooling to room temperature, the mixture was partitioned between EtOAc/H$_2$O (750 mL/750 mL). The organic layer was separated, dried (Na$_2$SO$_4$) and concentrated in vacuum. The residue was purified on ISCO twice (40 g silica gel column, EtOAc/hexanes 0˜100%; 80 g silica gel column, MeOH/dichloromethane 0˜5%). The colorless fractions were combined and dichloromethane was removed under reduced pressure on rotavap until a lot of white solid precipitated out. The white solid was collected by filtration and washed with cold MeOH. It was then mixed with MeCN/H$_2$O (10 mL/25 mL) and lyophilized to afford the title Compound 1 as a white solid (790 mg). m.p. 262-264° C. $^1$H NMR (300 MHz, DMSO-d$_6$) δ: 12.07 (s, 1H), 7.75 (s, 1H), 7.73 (d, J=2.2 Hz, 1H), 7.51 (dd, J=8.6, 2.3 Hz, 1H), 7.31 (d, J=8.8 Hz, 1H), 6.97 (d, J=8.0 Hz, 1H), 6.93 (d, J=7.7 Hz, 1H), 5.95 (d, J=8.0 Hz, 1H), 4.68 (m, 1H), 3.58 (s, 3H), 1.50 (d, J=6.6 Hz, 3H). LCMS (Method 2): 100% pure @ 254 nm, Rt 10.78 min, m/z 355, 357 [M+H]+. The filtrate and the colored fractions (TLC pure) from the second ISCO were combined and treated with activated charcoal and filtered (until the filtrate is colorless). The filtrate was then concentrated under reduced pressure on rotavap to remove dichloromethane until a lot of white solid precipitated out. The white solid was collected by filtration and washed with cold MeOH. It was then mixed with MeCN/H$_2$O (10 mL/25 mL) and lyophilized to afford the title Compound 1 as a white solid (970 mg). m.p. 262-264° C. $^1$H NMR (300 MHz, DMSO-d$_6$) δ: 12.06 (s, 1H), 7.75 (s, 1H), 7.73 (d, J=2.5 Hz, 1H), 7.51 (dd, J=8.6, 2.3 Hz, 1H), 7.31 (d, J=8.8 Hz, 1H), 6.97 (d, J=8.0 Hz, 1H), 6.92 (d, J=8.0 Hz, 1H), 5.95 (d, J=8.0 Hz, 1H), 4.68 (m, 1H), 3.58 (s, 3H), 1.50 (d, J=6.9 Hz, 3H). LCMS (Method 2): 100% pure @ 254 nm, m/z 355, 357 [M+H]+. The total yield for combined two batches is 67%.

Step 6: Solid Form of (S)-5-((1-(6-chloro-2-oxo-1,2-dihydroquinolin-3-yl)ethyl)amino)-1-methyl-6-oxo-1,6-dihydropyridine-2-carbonitrile Unless otherwise indicated, the clinical trial in Examples 10-13 were performed using a pharmaceutically acceptable solid form in an oral dosage form of Compound 1 that can be obtained by the method of Step 6 of Example 1. All volumes are with respect to the quantity of Compound 1 (v/w). Compound 1 is dissolved in 18 volumes of dichloromethane. The resulting solution is then concentrated under reduced pressure to approximately 5 volumes. To the mixture is added 5 volumes of ethyl acetate. The mixture is concentrated under reduced pressure to 5 volumes. To the mixture is added an additional 5 volumes of ethyl acetate, and the mixture again concentrated under reduced pressure to 5 volumes. The mixture is diluted to 10 volumes with ethyl acetate, and the mixture stirred at room temperature for 18 hours and then cooled to 0° C. The mixture is stirred at 0° C. for 3 hours and then filtered. The solids are rinsed with ethyl acetate and dried under vacuum (counterbalanced by nitrogen) at ambient temperature.

Figure 24:
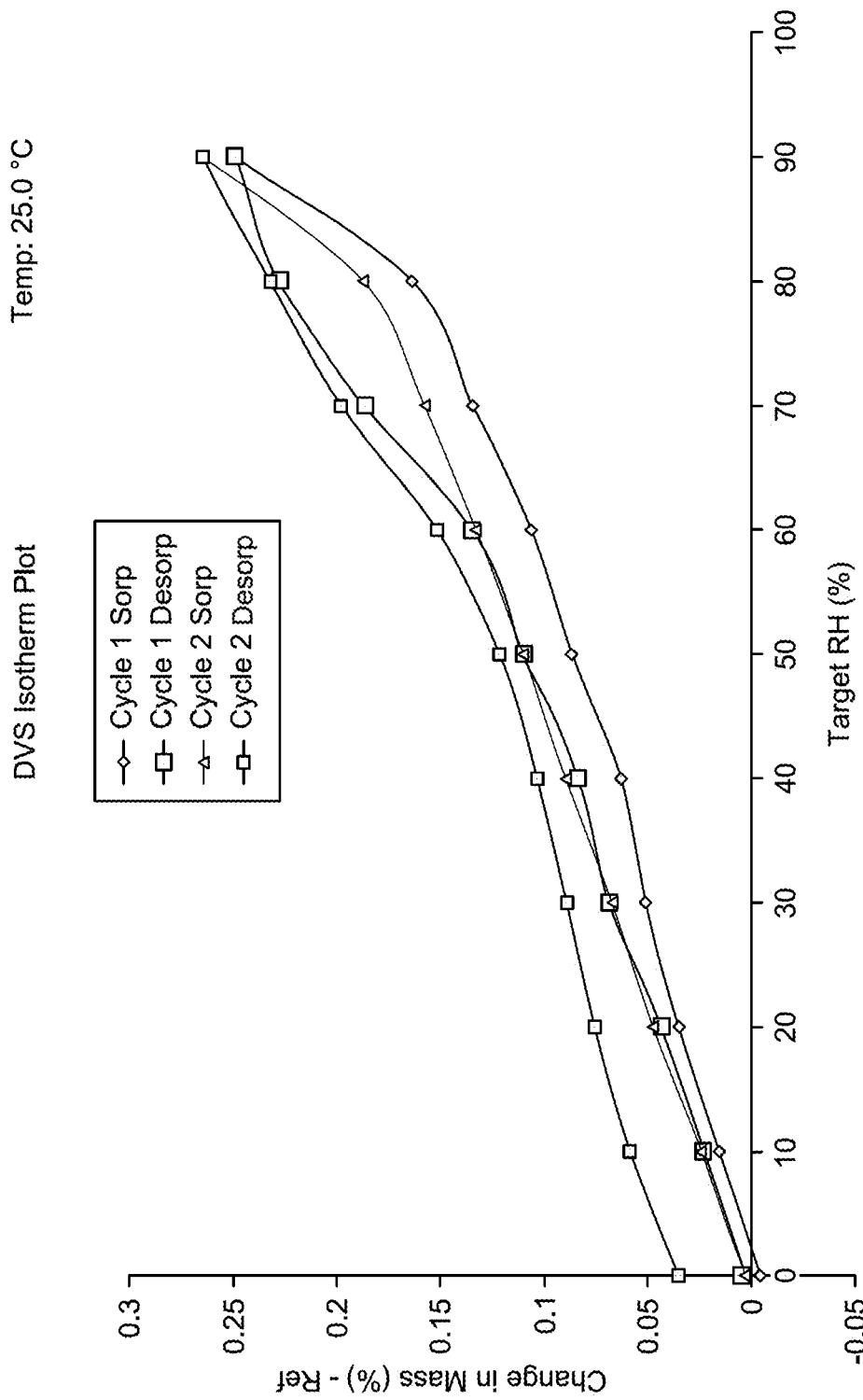
FIG. 24 depicts a dynamic vapor sorption (DVS) isotherm plot of Compound 1 Type A solid form.
Figure 25:
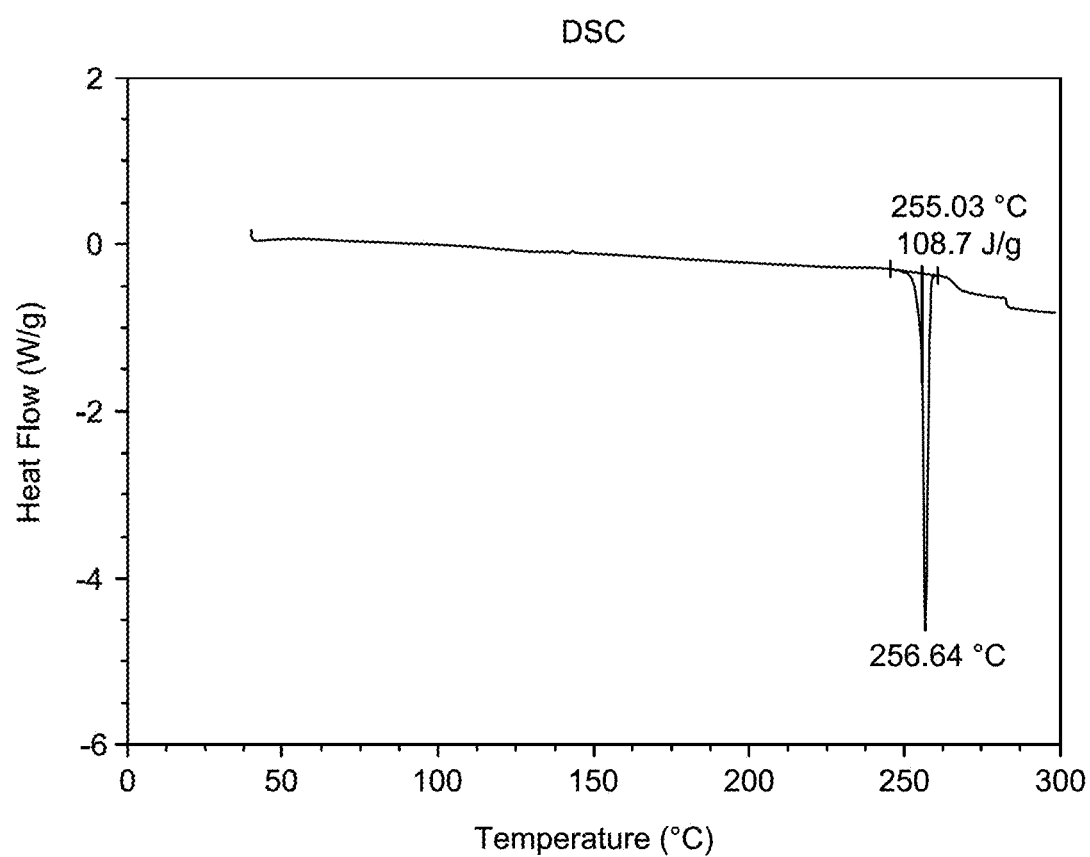
FIG. 25 depicts a differential scanning calorimetry (DSC) thermogram for Compound 1 Type A solid form.
Figure 26:
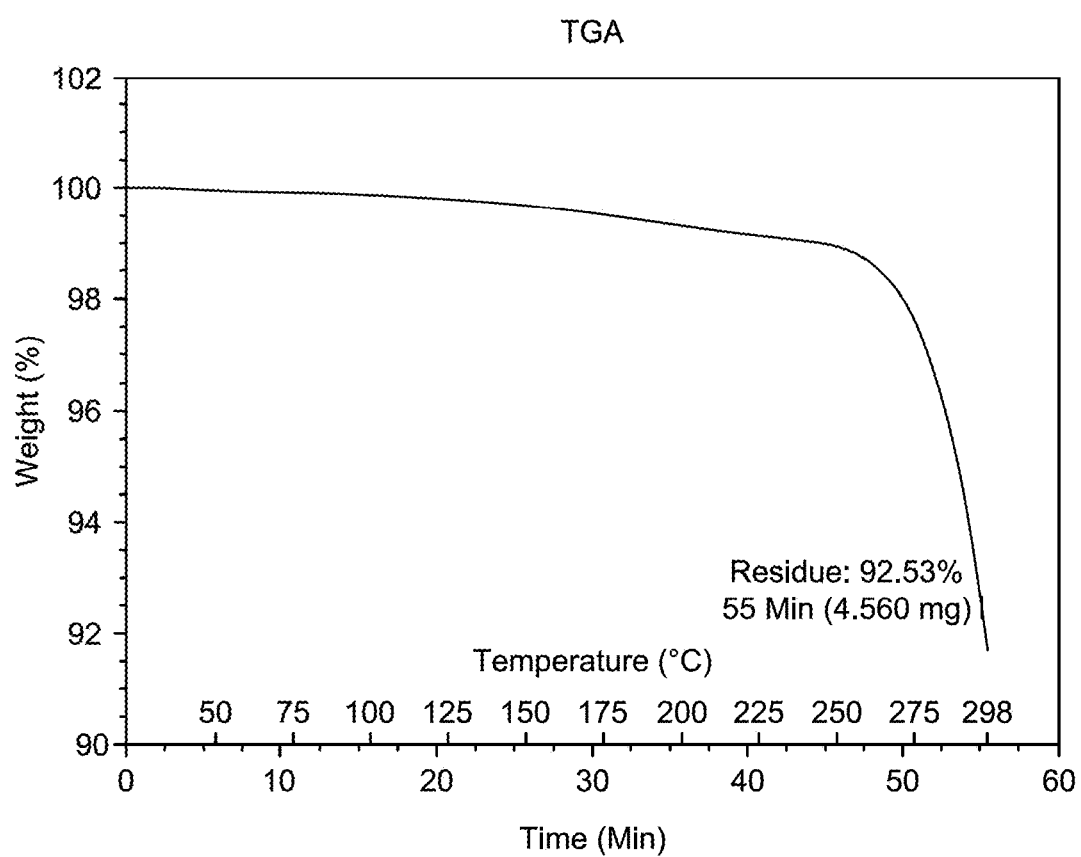
FIG. 26 depicts a thermogravimetric analysis (TGA) curve for Compound 1 Type A solid form.

The crystalline solid was determined to be the solid form of Compound 1 Type A. The DVS Isotherm of Compound 1 Type A is shown in FIG. 24. DVS shows maximum water uptake of 0.25% w/w at 25° C./90% RH, indicating Compound 1 Type A is not hygroscopic. The thermal behavior Compound 1 Type A was evaluated using DSC. An endothermic event was observed at 256.6° C. (peak max). The onset temperature and heat of fusion were 255.0° C. and 108.7 J/g respectively (FIG. 25). TGA data (FIG. 26) do not show significant release of moisture or nonaqueous residual volatiles from Compound 1 Type A.

Figure 27:
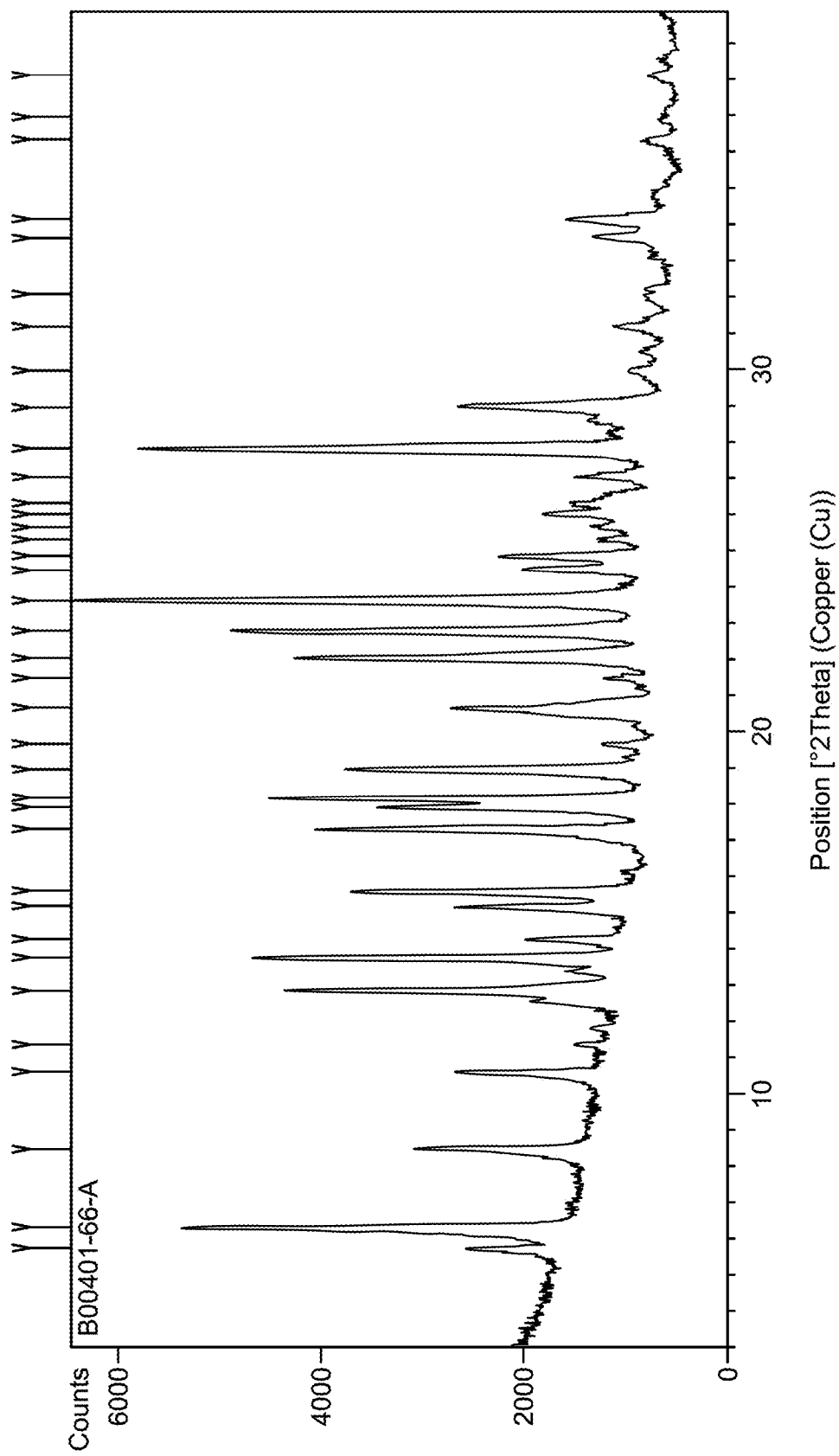
FIG. 27 depicts X-ray powder diffraction (XRPD) of Compound 1 Type A solid form.

The X-ray powder diffraction pattern of the crystalline Compound 1 Type A is depicted in FIG. 27, and the corresponding data is summarized in Table 9 below.

TABLE 9

| 2 theta ± 0.2 | d-spacing Å ± 0.2 |
|---|---|
| 5.7 | 15.4 |
| 6.3 | 14.0 |
| 8.5 | 10.4 |
| 10.6 | 8.4 |
| 11.4 | 7.8 |
| 12.8 | 6.9 |
| 13.8 | 6.4 |
| 14.2 | 6.2 |
| 15.2 | 5.8 |
| 15.6 | 5.7 |
| 17.3 | 5.1 |
| 17.9 | 5.0 |
| 18.2 | 4.9 |
| 18.9 | 4.7 |
| 19.6 | 4.5 |
| 20.6 | 4.3 |
| 21.5 | 4.1 |
| 22.0 | 4.0 |
| 22.8 | 3.9 |
| 23.6 | 3.8 |
| 24.5 | 3.6 |
| 24.8 | 3.6 |
| 25.3 | 3.5 |
| 25.6 | 3.5 |
| 26.0 | 3.4 |
| 26.3 | 3.4 |
| 27.0 | 3.3 |
| 27.8 | 3.2 |
| 28.9 | 3.1 |
| 30.0 | 3.0 |
| 31.2 | 3.0 |
| 32.1 | 2.8 |
| 33.6 | 2.7 |
| 34.1 | 2.6 |
| 36.3 | 2.5 |
| 37.0 | 2.4 |
| 38.1 | 2.4 |

Preferably, the oral dosage form of Compound 1 is a solid form designated Type A that is characterized by a reflection X-ray powder diffraction (XRPD) pattern comprising characteristic peaks at 6.3, 12.8, 13.8, 23.6, and 27.8 degrees ±0.2° 2θ. High resolution X-ray Powder Diffraction experiments were performed with Panalytical X'Pert3 Powder XRPD on a Si zero-background holder. The 2 theta position was calibrated against Panalytical 640 Si powder standard. Details of the XRPD method are listed below, with XRPD peaks reported as diffraction angles at 2 theta, with d-spacing measured in angstroms.

| Parameters for Reflection Mode | |
|---|---|
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2TH) | 3°-40° |
| Step size (°2TH) | 0.0131 |
| Scan speed (°/s) | 0.033 |

Compound 1 is preferably administered in an oral unit dosage form comprising a pharmaceutical composition that includes the following formulation: (a) Type A solid form of Compound 1 (e.g., in a relative weight of about 33), (b) a microcrystalline cellulose (e.g., in a relative weight of about 61), (c) a croscarmellose sodium (e.g., in a relative weight of about 5) and a magnesium stearate (e.g., in a relative weight of about 1). The pharmaceutical composition for oral administration can comprise Compound 1 (e.g. in a Type A solid form) with pharmaceutically acceptable excipients in a capsule or tablet. For example, a capsule may contain a total of 50 mg or 150 mg of Compound 1 in a unit dosage form. The capsule may encapsulate the pharmaceutical composition comprising Compound 1 in a relative weight of about 30-50% by weight relative to the weight of the pharmaceutical composition. In another embodiment, a GMP manufacturing batch can comprise Compound 1, optionally provided in the Type A solid form.

In particular, the Compound 1 Type A solid form can be characterized by an X-ray Powder Diffraction (XRPD), having diffractions at angles (2 theta±0.2) of 6.3, 12.8, 13.8, 23.6, and 27.8. In some embodiments, a novel Compound 1 Type A is characterized by an X-ray Powder Diffraction (XRPD), having diffractions at angles (2 theta±0.2) of 6.3, 12.8, 13.8, 23.6, and 27.8, corresponding to d-spacing (angstroms ±0.2) of 14.0, 6.9, 6.4, 3.8, and 3.2, respectively. In some embodiments, Compound 1 Type A can be identified by X-ray Powder Diffraction (XRPD), having characteristic diffractions at angles (2 theta±0.2) of 5.7, 6.3, 8.5, 10.6, 12.8, 13.8, 17.3, 22.0, 22.8, 23.6, and 27.8. In some embodiments, Compound 1 Type A can be identified by X-ray Powder Diffraction (XRPD), having characteristic diffractions at angles (2 theta}0.2) of 5.7, 6.3, 8.5, 10.6, 12.8, 13.8, 17.3, 22.0, 22.8, 23.6, and 27.8, corresponding to d-spacing (angstroms ±0.2) of 15.4, 14.0, 8.4, 6.9, 6.4, 5.1, 4.0, 3.9, 3.8, and 3.2, respectively.

In some embodiments, Compound 1 Type A solid form is characterized by a differential scanning calorimetry (DSC) endotherm having a minima at about 256.64° C. Differential Scanning Calorimetry (DSC) experiments were performed on TA Q2000 DSC from TA Instruments. Samples were heated at 10° C./min from about 20° C. to about 300° C. using dry nitrogen to purge the system. The details of the method are provided below:

| Parameters | DSC |
| --- | --- |
| Pan Type | Aluminum pan, closed |
| Temperature | RT-250° C. |
| Ramp rate | 10° C./min |
| Purge gas | $N_2$. |

Step 7: Oral Solid Dosage Form of (S)-5-((1-(6-chloro-2-oxo-1,2-dihydroquinolin-3-yl)ethyl)amino)-1-methyl-6-oxo-1,6-dihydropyridine-2-carbonitrile The oral dosage form of Compound 1 is a pharmaceutically acceptable solid form of the compound (S)-5-((1-(6-chloro-2-oxo-1,2-dihydroquinolin-3-yl)ethyl)amino)-1-methyl-6-oxo-1,6-dihydropyridine-2-carbonitrile, can be obtained using the method of Example 1 Step 6. The oral dosage form does not contain associated solvent or a counter ion. In particular, the oral dosage form of Compound 1 can be a capsule comprising drug substance (Compound 1) blended with excipients to improve powder flow and encapsulated in a Coni-Snap® hard gelatin capsule suitable for oral dosage in humans.

Example 2—Compound 1 Potently and Selectively Inhibited 2-HG Production in IDH1 R132H and IDH1 R132C Mutant Enzymes in Biochemical Assays, Compared to Wild Type IDH1 Enzyme and Mutant IDH2 Enzymes The biochemical potencies of Compound 1 against IDH1 R132H and IDH1 R132C mutants were determined in diaphorase-coupled assays, which measure activity by the determination of the level of remaining co-substrate NADPH after the enzymatic reaction is quenched. Recombinant homodimeric IDH1 R132H or IDH1 R132C mutant enzymes were used in these assays.

In order to evaluate the cellular potency of Compound 1 for other $IDH1^{R132}$ mutations that have been identified in human cancers, $IDH1^{R132L}$, $IDH1^{R132G}$ and $IDH1^{R132S}$ were expressed in U87MG human glioblastoma cells. Matched $IDH1^{R132H}$ and $IDH1^{R132C}$ lines were also prepared to allow direct comparisons in the same cellular background, as well as to compare the effects observed from the same mutation in different cell lines. As for the HT1080 and HCT-116 cell lines described above, the engineered mIDH1-expressing U87MG cells produced higher concentrations of 2-HG but exhibited a similar growth rate when compared to parental U87MG cells. Inhibition of 2-HG production by Compound 1 in the $IDH1^{R132H}$ and $IDH1^{R132C}$ U87 lines gave $IC_{50}$ values of 9.0 and 39.0 nM, respectively, which are in close agreement with those seen in the HT1080 and HCT-116 (Table 1). In addition, Compound 1 potently inhibited 2-HG production in $IDH1^{R132G}$, $IDH1^{R132S}$ and $IDH1^{R132L}$ expressing cells with $IC_{50}$ values of 5.6, 9.2, and 41.7 nM, respectively, suggesting that Compound 1 is a potent inhibitor against a broad spectrum of $IDH1^{R132}$ mutants. In agreement with the previous cell lines studies, Compound 1 was found to have minimal effects on the proliferation of mIDH1 expressing U87MG cells at 10 µM.

Additional results are shown in Table 10, relative to the $IC_{50}$ value obtained for R132H IDH1 mutated enzyme. Referring to data in Table 10, Compound 1 was found to selectively inhibit the enzymatic activity of the IDH1 R132H and IDH1 R132C mutations with an $IC_{50}$ value within a factor of about 5 (i.e., the $IC_{50}$ value measured for IDH1 R132C mutant enzyme was about 5 times higher than the $IC_{50}$ measured in the IDH1 R132H mutated enzyme). The selectivity of Compound 1 against other IDH isozymes was also tested utilizing diaphorase coupled assays employing either wild-type IDH1 or one of 2 alternate mutated forms of IDH2, namely IDH2 R172K and IDH2 R140Q.

TABLE 10

| Target | Relative Enzymatic $IC_{50}$ (Average +/− SEM, nM) |
| --- | --- |
| IDH1 R132H | 1.0 (±6.6%) |
| IDH1 R132C | 5.1 (±6.1%) |
| Wild Type IDH1 | 922 |
| IDH2 R172K | >1,000 |
| IDH2 R140Q | >4,000 (no activity measured) |

Compound 1 had comparatively very weak activity against wild type IDH1 ($IC_{50}$ value of about 922 times greater than the $IC_{50}$ value measured for IDH1 R132H). Compound 1 also demonstrated very weak activity against IDH2 R172K that was more than 1,000 greater than the $IC_{50}$ value measured for IDH1 R132H. Compound 1 did not show any inhibition of IDH2 R140Q up to a concentration of 100 µM. These selectivity data indicate that Compound 1 is a potent and selective inhibitor of IDH1 R132 mutations.

Example 3—In Vitro Activity of Compound 1 as a R132X mIDH-1 Inhibitor

In in vitro biochemical assays, Compound 1 significantly inhibited mutated IDH1-R132H and IDH1-R132C proteins. In contrast, Compound 1 displayed little or no inhibitory activity in biochemical assays of wild-type IDH1 protein or various mutated IDH2 proteins found in human cancers. Compound 1 suppressed 2-HG production in naturally occurring and genetically engineered cell lines expressing five different mutated IDH1 proteins (R132H, R132C, R132G, R132L, and R132S) with $IC_{50}$ values below about 0.5 micromolar. In addition, Compound 1 has displayed relevant levels of activity against multiple clinically relevant, mutated forms of IDH1, of which IDH1-R132H and IDH1-R132C are the most prevalent in hematologic and solid tumor malignancies. However, Compound 1 did not display appreciable activity against wild-type IDH1 or mutated IDH2.

The cellular potency of Compound 1 in suppressing intracellular 2-HG levels was determined in cell lines expressing five different mutated IDH1 proteins found in human cancers (R132H, R132C, R132G, R132L, R132S). The human fibrosarcoma cell line HT-1080 harbors a naturally occurring heterozygous IDH1-R132C mutation. The human colorectal carcinoma cell line HCT 116 is wild type for IDH1, but heterozygous mutations coding for IDH1-R132H or -R132C were introduced by knock-in into the endogenous IDH1 gene locus. Finally, the human astrocytoma cell line U-87 MG is also wild type for IDH1, but expression of five different mutated IDH1 proteins was achieved by stable transfection.

The parental HCT116 line (colon) line does not produce high levels of 2-HG, but the variants used herein (X-MAN HCT-116 lines obtained from Horizon Discovery Ltd.) are engineered to knock-in a heterozygous mutation of either IDH1 R132H or IDH1 R132C. This recapitulates the cellular context in mIDH1 cancer cells where there are both wild type and mutant IDH1 subunits that together form a heterodimer that is responsible for the production of elevated levels of 2-HG. These modified lines can be used as models of IDH1 mutant disease.

Each of these cell lines was treated with Compound 1 for 24 hr, and intracellular 2-HG levels were determined by mass spectroscopy. Compound 1 suppressed 2-HG production in each cell line, with $IC_{50}$ values ranging from <10 to <150 nM. Table 11 below indicates 2-HG $IC_{50}$ values: below 150 nM ("+"), below 100 nM ("++"), below 50 nM ("+++") and below 10 nM ("++++").

TABLE 11

| Cell Line | 2-HG IC50 (nM)* |
|---|---|
| HT-1080(IDH1-R132C/+) | ++ |
| HCT 116(IDH1-R132H/+) | +++ |
| HCT 116(IDH1-R132C/+) | + |
| U-87 MG/IDH1-R132H | +++ |
| U-87 MG/IDH1-R132C | ++ |
| U-87 MG/IDH1-R132G | ++++ |
| U-87 MG/IDH1-R132L | +++ |
| U-87 MG/IDH1-R132S | ++++ |
| Wild type-IDH1 $IC_{50}$ (μM) | +++ |
| mIDH2-R172K $IC_{50}$ (μM) | +++ |
| mIDH2-R140Q $IC_{50}$ (μM) | + |

*Mean +/− SEM where applicable

Compound 1 is therefore a potent inhibitor of a variety of clinically relevant IDH1 mutations in a cellular context.

In order to optimize the dosing schedule of Compound 1 to achieve sustained >90% 2-HG inhibition in mIDH1 in vivo, HCT116-IDH1$^{R132H}$ and HCT116-IDH1$^{R132C}$ xenograft-bearing mice were treated with Compound 1 at 25 and 50 mg/kg BID (3 doses). The free drug concentration of Compound 1 at 12 hour post final dose is above the in vivo $IC_{90}$ for all doses, and a greater than 90% reduction of 2-HG levels in tumor were achieved in each case. The free drug concentration decreased to 3-10× the in vivo $IC_{50}$ at 24 hour post final dose, and the compound showed 80-90% inhibition. There was less than 20 nM free drug concentration in tumor at 48 and 72 hours after final dose, and at that point there was less than 50% 2-HG inhibition in tumor samples, consistent with the reduced level of Compound 1.

In both IDH1 mutated models, the free concentration of Compound 1 was comparable in plasma and xenograft tumors, and exposures were dose-dependent. In comparison to the vehicle treated group, Compound 1 showed a time and dose-dependent inhibition of intratumoral 2-HG levels. At the highest dose tested in these studies (50 mg/kg), Compound 1 treatment inhibited 2-HG levels in tumor by >90% for up to 24 hours after the last dose in the HCT116-IDH1$^{R132H}$ xenograft model, and to similar levels for at least 12 hours in the HCT116-IDH1$^{R132C}$ model. Calculations based upon the percentage of suppression of 2-HG concentration in tumor versus the free drug concentration in tumor gave in vivo $IC_{50}$ values of less than 50 nM in both the HCT116-IDH1$^{R132H}$ or HCT116-IDH1$^{R132C}$ models.

Example 4—Comparative Compounds Demonstrated Greater Disparity Between 2-HG Inhibition in R132C and R132H IDH-1 Cells, Compared to Compound 1

The comparative activity of each of a series of mIDH-1 inhibitor compounds including Compound 1 were measured using the cell based assay in Example 3. The ratio of the $IC_{50}$ values obtained from IDH-1 R132C HCT116 mutant cells ($IC_{50}$ μM g mean)/$IC_{50}$ values obtained from IDH-1 R132H HCT116 mutant cells ($IC_{50}$ μM g mean) is provided in Table 4. Compound 1 had the lowest ratio among the tested compounds, indicating near equipotent activity of Compound 1 as measured with the R132C and R132H IDH-1 mutant cell assay of Example 3 (using the HCT 116 cells described in Example 3). Compound 1 showed comparative activity inhibiting 2-HG production from mIDH-1 R132C and R132H cell lines (using the assay of Example 3) that was within 5-fold, compared to more disparate differences in activity ranging from about 8-fold to over 200 fold (240) in comparative compounds A-H in Table 12.

TABLE 12

| Compound | Structure | Ratio of $IC_{50}$ measured for: [$IC_{50}$ for R132C]/[$IC_{50}$ for R132H] |
|---|---|---|
| 1 | 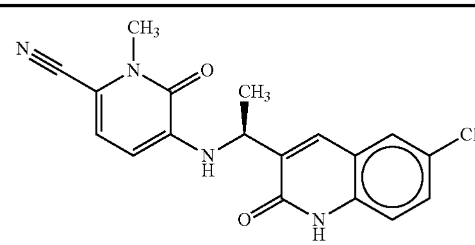 | 4.5 |

TABLE 12-continued

| Compound | Structure | Ratio of IC$_{50}$ measured for: [IC$_{50}$ for R132C]/ [IC$^{50}$ for R132H] |
|---|---|---|
| A | 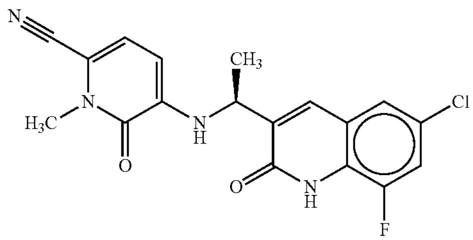 | 8.0 |
| B | 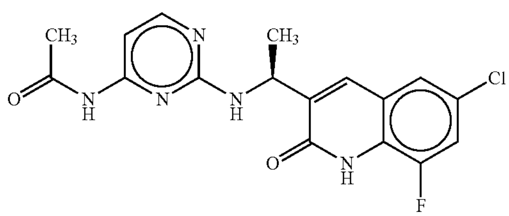 | 8.0 |
| C | 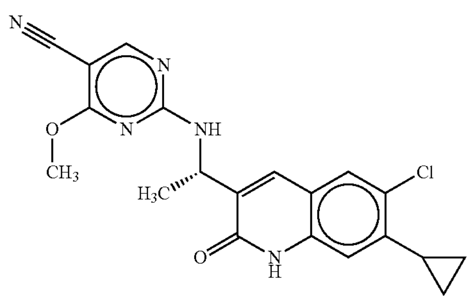 | 8.5 |
| D | 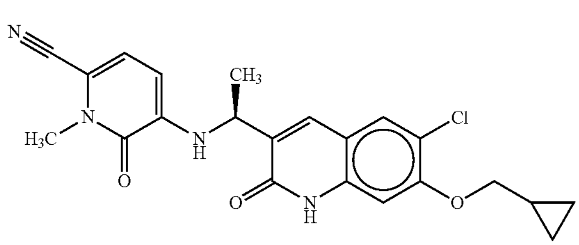 | 9.0 |

TABLE 12-continued

| Compound | Structure | Ratio of IC$_{50}$ measured for: [IC$_{50}$ for R132C]/ [IC$^{50}$ for R132H] |
|---|---|---|
| E | 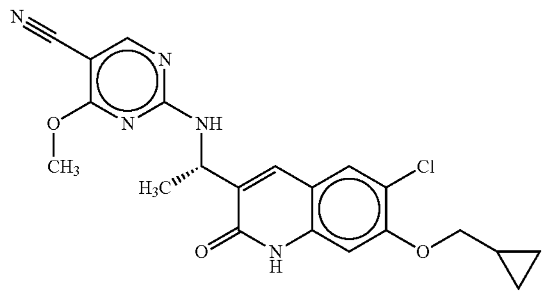 | 11.0 |
| F | 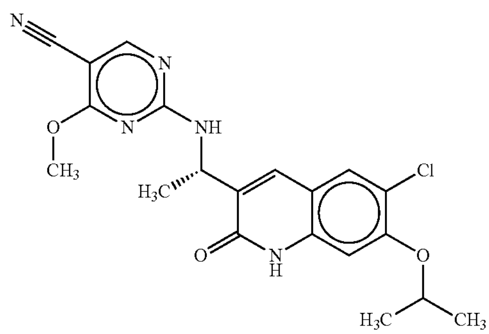 | 26 |
| G | 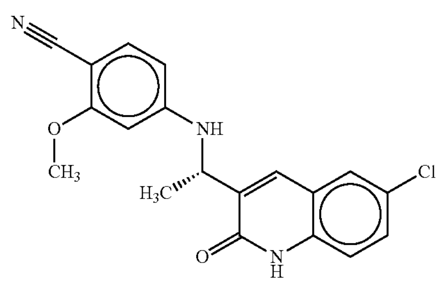 | 30 |
| H | 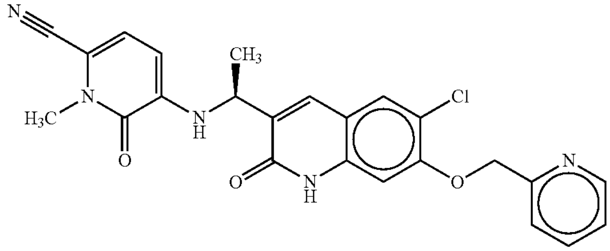 | 240 |

Example 5—Determination of Central Nervous System Multiparameter Optimization (CNS MPO)

Central nervous system multiparameter optimization (CNS MPO) may be used to prioritize compounds based on their likelihood to be brain-penetrant. The scoring function uses six key physicochemical properties (scoring each parameter on a scale of zero to one) to arrive at a composite score ranging from 0-6. Higher CNS MPO scores are correlated with a higher likelihood of a compound being brain-penetrant. The reported CNS MPO scores were calculated following the method reported in: Wager, T. T., Hou, X., Verhoest, P. R., and Villalobos, A. (2010) Moving beyond rules: The development of a central nervous system multiparameter optimization (CNS MPO) approach to enable alignment of druglike properties. *ACS Chem. Neurosci.* 1, 435-449.

A summary of the MPO scores for several IDHm inhibitors can be found in Table 13:

TABLE 13

| Cpd ID | Structure | IDH1 R132H IC$_{50}$ (μM) | IDH1 R132C IC$_{50}$ (μM) | CNS MPO Score[a] | BBB+[b] | Predicted BBB+[c] |
|---|---|---|---|---|---|---|
| AG-120[1] | 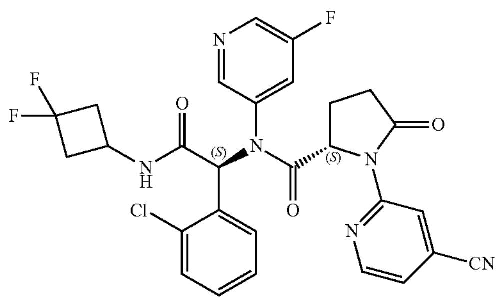 | 0.012 | 0.013 | 3.69 | No | No |
| AG-881[2] | 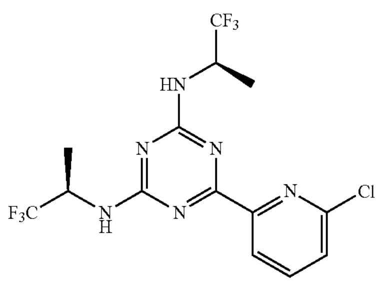 [SMILES: C[C@@H](Nc1nc(N[C@H](C)C(F)(F)F)nc(-c2cccc(Cl)n2)n1)C(F)(F)F] | >0.022 | >0.022 | 3.97 | Yes | Yes |
| IDH305[3] | 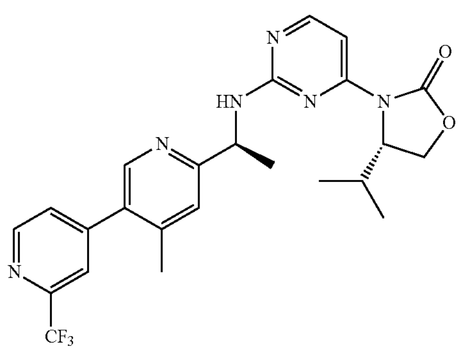 [SMILES: Cc1cc([C@H](C)Nc2nccc(N3C(=O)OC[C@@H]3C(C)C)n2)ncc1-c1ccnc(C(F)(F)F)c1] | 0.027 | 0.028 | 4.15 | Yes | Yes |
| IDH889[4] | 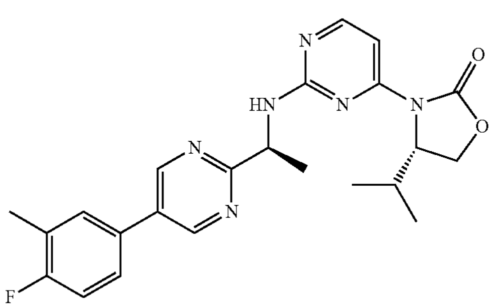 [SMILES: Cc1cc(-c2cnc([C@H](C)Nc3nccc(N4C(=O)OC[C@@H]4C(C)C)n3)nc2)ccc1F] | 0.020 | 0.072 | 4.50 | Yes | Yes |

TABLE 13-continued
| Cpd ID | Structure | IDH1 R132H IC$_{50}$ (μM) | IDH1 R132C IC$_{50}$ (μM) | CNS MPO Score[a] | BBB+[b] | Predicted BBB+[c] |
|---|---|---|---|---|---|---|
| GSK321[5] | 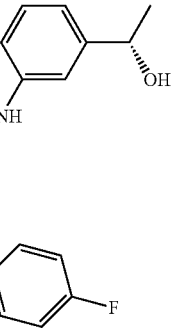 | 0.0048 | 0.0038 | 2.89 | nd | No |
| Bay1436032[6] | 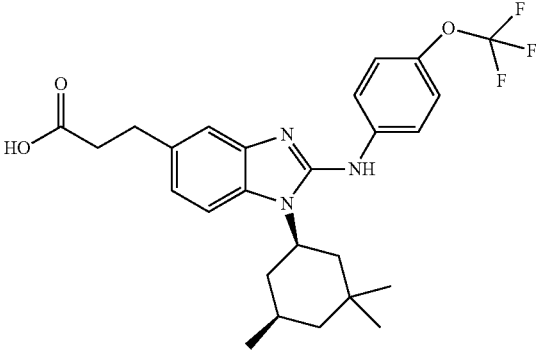 [SMILES: C[C@H]1C[C@@H](n2c(Nc3ccc(OC(F)(F)F)cc3)nc3cc(CCC(=O)O)ccc32)CC(C)(C)C1] | 0.015 | 0.015 | 3.05 | nd | No |
| Compound 1[d] | 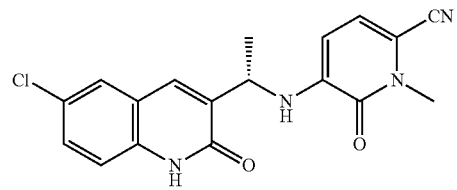 [SMILES: C[C@H](Nc1ccc(C#N)n(C)c1=O)c1cc2cc(Cl)ccc2[nH]c1=O] | +++ (0.0212) | +++ (0.1138) | 5.22 | Yes | Yes |
| I-1 | 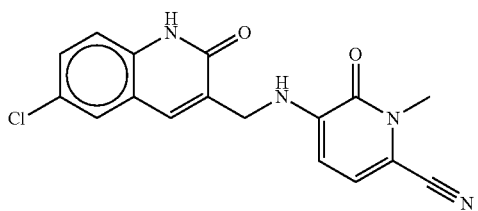 | +++ | nd | 5.30 | nd | Yes |
| I-2 | 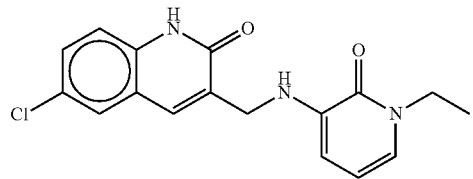 | ++ | + | 5.35 | nd | Yes |
| I-3 | 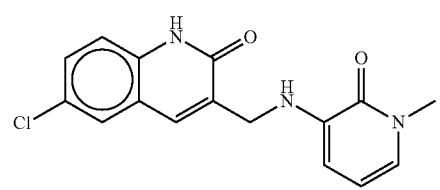 | ++ | + | 5.42 | nd | Yes |

TABLE 13-continued
| Cpd ID | Structure | IDH1 R132H IC$_{50}$ (μM) | IDH1 R132C IC$_{50}$ (μM) | CNS MPO Score[a] | BBB+[b] | Predicted BBB+[c] |
|---|---|---|---|---|---|---|
| I-5 | 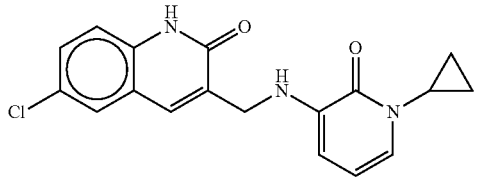 | ++ | + | 5.29 | nd | Yes |
| I-6 | 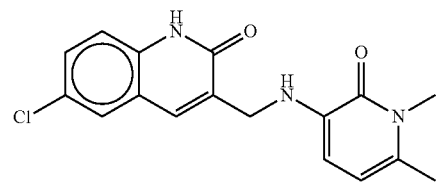 | ++ | + | 5.29 | nd | Yes |
| I-11 | 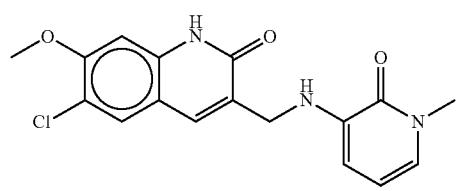 | ++ | + | 5.27 | nd | Yes |
| I-20 | 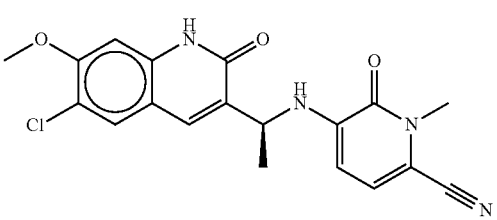 | +++ | ++++ | 4.93 | nd | Yes |
| I-22 | 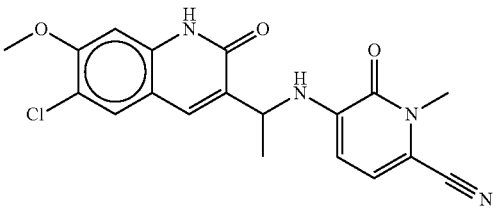 | +++ | ++++ | 4.93 | nd | Yes |
| I-23 | 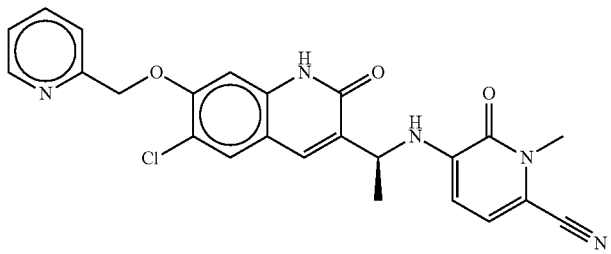 | +++ | ++++ | 3.97 | nd | Yes |
| I-25[e] | 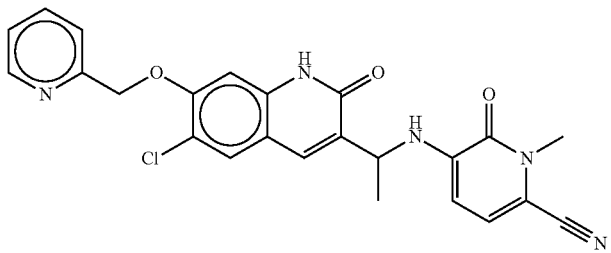 | +++ | nd | 3.97 | nd | Yes |

TABLE 13-continued

| Cpd ID | Structure | IDH1 R132H IC$_{50}$ (μM) | IDH1 R132C IC$_{50}$ (μM) | CNS MPO Score[a] | BBB+[b] | Predicted BBB+[c] |
|---|---|---|---|---|---|---|
| I-26 | 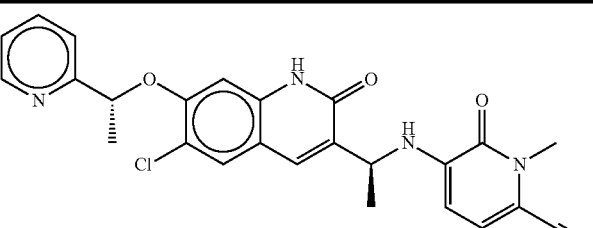 | ++++ | ++++ | 3.75 | nd | No |
| I-27 | 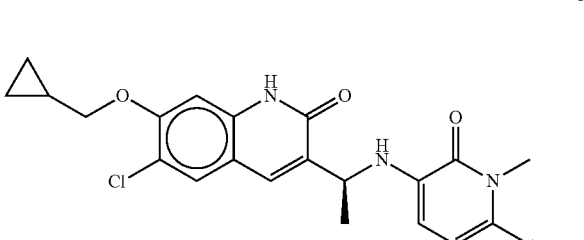 | ++++ | ++++ | 4.38 | nd | Yes |
| I-29 | 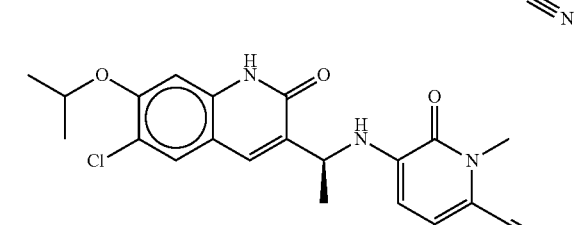 | ++++ | ++++ | 4.46 | nd | Yes |

For Compound 1 and Compounds I-1 through I-29, WO/2016044789 defines IC$_{50}$ values for IDH1 R132H as "++++": <0.01 μM; "+++": between 0.01 μM and 0.1 μM; "++": from 0.1 μM to 1 μM; and IC$_{50}$ values for IDH1 R132C as "++++": <0.1 μM; "+++": between 0.1 μM and 1 μM; "++": from 1 μM to 10 μM; and "+": >10 μM
[a]CNS MPO score calculated based on the method described in T. Wager, ACS Chem. Neurosci. (2010), 1, 435-449.
[b]Literature reported data
[c]Predicted BBB+: CNS MPO score >3.8
[d]WO/2016044789 also reports Compound 1 (as I-13) as having activity in HCT116 mutant IDH1 R132H and R132C cells as +++ and +++, respectively.
[e]WO/2016044789 also reports I-25 as having activity in HCT116 mutant IDH1 R132H and R132C cells as ++++ and ++++, respectively.
[1]Popovici-Muller, J., et al. Discovery of AG-120 (Ivosidenib): A First-in-Class Mutant IDH1 Inhibitor for the Treatment of IDH1 Mutant Cancers. ACS Med. Chem. Lett., 2018, 9(4), 300-305.
[2]Yen, K., et al. Abstract B126: AG-881, a brain penetrant, potent, pan-mutant IDH (mIDH) inhibitor for use in mIDH solid and hematologic malignancies, AACR-NCI-EORTC International Conference: Molecular Targets and Cancer Therapeutics; October 26-30, 2017; Philadelphia, PA.
[3]Cho, Y. S., et al. Discovery and evaluation of clinical candidate IDH305, a brain penetrant mutant IDH1 Inhibitor. ACS Med. Chem. Lett. 2017, 8, 1116-1121.
[4]Levell, J. R., et al. Optimization of 3-pyrimidin-4-yl-oxazolidin-2-ones as allosteric and mutant specific inhibitors of IDH1. ACS Med. Chem. Lett. 2017, 8, 151-156.
[5]Okoye-Okafor, U. C., etal. New IDH1 mutant inhibitors for treatment of acute myeloid leukemia. Nat. Chem. Biol. 2015, 11, 878-886.
[6]Pusch, S., et al. Pan-mutant IDH1 inhibitor BAY 1436032 for effective treatment of IDH1 mutant astrocytoma in vivo. Acta Neuropothologica 2017, 133(4), 629-644.

Example 6—Determination of Predicted C$_{brain}$ Ratio of IDHm Inhibitors

The distribution of Compound 1, AG-120 or AG-881 into the brain was measured ex-vivo, individually, in Sprague Dawley rats (n=4/molecule) following a 6 hour intravenous infusion of a 7.5 mg/kg dose. Brain tissue and plasma samples were collected at the end of the infusion time and were processed for bioanalysis via tandem HPLC-mass spectrometry analysis (LCMS) to determine the total amount of compound present. In parallel, brain and plasma samples were subjected to equilibrium dialysis as described by N. J. Waters et. al (J. Pharm Sci (2008) 97(10):4586-95) to determine the unbound fraction (Table x). The brain distribution or partitioning coefficient (Kpuu) was then calculated as the ratio of the unbound concentration of drug in brain (Fu, brain) to the unbound concentration of drug in plasma (Fu, plasma). Similarly, all calculations of effective plasma concentrations in rodents or humans were conducted using the unbound/free fraction measured for each molecule in each species using conventional equilibrium dialysis as described by Waters.

To determine the projected what the effective free concentration in humans, the plasma concentrations in tumor bearing mice were measured using 90% inhibition in tumors (IC$_{90}$) of the biomarker 2-HG, as the minimal effective concentration to provide therapeutic benefit. In tumor bearing mice studies the unbound plasma concentration at IC$_{90}$ was determined to be 90.7 ng/mL (Table 14). In human clinical trials a dose of 150 mg BID for Compound 1 showed a mean plasma concentration (C$_{free, avg}$) of 171 ng/mL, which when corrected by the expected brain partitioning (Kpuu=0.42) and free fraction in brain (Fu, brain=0.05) provides an estimate of 3.6 ng/mL unbound concentration in brain. The target effective concentration in human brain based on mouse models (to achieve IC$_{90}$) is 1.91 ng/mL. Hence Compound 1 partitions into the brain by 2-fold greater than projected levels required to achieve therapeutic benefit.

TABLE 14

| Parameters (ng/mL) | Compound 1 | AG-120 | AG-881 | |
|---|---|---|---|---|
| Brain Distribution (Kp, uu rat) | 0.4 | 0.01 | 0.5 | |
| *Predicted $C_{eff,\ brain,\ fu}$ | 1.9 | 0.7 | 0.5 | |
| Predicted Clinical | 150 mg bid: | 500 mg qd**: | 50 mg qd: | 10 mg qd: |
| $C_{Avg\_Brain,\ fu}$ | 4 | 0.4 | 0.03 | 0.01 |
| Predicted $C_{brain}$ Ratio ($C_{Avg\_Brain,\ fu}/C_{eff\_Brain,\ fu}$) | 2.0 | 0.6 | 0.06 | 0.02 |

*Calculated brain distribution of Ceff, fu plasma in mice
**Based Cycle 1 PK, 2-fold decrease over time

Figure 4A:
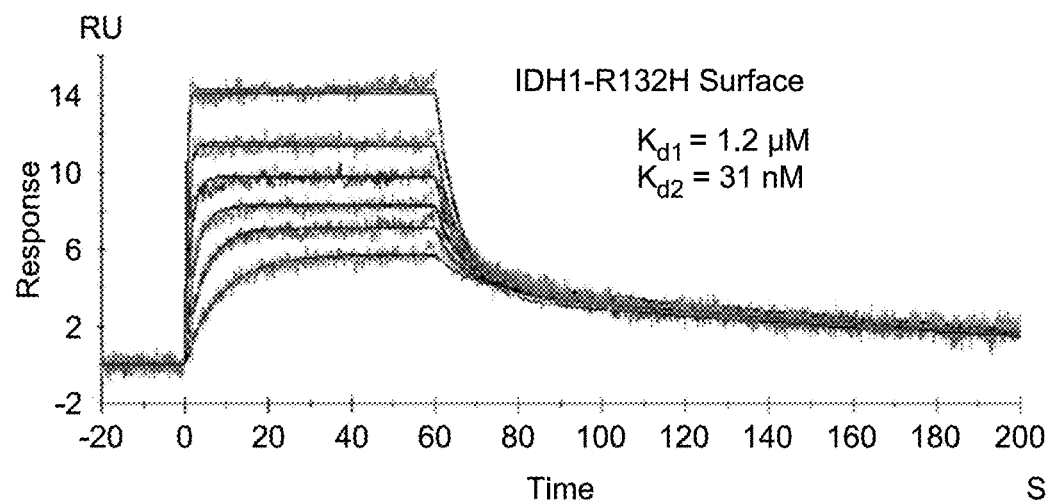
FIG. 4A is a graph showing the results from a surface plasmon resonance (SPR) biophysical characterization of the molecular interaction between mIDH-1 inhibitor Compound 1 and recombinant IDH-1-R132H protein.
Figure 4B:
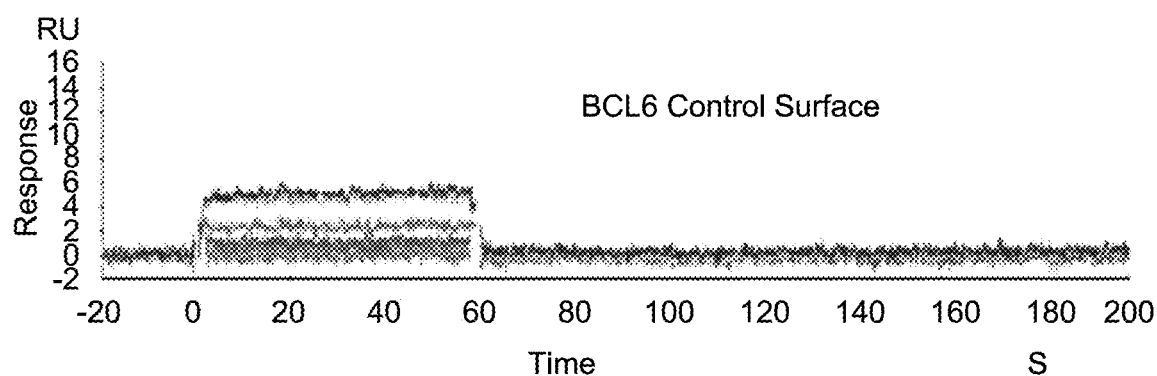
FIG. 4B is a comparator graph showing the SPR characterization of Compound 1 at a BCL6 control surface.

Example 7—Testing Compound 1 in Mouse Xenograft Models Using HCT 116 Cells with R132C and R132H Mutations In order to assess the in vivo activity of Compound 1, PK-PD experiments in mice bearing HCT-116 xenografts (derived from Horizon Discovery isogenic cell lines harboring IDH1-R132H and IDH1-R132C knock-in mutations) were used to determine the degree of exposure required to suppress 2-HG levels. Compound 1 was administered to HCT116-IDH1-R132H/+ xenograft bearing female BALB/c Nude mice at three oral doses (12.5, 25, and 50 mg/kg) in 12-hour intervals. Plasma and xenograft tumor samples were collected at 4, 12, and 24 hours post last dose to determine the exposure of Compound 1 in plasma and tumor, as well as to measure the inhibition of IDH1 mutant activity in tumor based on the reduction in levels of 2-HG. In IDH1-R132H/+ xenograft models, the free concentration of Compound 1 was comparable in plasma and xenograft tumors, and exposures were dose-dependent. In comparison to the vehicle treated group, Compound 1 showed a time and dose-dependent inhibition of 2-HG levels in plasma and in tumor) At the highest dose tested in these studies (50 mg/kg), treatment with Compound 1 inhibited 2-HG levels in the tumor by >90% for up to 24 hours after the last dose in the HCT116-IDH1-R132H/+ xenograft model (FIG. 4c), and to similar levels for at least 12 hours in the HCT116-IDH1-R132C/+ model. Calculations based upon the percentage of suppression of 2-HG concentration in tumor versus the free drug concentration in tumor gave in vivo $IC_{50}$ values of 26 nM and 36 nM in the HCT116-IDH1-R132H or HCT116-IDH1-R132C models, respectively. When corrected for unbound levels of Compound 1, there is an excellent correlation in potency among the biochemical assay, cellular assay, and in vivo studies.

TABLE 15

| mIDH1-R132H | | | mIDH1-R132C | | |
|---|---|---|---|---|---|
| Enzyme (nM) | Cell 2-HG (nM) | In vivo 2-HG (nM) | Enzyme (nM) | Cell 2-HG (nM) | In vivo 2-HG (nM) |
| 17 | 37 | 26 | 100 | 66 | 36 |

In order to optimize the dosing schedule of Compound 1 to achieve sustained >90% 2-HG inhibition in mIDH1 in vivo, HCT116-IDH1 R132H and HCT116-IDH1 R132C xenograft-bearing mice were treated with Compound 1 at 25 and 50 mg/kg BID (3 doses). The free drug concentration of Compound 1 at 12 hour post final dose is above the in vivo $IC_{90}$ for all doses, and a greater than 90% reduction of 2-HG levels in tumor were achieved in each case. The free drug concentration decreased to 3-10× the in vivo $IC_{50}$ at 24 hour post final dose, and Compound 1 showed 80-90% (or greater) inhibition. There was less than 20 nM free drug concentration in tumor at 48 and 72 hours after final dose, and at that point there was less than 50% 2-HG inhibition in tumor samples, consistent with the reduced level of Compound 1.

Briefly, 5×10⁶ HCT-116 IDH1-R132H/+ cells (Horizon Discovery) in PBS was inoculated subcutaneously at the right flank of the 6 weeks old female BALB/c nude mice. When the tumor size reached 360-400 mm³, mice were randomized by tumor volume into nine mice per group. The tumor bearing mice were treated with vehicle (9:1 PEG400:Ethanol) or Compound 1 for three doses with 12 hr dosing interval. The dosing volume was 10 μL/g. The plasma samples and tumor samples were collected at 4, 12 and 24 hr post final dose (N=3 mice per time point) for the subsequent measurement of compound level in plasma and tumor samples and of 2-HG level in the tumor samples by UPLC-MS-MS system.

In a separate dosing example, 5×10⁶ HCT-116 IDH1-R132C/+ cells (Horizon Discovery) in PBS was inoculated subcutaneously at the right flank of the 6-8 weeks old female BALB/c nude mice. When the tumor size reached ~250 mm³, mice were randomized by tumor volume into nine mice per group. The tumor bearing mice were treated with vehicle (9:1 PEG400:Ethanol) or Compound 1 for six doses with 12 hr dosing interval. The dosing volume was 10 μL/g. The plasma samples and tumor samples were collected at 4, 8 and 12 hr post final dose (N=4 mice per time point) for the subsequent measurement of compound level in plasma and tumor samples and of 2-HG level in the tumor samples by UPLC-MS-MS system.

For each assay, the total concentration of Compound 1 was determined in μM and free Compound 1 concentration was calculated by multiplying the total Compound 1 concentration by 0.043 given that Compound 1 is 95.7% protein binding in mouse plasma. The percentage of 2-HG inhibition in individual tumor sample in the treated groups was normalized to the average of 2-HG concentration in the vehicle group at the corresponding sampling time using the following calculation: % 2-HG inhibition=100*(A−B)/A, where A is the average of 2-HG concentration at the corresponding sampling time, B is the 2-HG concentration in the tumor treated with given dose of Compound 1 and sacked at the given sampling time. The in vivo potency of Compound 1 for suppressing 2-HG in tumor is calculated by plotting the percentage of 2-HG inhibition against corresponding free Compound 1 concentration in tumor and fitting the data with four-parameter logistic equation.

IDH1-R132H Mutation

IDH1-R132H mutation resulted in elevation of 2-HG level in hematological and solid cancers. HCT-116 IDH1-R132H/+ xenograft tumor was used to assess the in vivo potency of Compound 1 to suppress 2-HG in tumor lysates. The tumor bearing mice were randomized by tumor size into twelve mice per group. The mice were treated with Compound 1 at 6.25, 12.5, 25, or 50 mg/kg for six doses with dose interval of 12 hr. The plasma and tumor samples were collected at 4, 8, and 12 hr post last dose with four mice per time point. The Compound 1 concentration in plasma and tumor samples was analyzed by LC-MS method. The 2-HG level in tumor samples was analyzed by LC-MS method. The percentage of 2-HG suppression in tumor lysate at given dose of Compound 1 was then normalized to 2-HG level in the vehicle control group. The dose and time dependent 2-HG inhibition by Compound 1 was observed in this study. The degree of 2-HG inhibition in tumor lysates was correlated with the free drug concentration in the corresponding tumor lysate. The calculated in vivo potency of Compound 1 to suppress 2-HG in tumor was 26.0 nM.

Upon correcting for unbound Compound 1 concentration, there was a good correlation between the enzymatic, cellular 2-HG, and in vivo 2-HG potencies of Compound 1 for IDH1-R132H mutant.

IDH1-R132C Mutation

IDH1-R132C mutation resulted in elevation of 2-HG level in hematological and solid cancers. HCT-116 IDH1-R132C/+ xenograft tumor was used to assess the in vivo potency of Compound 1 to suppress 2-HG in tumor lysates. The tumor bearing mice were randomized by tumor size into nine mice per group. The mice were treated with Compound 1 at 12.5, 25, or 50 mg/kg for three doses with dose interval of 12 hr. The plasma and tumor samples were collected at 4, 12, and 24 hr post last dose with three mice per time point. The Compound 1 concentration in plasma and tumor samples was analyzed by LC-MS method. The 2-HG level in tumor samples was analyzed by LC-MS method. The percentage of 2-HG suppression in tumor lysate at given dose of Compound 1 was then normalized to 2-HG level in the vehicle control group. The dose and time dependent 2-HG inhibition by Compound 1 was observed in this study. The degree of 2-HG inhibition in tumor lysates was correlated with the free drug concentration in the corresponding tumor lysate. The calculated in vivo potency of Compound 1 to suppress 2-HG in tumor was 36.0 nM.

Upon correcting for unbound Compound 1 concentration, there was a good correlation between the enzymatic, cellular 2-HG, and in vivo 2-HG potencies of Compound 1 for IDH1-R132C mutant.

Results

Given the role of 2-HG in suppressing normal differentiation of mt-IDH1 cells (Figueria et al., 2010; Saha et al., 2014), it is hypothesized that in order to reverse and maintain this effect, it is necessary to achieve a very high degree of target inhibition on a continuous basis. Therefore, in order to optimize the dosing schedule of Compound 1, it is necessary to achieve sustained >90% 2-HG inhibition in mt-IDH1 in vivo. For the HCT116-IDH1$^{R132H}$ xenograft assay, the 12 and 24 hour time points were chosen to reflect the compound level and corresponding 2-HG inhibition at the $C_{trough}$ of BID and QD dosing schedules. The 48 and 72 hour time points were selected to investigate whether Compound 1 had long lasting effects on 2-HG inhibition. The free drug concentration of Compound 1 at 12 hour post final dose is above the in vivo $IC_{90}$ for all doses, and a greater than 90% reduction of 2-HG levels in tumor were achieved in each case. The free drug concentration decreased to 3-10× the in vivo $IC_{50}$ at 24 hour post final dose, and the compound showed 80-90% inhibition. There was less than 20 nM free drug concentration in tumor at 48 and 72 hours after final dose, and at that point there was less than 50% 2-HG inhibition in tumor samples, consistent with the reduced level of Compound 1. These data support the premise that constant target coverage by a significant margin is required to achieve sustained 2-HG inhibition. This experiment also suggests that a BID schedule is the preferred dosing regimen for Compound 1 in order to continuously achieve >90% 2-HG inhibition. This level of inhibition has recently been correlated to clinical efficacy with AG-221 in mt-IDH2 harboring AML patients (Fan et al., 2014)).

Figure 18:
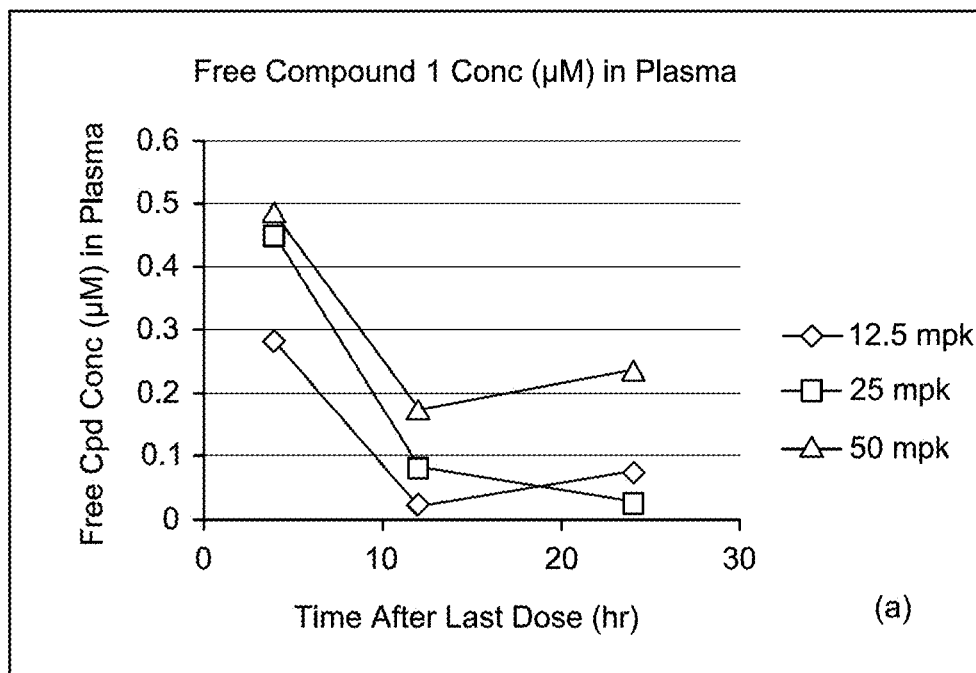
FIG. 18 consists of 4 panels: (a), (b), (c), and (d). Panel (a) illustrates free concentration of Compound 1 in plasma after three-dose oral administration (12.5, 25 and 50 mg/kg) with 12 hr dosing interval in mouse HCT116-IDH1-R132H/+ xenograft model. Panel (b) illustrates free concentration of Compound 1 in tumor after three-dose oral administration (12.5, 25 and 50 mg/kg) with 12 hr dosing interval in mouse HCT116-IDH1-R132H/+ xenograft model. Panel (c) illustrates percent 2-HG inhibition in tumors in a PO dose of 12.5 mpk, 25 mpk and 50 mpk at three different time points (4 h, 12 h, 24 h). Panel (d) illustrates in vivo activity (2-HG % inhibition) of Compound 1 vs free compound concentration in tumor.
Figure 18:
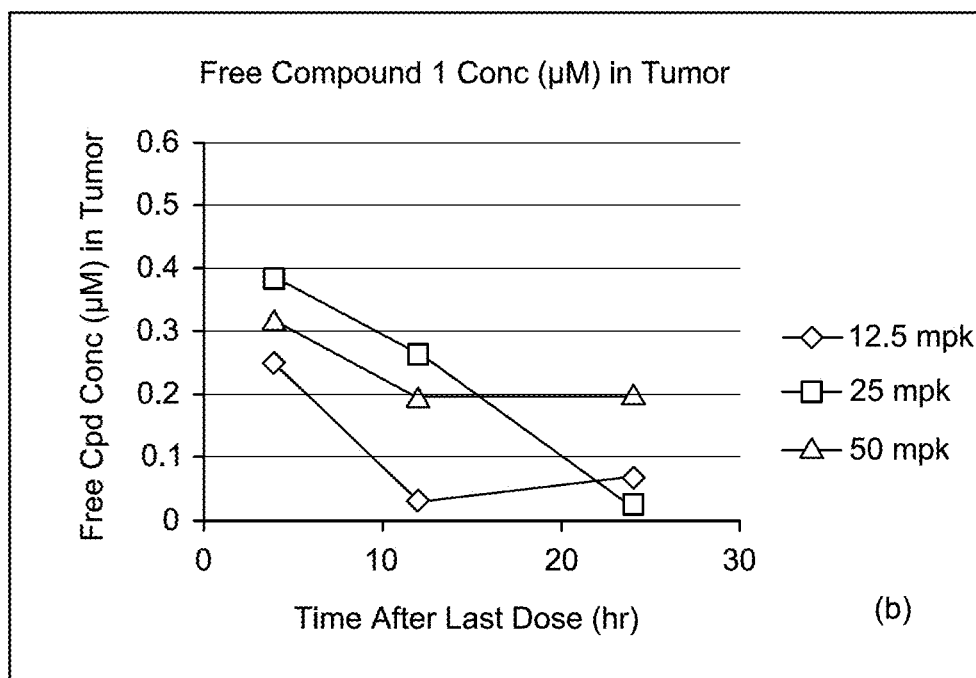
Figure 18:
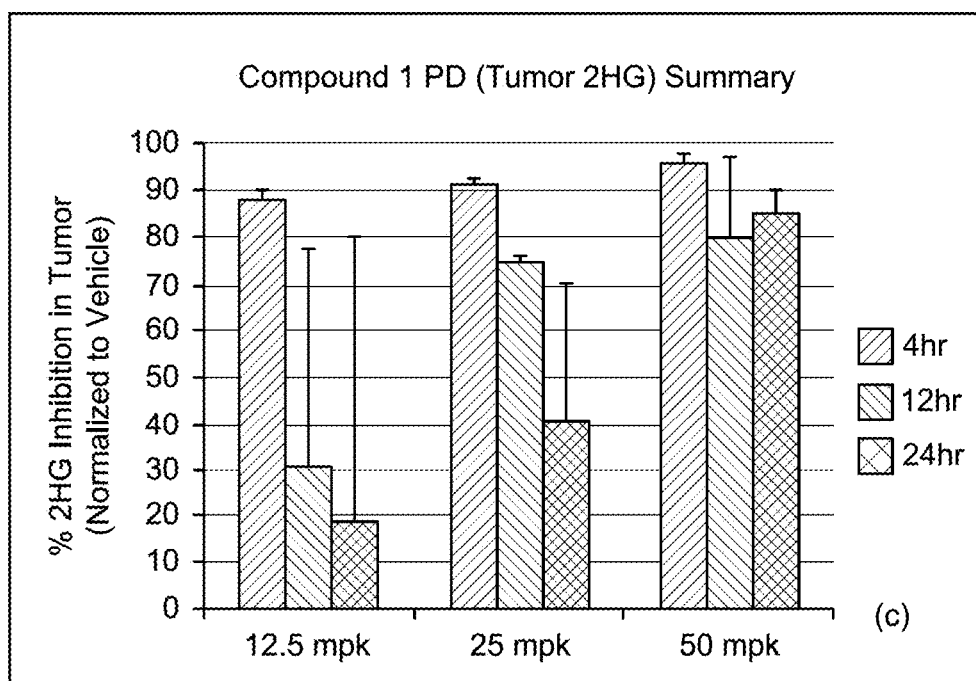
Figure 18:
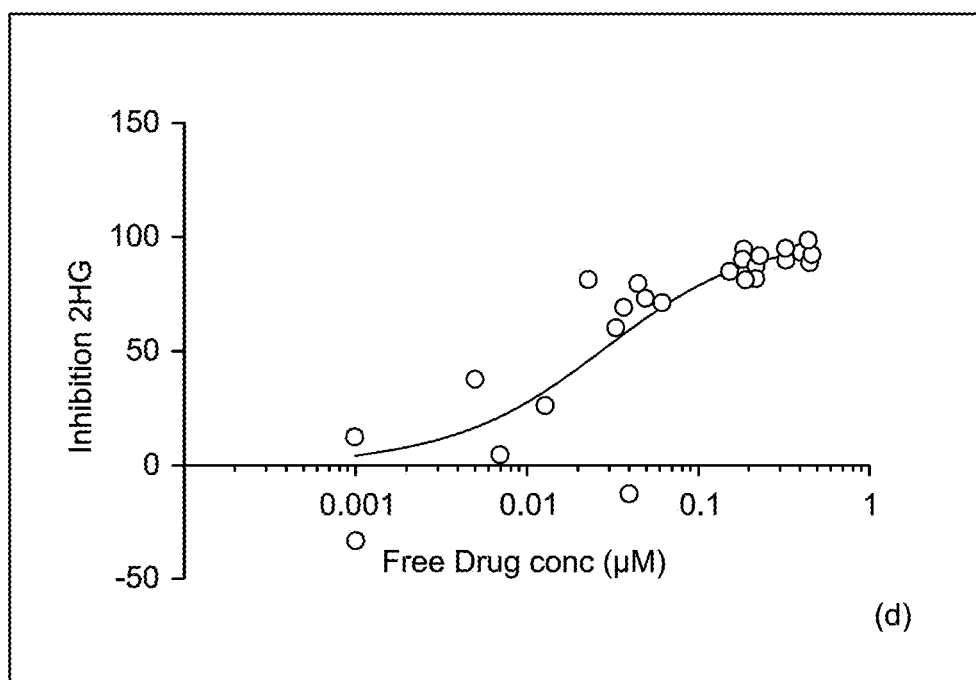

The present disclosure contemplates, among other things, recognition that the total concentration ($C_{eff}$) of Compound 1 must be above 1652 ng/mL in human patients in order to achieve 90% inhibition of 2-HG and above 2000 ng/mL to achieve greater than 90% inhibition of 2-HG. $C_{eff}$ was determined using assays outlined in Example 7. In two separate mouse experiments, HCT-116 IDH1-R132H/+ xenografts and HCT-116 IDH1-R132C/+ xenograft tumor were used to assess the in vivo potency of Compound 1 to suppress 2-HG in tumor lysates. Compound 1 concentration in plasma and tumor samples and 2-HG level in tumor samples was measured. The degree of 2-HG inhibition in tumor lysates was correlated with the free drug concentration in the corresponding tumor lysate (see FIG. 18D). Given the role of 2-HG in suppressing normal differentiation of mt-IDH1 cells (Figueria et al., 2010; Saha et al., 2014), the present disclosure hypothesized that in order to reverse and maintain this effect, it is necessary to achieve a very high degree of target inhibition with Compound 1 on a continuous basis. It was previously proposed that >90% inhibition of 2-HG correlates to clinical efficacy in mt-IDH2 harboring AML patients (FAN, B. et al., Evaluation of the pharmacokinetic/pharmocodynamic (PK/PD) relationships of an oral, selective, first-in-class, potent IDH1 inhibitor, AG-221, from a phase 1 trial in patients with advanced IDH2 mutant positive hematologic malignancies, Blood, 124: 3737, 6 pages (2014)). Using the curve from FIG. 18D, the level of free drug concentration of Compound 1 was determined to be 0.256 µM in order to achieve 90% inhibition of 2-HG.

Using a rapid equilibrium dialysis approach, the plasma protein binding for a human patient was determined to be 94.5%. (Waters, N. J., et al. (2008)). Validation of a rapid equilibrium dialysis approach for the measurement of plasma protein binding. J Pharm Sci 97(10): 4586-95.) Accordingly, the total concentration ($C_{eff}$) can be determined: 0.256/((100−94.5)/100)=4.65 µM=1652 ng/mL.

Example 8—Compound 1 Penetrates the Blood Brain Barrier in Murine Models

Figure 5:
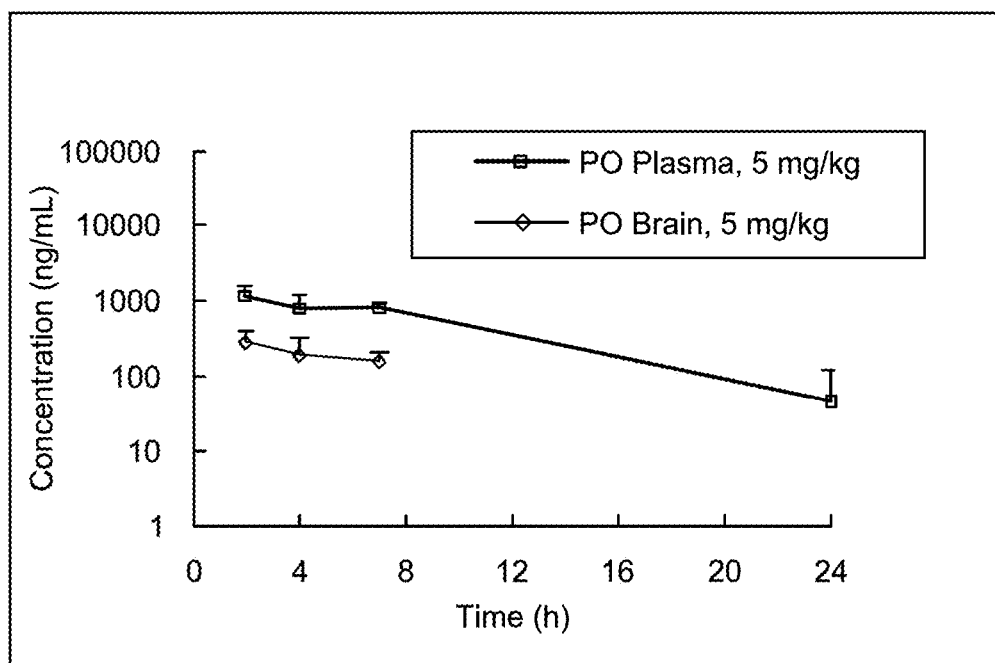
FIG. 5 is a graph showing plasma and brain exposure for Compound 1 following 5 mg/kg PO dose in a CD-1 Mouse.

The blood brain barrier penetration and free brain exposure of Compound 1 was investigated in the male CD-1 mouse (FIG. 5). The brain exposure of Compound 1 following oral dosing (5 mg/kg) was evaluated. Following a 5 mg/kg oral dose in CD1 mice, the brain to plasma ratio of Compound 1 was found to be 0.24 suggesting that the compound has reasonable brain penetration characteristics, and that at higher doses Compound 1 would have the potential to achieve therapeutic brain levels.

Figure 6:
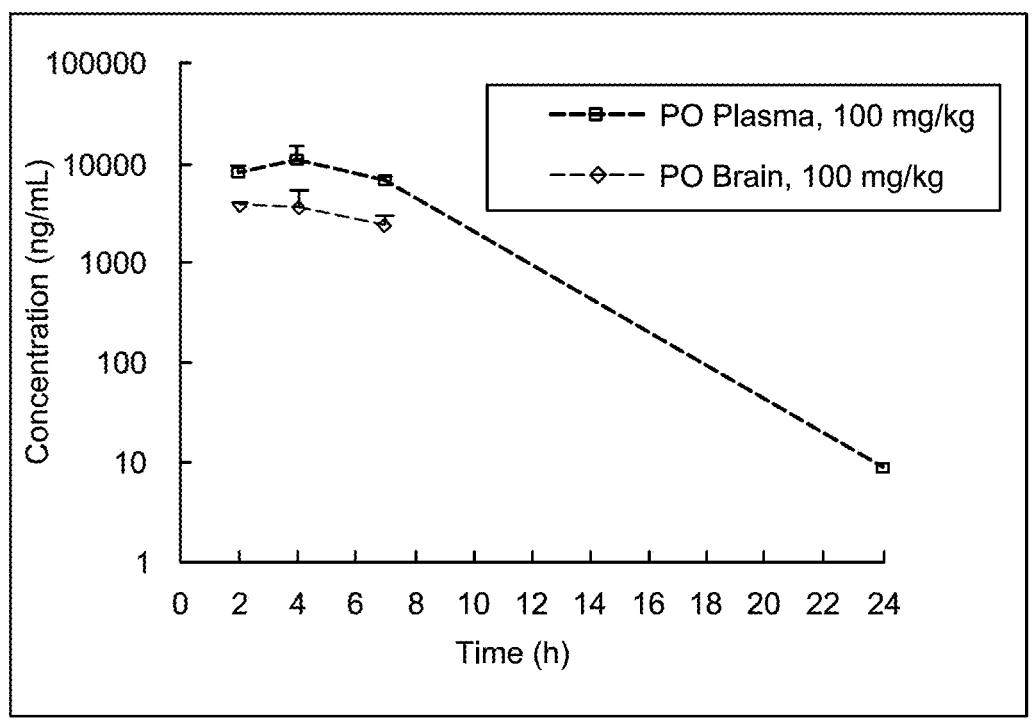
FIG. 6 is a graph showing plasma and brain exposure for Compound 1 following 100 mg/kg PO dose in a CD-1 Mouse.

This was confirmed by dosing at 100 mg/kg (FIG. 6), where the brain to plasma ratio was determined to be 0.38. Importantly, following a single 100 mg/kg PO dose, the free C max concentration of Compound 1 was about 200 nM (approximately ten fold $IC_{50}$), dropping to about 130 nM (about six fold $IC_{50}$) at the 7 hour time point, which is consistent with exposures that produced >90% suppression of 2-HG in both HCT116 (IDH-1 R132H) and HCT116 (IDH-1 R132C) xenograft PK-PD studies. Based on assessment in the mouse, Compound 1 crosses the blood-brain barrier to reach free concentration levels in the brain consistent with pharmacological activity. An oral 100 mg/kg dose gives a free C max in brain of 200 nM, dropping to about 130 nM at the 7 hr time point.

Example 9—Testing Compound 1 in Cynomolgus Monkey Models

Animal Acquisition and Acclimation

A total of 22 male and 22 female experimentally naïve cynomolgus monkeys, approximately 2 years and 7 months to 3 years and 11 months of age at transfer, were transferred from the stock colony. The animals were originally received from Worldwide Primates Inc.

Animals were quarantined upon arrival and quarantine activities, including intrapalpebral tuberculin skin tests, were performed. The animals were considered suitable prior to being released from quarantine. During acclimation as part of the stock colony, the monkeys were examined by a staff veterinarian, weighed, and observed daily with respect to general health and any signs of disease.

Randomization, Assignment to Study, and Maintenance

Using a standard, by weight, measured value randomization procedure, 20 male and 20 female animals (weighing 2.50 to 3.15 kg and 2.35 to 3.20 kg, respectively, at randomization) were assigned to the control and 3 treatment groups. Animals assigned to study had body weights within ±20% of the mean body weight for each sex. Extra animals obtained for the study, but not placed on study, were transferred to the stock colony. Each animal was assigned an animal number to be used in the data collection system and was implanted with a microchip bearing a unique identification number. Each animal was also identified by a permanent tattoo with the vendor animal number. The individual animal number, implant number, tattoo number and study number comprised a unique identification for each animal. Each cage was identified by the animal number, study number, group number, and sex.

Administration

Male and female cynomolgus monkeys were assigned to four groups. Animals were assigned to the study as indicated below in Table A. Six animals per sex in Group 1 were administered vehicle control article only. Four animals per sex in Groups 2 and 3, and 6 animals per sex in Group 4 were administered test article. Animals in Groups 2 through 4 were dosed for 28 days. 2 animals/sex in Groups 1 & 4 were assigned for 28-day recovery assessment. Animals were dosed via oral gavage twice daily, every 12 hours, at a volume of 10 mL/kg/dose (20 mL/kg/day). Animals in Groups two through four were administered 30, 100/50, or 300/200/100 mg/kg/day (15, 50/25, or 150/100/50 mg/kg/dose) respectively. The dose levels were lowered for Group 3 and Group 4 animals based clinical observations during the dosing phase. The vehicle control article was Kolliphor EL:Tween 80 (70:30, v/v). Animals designated for recovery sacrifice (2 animals/sex in Groups 1&4) underwent 4 weeks of recovery assessment.

Assessment of toxicity was based on mortality, clinical observations, body weights, food consumption, ophthalmic observations, electrocardiographic (ECG) measurements, and clinical and anatomic pathology. Blood samples were collected for toxicokinetic evaluations.

Electrocardiographic Assessment

With the exception of one animal in the high dose group, there was no effect of Compound 1 on qualitative ECG parameters. Frequent ventricular premature complexes (Day 1, 3-4 hours post-dose) and ventricular tachycardia (Day 28 pre-dose and 3-4 hours post-dose) were observed in one animal following administration of the 300/200/100 mg/kg/day dose. As these ventricular arrhythmias are not considered normal variants and were observed following the high dose, these findings may have been test article-related. Noteworthy effects on quantitative ECG parameters were limited to QTc interval duration. When evaluated statistically by sex, mean QTc interval duration was longer (vs. concurrent vehicle control value) in 300/200/100 mg/kg/day males at the Day 1 post-dose interval and at the Day 28 pre-dose and post-dose intervals and in 100/50 mg/kg/day females at the pre-test and Day 28 intervals. The difference in 100/50 mg/kg/day females was not considered to be test article-related as it was present prior to initiation of test article administration. In 300/200/100 mg/kg/day males, the increase in mean QTc interval duration may have been test article-related as it was observed at the highest dose level and exhibited a progressive increase with continued dosing. The magnitude of change from pretest values was mild to moderate (Day 1 post-dose: 7.14%; Day 28 pre-dose: 7.73%; Day 28 post-dose: 10.6%). Compared to pretest values, the magnitude of the increase in QTc interval duration in males at the Day 28 post-dose interval was 10.61%, which approximates the 10% change seen in the Japanese QT PRODACT studies (Ando, K., Hombo, T., Kanno, A., Ikeda, H., et al. QT PRODACT: in vivo QT assay with a conscious monkey for assessment of the potential for drug induced QT interval prolongation. J Pharmacol Sci. 2005; 99(5):487-500) of drugs known to cause QT prolongation in people. The effect on QTc interval duration was reversible, not being present at the recovery interval. The threshold $C_{max}$ plasma concentration in a monkey that experienced an average group $QT_c$ prolongation of 10.6% was 7840 ng/mL.

Conclusion

Cynomolgus monkeys tolerated oral doses of Compound 1 twice daily at 15 mg/kg/dose (30 mg/kg/day) and once daily at 50 mg/kg/day. Compound 1-related post-mortem findings at the end of the treatment period included macro-

TABLE A

Group Assignments

| Group Number | Dose Level (mg/kg/day) | Dose Level (mg/kg/dose) | Dose Volume (mL/kg/dose) | Dose Concentration (mg/mL) | Number of Animals Male | Number of Animals Female |
|---|---|---|---|---|---|---|
| 1 | 0[a] | 0 | 10 | 0 | 6[b] | 6[b] |
| 2 | 30 | 15 | 10 | 1.5 | 4 | 4 |
| 3 | 100/50[c] | 50[c] | 10 | 5 | 4 | 4 |
| 4 | 300/200/100[d] | 150/100[d] | 10 | 15/10[d] | 6[b] | 6[b] |

[a]Animals in Group 1 received the vehicle, Kolliphor EL:Tween 80 (70:30, v/v).
[b]Two animals/sex were maintained for a 28-day recovery period.
[c]Beginning on Day 14, the 50 mg/kg/dose twice daily (BID) dose (100 mg/kg/day) was reduced to 50 mg/kg/dose once daily (50 mg/kg/day) for the remainder of the study.
[d]Animals at 300 mg/kg/day were placed on a dosing holiday beginning with the second dose on Days 4 through Day 11. The 150 mg/kg/dose twice daily (BID) dose (300 mg/kg/day) was reduced to 100 mg/kg/dose twice daily (200 mg/kg/day) at a concentration of 10 mg/mL for Days 12 and 13. Beginning on Day 14, the 100 mg/kg/dose twice daily (BID) dose (200 mg/kg/day) was reduced to 100 mg/kg/dose once daily (100 mg/kg/day) for the remainder of the study.

scopic findings of black discoloration in the liver of 3/4 males and 2/4 females at 300/200/100 mg/kg/day, which correlated to multinucleated cells in the sinusoids. Lower thymus weights, which correlated to an increased incidence and/or severity of lymphoid depletion, were observed in Compound 1-treated animals and were considered secondary to stress and ill-health. Microscopically, Compound 1 was associated with multinucleated cells in the sinusoids of the liver and mucosal atrophy of the intestinal tract in males and females at 100/50 and/or 300/200/100 mg/kg/day. The histological changes in the liver were considered adverse and correlated with a number of the serum chemistry changes. At the recovery interval, intestinal changes were absent, suggesting reversibility, and multinucleated cells in the sinusoids of the liver were decreased in severity, indicating partial recovery. Test article-related increase in the mean $QT_c$ level was observed at the highest dose level 300/200/100 mg/kg/day in the male monkeys. The threshold plasma $C_{max}$ concentration in a monkey that experienced an average group $QT_c$ prolongation of 10.6% was 7840 ng/mL.

The no-observed-adverse effect-level (NOAEL) for Compound 1 was considered to be 30 mg/kg/day (15 mg/kg/dose BID). Systemic exposure (C max and AUClast; combined-sex) at the NOAEL on Day 28 was 2490 ng/mL and 23600 ng·h/mL, respectively. Based on the expected reversibility of adverse hepatic findings, 50 mg/kg/day was considered the highest nonseverely toxic dose (HNSTD). Systemic exposure (C max and AUClast; combined-sex) at the HNSTD on Day 28 was 4350 ng/mL and 53900 ng·h/mL, respectively.

Example 10—A Phase 1 Dose Escalation Study of the mIDH-1 Inhibitor, Compound 1, in Patients with AML or Myelodysplastic Syndrome MDS Isocitrate dehydrogenase 1 mutations (mIDH-1) occur in 7-14% of AML patients ("pts.") and 3% of MDS pts. Compound 1 is a highly potent, selective small molecule inhibitor of mIDH-1 without anticipated CYP or QTc liabilities at the recommended phase 2 dose. Compound 1 was tested in a Phase 1/2 study to evaluate the safety, efficacy, PK, and PD of Compound 1 as a single agent or in combination with azacitidine or cytarabine.

FIG. 13A illustrates the summary of cohorts from a phase 1 study in IDH1m AML and MDS, described in this example. The Phase 1/2 study of Compound 1 was initiated to evaluate the safety, PK/PD, and clinical activity of Compound 1 alone or in combination with azacitidine (AZA) or cytarabine in mIDH-1 AML/MDS pts. In the phase 1 portion of the study, Compound 1 was dose escalated in a 3+3 design to define the maximum tolerated doses (MTDs) or maximum evaluated doses (MEDs) as a single-agent (SA) and in combination with azacitidine (CO) followed by expansion cohorts. Doses evaluated were 150 mg QD (SA, CO), 300 mg QD (SA), and 150 mg BID (SA, CO). Safety was assessed by incidence and severity of treatment emergent AEs (TEAEs) for all pts and efficacy derived by IWG criteria (2003 AML and 2006 MDS) based on investigator assessment for evaluable pts.

Figure 15:
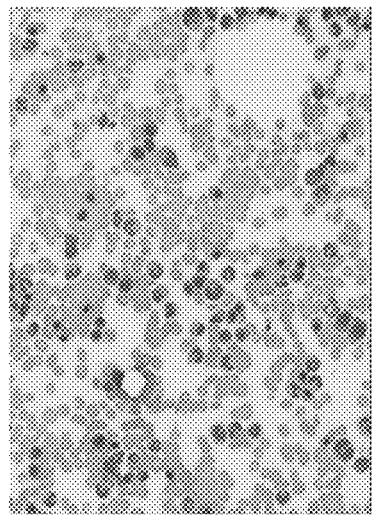
FIG. 15 is a graph showing cycle 1, grade 2 IDH-DS is resolved with dexamethasone and hydroxyurea. C2D1: CRp (1% blasts) to SCT in MLFS.
Figure 15:
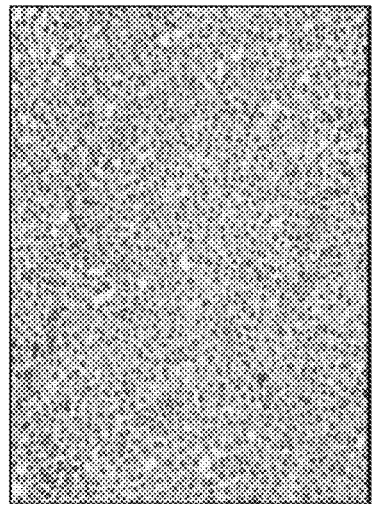

FIG. 15 illustrates cycle 1, grade 2 IDH-DS is resolved with dexamethasone and hydroxyurea. C2D1: CRp (1% blasts) to SCT in MLFS, during the clinical trial of Example 10.

Subject Inclusion Criteria can Include:
1. Pathologically proven AML or intermediate, high-risk, or very high risk MDS as defined by the World Health Organization (WHO) criteria or Revised International Prognostic Scoring System (IPSS-R) which is relapsed or refractory (R/R) to standard therapy and/or for which standard therapy is contraindicated or which has not adequately responded to standard therapy, e.g. Compound 1 as a single agent: patient has received no prior IDH1 inhibitor or Compound 1 in combination with Aza: patients are treat-naïve & eligible for Aza, patients can have received IDH1m inhibitor or HMA.
2. Patients must have documented IDH1-R132 gene-mutated disease as evaluated by the site.
3. Good performance status.
4. Good kidney and liver function.
5. Baseline QTcF≤450 msec.
6. No exclusions for concomitant medications.

Exclusion Criteria:
1. Patients with symptomatic central nervous system (CNS) metastases or other tumor location (such as spinal cord compression, other compressive mass, uncontrolled painful lesion, bone fracture, etc.) necessitating an urgent therapeutic intervention, palliative care, surgery or radiation therapy.
2. Congestive heart failure (New York Heart Association Class III or IV) or unstable angina pectoris. Previous history of myocardial infarction within 1 year prior to study entry, uncontrolled hypertension or uncontrolled arrhythmias.
3. Pulmonary disease (e.g. COPD, asthma, etc) that is not controlled (moderate to severe symptoms) with current medication.
4. Active, uncontrolled bacterial, viral, or fungal infections, requiring systemic therapy.

Treatment/Intervention Plan

Compound 1 was administered as a single agent or in combination with azacitidine or cytarabine. Compound 1 was supplied as 50 mg or 150 mg capsules and was administered per the protocol defined frequency and dose level. Azacitidine was administered per site's standard of care. Cytarabine will be administered per site's standard of care.

The Phase 1 stage of the study was split into 2 distinct parts: a dose escalation part, which will utilize an open-label design of Compound 1 (single agent), or Compound 1+azacitidine (combination agent), or Compound 1+cytarabine (combination agent) administered via one or more intermittent dosing schedules followed by a dose expansion part. The dose expansion part will enroll patients in up to 5 expansion cohorts, exploring single-agent Compound 1 activity as well as combination activity with azacitidine or cytarabine. Patients may receive only a single dose of study drug (single-agent arm and combination arm) on Cycle 1 Day 1. Following the completion of the relevant Phase 1 cohorts, Phase 2 begins enrollment. Patients are enrolled across 6 different cohorts, examining the effect of Compound 1 (as a single agent) and Compound 1 with azacitidine (combination) on various AML/MDS disease states. Conditions examined include acute myeloid leukemia (also known as acute myelogenous leukemia) and myelodysplastic syndrome.

TABLE 16

Arms and Interventions of Phase 1 Trial.

| Arms | Assigned Interventions |
|---|---|
| Experimental: PH1 Dose Escalation & Expansion Compound 1 | Drug: Compound 1<br>Compound 1 is supplied as 50 mg or 150 mg capsules and is administered per the protocol defined frequency and dose level |
| Experimental: PH1 Esc. and Exp. Compound 1 + Azacitidine | Drug: Compound 1<br>Compound 1 is supplied as 50 mg or 150 mg capsules and is administered per the protocol defined frequency and dose level<br>Drug: Azacitidine (Vidaza)<br>azacitidine is administered per site's standard of care |
| Experimental: PH1 Esc. and Exp. Compound 1 + Cytarabine | Drug: Compound 1<br>Compound 1 is supplied as 50 mg or 150 mg capsules and is administered per the protocol defined frequency and dose level<br>Drug: Cytarabine<br>low-dose cytarabine are administered per site's standard of care |
| Experimental: PH2 Cohort 1 Compound 1 Single Agent Relapsed or Refractory (R/R) AML | Drug: Compound 1<br>Compound 1 is supplied as 50 mg or 150 mg capsules and is administered per the protocol defined frequency and dose level |
| Experimental: PH2 Cohort 2 Compound 1 Single Agent AML/MDS in morphologic complete remission or complete remission with incomplete blood count recovery (CR/CRi) after cytotoxic-containing induction therapy with residual IDH-R132 mutation | Drug: Compound 1<br>Compound 1 is supplied as 50 mg or 150 mg capsules and is administered per the protocol defined frequency and dose level |
| Experimental: PH2 Cohort 3 Compound 1 Single Agent R/R AML/MDS, previously treated with an IDH1 inhibitor | Drug: Compound 1<br>Compound 1 is supplied as 50 mg or 150 mg capsules and is administered per the protocol defined frequency and dose level |
| Experimental: PH2 Cohort 4 Compound 1 + Azacitidine R/R AML/MDS that are naïve to prior hypomethylating therapy and IDH1 inhibitor therapy | Drug: Compound 1<br>Compound 1 is supplied as 50 mg or 150 mg capsules and is administered per the protocol defined frequency and dose level<br>Drug: Azacitidine (Vidaza)<br>Azacitidine is administered per site's standard of care |
| Experimental: PH2 Cohort 5 Compound 1 + Azacitidine R/R AML/MDS that have inadequately responded or have progressed immediately preceeding hypomethylating therapy | Drug: Compound 1<br>Compound 1 is supplied as 50 mg or 150 mg capsules and is administered per the protocol defined frequency and dose level<br>Drug: Azacitidine (Vidaza)<br>Azacitidine is administered per site's standard of care |
| Experimental: PH2 Cohort 6 Compound 1 + Azacitidine R/R AML/MDS that have been previously treated with single-agent IDH1 inhibitor therapy as their last therapy prior to study enrollment | Drug: Compound 1<br>Compound 1 is supplied as 50 mg or 150 mg capsules and is administered per the protocol defined frequency and dose level<br>Drug: Azacitidine (Vidaza)<br>azacitidine is administered per site's standard of care |

Following the completion of Phase 1, Phase 2 enrollment began. Patients were enrolled across 6 different cohorts, examining the effect of Compound 1 (as a single agent) and Compound 1+azacitidine (combination) on various AML/MDS disease states. The Phase 2 cohorts are summarized in Table 17 below:

TABLE 17

| Cohort | Patient Population | Intervention |
|---|---|---|
| I | Patients with relapsed or refractory (R/R) AML | Recommended phase II dose ("RP2D") of Compound 1 as a single-agent |
| II | Patients with AML/MDS in morphologic complete remission or complete remission with incomplete blood count recovery (CR/CRi) after cytotoxic-containing induction therapy with residual IDH-R132 mutation | RP2D of Compound 1 as a single-agent |
| III | Patients with R/R AML/MDS, previously treated with an IDH1 inhibitor | RP2D of Compound 1 as a single-agent |

TABLE 17-continued

| Cohort | Patient Population | Intervention |
|---|---|---|
| IV | Patients with R/R AML/MDS that are naïve to prior hypomethylating therapy and IDH1 inhibitor therapy | RP2D of Compound 1 in combination with azacitidine |
| V | Patients with R/R AML/MDS that have inadequately responded or have progressed immediately preceding hypomethylating therapy | RP2D of Compound 1 in combination with azacitidine |
| VI | Patients with R/R AML/MDS that have been previously treated with single-agent IDH1 inhibitor therapy as their last therapy prior to study enrollment | RP2D of Compound 1 in combination with azacitidine |

Primary Outcome Measures

The outcome of the study can be evaluated using the following criteria:
1. Maximum Tolerated Doses (MTDs) or Maximum Evaluated Doses (MEDs) [Phase 1]. Time Frame: Within first 4 weeks of treatment.
2. Number of Participants with a Dose Limiting Toxicity (DLT) [Phase 1]. Time Frame: Within first 4 weeks of treatment. DLT Criteria can include:
   ≥Gr 3 non-hematologic toxicity or laboratory finding
   Gr 4 hematologic toxicity by Day 42 in absence of disease
   Inability to tolerate at least 75% of Cycle 1 treatment
3. Doses recommended for future studies [Phase 1]. Time Frame: Within first 4 weeks of treatment.
4. Complete Response (CR, CRi, MLFS, Marrow CR) Rate of Compound 1 as a single-agent or in combination with Azacitidine in patients with AML/MDS [Phase 2]. Time Frame: As per IWG Response Assessment Guidelines for AML and MDS based on investigator's assessment through study completion, e.g. modified IWG AML 2003/MDS 2006.

Secondary Outcome Measures

The outcome of the study can also be evaluated using the following criteria:
1. Area under the plasma concentration versus time curve (AUC) [Phase 1 and Phase 2]. Time Frame: Blood samples for PK analysis collected at multiple visits during the first 60 days of treatment and on day 1 of all cycles following the first 30 days.
2. Peak Plasma Concentration (C max) [Phase 1 and Phase 2]. Time Frame: Blood samples for PK analysis collected at multiple visits during the first 60 days of treatment and on day 1 of all cycles following the first 30 days.
3. Time of peak plasma concentration (T max) [Phase 1 and Phase 2]. Time Frame: Blood samples for PK analysis collected at multiple visits during the first 60 days of treatment and on day 1 of all cycles following the first 30 days.
4. Time for half of the drug to be absent in blood stream following dose (T ½) [Phase 1 and Phase 2]. Time Frame: Blood samples for PK analysis collected at multiple visits during the first 60 days of treatment and on day 1 of all cycles following the first 30 days.
5. Rate at which drug is removed from blood stream (CL/F) [Phase 1 and Phase 2]. Time Frame: Blood samples for PK analysis collected at multiple visits during the first 60 days of treatment and on day 1 of all cycles following the first 30 days.
6. Rate of drug distribution within the blood stream (Vd/F) [Phase 1 and Phase 2]. Time Frame: Blood samples for PK analysis collected at multiple visits during the first 60 days of treatment and on day 1 of all cycles following the first 30 days.
7. Reduction of 2-HG levels in plasma [Phase 1 and Phase 2]. Time Frame: Blood samples for PK/PD analysis collected at multiple visits during the first 60 days of treatment and on day 1 of all cycles following the first 30 days.
8. Evidence of antileukemic or antimyelodysplastic activity of Compound 1 as determined by complete response (CR), CRi (complete remission with incomplete hematologic recovery), morphologic leukemia-free state (MLFS), Marrow CR, partial remission (PR), and stable disease (SD) as a single-agent or in combination with azacitidine or cytarabine [Phase 1]. Time Frame: As per IWG Response Assessment Guidelines for AML and MDS based on investigator's assessment through study completion.
9. Incidence and severity of adverse events, clinical laboratory abnormalities, and changes in ECG parameters as assessed by CTCAE v4.0 as a single-agent or in combination with azacitidine [Phase 2]. Time Frame: Safety will be assessed from time of first dose through 28 days post last dose.
10. Additional measures of antileukemic or antimyelodysplastic activity as determined by CRh, Overall Response (OR), and Stable Disease of Compound 1 alone or in combination with azacitidine [Phase 2]. Time Frame: As per IWG Response Assessment Guidelines for AML and MDS based on investigator's assessment through study completion.
11. Time to Response (TTR) [Phase 2]. Time Frame: From first dose of study drug through time of first response by blood recovery count.
12. Duration of Response (DOR) [Phase 2]. Time Frame: From time of first response by blood recovery count through relapse.
13. Event-Free Survival (EFS) [Phase 2]. Time Frame: From time of entry on study through progression.
14. Overall Survival (OS) [Phase 2]. Time Frame: From time of entry on study through death or date last known alive at end of follow-up.

Disease History and Baseline Characteristics of Exemplary Participants

A summary the disease history and baseline characteristics of exemplary participants is shown in Table 18.

TABLE 18

| Characteristic | Compund 1 n = 31 | Compund 1 + Azacitidine n = 41 |
|---|---|---|
| Age, median (range), years | 71 (35-87) | 66 (31-88) |
| Female, % | 52 | 51 |
| ECOG PS - 0/1/2, % | 25/65/10 | 32/51/17 |
| IDH1 mutation type R132-, n | C (13)/H (9)/S (4)/ G (4)/L (1) | C (22)/H (12)/S (4)/ G (2)/Others (1*) |
| AML, n | 25 | 35 |
| Relapsed (>12 mo) | 14 | 1 |
| Relapsed (≤12 mo) | 4 | 10 |
| Refractory | 8 | 15 |
| Treatment- naïve | 3 | 9 |
| Secondary AML | 3 | 12 |
| t-AML | 1 | 1 |
| Prior regimens, median (range) | 2 (0-10) | 3 (0-6) |
| Prior HMA/IDHm inhibitor/ Both | no prior IDHm inhibitor | 6/3/1 |
| MDS, n | 6 | 6 |

TABLE 18-continued

| Characteristic | Compund 1 n = 31 | Compund 1 + Azacitidine n = 41 |
|---|---|---|
| Relapsed/Refractory | 4 | 2 |
| Treatment naive | 2 | 4 |
| Prior regimens, median (range) | 1 (0-4) | 1 (0-4) |
| Prior HMA/IDHm inhibitor/Both | no prior IDHm inhibitor | 2/0/0 |

*One patient with a different non-R132 mutation variant

Results

In the human clinical trial described in Example 10, when Compound 1 was administered as a single agent, it provided a 41% overall response rate (ORR) and 27% CR/CRh in R/R AML. Combination of Compound 1 with azacitidine provided a 46% ORR and 16% CR/CRh in R/R AML.

At the data cutoff, 35 pts with a median of 2 prior regimens (range 1-9) had received Compound 1 in dose-escalation, including 31 single-agent (SA) and 41 azacitidine combination (CO) pts. Steady-state exposure that exceeded the target $IC_{90}$ for mIDH-1 was achieved at 150 mg BID, resulting in a reduction of 2-HG to normal levels in the majority of pts. Furthermore, administration of Compound 1, both as SA and in CO at 150 mg BID, enabled all pts to achieve the target Css that exceeded the $IC_{90}$ for mIDH-1 while staying below the exposures projected from the monkey toxicology studies that could be associated with QT prolongation. PK data were available through Cycle 10; steady state plasma drug levels were maintained at target Css over the evaluated period. A reduction of 2-HG was observed across all dose levels, with pts receiving 150 mg BID having a median within the normal 2-HG limits.

Figure 16A:
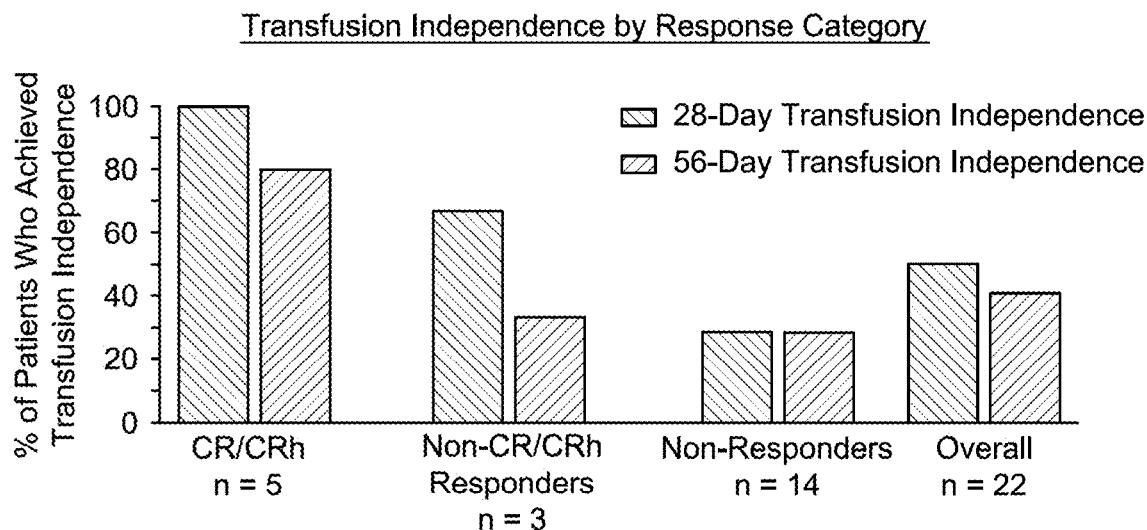
FIG. 16A is a graph of % patients who achieved transfusion independence (28- and 56-day) by category (CR/CRh, Non-CR/CRh, non-responders and overall), illustrating transfusion independence by response category for patients treated with Compound 1 as a single agent.
Figure 16B:
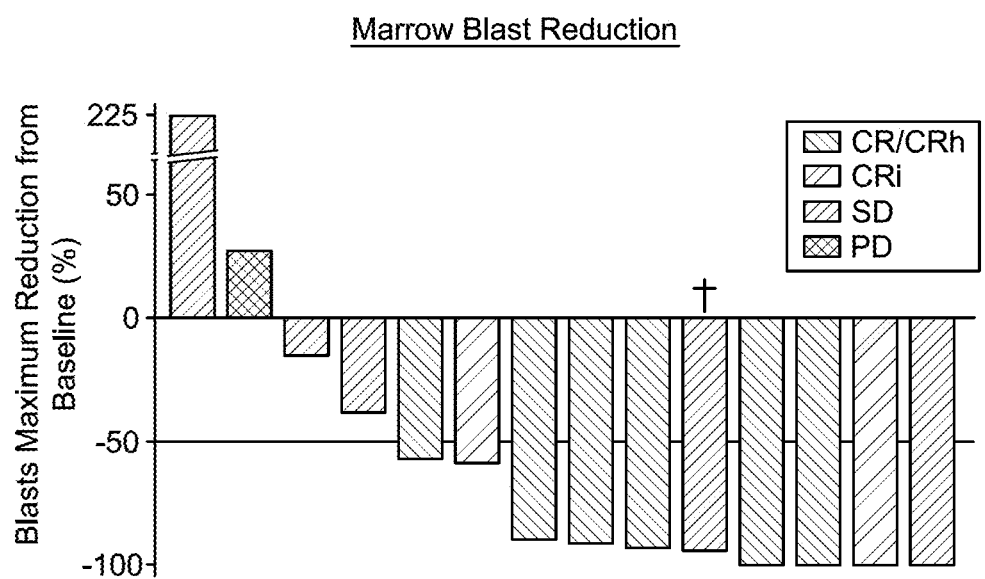
FIG. 16B is a graph showing blasts maximum reduction from baseline (%) based on category (CR/CRh, CRi, SD and PD), illustrating marrow blast reduction for patients treated with Compound 1 as a single agent.

As shown in FIG. 16A, transfusion independence (platelets and/or red blood cells) was observed in all response categories in AML patients treated with Compound 1 as a single agent who were transfusion-dependent at baseline. As shown in FIG. 16B, significant reduction in bone marrow blast content was observed in patients with a CR/CRi response per IWG response criteria. Reductions in bone marrow blast content were also observed in patients in the absence of IWG response (stable disease) including 1 subject (denoted with t in FIG. 16B) with bone marrow blast count <5% but with blasts present in peripheral blood.

The responses per Investigator assessment per modified IWG are summarized in Table 19:

TABLE 19

Responses to Compound 1 as a single agent.

| Response | R/R AML N = 22 | All AML & MDS N = 31 |
|---|---|---|
| ORR, n (%)* | 9 (41) | 11 (35) |
| [95% CI] | [21, 64] | [19, 55] |
| CR, n (%) | 4 (18) | 5 (16) |
| CRh, n (%) | 2 (9) | 2 (6) |
| CRi, n (%) | 3 (14) | 4 (13) |
| PR, n (%) | 0 | 0 |
| MLFS, n (%) | 0 | 0 |
| SD, n (%) | 5 (23) | 11 (35) |
| PD, n (%) | 1 (5) | 1 (3) |
| NE, n (%) | 7 (32) | 8 (26) |

Figure 17A:
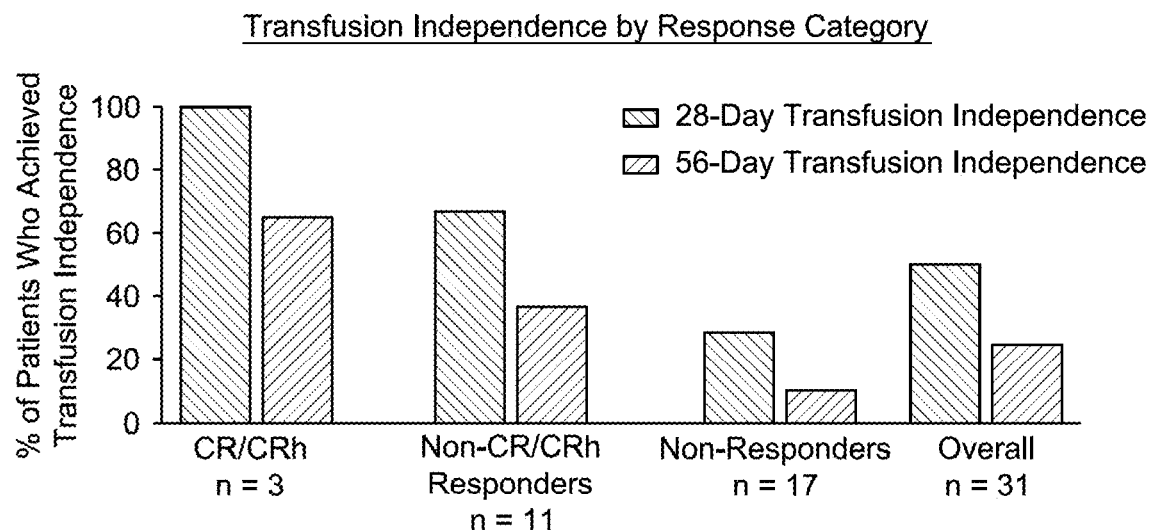
FIG. 17A is a graph of % patients who achieved transfusion independence (28- and 56-day) by category (CR/CRh, Non-CR/CRh, non-responders and overall), illustrating transfusion independence by response category for patients treated with Compound 1 in combination with azacitidine.
Figure 17B:
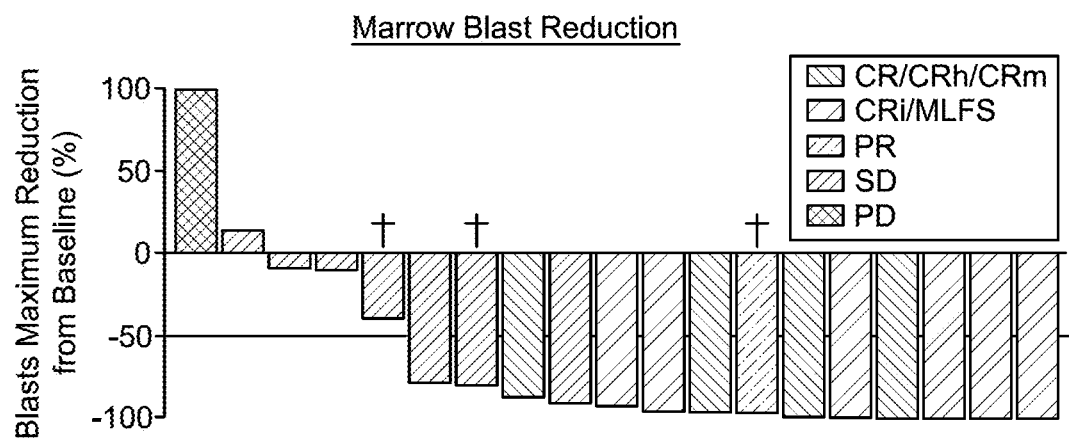
FIG. 17B is a graph showing blasts maximum reduction from baseline (%) based on category (CR/CRh, CRi, SD and PD), illustrating marrow blast reduction for patients treated with Compound 1 in combination with azacitidine.

As shown in FIG. 17A, transfusion independence (platelets and/or red blood cells) was observed in all response categories in AML patients treated with Compound 1 and azacitidine who were transfusion-dependent at baseline. As shown in FIG. 17B, reduction in bone marrow blast content was observed in patients with a CR/CRi response per IWG response criteria. Reductions in bone marrow blast content were also observed in patients in the absence of IWG response (stable disease) including 1 subject (denoted with t in FIG. 17B) with bone marrow blast count <5% but with blasts present in peripheral blood. Marrow blast reduction >50% in patients with SD indicates clinical activity in the absence of IWG response.

The responses per Investigator assessment per modified IWG are summarized in Table 20.

TABLE 20

Responses to Compound 1 + azacitidine.

| Response | R/R AML N = 26 | TN AML N = 9 | All AML & MDS N = 41 |
|---|---|---|---|
| ORR, n (%)* | 12 (46) | 7 (78) | 22 (54) |
| [95% CI] | [27, 67] | [40, 97] | [37, 69] |
| CR, n (%) | 3 (12) | 2 (22) | 8 (20) |
| CRh, n (%) | 1 (4) | 0 | 1 (2) |
| CRi, n (%) | 5 (19) | 4 (44) | 9 (22) |
| PR, n (%) | 1 (4) | 1 (11) | 2 (5) |
| MLFS, n (%) | 2 (8) | 0 | 2 (5) |
| SD, n (%) | 11 (42) | 1 (11) | 14 (34) |
| PD, n (%) | 1 (4) | 0 | 1 (2) |
| NE, n (%) | 2 (8) | 1 (11) | 4 (10) |

Exemplary Patient Disposition

A summary of the patient disposition is shown in Table 21.

TABLE 21

| | Compound 1 n = 31 (%) | Compound 1 + Azacitidine n = 27 (%) |
|---|---|---|
| Characteristic | | |
| Patients enrolled, n | 31 | 27 |
| Patients treated | 31 (100) | 26 (96) |
| Median months on treatment (range) | 3 (<1-20 m) | 3 (<1-12 m) |
| Patients on treatment | 13 (42) | 13 (50) |
| Discontinued treatment | 18 (58) | 13 (50) |
| Reason for Discontinuation | | |
| Death | 6 | 4 |
| Progressive disease | 9 | 6 |
| Transplant | 4 | 6 |
| Other * | 3 | 3 |
| Investigator decision | 2 | 5 |
| Withdrawal of consent | 1 | 0 |
| Adverse event | 3 | 2 |

* SA: 3 patients discontinued due to resistant disease/lack of response
Combo: 1 patient discontinued for refusal of treatment, 1 patient to enter hospice, and 1 patient with no reason for discontinuation given.

Treatment-Emergent Adverse Events (TEAEs) ≥15% All Grades

A summary of TEAEs can be found in Tables 22A and 22B.

TABLE 22A

| | Compound 1, n = 31 (Single Agent) | |
|---|---|---|
| AE Preferred Term | All Grade (%) | Grade 3/4 (%) |
| Fatigue | 13 (42) | 1 (3) |
| Nausea | 13 (42) | 0 |
| Pyrexia | 10 (32) | 2 (7) |

TABLE 22A-continued

| AE Preferred Term | Compound 1, n = 31 (Single Agent) | |
|---|---|---|
| | All Grade (%) | Grade 3/4 (%) |
| Pneumonia | 7 (23) | 5 (16) |
| Vomiting | 7 (23) | 0 |
| Dyspnea | 7 (23) | 0 |
| Diarrhea | 6 (19) | 0 |
| Dizziness | 6 (19) | 1 (3) |
| Decreased Appetite | 6 (19) | 0 |
| Constipation | 6 (19) | 1 (3) |
| Hypokalemia | 6 (19) | 2 (7) |
| AST | 5 (16) | 2 (7) |
| Abdominal distention | 5 (16) | 0 |
| Epistaxis | 5 (16) | 1 (3) |
| Headache | 5 (16) | 0 |
| Thrombocytopenia[1] | 9 (29) | 9 (29) |
| Leukocytosis | 8 (26) | 4 (13) |
| Anemia | 7 (23) | 7 (23) |
| Febrile neutropenia | 7 (23) | 7 (23) |

[1] Includes preferred term of platelet count decreased

TABLE 22B

| AE Preferred Term | Compound 1, n = 41 (Cpd 1 + AZA) | |
|---|---|---|
| | All Grade (%) | Grade 3/4 (%) |
| Nausea | 20 (49) | 3 (7) |
| Constipation | 20 (49) | 1 (2) |
| Hypokalemia | 15 (37) | 4 (10) |
| Fatigue | 15 (37) | 7 (17) |
| Diarrhea | 13 (32) | 2 (5) |
| Vomiting | 9 (22) | 0 |
| Headache | 9 (22) | 1 (2) |

TABLE 22B-continued

| AE Preferred Term | Compound 1, n = 41 (Cpd 1 + AZA) | |
|---|---|---|
| | All Grade (%) | Grade 3/4 (%) |
| Decreased Appetite | 8 (20) | 1 (2) |
| Cough | 7 (17) | 1 (2) |
| Pneumonia | 7 (17) | 6 (15) |
| Pruritus | 7 (17) | 0 |
| Dysgeusia | 7 (17) | 0 |
| Creatinine increased | 7 (17) | 1 (2) |
| Dizziness | 6 (15) | 1 (2) |
| Asthenia | 6 (15) | 2 (5) |
| Abdominal Pain | 6 (15) | 1 (2) |
| Thrombocytopenia[1] | 15 (37) | 12 (29) |
| Febrile neutropenia | 12 (29) | 12 (29) |
| Neutropenia[2] | 10 (24) | 7 (17) |
| Anemia | 9 (22) | 7 (17) |
| Leukocytosis | 9 (22) | 6 (15) |
| Leukpenia | 7 (17) | 5 (12) |

[1] Includes preferred term of platelet count decreased
[2] Includes preferred term of neutrophil count decreased Adverse Events (AE) of Interest and Deaths AEs were assessed per National Cancer Institute's Common Terminology Criteria for Adverse Events (NCI CTCAE), version 4.03.

No DLTs were observed in dose escalation.

Compound 1 as Single Agent 4 (13%) patients receiving Compound 1 as a single agent exhibited IDH-DS; all resolved with treatment interruption, dexamethasone, hydroxyurea and supportive care and then resumed treatment with Compound 1.

The QTcF maximum change from baseline for patients treated with Compound 1 as a single agent is reported in Table 23.

TABLE 23

| Treatment Group | Baseline Value | Maximum Post-Baseline Value | | | |
|---|---|---|---|---|---|
| | | ≤480 msec n (%) | >480-≤500 msec n (%) | >500 msec n (%) | >60 msec Δ from BL n (%) |
| Total Compound 1 SA | ≤480 msec | 27 (90) | 0 | 0 | 1 (3.3)[‡] |
| | >480-≤500 msec | 0 | 1 (3.3)[†] | 0 | 0 |
| | >500 msec | 0 | 0 | 1 (3.3) | 0 |
| (N = 30) | Total | 27 (90) | 1 (3.3) | 1 (3.3) | 1 (3.3) |

2 patients with BBB († in Table 23) enrolled with QTc readings above normal at baseline remained stable within the same QTc range on treatment. One patient (‡ in Table 23) had an increase of >60 msec but remained within the normal limits (<450 msec).

9 patients receiving Compound 1 as a single agent died within 30 days of last dose due to AEs unrelated to treatment with Compound 1. The AEs unrelated to treatment with Compound 1 which resulted in death are summarized below:
  Progressive Disease (PD) (n=3)
  Central Nervous System (CNS) Events (n=2)
  Sepsis (n=1)
  Cardiac Arrest (n=1)
  Multiorgan failure (n=1)
  toxicity to HSCT regime (n=1)

Compound 1 in Combination with Azacitidine

The QTcF maximum change from baseline (BL) for patients treated with Compound 1 and azacitidine in combination is reported in Table 24.

TABLE 24

| Treatment Group | Baseline Value | Maximum Post-Baseline Value | | | |
|---|---|---|---|---|---|
| | | ≤480 msec n (%) | >480-≤500 msec n (%) | >500 msec n (%) | >60 msec Δ from BL n (%) |
| Total Compound 1 + AZA 75 mg/m² | ≤480 msec | 37 (90.0) | 2 (5) | 2 (5) | 4 (10) |
| | >480-≤500 msec | 0 | 0 | 0 | 0 |
| | >500 msec | 0 | 0 | 0 | 0 |
| (N = 41) | Total | 37 (90.0) | 2 (5) | 2 (5) | 4 (10) |

Referring to Table 24, 4 patients with >60 msec which increased from BL included the 2 patients with suspect concomitant medications, 1 patient developed G1 prolongation and 1 patient remained within normal limits. Among the patients with QTcF <480 msec at BL, 2 had values of 480-500 msec, and 2 had values >500 msec. 1 of each group (including 1 with pacemaker) had prolonged QTcF before treatment start. The other 2 had transient prolongation that normalized once suspect concomitant medications discontinued 2 AEs of QTcF prolongation reported on study (G2 and G3). These were transient and patients resumed treatment once suspect concomitant medications discontinued.

7 patients receiving Compound 1 and azacitidine died within 30 days of last dose due to AEs unrelated to treatment with Compound 1. The AEs unrelated to treatment with Compound 1 which resulted in death are summarized below:
  Progressive Disease (PD) (n=3)
  Central Nervous System (CNS) Events (n=2)
  Pneumonia (n=1)
  Gastrointestinal fistula (n=1)

The present disclosure includes, among other things, the novel understanding that administration of 300 mg of Compound 1 (e.g., 150 mg BID or 300 mg QD) to a patient or population of patients results in a sustained therapeutically effective trough blood plasma concentration ($C_{ss}$). Such a $C_{ss}$ of Compound 1 resulted in a durable reduction in 2-HG plasma level over the course of at least 6 treatment cycles.

As outlined in Example 10, the concentration total plasma concentration of Compound 1 and the plasma concentration of 2-HG was measured in the blood of patients receiving one of three different dose and dose intervals: 150 mg QD, 300 mg QD or 150 mg BID (either receiving Compound 1 as a single agent or in combination with azacitidine as described in the clinical trial of Example 10, in each category). The 2-HG levels were measured prior to administration of Compound 1, and then measured after administration of Compound 1 up to cycle 2, day 1 after first receiving Compound 1 (as the solid form obtained from Example 1).

Figure 19:
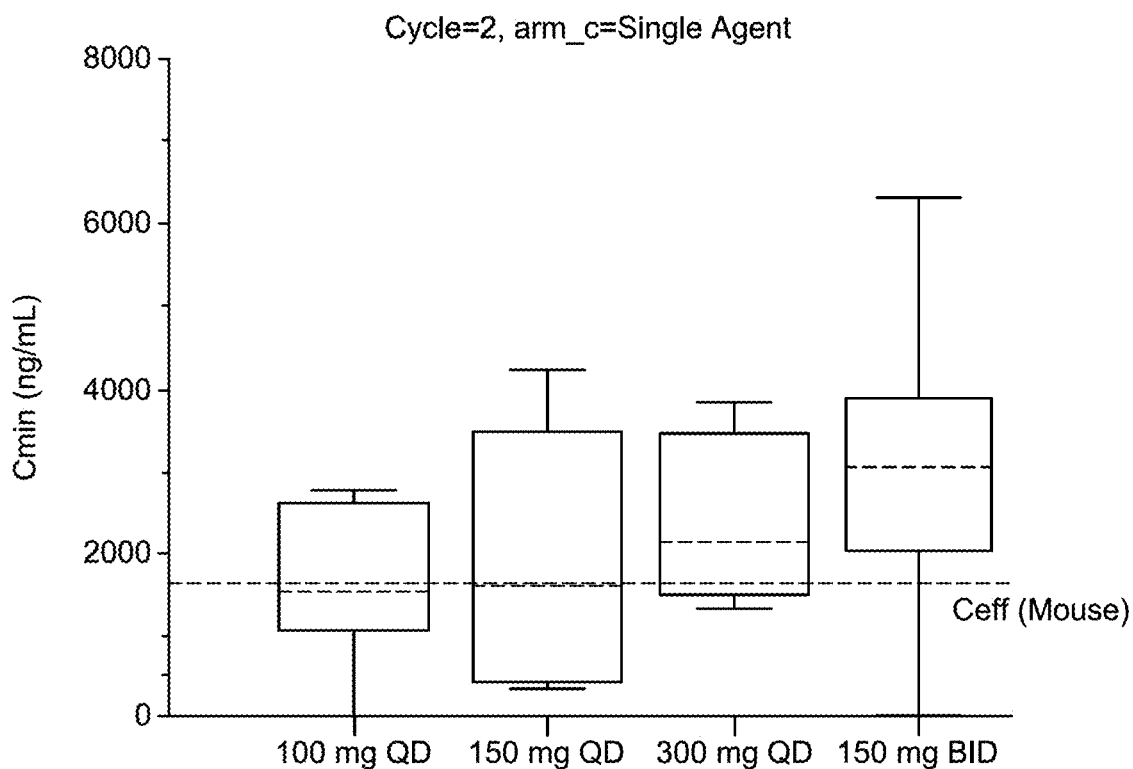
FIG. 19 is a graph of the minimum blood plasma concentration (C min) of Compound 1 measured in groups of human patients receiving Compound 1 as a single agent at different dose amounts and dose intervals: day 15 trough (ng/mL) of Compound 1 after administration to patients of 100 QD, 150 mg QD, 300 mg QD, and 150 mg BID Compound 1 as a single agent.
Figure 20:
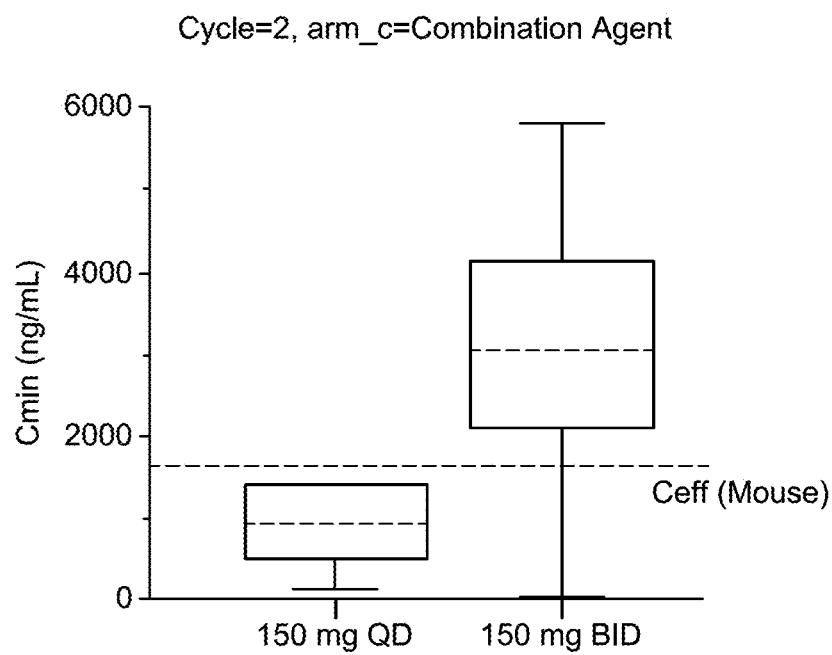
FIG. 20 is a graph of the minimum blood plasma concentration (C min) of Compound 1 measured in groups of human patients receiving Compound 1 at different dose amounts and dose intervals, in combination with azacitidine: day 15 trough (ng/mL) of Compound 1 after administration to patients of 150 mg QD and 150 mg BID of Compound 1 in combination with azacitidine.
Figure 21:
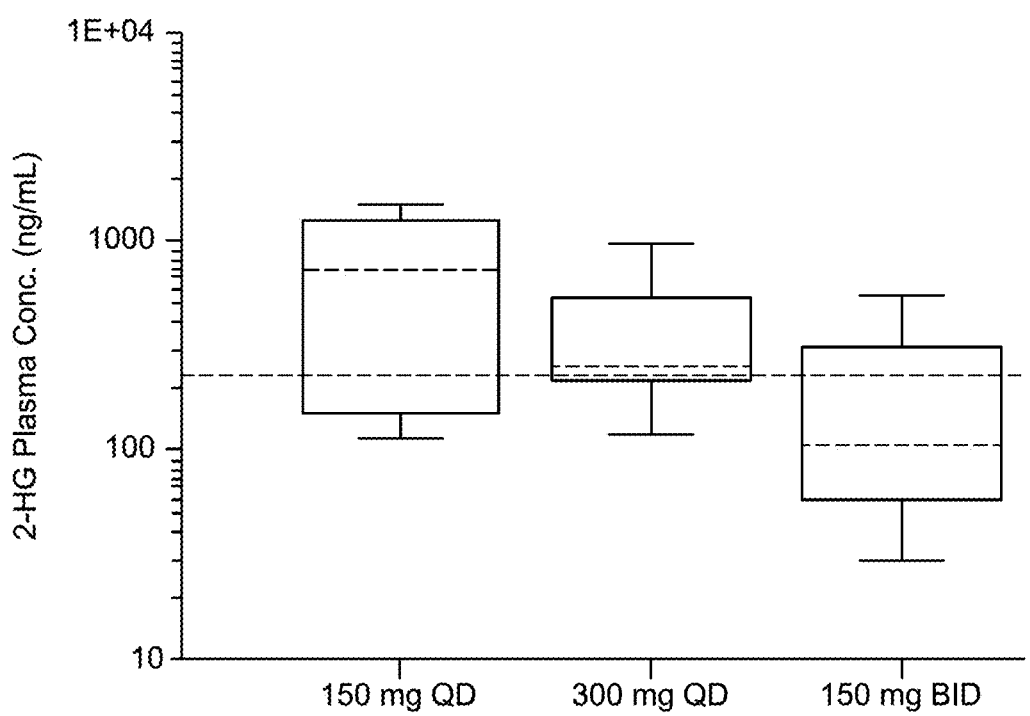
FIG. 21 illustrates a therapeutically reduced level of 2-HG in the patient plasma after consecutive treatment cycles of treatment with Compound 1 as a single agent.

As shown in FIGS. 19-20, the administration of Compound 1 at 150 mg BID resulted in a trough blood plasma concentration above 1,652 ng/mL after cycle 2 of a 28-day treatment cycle as both a single agent and in combination with azacitidine. Additionally, as shown in FIGS. 21-22, a reduction of 2-HG level was observed. The decrease in 2-HG concentration observed in patients receiving Compound 1 at 150 mg BID or 300 mg QD is unexpectedly better than those who received Compound 1 at 150 mg QD, both in terms of magnitude and variability of effect.

Figure 9A:
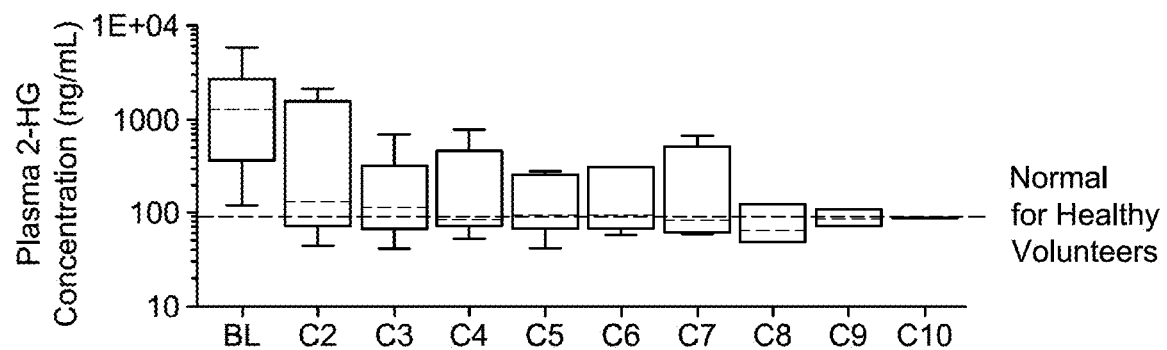
FIG. 9A is a graph of the level of 2-HG in plasma of a group of human patients after consecutive treatment cycles of treatment with Compound 1 as a single agent.
Figure 9B:
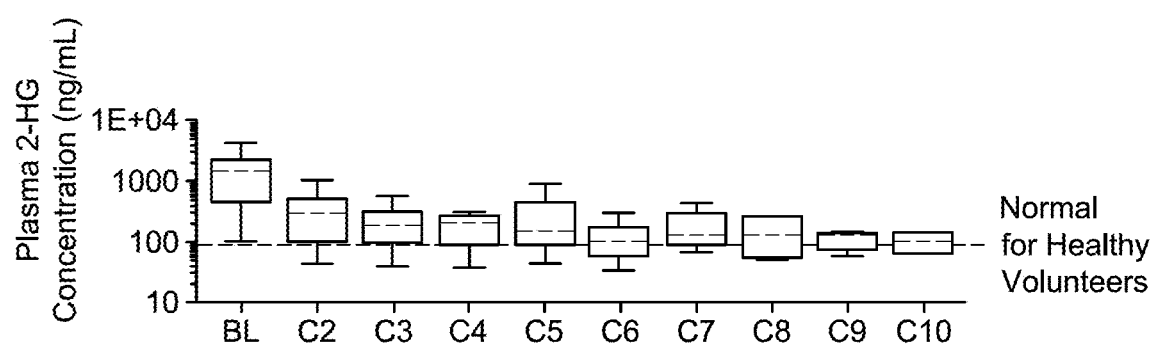
FIG. 9B is a graph of the level of 2-HG in plasma of a group of human patients after consecutive treatment cycles of treatment with Compound 1 and azacitidine.
Figure 9C:
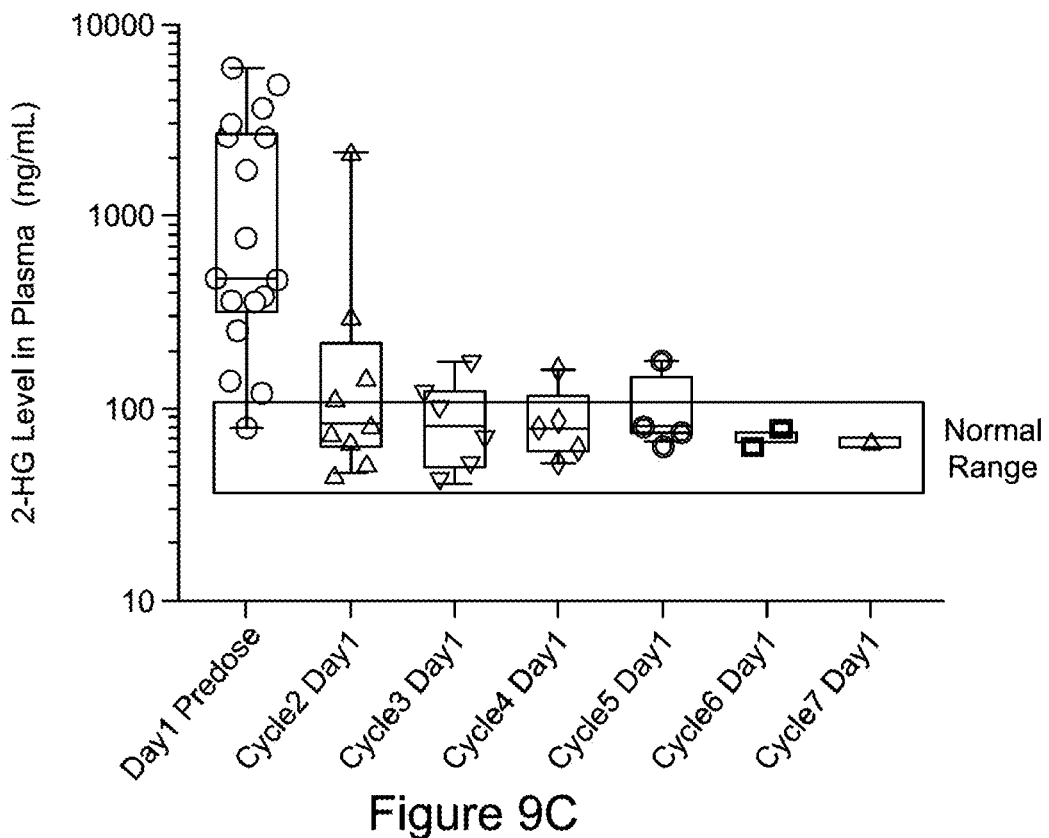
FIG. 9C is a graph of the level of 2-HG in plasma of a group of patients after two consecutive treatment cycles.
Figure 9D:
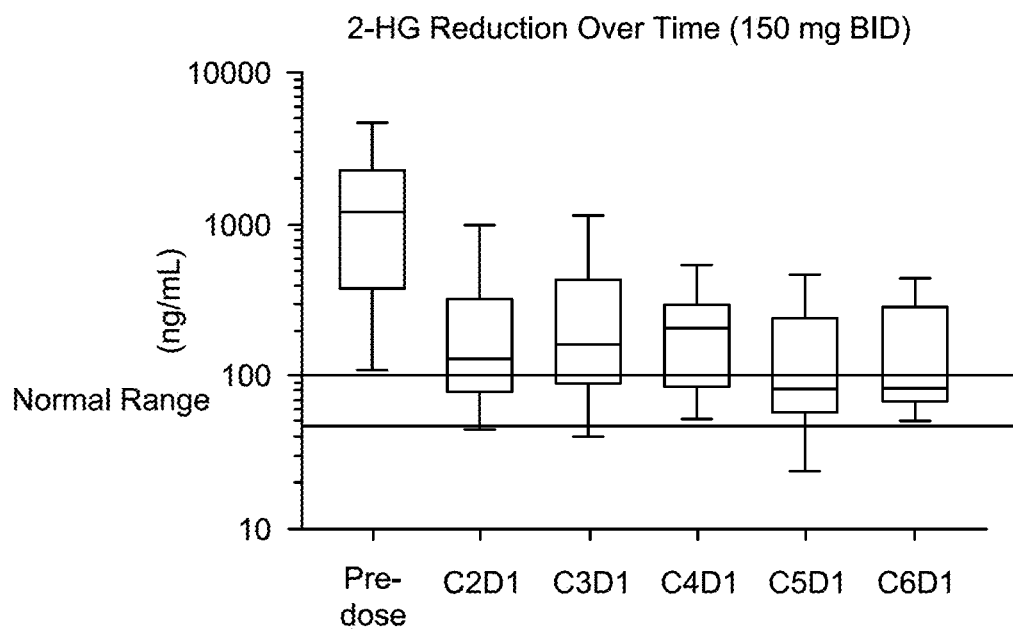
FIG. 9D is a graph showing the reduced level of 2-HG measured over time in a group of human patients treated with 150 mg of Compound 1 BID; the PD response is sustained throughout treatment with 150 mg of Compound 1 BID.

As shown in FIG. 8A-8E, the plasma exposures (steady state blood plasma concentration) of Compound 1 were durable (i.e., sustained) throughout at least a 6 cycle treatment duration. As shown in FIGS. 9A-9C the plasma 2-HG concentrations were reduced within 1 cycle (C2D1) and maintained throughout the treatment duration.

Example 11—Pharmacokinetics and Pharmacodynamics from Human Clinical Trial Testing Prior to Phase 1 trials, evaluation of Compound 1 in in vivo rat and in vitro human tissue indicated hepatic metabolism by CYP enzymes (CPY3A4, 2C9, 1A1) as the major route of excretion. Animal toxicology studies predicted the threshold for QTc prolongation risk occurred at exposures >6-fold the in vivo $C_{eff}$ observed in preclinical studies resulting in ≥90% reduction in plasma 2-HG.

In human clinical testing described above in Example 10, Compound 1 plasma concentrations were determined by a validated and sensitive bioanalytical method. Compound 1 was administered to patients QD (once per day) and BID (twice per day) as a single agent or in combination with azacitidine. On the 1st day of dosing (Cycle 1 Day 1), patients were administered a single dose of Compound 1 and the plasma was collected for pharmacokinetics analysis for 24 hours. Based on limited numbers of evaluable patients (n=5), a plasma half-life of about 60 hours was estimated for Compound 1 (steady state by week 2) for 150 mg BID administration of Compound 1, with a C max of about 570 ng/mL (well below the levels expected to increase QTcF potential (corrected QT interval) and an Area Under Curve (0-24 hours) of about 10,000 to 10,050 h ng/mL.

A lack of dose proportional response was noted in the C max and AUC after a single dose of Compound 1. Similarly, the steady state trough values did not increase with dose from 150 mg QD to 300 mg QD (see FIG. 10A). The lack of increasing C max, and steady trough values is believed to be caused by a dissolution limited absorption, which led to exploration of dose partition. As demonstrated in FIG. 10A, splitting the 300 mg QD dose to 150 mg BID dose improved the steady state exposure of Compound 1, as a single agent and in combination with azacitidine. Notably, concentrations observed in the 150 mg BID dose as a single agent or in combination with azacitidine span the $IC_{90}$ values for inhibition of all R132X mutations.

Changes in serum 2-HG levels collected at pre-dose and several time points through C2D1 (cycle 2, day 1) were measured to assess the pharmacodynamics effect of Compound 1 (See Example 10). A reduction in 2-HG was observed across all dosing cohorts with normalization of 2-HG levels observed with the BID dosing schedule of Compound 1. FIG. 10B shows the nadir of 2-HG levels in Cycle 1 of Compound 1 dosing observed in patients receiving single agent Compound 1 QD or BID dosing. The median level for pre-treatment, QD (150 mg or 300 mg), and BID (150 mg) is about 700, 200, and 70 ng/mL, respectively. Accordingly, the median 2-HG levels were reduced by about 10-fold in the 150 mg BID dose of Compound 1 compared to the 150 mg QD dose of Compound 1.

Example 12—Case Study of Human Clinical Trial Testing of Compound 1

Patient X is 66 y/o female, diagnosed with AML who initially received induction treatment with high dose cytarabine to which the patient was refractory. Subsequently, the patient enrolled in a clinical trial study, where she was treated with single agent (SA) Compound 1 150 mg BID and achieved a complete remission (CR) after one cycle of treatment (28 days). Patient continued treatment while in CR for 7 additional cycles. Patient then relapsed and discontinued study treatment.

Patient Y is 62 y/o male, diagnosed with FLT3-positive secondary AML (secondary to MDS). Patient received intensive chemotherapy induction with cytarabine and daunorubicin in combination with midostaurin (FLT3 inhibitor) but unfortunately was refractory. He enrolled in a clinical trial study, where he was treated with Compound 1 150 mg BID in combination with azacitidine for a total of 8 cycles (1 cycle=28 days). He achieved complete remission with IDH1 mutation clearance (CRm) by cycle 6 and discontinued study treatment after cycle 8 to undergo bone marrow transplant (HSCT).

Patient Z is a 50 year old diagnosed with grade III IDH1m glioma (anaplastic astrocytoma) previously treated with chemotherapy and radiation according to the applicable standard of care. This patient was subsequently enrolled on the clinical study treated with Compound 1 at 150 mg twice daily (BID) each day. Following treatment with Compound 1 for 2 cycles (each cycle=28 consecutive days receiving 150 mg Compound 1 BID), by MRI, patient was determined by the investigator to have experienced a partial response by RANO criteria (≥50% decrease in tumor, no new lesions, on stable dose corticosteroids, no progression of measurable disease). After receiving 2 cycles of Compound 1 (150 mg BID), the patient remains on treatment with 150 mg BID Compound 1 per protocol.

3 Patients received a Compound 1 at 100 mg once daily (QD) each day. Blood samples were collected every 28 days for measurement of plasma concentrations of Compound (single agent) Blood was collected at the following times relative to Compound 1 administration:

Cycle 1 Day 1: predose, and postdose at 30 minutes, 1, 2, 4, and 8 hours
Cycle 1 Days 2, 8, 15, and 22: predose
Cycle 2 Day 1: predose, and postdose at 30 minutes, 1, 2, 4, and 8 hours
Cycle 2 Day 2: 24 hours after C2D1 dosing (±2 hours) for patients in dose expansion
Cycle 2 Day 4: predose [72 hours after C2D1 dosing (±4 hours)] for patients in dose expansion only
Cycle 2 Day 15: predose
Cycle 3 and Beyond: Predose on Day 1 of every cycle The observed $C_{min}$ associated with this case study can be found in FIG. 19.

Example 13—A Phase 1b/2 Study of Compound 1 in Patients with Advanced CNS and Solid Tumors with an IDH1 Mutation Patients having any of the following solid tumors that harbor a IDH1 mutation receive Compound 1 (unless otherwise indicated, at a dose of 150 mg of the solid form provided in Example 1, administered orally BID) as a single agent or in combination with additional therapies:

Compound 1 is administered to patients diagnosed with glioma or chondrosarcoma as a single agent or in combination with 5-azacitidine (also referred to herein as "5-azacytidine" or "azacytidine" or "azacitidine");

Compound 1 is administered to patients diagnosed with hepatobiliary cancers as a single agent or in combination with a PD-1 inhibitor (preferably, nivolumab);

Compound 1 is administered to patients diagnosed with intrahepatic cholangiocarcinoma as a single agent or in combination with gemcitabine and cisplatin ("GemCis"); and Compound 1 is administered to patients diagnosed with other non-CNS solid tumors as a single agent.

Each patient has a histologically or cytologically-confirmed IDH1 R132X gene-mutated advanced solid tumor prior to receiving Compound 1. In particular, some patients receiving Compound 1 can have a histologically or cytologically-confirmed IDH1 R132X gene-mutated advanced glioma that has recurred or progressed following standard therapy. Patients receiving Compound 1 can have relapsed or refractory glioma (per WHO criteria 2016) with confirmed IDH1 mutation. Other patients receiving Compound 1 can have relapsed or refractory hepatobiliary tumors with confirmed IDH1 mutation previously treated with an approved therapy for HBC. Other patients receiving Compound 1 can have recurrent, refractory or either locally advanced or metastatic chondrosarcoma with confirmed IDH1 mutation not amenable to complete surgical excision. Other patients receiving Compound 1 can have advanced, nonresectable or metastatic intrahepatic cholangiocarcinoma with confirmed IDH1 mutation not eligible for curative resection or transplantation. Patients can be assessed for pharmacokinetics (PK) (e.g., by collecting a blood sample) at regular intervals throughout a course of treatment. In particular, pre-dose PK assessment is performed at least on days 1, 2, 8, 15, and 22 of the course of treatment for patients having a course of treatment comprising one or more 28-day treatment cycles. (Additional post dose assessment can be performed at cycle 1 day 1 and cycle 2 day 1.) In addition, pre-dose PK assessments are collected on day 1, 2 and 15 of cycle 2 of a 28-day treatment cycle during the course of treatment. Additional pre-dose PK assessment is performed on day 1 of Cycle 3 and subsequent 28-day treatment cycles during the course of treatment. Some patients receiving Compound 1 can have relapsed or refractory other solid tumors with confirmed IDH1 mutation.

In addition, methods of treatment can comprise the administration of Compound 1 to patients who meet the following criteria for inclusion: ≥18 years of age; Life expectancy of ≥4 months; Documented IDH1 gene-mutated malignancy based on local test evaluation; Able to provide tumor tissue sample (archival); and cancer diagnosis as detailed in below. Preferably, the methods comprise administering Compound 1 to a patient who also meets one or more of the following additional inclusion criteria:

Recovered to ≤Grade 2 or baseline toxicity (except alopecia) from prior therapy (per CTCAE v 4.03);

Eastern Cooperative Oncology Group (ECOG) performance status 0-2;

Adequate bone marrow function (e.g., Absolute neutrophil count (ANC) ≥1.5×109/L without any growth factors in prior 7 days and Hemoglobin ≥8.0 g/dL (with or without transfusion support); Platelet count ≥75× $10^9$/L (with or without transfusion support); Cohort 4b (GemCis combination); and platelet count ≥100×109/L (with or without transfusion support));

Child-Pugh Class A (HBC only)

Adequate hepatic function (e.g, Aspartate aminotransferase (AST) (serum glutamic oxaloacetic transaminase

[SGOT])/alanine aminotransferase (ALT) (serum glutamic pyruvate transaminase [SGPT])≤2.5× institutional upper limit of normal (ULN). For patients with suspected malignancy related elevations, <5×ULN; and Total bilirubin ≤1.5×ULN. For patients with suspected malignancy related elevation <3× institutional upper limit of normal); and Adequate renal function (e.g, Creatinine clearance per Cockcroft-Gault equation of ≥60 mL/min).

In some embodiments, Compound 1 is not administered to patients who meet one or more of the following exclusion criteria:

Previous solid organ or hematopoietic cell transplant

Prior anticancer treatment (e.g, No prior treatment with small molecule, antibody, or other anticancer therapeutic within 21 days (or 5 half-lives), whichever is shorter of first dose of study treatment (6 weeks for nitrosoureas or mitomycin C); No previous treatment with an IDH1 inhibitor; No prior radiation therapy (including radiofrequency ablation) within 4 weeks prior to initiation of study treatment; No prior stereotactic body radiation therapy (SBRT) within 2 weeks prior to initiation of study treatment; and No prior chemoembolization or radioembolization within 4 weeks)

Congestive heart failure (New York Heart Association Class III or IV) or unstable angina pectoris; previous history of myocardial infarction within one year prior to study entry, uncontrolled hypertension, or uncontrolled arrhythmias History of QT prolongation or baseline QT interval corrected with Fridericia's method (QTcF) >450 ms (average of triplicate readings) (NOTE: criterion does not apply to patients with a right or left bundle branch block)

Concomitant medication(s) associated with QTc interval prolongation or Torsades de Pointes (TdP) initiated less than the duration required to reach steady-state plasma concentration (approximately five half-lives) before first dose of study drug (medications used as needed [PRN] (e.g. Zofran) are exempt).

Pregnant or nursing women or women of childbearing potential not using adequate contraception; male patients not using adequate contraception Other malignancy within the last 5 years except: adequately treated non-melanoma skin cancer, curatively treated in situ cancer of the cervix, ductal carcinoma in situ (DCIS), stage 1, grade 1 endometrial carcinoma, or other solid tumors including lymphomas (without bone marrow involvement) curatively treated with no evidence of disease for ≥5 years Major surgery within 4 weeks of starting study treatment or not recovered from any effects of prior major surgery (uncomplicated central line placement or fine needle aspirate are not considered major surgery);

Patients receiving >6 mg/day of dexamethasone or equivalent

Patients with gastrointestinal disorders likely to interfere with absorption of the study medication Known history of HIV positivity Active infection with hepatitis B or C virus (Hep B or C viral load>100 international units/milliliter or local institutional equivalent)

Unstable or severe uncontrolled medical condition (e.g., unstable cardiac function, unstable pulmonary condition including pneumonitis and/or interstitial lung disease, uncontrolled diabetes) or any important medical or psychiatric illness or abnormal laboratory finding that would, in the Investigator's judgment, increase the risk to the patient associated with his or her participation in the study and PD-1 combination only: Patients with active autoimmune disease (Note: patients with well controlled diabetes or hypothyroidism are eligible).

Each patient receives Compound 1 throughout a medically appropriate course of treatment. In general, patients receive Compound 1 (either single-agent Compound 1 or combination therapy as indicated above) until disease progression or unacceptable toxicity. At the start of the course of treatment, each patient receives Compound 1 as the solid form obtainable by the method of Example 1 at a dose of 150 mg BID administered continuously in one or more 28-day treatment cycles.

The DLT-Evaluable Analysis Set is defined as all patients in the Safety Lead-in Periods (single agent Compound 1, combination Compound 1+5-azacitidine, combination Compound 1+GemCis and combination Compound 1+PD-1 inhibitor such as nivolumab) who either experienced a DLT during Cycle 1 or completed at least 75% of the prescribed Cycle 1 dose. This analysis sets will be used to assess the tolerability of Compound 1.

The Safety Analysis Set is defined as all patients who received any amount of study drug(s) (Compound 1 and combination agents, if appropriate).

This analysis set will be the primary analysis set for all safety endpoints, excluding DLT evaluation. Safety analysis will be by cohort and by treatment within cohort if more than 1 dose or dosing combination are initiated for a particular indication cohort.

The Response-Evaluable Analysis Set is defined as all patients with measurable disease at baseline who received the study drug(s) specific to the part of their particular cohort (either Compound 1 monotherapy or Compound 1 in combination), and had at least 1 post-baseline response assessment or discontinued the treatment phase due to disease progression (including death caused by disease progression) within 8 weeks (+2-week window) of the first dose of study treatment. This analysis set will be the primary analysis set for efficacy endpoints such as ORR. All response evaluations will be by cohort, and by treatment within cohort if more than 1 doses or dosing combinations are initiated for a particular indication cohort.

Patient safety measurements and clinical laboratory measurements are performed throughout the course of treatment for each cohort. Safety measurements include assessment of patient concomitant medications and procedures, AE/SAE assessment, symptom-directed physical examination and ECOG performance status. Clinical laboratory measurement assessment includes blood chemistry and hematology and other measurements specific to individual cohorts.

For patients receiving Compound 1 as a single agent, or in combination with 5-azacitidine (glioma, chondrosarcoma) or in combination with a PD-1 inhibitor (HBC), Compound 1 is administered in a 28-day treatment cycle (28 consecutive days, at a dose of 150 mg BID) and patient safety measurement and clinical blood chemistry and hematology are obtained on the following days during the course of treatment for patients in the first 28-day treatment cycle during the clinical trial: day 1, day 8 (+/−2), day 15 (+/−2), day 22 (+/−2). In treatment cycle 2 and beyond, these assessments are obtained at day 1 (+/−2) and day 15 (+/−2).

For patients receiving Compound 1 in combination with chemotherapy (e.g., GemCis for cholangiocarcinoma), Compound 1 is administered in a 28-day treatment cycle (28 consecutive days, at a dose of 150 mg BID) and patient safety measurement and clinical blood chemistry and hematology are obtained on the following days during the course of treatment for patients in the first six 28-day treatment cycle during the clinical trial: day 1, day 8 (+/−2), day 15 (+/−2), day 22 (+/−2). The combination is given for a total of six treatment cycles. In treatment cycle 7 and beyond, these assessments are obtained at day 1 (+/−2) and day 15 (+/−2). The patient can continue on single agent Compound 1 treatment without combination agent as directed by treating physician.

Safety Lead-In Period

The study includes a Safety Lead-in Period where single-agent 150 mg Compound 1 BID administered over 28 days (1 cycle). The Safety-Lead-in Period employs a traditional 3+3 design, whereby 3 patients with solid tumors and 3 patients with gliomas are treated with Compound 1 150 mg BID and monitored for dose-limiting toxicities (DLTs) during the first cycle of study treatment.

- If no DLTs occur in the first 3 patients in either group (solid tumors or glioma), and available pharmacokinetic (PK)/pharmacodynamic (PD) data support the dose, enrollment continues in the 4 disease-specific cohorts described below.
- If a DLT occurs in the first 3 patients in either group, an additional 3 patients are treated at that dose level in the relevant group. If no DLTs occur in these additional 3 patients (i.e. <2 DLTs per 6 patients) and available PK/PD data support the dose, enrollment continues in the 4 disease-specific cohorts described below.
- If there are ≥2 DLTs at the starting dose, lower doses or an altered dosing schedule of Compound 1 can be considered. Likewise, higher doses may be evaluated based upon safety, PK, and PD data as determined by the SRC.

Cohort 1: Glioma (n=16-31)

Compound 1 is used to treat patients diagnosed with a glioma cancer diagnosis. In particular, Compound 1 is administered to patients meeting the inclusion criteria above and one or more the following disease related inclusion criteria: histologically or cytologically confirmed IDH1 gene-mutated advanced glioma, and a diagnosis of glioblastoma multiforme with confirmed IDH1 gene-mutated disease with first or second recurrence. Cohort 1 includes patients with glioma harboring an IDH1 mutation that is relapsed or refractory. Glioma patients are treated with single-agent Compound 1 (Cohort 1a). Cohort 1a employs a Simon's 2-stage design, in which 8 patients are treated with single-agent Compound 1 for a minimum of 4 cycles (cycle=28 days) and assessed for efficacy and safety (Stage 1). If ≥1 clinical response is observed in Stage 1, then Stage 2 (n=15) initiates with single-agent Compound 1. If no clinical responses are observed in Stage 1 with single-agent Compound 1, then combination therapy is examined (Compound 1+5-azacytidine) (Cohort 1b). Cohort 1b employs a Simon's 2-stage design, whereby 8 patients are treated in Stage 1 with combination therapy for a minimum of 4 cycles (cycle=28 days) and assessed for efficacy and safety. If ≥1 clinical response is observed in Stage 1 of Cohort 1b, then Stage 2 (n=15) is initiated with combination therapy. During Stage 1 aggregate safety data are monitored by the SRC. If unacceptable toxicity is observed in Stage 1, then the dose and schedule may be modified by the SRC. (Note: any glioma patients enrolled in the safety Lead-in Period are considered part of Stage 1 enrollment.)

Cohort 2: Hepatobiliary Carcinoma (HBC) (n=21-63)

Compound 1 is used to treat patients diagnosed with a hepatobiliary carcinoma (HBC) cancer diagnosis. In particular, Compound 1 is administered to patients meeting the inclusion criteria above and one or more the following disease related inclusion criteria: Relapsed/refractory or intolerant to approved standard-of-care therapy (included: hepatocellular carcinoma, biliary carcinoma or other hepatobiliary carcinomas); Histologically or cytologically confirmed IDH1 gene-mutated with measurable disease per RECIST 1.1 criteria; and Child-Pugh Class A.

Cohort 2 includes patients with relapsed/refractory HBC harboring an IDH1 mutation. HBC patients are initially treated with single-agent Compound 1 (Cohort 2a). Prior exposure to nivolumab is permitted for patients of Cohort 2a. Cohort 2a employs a Simon's 2-stage design, in which 8 patients are treated with single-agent Compound 1 for a minimum of 4 cycles (cycle=28 days) and assessed for efficacy and safety (Stage 1). If ≥1 clinical response is observed in Stage 1, then Stage 2 (n=15) is initiated with single-agent Compound 1. If no clinical responses are observed in Stage 1 with single-agent Compound 1, then combination therapy can be examined (Compound 1+PD1 inhibitor) (Cohort 2b). Cohort 2b employs a Simon's 2-stage design, whereby 13 patients are treated in Stage 1 with combination therapy for a minimum of 4 cycles (cycle=28 days) and assessed for efficacy and safety. If ≥4 clinical response is observed in Stage 1 of Cohort 2b, then Stage 2 (n=42) can initiate with combination therapy. Prior exposure to nivolumab is not permitted for patients of Cohort 2b. During Stage 1 aggregate safety data is monitored by the SRC. If unacceptable toxicity is observed in Stage 1, then the dose and schedule may be modified by the SRC. (Note: any HBC patients enrolled in the Safety Lead-in Period are considered part of Stage 1 enrollment.)

Cohort 3: Chondrosarcoma (n=16-31)

Compound 1 is used to treat patients diagnosed with a chondrosarcoma cancer diagnosis. In particular, Compound 1 is administered to patients meeting the inclusion criteria above and one or more the following disease related inclusion criteria: Relapsed or refractory and either locally advanced or metastatic and not amenable to complete surgical excision; and histologically or cytologically confirmed IDH1 gene-mutated with measurable disease per RECIST 1.1 criteria. Cohort 3 includes patients with relapsed/refractory, locally advanced or metastatic chondrosarcoma harboring an IDH1 mutation. Chondrosarcoma patients are treated with single-agent Compound 1 (Cohort 3a). Cohort 3a will employ a Simon's 2-stage design, in which 8 patients will be treated with single-agent Compound 1 for a minimum of 4 cycles (cycle=28 days) and assessed for efficacy and safety (Stage 1). If ≥1 clinical response is observed in Stage 1, then Stage 2 (n=15) will initiate with single-agent Compound 1. If no clinical responses are observed in Stage 1 with single-agent Compound 1, then combination therapy is examined (Compound 1+5-azacytidine) (Cohort 3b). Cohort 3b employs a Simon's 2-stage design, whereby 8 patients are treated in Stage 1 with combination therapy for a minimum of 4 cycles (cycle=28 days) and assessed for efficacy and safety. If ≥1 clinical response is observed in Stage 1 of Cohort 3b, then Stage 2 (n=15) initiates with combination therapy. During Stage 1 aggregate safety data are monitored by the SRC. If unacceptable toxicity is observed in Stage 1, then the dose and schedule may be modified by the SRC. (Note: any chondrosarcoma patients enrolled in the Safety Lead-in Period are considered part of Stage 1 enrollment.)

Cohort 4: Intrahepatic Cholangiocarcinoma (n=21-63)

Compound 1 is used to treat patients diagnosed with an intrahepatic cholangiocarcinoma (IHCC) cancer diagnosis. In particular, Compound 1 is administered to patients meeting the inclusion criteria above and one or more of the following disease related inclusion criteria: Advanced non-resectable or metastatic IHCC not eligible for curative resection or transplantation; Phase 1b/Safety Lead-in of Phase 2: relapsed or refractory disease; and histologically or cytologically confirmed IDH1 gene-mutated with measurable disease per RECIST 1.1 criteria. Cohort 4 includes patients with advanced IHCC harboring an IDH1 mutation. IHCC patients are treated with single-agent Compound 1 (Cohort 4a). Patients of cohort 4a must be ineligible for standard therapies. Cohort 4a employs a Simon's 2-stage design, in which 8 patients are treated with single-agent Compound 1 for a minimum of 4 cycles (cycle=28 days) and assessed for efficacy and safety (Stage 1). If ≥2 clinical responses are observed in Stage 1, then Stage 2 (n=15) initiates with single-agent Compound 1. If <2 clinical responses are observed in Stage 1 with single-agent Compound 1, then combination therapy is examined (Compound 1+GemCis) (Cohort 4b). Patients in Cohort 4b have received no more than one cycle of Gem/Cis therapy. Cohort 4b employs a Simon's 2-stage design, whereby 13 patients are treated in Stage 1 with combination therapy for a minimum of 4 cycles (cycle=21 days) and assessed for efficacy and safety. If ≥4 clinical responses are observed in Stage 1 of Cohort 4b, then Stage 2 (n=42) initiates with combination therapy. During Stage 1 aggregate safety data are monitored by the SRC. If unacceptable toxicity is observed in Stage 1, then the dose and schedule may be modified by the SRC. (Note: any IHCC patients enrolled in the Safety Lead-in Period are considered part of Stage 1 enrollment.)

In some examples, patients diagnosed with relapsed/refractory IHCC receive Compound 1 single agent, whereas patients newly diagnosed and treatment naïve IHCC receive Compound 1 in combination with GemCis chemotherapy.

Cohort 5: Other Non-CNS Solid Tumors with IDH1 Mutations (n=12)

Compound 1 is used to treat patients diagnosed with non-CNS solid tumors with IDH1 mutations (preferably detectable 2-HG in plasma). Cohort 5 includes patients with relapsed or refractory non-CNS solid tumors harboring an IDH1 mutation. In particular, Compound 1 is administered to patients meeting the inclusion criteria above and one or more of the following disease related inclusion criteria: relapsed or refractory to standard-of-care therapy with no other available therapeutic options; and histologically or cytologically confirmed IDH1 gene-mutated with measurable disease per disease appropriate response criteria. This cohort includes treatment with single agent Compound 1. Due to the diverse population, this is an exploratory cohort without pre-defined efficacy/futility determinations. Aggregate safety data is monitored by the SRC and if unacceptable toxicity is observed in ≥2 patients, the cohort can be closed for additional enrollment.

Table 25 Schedule of Efficacy Assessment by Cohort

For Cohorts 1-5 above, the efficacy assessments obtained include those listed in the table below. (MRS=1H magnetic resonance spectroscopy; MRI=magnetic resonance imaging).

TABLE 25

| Cohort | Population | Assessment Criteria | Response Assessment | Biomarkers | Cycles (day 1) |
|---|---|---|---|---|---|
| 1 | Glioma | Modified RANO Criteria 2017, Low Grade Glioma RANO 2011 | Contrast-enhanced MRI and MRS for 2-HG (central) | N/A | C3, C5, C7, C9, C12, every 3 cycles thereafter |
| 2 | HBC | Modified RECIST RECIST v1.1 | CT/MRI | Serum AFP, CA19-9, and CEA | C3, C5, C7, C9, C12, every 3 cycles thereafter |
| 3 | Chondrosarcoma | RECIST v 1.1 | CT/18FDG-PET | N/A | C3, C5, C7, C9, C12, every 3 cycles thereafter |
| 4 | Cholangiocarcinoma (IHCC) | RECIST v1.1 | CT/MRI | Serum CA19-9, and CEA | C3, C5, C7, C9, C12, every 3 cycles thereafter |
| 5 | Other IDH1 Solid Tumors | Disease appropriate | CT/MRI | N/A | C3, C5, C7, C9, C12, every 3 cycles thereafter |

We claim:

1. A method of treating a patient diagnosed with a relapsed or refractory glioma having a R132H IDH1 mutation, the method comprising orally administering to the patient in need thereof a pharmaceutical composition comprising 150 mg of a compound of Formula (1) twice per day (BID):

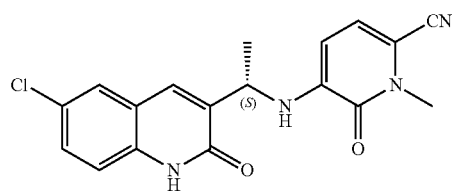

in an oral unit dosage form, on consecutive days throughout a course of treatment of at least 15 consecutive days.

2. The method of claim 1, wherein the patient is diagnosed with histologically or cytologically confirmed IDH1 gene-mutated advanced glioma or glioblastoma multiforme with confirmed IDH1 gene-mutated disease with first or second recurrence, prior to the administration of the compound of Formula (1).

3. The method of claim 1, wherein the compound of Formula (1) is administered to the patient as a single agent for the treatment of the glioma.

* * * * *